US009394555B2

(12) United States Patent
Sweeney et al.

(10) Patent No.: US 9,394,555 B2
(45) Date of Patent: Jul. 19, 2016

(54) COMPOSITIONS COMPRISING A POLYPEPTIDE HAVING CELLULOLYTIC ENHANCING ACTIVITY AND A DIOXY COMPOUND AND USES THEREOF

(75) Inventors: Matthew Sweeney, Sacramento, CA (US); Feng Xu, Davis, CA (US); Jason Quinlan, Woodland, CA (US)

(73) Assignee: NOVOZYMES, INC., Davis, CA (US)

( * ) Notice: Subject to any disclaimer, the term of this patent is extended or adjusted under 35 U.S.C. 154(b) by 338 days.

(21) Appl. No.: 13/814,919

(22) PCT Filed: Aug. 5, 2011

(86) PCT No.: PCT/US2011/046780
§ 371 (c)(1),
(2), (4) Date: Feb. 27, 2013

(87) PCT Pub. No.: WO2012/021408
PCT Pub. Date: Feb. 16, 2012

(65) Prior Publication Data
US 2013/0157317 A1      Jun. 20, 2013

Related U.S. Application Data

(60) Provisional application No. 61/373,210, filed on Aug. 12, 2010, provisional application No. 61/373,170, filed on Aug. 12, 2010, provisional application No. 61/373,166, filed on Aug. 12, 2010, provisional application No. 61/373,157, filed on Aug. 12, 2010, provisional application No. 61/373,150, filed on Aug. 12, 2010, provisional application No. 61/373,145, filed on Aug. 12, 2010, provisional application No. 61/373,128, filed on Aug. 12, 2010, provisional application No. 61/373,124, filed on Aug. 12, 2010.

(51) Int. Cl.
*C12N 9/42* (2006.01)
*C12P 7/10* (2006.01)
*C12P 19/02* (2006.01)
*C12P 19/14* (2006.01)
*C12N 9/24* (2006.01)
*C12N 9/96* (2006.01)
*C12P 7/14* (2006.01)
*B01J 31/06* (2006.01)

(52) U.S. Cl.
CPC .............. *C12P 19/14* (2013.01); *B01J 31/06* (2013.01); *C12N 9/2402* (2013.01); *C12N 9/2437* (2013.01); *C12N 9/2445* (2013.01); *C12N 9/96* (2013.01); *C12P 7/10* (2013.01); *C12P 7/14* (2013.01); *C12P 19/02* (2013.01); *C12Y 302/01021* (2013.01); *C12P 2203/00* (2013.01); *Y02E 50/16* (2013.01); *Y02P 20/52* (2015.11)

(58) Field of Classification Search
CPC ........ C12P 2201/00; C12P 7/10; C12P 19/14; C12N 9/2437; C12Y 302/0102

USPC .................................................. 435/209, 201
See application file for complete search history.

(56) References Cited

U.S. PATENT DOCUMENTS

| 4,248,663 | A | 2/1981 | Kubes et al. |
|---|---|---|---|
| 4,305,566 | A | 12/1981 | Grawunde |
| 4,310,383 | A | 1/1982 | Fujii et al. |
| 4,540,664 | A | 9/1985 | Johnson et al. |
| 5,871,663 | A | 2/1999 | Turner |
| 8,236,551 | B2 | 8/2012 | Dhawan et al. |
| 8,309,328 | B1 | 11/2012 | Dhawan et al. |
| 8,338,121 | B2 | 12/2012 | Sweeney et al. |
| 8,518,684 | B2 | 8/2013 | Brown et al. |
| 8,569,581 | B2 | 10/2013 | Maiyuran et al. |
| 2009/0019608 | A1 | 1/2009 | Lopez de Leon et al. |
| 2009/0056889 | A1 | 3/2009 | Ren et al. |
| 2009/0090480 | A1 | 4/2009 | Edwards |
| 2010/0129860 | A1 | 5/2010 | McFarland et al. |
| 2011/0002832 | A1 | 1/2011 | Hosono et al. |

FOREIGN PATENT DOCUMENTS

| WO | 2005074647 | A2 | 8/2005 |
|---|---|---|---|
| WO | 2005074656 | A2 | 8/2005 |
| WO | 2007089290 | A2 | 8/2007 |
| WO | 2008148131 | A1 | 12/2008 |
| WO | 2008151043 | A1 | 12/2008 |
| WO | 2009026722 | A1 | 3/2009 |
| WO | 2009085859 | A2 | 7/2009 |
| WO | 2009085864 | A2 | 7/2009 |
| WO | 2009085868 | A1 | 7/2009 |
| WO | 2009085935 | A2 | 7/2009 |
| WO | 2010065830 | A1 | 6/2010 |
| WO | 2010080532 | A1 | 7/2010 |

(Continued)

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Arantes et al, 2010, Biotechnol Biofuel 3(1,4), 1-11.
Gilbert et al, 2010, Plant Physiol 153(2), 444-455.
Harris et al, 2010, Biochem 49(15), 3305-3316.
Berlin et al, 2006, J Biotechnol 125(2), 198-209.
Davin et al, 2005, Curr Opinion Biotechnol 16 (4), 407-415.
Klinke et al, 2004, Appl Microbiol Biotechnol 66(1), 10-26.

(Continued)

*Primary Examiner* — Md. Younus Meah
(74) *Attorney, Agent, or Firm* — Robert Starnes

(57) ABSTRACT

The present invention relates to compositions comprising: a polypeptide having cellulolytic enhancing activity and a dioxy compound. The present invention also relates to methods of using the compositions.

54 Claims, 36 Drawing Sheets

(56) References Cited

FOREIGN PATENT DOCUMENTS

| | | |
|---|---|---|
| WO | 2010138754 A1 | 12/2010 |
| WO | 2011005867 A1 | 1/2011 |
| WO | 2011035027 A2 | 3/2011 |
| WO | 2011039319 A1 | 4/2011 |
| WO | 2011041397 A1 | 4/2011 |
| WO | 2011041504 A1 | 4/2011 |

OTHER PUBLICATIONS

Moser et al, 2008, Biotechnol Bioengg 100 (6), 1066-1077.
Quinlan et al, 2011, P N A S 108(37), 15079-15084.
Vaaje-Kolstad et al, 2010, Sci 330(6001), 219.
Li et al, 2012, Structure 20, 1051-1061.
Wilmot et al, 2012,Structure 20, 938-940.
Ximenes et al., 2010 Enz. Microb. Technol. 46,170-176.

* cited by examiner

COMPOSITIONS COMPRISING A POLYPEPTIDE HAVING CELLULOLYTIC ENHANCING ACTIVITY AND A DIOXY COMPOUND AND USES THEREOF

CROSS-REFERENCE TO RELATED APPLICATIONS

This application is a 35 U.S.C. 371 national application of PCT/US2011/046780 filed Aug. 5, 2011, which claims priority or the benefit under 35 U.S.C. 119 of U.S. Provisional Application Ser. No. 61/373,124, filed Aug. 12, 2010, U.S. Provisional Application Ser. No. 61/373,128, filed Aug. 12, 2010, U.S. Provisional Application Ser. No. 61/373,145, filed Aug. 12, 2010, U.S. Provisional Application Ser. No. 61/373, 150, filed Aug. 12, 2010, U.S. Provisional Application Ser. No. 61/373,157, filed Aug. 12, 2010, U.S. Provisional Application Ser. No. 61/373,166, filed Aug. 12, 2010, U.S. Provisional Application Ser. No. 61/373,170, filed Aug. 12, 2010, and U.S. Provisional Application Ser. No. 61/373,210, filed Aug. 12, 2010, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to compositions comprising a polypeptide having cellulolytic enhancing activity and a dioxy compound, and to methods of using the compositions.

2. Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

WO 2005/074647, WO 2008/148131, WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 discloses an isolated GH61 polypeptide having cellulolytic enhancing activity and the polynucleotide thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses isolated GH61 polypeptides having cellulolytic enhancing activity and the polynucleotides thereof from *Aspergillus fumigatus*. WO 2011/005867 discloses isolated GH61 polypeptides having cellulolytic enhancing activity and the polynucleotides thereof from *Penicillium pinophilum*. WO 2011/039319 discloses isolated GH61 polypeptides having cellulolytic enhancing activity and the polynucleotides thereof from *Thermoascus* sp. WO 2011/041397 discloses isolated GH61 polypeptides having cellulolytic enhancing activity and the polynucleotides thereof from *Penicillium* sp. WO 2011/041504 discloses isolated GH61 polypeptides having cellulolytic enhancing activity and the polynucleotides thereof from *Thermoascus crustaceous*. WO 2008/151043 discloses methods of increasing the activity of a GH61 polypeptide having cellulolytic enhancing activity by adding a soluble activating divalent metal cation to a composition comprising the polypeptide.

It would be advantageous in the art to improve the ability of polypeptides having cellulolytic enhancing activity to enhance enzymatic hydrolysis of lignocellulosic feedstocks.

The present invention relates to compositions comprising a polypeptide having cellulolytic enhancing activity and a dioxy compound, and to methods of using the compositions.

SUMMARY OF THE INVENTION

The present invention relates to compositions comprising: (a) a polypeptide having cellulolytic enhancing activity; and (b) a dioxy compound, wherein the combination of the polypeptide having cellulolytic enhancing activity and the dioxy compound enhances hydrolysis of a cellulosic material by a cellulolytic enzyme.

The present invention also relates to methods for degrading or converting a cellulosic material, comprising: treating the cellulosic material with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition.

The present invention also relates to methods for producing a fermentation product, comprising:
(a) saccharifying a cellulosic material with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition;
(b) fermenting the saccharified cellulosic material with one or more fermenting microorganisms to produce the fermentation product; and
(c) recovering the fermentation product from the fermentation.

The present invention also relates to methods of fermenting a cellulosic material, comprising: fermenting the cellulosic material with one or more fermenting microorganisms, wherein the cellulosic material is saccharified with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition.

In one aspect, the dioxy compound is a compound of formula (I):

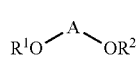
(I)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

A is a bond or an optionally substituted moiety selected from alkylene, alkenylene, alkynylene, cycloalkylene, heterocycloalkylene, arylene, and heteroarylene;

or a salt or solvate thereof.

DEFINITIONS

Figure 1A:
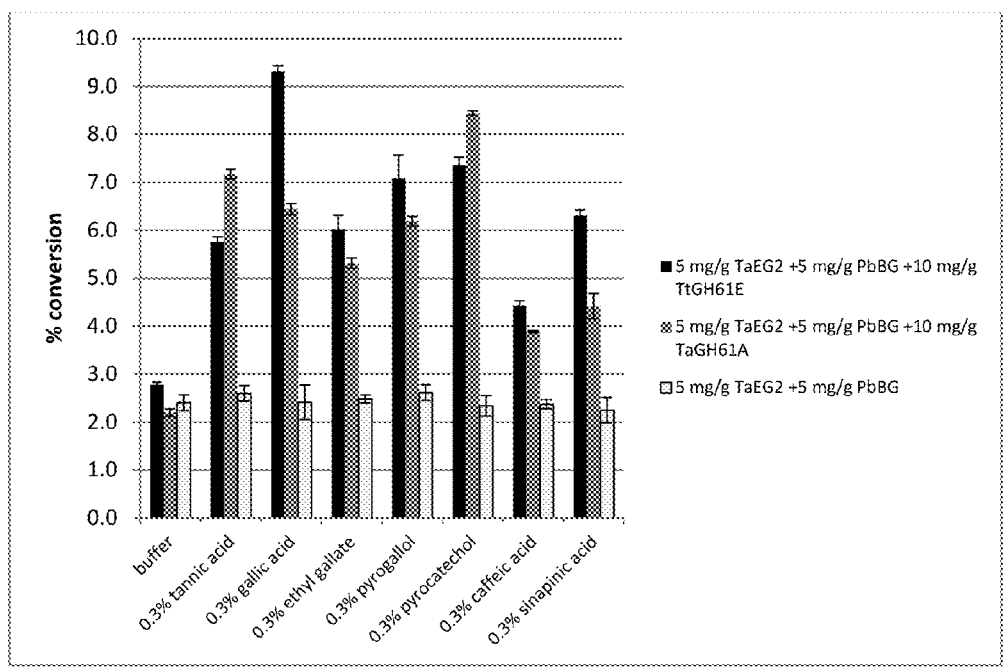
FIGS. 1A and 1B show the effect of combinations of *Thermoascus aurantiacus* GH61A polypeptide or *Thielavia terrestris* GH61E polypeptide with dioxy compounds, *Penicillium brasilianum* CEL3A beta-glucosidase, and *Thermoascus aurantiacus* CEL5A endoglucanase II on the conversion of microcrystalline cellulose.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alkyl: The term "alkyl," by itself or as part of another substituent, means, unless otherwise stated, a fully saturated straight-chain (linear; unbranched) or branched chain, or combination thereof, having the number of carbon atoms specified, if designated (i.e., $C_1$-$C_{10}$ means one to ten carbons). Examples include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. If no size is designated, the alkyl groups mentioned herein contain 1-20 carbon atoms, typically 1-10 carbon atoms, or 1-8 carbon atoms, or 1-6 carbon atoms, or 1-4 carbon atoms. The term "alkylene" is by itself or in combination with other terms, represents a divalent radical derived from an alkyl, as exemplified, but not limited, by —$CH_2CH_2CH_2CH_2$—.

Alkenyl: The term "alkenyl" refers to unsaturated aliphatic groups including straight-chain (linear; unbranched), branched-chain groups, and combinations thereof, having the number of carbon atoms specified, if designated, which contain at least one double bond (—C=C—). All double bonds may be independently either (E) or (Z) geometry, as well as mixtures thereof. Examples of alkenyl groups include, but are not limited to, —$CH_2$—CH=CH—$CH_3$; —CH=CH—CH=$CH_2$ and —$CH_2$—CH=CH—CH($CH_3$)—$CH_2$—$CH_3$. If no size is designated, the alkenyl groups mentioned herein contain 2-20 carbon atoms, typically 2-10 carbon atoms, or 2-8 carbon atoms, or 2-6 carbon atoms, or 2-4 carbon atoms. The term "alkenylene" is by itself or in combination with other terms, represents a divalent radical derived from an alkenyl, as exemplified, but not limited, by —$CH_2CHCHCH_2$—.

Alkynyl: The term "alkynyl" refers to unsaturated aliphatic groups including straight-chain (linear; unbranched), branched-chain groups, and combinations thereof, having the number of carbon atoms specified, if designated, which contain at least one carbon-carbon triple bond (—C≡C—). Examples of alkynyl groups include, but are not limited to, —$CH_2$—C≡C—$CH_3$; —C≡C—C≡CH and —$CH_2$—C≡C—CH($CH_3$)—$CH_2$—$CH_3$. If no size is designated, the alkynyl groups mentioned herein contain 2-20 carbon atoms, typically 2-10 carbon atoms, or 2-8 carbon atoms, or 2-6 carbon atoms, or 2-4 carbon atoms. The term "alkynylene" is by itself or in combination with other terms, represents a divalent radical derived from an alkynyl, as exemplified, but not limited, by —$CH_2CCCH_2$—.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Aralkyl: The term "aralkyl" designates an alkyl-substituted aryl group, where the alkyl portion is attached to the parent structure. Examples are benzyl, phenethyl, and the like. "Heteroaralkyl" designates a heteroaryl moiety attached to the parent structure via an alkyl residue. Examples include furanylmethyl, pyridinylmethyl, pyrimidinylethyl, and the like. Aralkyl and heteroaralkyl also include substituents in which at least one carbon atom of the alkyl group is present in the alkyl group and wherein another carbon of the alkyl group has been replaced by, for example, an oxygen, nitrogen or sulfur atom (e.g., phenoxymethyl, 2-pyridylmethoxy, 3-(1-naphthyloxy)propyl, and the like).

Aryl: The term "aryl" means, unless otherwise stated, a polyunsaturated, aromatic, hydrocarbon substituent. Aryl may contain additional fused rings (e.g., from 1 to 3 rings), including additionally fused aryl, heteroaryl, cycloalkyl, and/or heterocycloalkyl rings. Examples of aryl groups include, but are not limited to, phenyl, 1-naphthyl, 2-naphthyl, and 4-biphenyl.

Arylene/heteroarylene: The term "arylene" and "heteroarylene" means a divalent radical derived from an aryl and heteroaryl, respectively. Each of the two valencies of arylene and heteroarylene may be located at any suitable portion of the ring (e.g.,

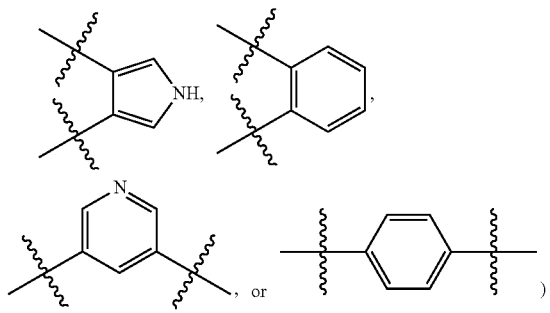

and may be fused to another ring, as appropriate. Non-limiting examples of arylene include phenylene, biphenylene, naphthylene, and the like. Examples of heteroarylene groups include, but are not limited to, pyridinylene, oxazolylene, thioazolylene, pyrazolylene, pyranylene, and furanylene.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-β-D-lactoside.

Cellulolytic enhancing activity: The term "cellulolytic enhancing activity" means a biological activity catalyzed by a GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N° 1 filter paper, microcrystalline cellulose, bacterial cellulose, algal cellulose, cotton, pretreated lignocellulose, etc. The most common total cellulolytic activity assay is the filter paper assay using Whatman N° 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-20 mg of cellulolytic enzyme protein/g of cellulose in PCS for 3-7 days at 50° C. compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means all components necessary for the expression of a polynucleotide encoding a polypeptide. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Cycloalkyl: The term "cycloalkyl" by itself or in combination with other terms, represents, unless otherwise stated, a saturated or unsaturated cyclic non-aromatic hydrocarbon radical (e.g., cyclic versions of alkyl, alkenyl, or alkynyl, or mixtures thereof). Cycloalkyl may contain additional fused rings (e.g., from 1 to 3 rings), including additionally fused cycloalkyl and/or heterocycloalkyl rings, but excludes additionally fused aryl and/or heteroaryl groups. Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like. If no size is designated, the alkynyl groups mentioned herein contain 3-9 carbon atoms, typically 3-7 carbon atoms. The term "cycloalkylene" by itself or as part of another substituent means a divalent radical derived from a cycloalkyl, as exemplified, but not limited, by -cyclohexyl-.

Cycloalkyl-alkyl/heterocycloalkyl-alkyl: The terms "cycloalkyl-alkyl" and "heterocycloalkyl-alkyl" designate an alkylsubstituted cycloalkyl group and alkyl-substituted heterocycloalkyl, respectively, where the alkyl moiety is attached to the parent structure. Non-limiting examples include cyclopropylethyl, cyclobutyl-propyl, cyclopentyl-hexyl, cyclohexyl-isopropyl, 1-cyclohexenyl-propyl, 3-cyclohexenyl-t-butyl, cycloheptyl-heptyl, norbornyl-methyl, 1-piperidinyl-ethyl, 4-morpholinyl-propyl, 3-morpholinyl-t-butyl, tetrahydrofuran-2-yl-hexyl, tetrahydrofuran-3-ylisopropyl, and the like. Cycloalkyl-alkyl and heterocycloalkyl-alkyl also include substituents in which at least one carbon atom is present in the alkyl group and wherein another carbon atom of the alkyl group has been replaced by, for example, an oxygen, nitrogen or sulfur atom (e.g., cyclopropoxymethyl, 2-piperidinyloxy-t-butyl, and the like).

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Halogen: The terms "halo" or "halogen," by themselves or as part of another substituent, mean, unless otherwise stated, a fluorine, chlorine, bromine, or iodine atom.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752.

Heteroaryl: The term "heteroaryl" refers to aryl groups (or rings) that contain from one to four annular heteroatoms selected from N, O, and S, wherein the nitrogen and sulfur atoms are optionally oxidized, and the nitrogen atom(s) are optionally quaternized. A heteroaryl group can be attached to the remainder of the molecule at an annular carbon or annular heteroatom. Heteroaryl may contain additional fused rings (e.g., from 1 to 3 rings), including additionally fused aryl, heteroaryl, cycloalkyl, and/or heterocycloalkyl rings. Non-limiting examples of heteroaryl groups are 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Heterocycloalkyl: The term "heterocycloalkyl," by itself or in combination with other terms, represents a saturated or unsaturated cyclic non-aromatic hydrocarbon radical containing of at least one carbon atom and at least one annular heteroatom selected from the group consisting of O, N, P, Si and S, and wherein the nitrogen and sulfur atoms may optionally be oxidized and the nitrogen heteroatom may optionally be quaternized. The heteroatom(s) O, N, P, S and Si may be placed at any interior position of the heterocycloalkyl group or at the position at which the heterocycloalkyl group is attached to the remainder of the molecule. Heterocycloalkyl may contain additional fused rings (e.g., from 1 to 3 rings), including additionally fused cycloalkyl and/or heterocycloalkyl rings, but excludes additionally fused aryl and/or heteroaryl groups. Examples of heterocycloalkyl include, but are not limited to, thiazolidinonyl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The term "heterocycloalkylene" by itself or as part of another substituent means a divalent radical derived from a heterocycloalkyl, as exemplified, but not limited, by

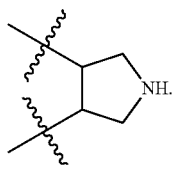 [SMILES: *C1CNCC1*]

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Isolated or Purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. The mature polypeptide can be predicted using the SignalP program (Nielsen et al., 1997, Protein Engineering 10:1-6).

Mature polypeptide coding sequence: The term "mature polypeptide coding sequence" is defined herein as a nucleotide sequence that encodes a mature polypeptide having biological activity. The mature polypeptide coding sequence can be predicted using the SignalP program (Nielsen et al., 1997, supra).

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide such that the control sequence directs the expression of the coding sequence.

Polypeptide fragment: The term "fragment" means a polypeptide having one or more (e.g., several) amino acids deleted from the amino and/or carboxyl terminus of a mature polypeptide; wherein the fragment has biological activity.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0, 5.0.0, or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides deleted from the 5' and/or 3' end of a mature polypeptide coding sequence; wherein the subsequence encodes a fragment having biological activity.

Substituted: The term "substituted" refers to the replacement of one or more (e.g., several) hydrogen atoms of a moiety with a monovalent or divalent radical. "Optionally substituted" indicates that the moiety may be substituted or unsubstituted. A moiety lacking the terms "optionally substituted" and "substituted" is intended an unsubstituted moiety (e.g., "phenyl" is intended an unsubstituted phenyl unless indicated as a substituted phenyl or an optionally substituted phenyl). Suitable substituent groups for indicated optionally substituted moieties include, for example, hydroxyl, nitro, amino (e.g., —NH$_2$ or dialkyl amino), imino, cyano, halo (such as F, Cl, Br, I), halo alkyl (such as —CCl$_3$ or —CF$_3$), thio, sulfonyl, thioamido, amidino, imidino, oxo, oxamidino, methoxamidino, imidino, guanidino, sulfonamido, carboxyl, formyl, alkyl, alkoxy, alkoxy-alkyl, alkylcarbonyl, alkylcarbonyloxy (—OCOR), aminocarbonyl, arylcarbonyl, aralkylcarbonyl, carbonylamino, heteroarylcarbonyl, heteroaralkylcarbonyl, alkylthio, amino alkyl, cyanoalkyl, carbamoyl (—NHCOOR— or —OCONHR—), urea (—NH-CONHR—), aryl and the like, where R is any suitable group, e.g., alkyl or alkylene. In some embodiments, the optionally substituted moiety is optionally substituted only with select radicals, as described. In some embodiments, the above groups (e.g., alkyl groups) are optionally substituted with, for example, alkyl (e.g., methyl or ethyl), halo alkyl (e.g., —CCl$_3$, —CH$_2$CHCl$_3$ or —CF$_3$), cycloalkyl (e.g., —C$_3$H$_5$, —C$_4$H$_7$, —C$_5$H$_9$), amino (e.g., —NH$_2$ or dialkyl amino), alkoxy (e.g., methoxy), heterocycloalkyl (e.g., as morpholine, piperazine, piperidine, azetidine), hydroxyl, and/or heteroaryl (e.g., oxazolyl). Other suitable substituent groups for indicated optionally substituted moieties are described herein. In some embodiments, a substituent group is itself optionally substituted. In some embodiments, a substituent group is not itself substituted. The group substituted onto the substitution group can be, for example, carboxyl, halo, nitro, amino, cyano, hydroxyl, alkyl, alkenyl, alkynyl, alkoxy, aminocarbonyl, —SR, thioamido, —SO$_3$H, —SO$_2$R or cycloalkyl, where R is any suitable group, e.g., a hydrogen or alkyl.

When the substituted substituent includes a straight chain group, the substituent can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms (N, O or S).

Variant: The term "variant" means a polypeptide having cellulolytic enhancing activity comprising an alteration, i.e., a substitution, insertion, and/or deletion of one or more (e.g., several) amino acid residues at one or more (e.g., several) positions. A substitution means a replacement of an amino acid occupying a position with a different amino acid; a deletion means removal of an amino acid occupying a position; and an insertion means adding one or more (e.g., several) amino acids, e.g., 1-5 amino acids, adjacent to an amino acid occupying a position.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580 (19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

As used herein and in the appended claims, the singular forms "a," "or," and "the" include plural referents unless the context clearly dictates otherwise. It is understood that the aspects of the invention described herein include "consisting" and/or "consisting essentially of" aspects.

DETAILED DESCRIPTION OF THE INVENTION

The present invention relates to compositions comprising: (a) a polypeptide having cellulolytic enhancing activity; and (b) a dioxy compound, wherein the combination of the polypeptide having cellulolytic enhancing activity and the dioxy compound enhances hydrolysis of a cellulosic material by a cellulolytic enzyme. In one aspect, the compositions further comprise (c) one or more (e.g., several) enzymes selected from the group consisting of a cellulase, a hemicellulase, an esterase, an expansin, a laccase, a ligninolytic enzyme, a pectinase, a peroxidase, a protease, and a swollenin.

The present invention also relates to methods for degrading or converting a cellulosic material, comprising: treating the cellulosic material with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition. In one aspect, the method above further comprises recovering the degraded or converted cellulosic material. Soluble products of degradation or conversion of the cellulosic material can be separated from the insoluble cellulosic material using technology well known in the art such as, for example, centrifugation, filtration, and gravity settling.

The present invention also relates to methods for producing a fermentation product, comprising:

(a) saccharifying a cellulosic material with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition;

(b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition. In one aspect, the fermenting of the cellulosic material produces a fermentation product. In another aspect, the method further comprises recovering the fermentation product from the fermentation.

Dioxy Compounds

The dioxy compounds used in the methods and compositions of the present invention include any compound containing two or more oxygen atome. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives.

In one aspect of the methods and compositions of the present invention, the dioxy compound is of formula (I):

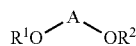

(I)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

A is a bond or an optionally substituted moiety selected from alkylene, alkenylene, alkynylene, cycloalkylene, heterocycloalkylene, arylene, and heteroarylene;

or a salt or solvate thereof.

In another aspect, A is an optionally substituted moiety selected from alkylene, alkenylene, alkynylene, and cycloalkylene. In another aspect, A is an optionally substituted alkylene (e.g., an optionally substituted $C_1$-$C_6$ alkylene, such as a methylene, ethylene, n-propylene, isopropylene, n-butylene, t-butylene, or n-pentylene substituted with one or more (e.g., several) alkyl, alkoxy, =O, or carboxyl moieties). In another aspect, A is an optionally substituted alkenylene (e.g., an optionally substituted $C_2$-$C_6$ alkenylene, such as a $C_2$-$C_6$ alkenylene substituted with one or more (e.g., several) alkyl, alkoxy, =O, or carboxyl moieties). In another aspect, A is an optionally substituted alkynylene (e.g., an optionally substituted $C_2$-$C_6$ alkynylene, such as a $C_2$-$C_6$ alkynylene substituted with one or more (e.g., several) alkyl, alkoxy, =O, or carboxyl moieties). In another aspect, A is an optionally substituted cycloalkylene (e.g., an optionally substituted $C_5$-$C_6$ cycloalkylene, such as a $C_5$-$C_6$ cycloalkylene substituted with one or more (e.g., several) alkyl, alkoxy, =O, or carboxyl moieties).

In some aspects, A is an optionally substituted moiety selected from arylene and heteroarylene. In some aspects, A is an optionally substituted arylene (e.g., an optionally substituted 5 or 6-membered arylene). In some aspects, A is an optionally substituted heteroarylene (e.g., an optionally substituted 5 or 6-membered heteroarylene). In some aspects, A is an optionally substituted moiety selected from phenylene, pyrazolylene, furanylene, imidazolylene, isoxazolylene, oxadiazolylene, oxazolylene, pyrrolylene, pyridylene, pyrimidylene, pyridazinylene, thiazolylene, triazolylene, thienylene, dihydrothieno-pyrazolylene, thianaphthenylene, carbazolylene, benzimidazolylene, benzothienylene, benzofuranylene, indolylene, quinolinylene, benzotriazolylene, benzothiazolylene, benzooxazolylene, benzimidazolylene, isoquinolinylene, isoindolylene, acridinylene, benzoisazolylene, dimethylhydantoinene, pyrazinylene, tetrahydrofuranylene, pyrrolinylene, pyrrolidinylene, morpholinylene, indolylene, diazepinylene, azepinylene, thiepinylene, piperidinylene, and oxepinylene. In some aspects, A is an optionally substituted phenylene.

In some aspects of formula (I), the dioxy compound is an organic acid. In some aspects of formula (I), the dioxy compound is not an organic acid (e.g., the dioxy compound is other than one or more of glutathione, coumaric acid, gallic acid, ascorbic acid, succinic acid, humic acid and/or ferulic acid).

In another aspect, the dioxy compound is of formula (II):

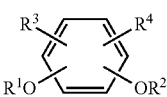

(II)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

$R^3$ and $R^4$ are independently hydrogen, halogen, —O$R^8$, —NO$_2$, —N($R^9$)($R^{10}$), —CN, —C(O)$R^5$, —C(O)O$R^6$, —C(O)NH$R^7$, —OC(O)$R^{11}$, —NHC(O)$R^{12}$, —OC(O)

$OR^{13}$, —$NHC(O)OR^{14}$, —$OC(O)NHR^{15}$, —$NHC(O)NHR^{16}$, —$SO_2R^{17}$, —$SO_2N(R^{18})(R^{19})$, —$SR^{20}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^3$ and $R^4$ combine to form an optionally substituted fused ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, and $R^{20}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and $R^{17}$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or a salt or solvate thereof.

In another aspect of formula (I) or (II), when one of $R^1$ and $R^2$ is hydrogen, the other of $R^1$ and $R^2$ is not methyl. In another aspect, when one of $R^1$ and $R^2$ is hydrogen, the other of $R^1$ and $R^2$ is not alkyl. In another aspect, when one of $R^1$ and $R^2$ is hydrogen, the other of $R^1$ and $R^2$ is hydrogen, —$C(O)R^5$, —$C(O)OR^6$, —$C(O)NHR^7$, or an optionally substituted moiety selected from alkenyl, alkynyl, cycloalkyl, cycloalkyl-alkyl, heterocycloalkyl, heterocycloalkyl-alkyl, aryl, aralkyl, heteroaryl, and heteroaralkyl.

In any of these aspects of formula (I) or (II), $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether. In some aspects, $R^1$ and $R^2$ are independently hydrogen, or an optionally substituted moiety selected from alkyl, alkenyl, alkynyl, cycloalkyl, or cycloalkyl-alkyl. In some aspects, $R^1$ and $R^2$ are independently hydrogen, or an optionally substituted moiety selected from alkyl, alkenyl, and alkynyl. In some aspects, $R^1$ and $R^2$ are independently hydrogen, or an optionally substituted alkyl. In some aspects, $R^1$ and $R^2$ are independently hydrogen, or an optionally substituted $C_1$-$C_5$ alkyl. In some aspects, $R^1$ and $R^2$ are independently hydrogen, or a $C_1$-$C_5$ alkyl. In some aspects, $R^1$ and $R^2$ are independently hydrogen, or an optionally substituted methyl. In some aspects, $R^1$ and $R^2$ are independently hydrogen or methyl. In some aspects, at least one of $R^1$ and $R^2$ is hydrogen. In some aspects, both $R^1$ and $R^2$ are hydrogen. In some aspects, at least one of $R^1$ and $R^2$ is an optionally substituted $C_1$-$C_5$ alkyl. In some aspects, at least one of $R^1$ and $R^2$ is an optionally substituted methyl. In some aspects, at least one of $R^1$ and $R^2$ is methyl. In some aspects, both $R^1$ and $R^2$ are an optionally substituted $C_1$-$C_5$ alkyl. In some aspects, both $R^1$ and $R^2$ are $C_1$-$C_5$ alkyl. In some aspects, both $R^1$ and $R^2$ are methyl.

In any of these aspects of formula (II), $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some aspects, $R^3$ and $R^4$ are independently hydrogen, or an optionally substituted moiety selected from alkyl, alkenyl, alkynyl, cycloalkyl, or cycloalkyl-alkyl. In some aspects, $R^3$ and $R^4$ are independently hydrogen, or an optionally substituted moiety selected from alkyl, alkenyl, and alkynyl. In some aspects, $R^3$ and $R^4$ are independently hydrogen, halogen, —OH, —$OR^8$, —$NO_2$, —$N(R^9)(R^{10})$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, —$SO_2R^{17}$, or —$SO_2N(R^{18})(R^{19})$. In some aspects, $R^3$ and $R^4$ are independently hydrogen, halogen, —OH, —$OR^8$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, or an optionally substituted moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl. In some aspects, one of $R^3$ and $R^4$ is —OH. In some aspects, at least one of $R^3$ and $R^4$ is hydrogen. In some aspects, both $R^3$ and $R^4$ are hydrogen. In some aspects, at least one of $R^3$ and $R^4$ is other than hydrogen. In some aspects, both $R^3$ and $R^4$ are other than hydrogen. In some aspects, $R^3$ and $R^4$ combine to form an optionally substituted fused ring (e.g., an optionally substituted cycloalkylene, heterocycloalkylene, arylene, or heteroarylene).

In some aspects of formula (II), the dioxy compound is an organic acid. In some aspects of formula (II) the dioxy compound is not an organic acid (e.g., the dioxy compound is other than one or more of gallic acid, humic acid and/or ferulic acid).

In some of these aspects of formula (I) or (II), both $R^1$ and $R^2$ are hydrogen; and wherein one of $R^3$ and $R^4$ is —OH. In some aspects, both $R^1$ and $R^2$ are optionally substituted alkyl; and wherein one of $R^3$ and $R^4$ is —OH. In some aspects, both $R^1$ and $R^2$ are optionally substituted —($C_1$-$C_5$)alkyl; and wherein one of $R^3$ and $R^4$ is —OH. In some aspects, both $R^1$ and $R^2$ are optionally substituted methyl; and wherein one of $R^3$ and $R^4$ is —OH.

In another aspect, the dioxy compound has the formula (II-A):

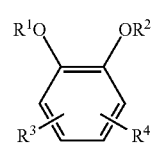

(II-A)

wherein $R^1$, $R^2$, $R^3$, and $R^4$ are as defined in any one of the aspects above; or a salt or solvate thereof.

In some aspects of formula (II-A), one of $R^1$ and $R^2$ is hydrogen, the other of $R^1$ and $R^2$ is not methyl. In some aspects, one of $R^1$ and $R^2$ is hydrogen, the other of $R^1$ and $R^2$ is not alkyl. In some aspects, one of $R^1$ and $R^2$ is hydrogen, the other of $R^1$ and $R^2$ is hydrogen, —$C(O)R^5$, —$C(O)OR^6$, —$C(O)NHR^7$, or an optionally substituted moiety selected from alkenyl, alkynyl, cycloalkyl, cycloalkyl-alkyl, heterocycloalkyl, heterocycloalkyl-alkyl, aryl, aralkyl, heteroaryl, and heteroaralkyl. In some aspects, $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether. In some aspects, $R^1$ and $R^2$ are independently hydrogen, or an optionally substituted moiety selected from alkyl, alkenyl, alkynyl, cycloalkyl, or cycloalkyl-alkyl. In some aspects, $R^1$ and $R^2$ are independently hydrogen, or an optionally substituted moiety selected from alkyl, alkenyl, and alkynyl. In some aspects, $R^1$ and $R^2$ are independently hydrogen, or an optionally substituted alkyl. In some aspects, $R^1$ and $R^2$ are independently hydrogen, or an optionally substituted $C_1$-$C_5$ alkyl. In some aspects, $R^1$ and $R^2$ are independently hydrogen, or a $C_1$-$C_5$ alkyl. In some aspects, $R^1$ and $R^2$ are independently hydrogen, or an optionally substituted methyl. In some aspects, $R^1$ and $R^2$ are independently hydrogen or methyl. In some aspects, at least one of $R^1$ and $R^2$ is hydrogen. In some aspects, both $R^1$ and $R^2$ are hydrogen. In some aspects, at least one of $R^1$ and $R^2$ is an optionally substituted $C_1$-$C_5$ alkyl. In some aspects, at least one of $R^1$ and $R^2$ is an optionally substituted methyl. In some aspects, at least one of $R^1$ and $R^2$ is methyl. In some aspects, both $R^1$ and $R^2$ are an optionally substituted $C_1$-$C_5$ alkyl. In some aspects, both $R^1$ and $R^2$ are $C_1$-$C_5$ alkyl. In some aspects, both $R^1$ and $R^2$ are methyl.

In some aspects of formula (II-A), the dioxy compound is an organic acid. In some aspects of formula (II-A), the dioxy compound is not an organic acid (e.g., the dioxy compound is other than one or more of gallic acid, humic acid and/or ferulic acid).

In another aspect, the dioxy compound has the formula (II-B):

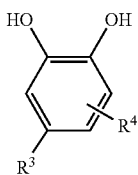

(II-B)

wherein $R^3$ and $R^4$ are as defined in any one of the aspects above; or a salt or solvate thereof.

In some aspects of formula (II-B), the dioxy compound is an organic acid. In some aspects of formula (II-B), the dioxy compound is not an organic acid (e.g., the dioxy compound is other than one or more of gallic acid, humic acid and/or ferulic acid).

In some aspects of formula (II-A) or formula (II-B), $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some aspects, $R^3$ and $R^4$ are independently hydrogen, or an optionally substituted moiety selected from alkyl, alkenyl, alkynyl, cycloalkyl, or cycloalkyl-alkyl. In some aspects, $R^3$ and $R^4$ are independently hydrogen, or an optionally substituted moiety selected from alkyl, alkenyl, and alkynyl. In some aspects, $R^3$ and $R^4$ are independently hydrogen, halogen, —OH, —$OR^8$, —$NO_2$, —$N(R^9)(R^{10})$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, —$SO_2R^{17}$, or —$SO_2N(R^{18})(R^{19})$. In some aspects, $R^3$ and $R^4$ are independently hydrogen, halogen, —OH, —$OR^8$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, or an optionally substituted moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl. In some aspects, one of $R^3$ and $R^4$ is —OH. In some aspects, at least one of $R^3$ and $R^4$ is hydrogen. In some aspects, both $R^3$ and $R^4$ are hydrogen. In some aspects, at least one of $R^3$ and $R^4$ is other than hydrogen. In some aspects, both $R^3$ and $R^4$ are other than hydrogen. In some aspects, both $R^1$ and $R^2$ are hydrogen; and wherein one of $R^3$ and $R^4$ is —OH. In some aspects, both $R^1$ and $R^2$ are optionally substituted alkyl; and wherein one of $R^3$ and $R^4$ is —OH. In some aspects, both $R^1$ and $R^2$ are optionally substituted —($C_1$-$C_5$)alkyl; and wherein one of $R^3$ and $R^4$ is —OH. In some aspects, both $R^1$ and $R^2$ are optionally substituted methyl; and wherein one of $R^3$ and $R^4$ is —OH. In some aspects, $R^3$ and $R^4$ combine to form an optionally substituted fused ring (e.g., an optionally substituted cycloalkylene, heterocycloalkylene, arylene, or heteroarylene).

In another aspect, the dioxy compound has of the formula (II-C):

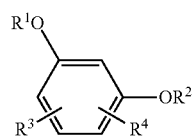

(II-C)

wherein $R^1$, $R^2$, $R^3$ and $R^4$ are as defined in any one of the aspects above; or a salt or solvate thereof.

In some aspects of formula (II-C), the dioxy compound is an organic acid. In some aspects of formula (II-C), the dioxy compound is not an organic acid (e.g., the dioxy compound is other than one or more of gallic acid and/or humic acid).

In another aspect, the dioxy compound has the formula (II-D):

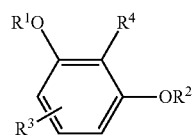

(II-D)

or a salt or solvate thereof.

wherein $R^1$, $R^2$, $R^3$ and $R^4$ are as defined in any one of the aspects above; or a salt or solvate thereof.

In some aspects of formula (II-D), the dioxy compound is an organic acid. In some aspects of formula (II-D), the dioxy compound is not an organic acid (e.g., the dioxy compound is other than one or more of gallic acid and/or humic acid).

In some aspects of formula (II-C) or formula (II-D), $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some aspects, $R^1$ and $R^2$ are independently hydrogen, or an optionally substituted moiety selected from alkyl, alkenyl, alkynyl, cycloalkyl, or cycloalkyl-alkyl. In some aspects, $R^1$ and $R^2$ are independently hydrogen, or an optionally substituted moiety selected from alkyl, alkenyl, and alkynyl. In some aspects, $R^1$ and $R^2$ are independently hydrogen, or an optionally substituted alkyl. In some aspects, $R^1$ and $R^2$ are independently hydrogen, or an optionally substituted $C_1$-$C_5$ alkyl. In some aspects, $R^1$ and $R^2$ are independently hydrogen, or a $C_1$-$C_5$ alkyl. In some aspects, $R^1$ and $R^2$ are independently hydrogen, or an optionally substituted methyl. In some aspects, $R^1$ and $R^2$ are independently hydrogen or methyl. In some aspects, at least one of $R^1$ and $R^2$ is hydrogen. In some aspects, both $R^1$ and $R^2$ are hydrogen. In some aspects, at least one of $R^1$ and $R^2$ is an optionally substituted $C_1$-$C_5$ alkyl. In some aspects, at least one of $R^1$ and $R^2$ is an optionally substituted methyl. In some aspects, at least one of $R^1$ and $R^2$ is methyl. In some aspects, both $R^1$ and $R^2$ are an optionally substituted $C_1$-$C_5$ alkyl. In some aspects, both $R^1$ and $R^2$ are $C_1$-$C_5$ alkyl. In some aspects, both $R^1$ and $R^2$ are methyl.

In some of these aspects of formula (II-C) or formula (II-D), $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some aspects, $R^3$ and $R^4$ are independently hydrogen, or an optionally substituted moiety selected from alkyl, alkenyl, alkynyl, cycloalkyl, or cycloalkyl-alkyl. In some aspects, $R^3$ and $R^4$ are independently hydrogen, or an optionally substituted moiety selected from alkyl, alkenyl, and alkynyl. In some aspects, $R^3$ and $R^4$ are independently hydrogen, halogen, —OH, —$OR^8$, —$NO_2$, —$N(R^9)(R^{10})$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, —$SO_2R^{17}$, or —$SO_2N(R^{18})(R^{19})$. In some aspects, $R^3$ and $R^4$ are independently hydrogen, halogen, —OH, —$OR^8$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, or an optionally substituted moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl. In some aspects, $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl. In some aspects, one of $R^3$ and $R^4$ is —OH. In some aspects, at least one of $R^3$ and $R^4$ is hydrogen. In some aspects, both $R^3$ and $R^4$ are hydrogen. In some aspects, at least one of $R^3$ and $R^4$ is other than hydrogen. In some aspects, both $R^3$ and $R^4$ are other than hydrogen. In some aspects, $R^3$ and $R^4$ combine to form an optionally substituted fused ring (e.g., an optionally substituted cycloalkylene, heterocycloalkylene, arylene, or heteroarylene).

In some of aspects of formula (II-C) or formula (II-D), both $R^1$ and $R^2$ are hydrogen; and wherein one of $R^3$ and $R^4$ is —OH. In some aspects, both $R^1$ and $R^2$ are optionally substituted alkyl; and wherein one of $R^3$ and $R^4$ is —OH. In some aspects, both $R^1$ and $R^2$ are optionally substituted —($C_1$-$C_5$) alkyl; and one of $R^3$ and $R^4$ is —OH. In some aspects, both $R^1$ and $R^2$ are optionally substituted methyl; and one of $R^3$ and $R^4$ is —OH.

In another aspect, the dioxy compound has the formula (II-E):

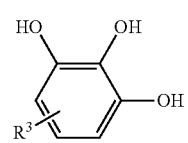

(II-E)

wherein $R^3$ is as defined in any one of the aspects above; or a salt or solvate thereof.

In some of these aspects of formula (II-E), $R^3$ is hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some aspects, $R^3$ is hydrogen, or an optionally substituted moiety selected from alkyl, alkenyl, alkynyl, cycloalkyl, or cycloalkyl-alkyl. In some aspects, $R^3$ is hydrogen, or an optionally substituted moiety selected from alkyl, alkenyl, and alkynyl. In some aspects, $R^3$ is hydrogen, halogen, —OH, —$OR^8$, —$NO_2$, —$N(R^9)(R^{10})$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, —$SO_2R^{17}$, or —$SO_2N(R^{18})(R^{19})$. In some aspects, $R^3$ is hydrogen, halogen, —OH, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, or an optionally substituted moiety selected from alkyl, alkenyl, and alkynyl. In some aspects, $R^3$ is hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl. In some aspects, $R^3$ is hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl. In some aspects, $R^3$ is hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl. In some aspects, one of $R^3$ is —OH. In some aspects, $R^3$ is hydrogen. In some aspects, $R^3$ is other than hydrogen.

In some aspects of formula (II-E), the dioxy compound is an organic acid. In some aspects of formula (II-E), the dioxy compound is not an organic acid (e.g., the dioxy compound is other than gallic acid).

In some of these aspects of the dioxy compounds (e.g., a dioxy compound of formula I, II, II-A, II-B, II-C, II-D, or II-E), each optionally substituted moiety is the indicated moiety optionally substituted with one or more (e.g., several) groups selected from hydroxyl, nitro, amino, imino, cyano, halo, haloalkyl, thiol, thioalkyl, sulfonyl, thioamido, amidino, oxo, oxamidino, methoxamidino, imidino, guanidino, sulfonamido, carboxyl, formyl, alkyl, cycloalkyl, alkoxy, alkoxy-alkyl, alkylcarbonyl, alkylcarbonyloxy, aminocarbonyl, aryl, heteroaryl, arylcarbonyl, aralkylcarbonyl, carbonylamino, heteroarylcarbonyl, heteroaralkyl-carbonyl, alkylthio, amino alkyl, cyanoalkyl, carbamoyl, and urea. In some embodiments, each optionally substituted moiety is the indicated moiety optionally substituted with one or more (e.g., several) groups selected from hydroxyl, nitro, amino, cyano, halo, haloalkyl, thiol, thioalkyl, sulfonyl, thioamido, amidino, carboxyl, formyl, alkyl, cycloalkyl, alkoxy, and alkoxy-alkyl.

In another aspect, the dioxy compound is selected from the group consisting of:

(I-1):

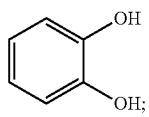

Pyrocatechol or catechol (I-2):

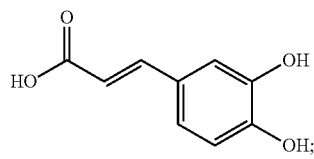

Caffeic acid (I-3):

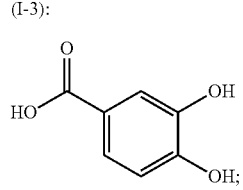

3,4-Dihydroxybenzoic acid (I-4):

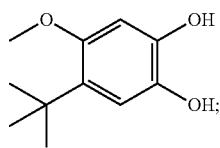

4-tert-Butyl-5-methoxy-1,2-benzenediol (I-5):

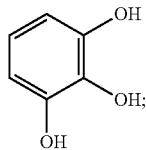

Pyrogallol (I-6):

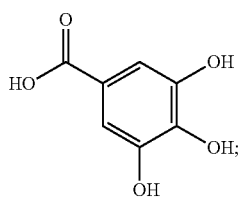

Gallic acid (I-7):

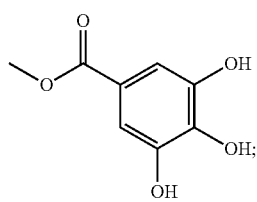

Methyl-3,4,5-trihydroxybenzoate (I-8):

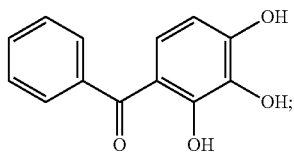

2,3,4-Trihydroxybenzophenone (I-9):

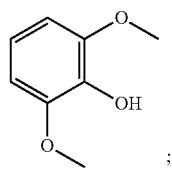

2,6-Dimethoxyphenol (I-10):

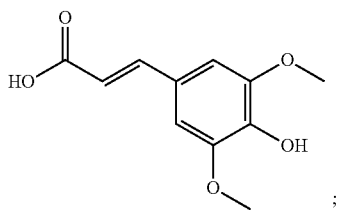

Sinapinic Acid (I-11):
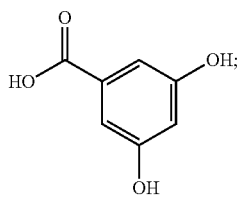
3,5-Dihydroxybenzoic acid
(I-12):
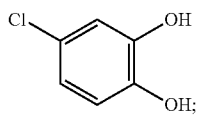
4-chloro-1,2-benzenediol
(I-13):
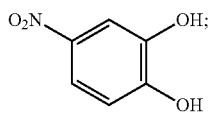
4-Nitro-1,2-benzenediol
(I-14):
Tannic acid
(I-15):
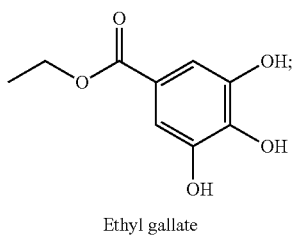
Ethyl gallate
(I-16):
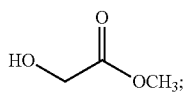
Methyl glycolate
(I-17):
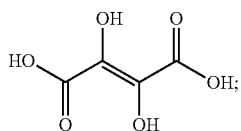
Dihydroxyfumaric acid
(I-18):
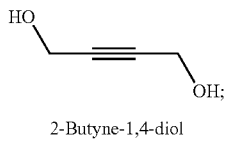
2-Butyne-1,4-diol
(I-19):
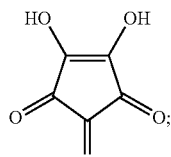
Croconic acid
(I-20):
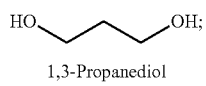
1,3-Propanediol
(I-21):
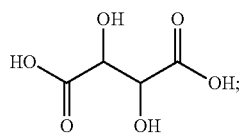
Tartaric acid
(I-22):
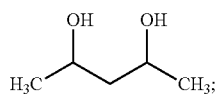
2,4-Pentanediol
(I-23):
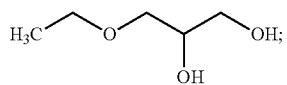
3-Ethyoxy-1,2-propanediol
(I-24):
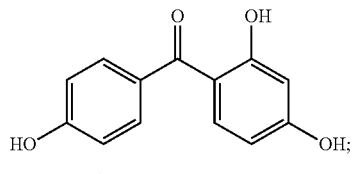
2,4,4'-Trihydroxybenzophenone
(I-25):
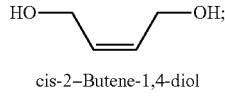
cis-2–Butene-1,4-diol
(I-26):
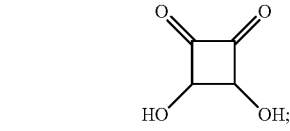
3,4-Dihydroxy-3-cyclobutene-1,2-dione or squaric acid
(I-27):
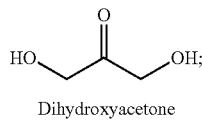
Dihydroxyacetone (I-28):

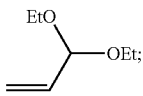

Acrolein acetal (I-29):

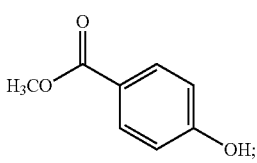

Methyl-4-hydroxybenzoate (I-30):

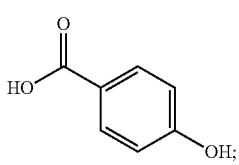

4-Hydroxybenzoic acid (I-31):

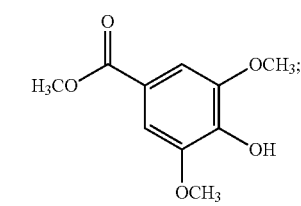

Methyl-3,5-dimethoxy-4-hydroxybenzoate (I-32):

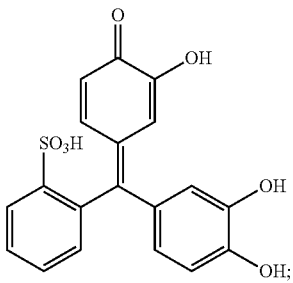

Pyrocatechol violet or a salt or solvate thereof.

In some aspects (e.g., any aspect of formula I, II, II-A, II-B, II-C, II-D, or II-E), the dioxy compound is an organic acid. In some of aspects of the dioxy compounds (e.g., a dioxy compound of formula I, II, II-A, II-B, II-C, II-D, or II-E), the dioxy compound is not an organic acid (e.g., the dioxy compound is not one or more of glutathione, coumaric acid, gallic acid, ascorbic acid, succinic acid, humic acid and/or ferulic acid).

In some aspects, the dioxy compound described herein (e.g., a dioxy compound of formula I, II, II-A, II-B, II-C, II-D, or II-E) is in substantially pure form. With respect to the dioxy dioxy compounds, unless otherwise stated, "substantially pure" intends a preparation of the dioxy compound that contains no more than 15% impurity, wherein the impurity intends compounds other than the dioxy compound, but does not include other forms of the dioxy compound (e.g., different salt form or a different stereoisomer, conformer, rotamer, or tautomer of the analog depicted). In one variation, a preparation of substantially pure dioxy compound is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

In some aspects the dioxy compound described herein (e.g., a compound of formula I, II, II-A, II-B, II-C, II-D, or II-E) is not in substantially pure form. For example, the dioxy compound may be added or supplemented as part of an impure composition (e.g., unpurified biological material) wherein the composition is rich in the compound or one or more (e.g., several) chemical precursors thereof. In a one aspect, an impure composition (e.g., unpurified biological material) comprising a dioxy compound is pretreated, e.g., as described herein for cellulosic material, and/or added to cellulosic material and/or combined with the cellulosic material prior to pretreatment of the cellulosic material. In another aspect, an impure composition (e.g., unpurified biological material) comprising a dioxy compound is added to an enzyme composition involved in saccharification, enhancement of saccharification, liquefaction, etc. In another aspect, an impure composition (e.g., unpurified biological material) comprising a dioxy compound is added to a fermentation or simultaneous saccharification-fermentation reaction. In any of these aspects, the impure composition comprising a dioxy compound (e.g., unpurified biological material) is a preparation that contains more than 0.5% impurity, or more than 1% impurity, or more than 3% impurity, or more than 5% impurity, or more than 10% impurity, or more than 20% impurity, or more than 30% impurity, or more than 40% impurity, or more than 50% impurity, or more than 60% impurity, or more than 70% impurity, or more than 80% impurity, or more than 90% impurity, or more than 95% impurity, or more than 97% impurity, or more than 98% impurity, or more than 99% impurity.

The dioxy compounds described herein (e.g., a dioxy compound of formula I, II, II-A, II-B, II-C, II-D, or II-E) and methods of using the same, unless otherwise stated, include all solvate and/or hydrate forms. In some aspects, the dioxy compounds described herein can exist in unsolvated forms as well as solvated forms (i.e., solvates). The dioxy compounds may also include hydrated forms (i.e., hydrates).

The dioxy compounds described herein (e.g., a dioxy compound of formula I, II, II-A, II-B, II-C, II-D, or II-E), as well as methods of using such compounds, unless otherwise stated, include all salt forms of the compounds. The compounds also include all non-salt forms of any salt of a dioxy compound described herein, as well as other salts of any salt of a dioxy compound described herein. The desired salt of a basic functional group of a dioxy compound may be prepared by methods known to those of skill in the art by treating the compound with an acid. The desired salt of an acidic functional group of a dioxy compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts. Examples of inorganic salts of base compounds include, but are not limited to, hydrochloride and hydrobromide salts. Examples of organic salts of base compounds include, but are not limited to, tartrate, citrate, maleate, fumarate, and succinate.

Unless stereochemistry is explicitly indicated in a chemical structure or chemical name, the chemical structure or chemical name is intended to embrace all possible stereoisomers, conformers, rotamers, and tautomers of the dioxy compounds depicted. For example, a dioxy compound containing a chiral carbon atom is intended to embrace both the (R) enantiomer and the (S) enantiomer, as well as mixtures of enantiomers, including racemic mixtures; and a dioxy compound containing two chiral carbons is intended to embrace all enantiomers and diastereomers (including (R,R), (S,S), (R,S), and (R,S) isomers). In some aspects, a dioxy compound described herein (e.g., a dioxy compound of formula I, II, II-A, II-B, II-C, II-D, or II-E) is in the form of the (R) enantiomer. In some aspects, a dioxy compound described herein (e.g., a dioxy compound of formula I, II, II-A, II-B, II-C, II-D, or II-E) is in the form of the (S) enantiomer. Included in all uses of the dioxy compounds disclosed herein, is any or all of the stereochemical, enantiomeric, diastereomeric, conformational, rotomeric, tautomeric, solvate, hydrate, and salt forms of the compounds as described.

The effective amount of the dioxy compound can depend on one or more (e.g., several) factors including, but not limited to, the mixture of component cellulolytic enzymes, the cellulosic substrate, the concentration of cellulosic substrate, the pretreatment(s) of the cellulosic substrate, non-cellulosic components (e.g., native or degraded lignin or hemicellulose), non-cellulase components, temperature, and reaction time.

The dioxy compound is preferably present in an amount that is not limiting with regard to the GH61 polypeptide having cellulolytic enhancing activity, cellulolytic enzyme(s), and cellulose. In another aspect, the compound is present in an amount that is not limiting with regard to the GH61 polypeptide having cellulolytic enhancing activity. In another aspect, the compound is present in an amount that is not limiting with regard to the cellulolytic enzyme(s). In another aspect, the compound is present in an amount that is not limiting with regard to the cellulose. In another aspect, the compound is present in an amount that is not limiting with regard to the GH61 polypeptide having cellulolytic enhancing activity and the cellulolytic enzyme(s). In another aspect, the compound is present in an amount that is not limiting with regard to the GH61 polypeptide having cellulolytic enhancing activity and the cellulose. In another aspect, the compound is present in an amount that is not limiting with regard to the cellulolytic enzyme(s) and the cellulose. In another aspect, the compound is present in an amount that is not limiting with regard to the GH61 polypeptide having cellulolytic enhancing activity, the cellulolytic enzyme(s), and the cellulose.

In another aspect, an effective amount of the dioxy compound to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of the dioxy compound to cellulosic material as a molar ratio to glucosyl units of cellulose is about $10^{-6}$ to about 10. In another aspect, an effective amount of the dioxy compound to cellulosic material as a molar ratio to glucosyl units of cellulose is about $10^{-6}$ to about 7.5. In another aspect, an effective amount of the dioxy compound to cellulosic material as a molar ratio to glucosyl units of cellulose is about $10^{-6}$ to about 5. In another aspect, an effective amount of the dioxy compound to cellulosic material as a molar ratio to glucosyl units of cellulose is about $10^{-6}$ to about 2.5. In another aspect, an effective amount of the dioxy compound to cellulosic material as a molar ratio to glucosyl units of cellulose is about $10^{-6}$ to about 1. In another aspect, an effective amount of the dioxy compound to cellulosic material as a molar ratio to glucosyl units of cellulose is about $10^{-5}$ to about 1. In another aspect, an effective amount of the dioxy compound to cellulosic material as a molar ratio to glucosyl units of cellulose is about $10^{-5}$ to about $10^{-1}$. In another aspect, an effective amount of the dioxy compound to cellulosic material as a molar ratio to glucosyl units of cellulose is about $10^{-4}$ to about $10^{-1}$. In another aspect, an effective amount of the dioxy compound to cellulosic material as a molar ratio to glucosyl units of cellulose is about $10^{-3}$ to about $10^{-1}$. In another aspect, an effective amount of the dioxy compound to cellulosic material as a molar ratio to glucosyl units of cellulose is about $10^{-3}$ to about $10^{-2}$.

In another aspect, an effective amount of the dioxy compound to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose. In another aspect, an effective amount of the dioxy compound to cellulose is about $10^{-6}$ to about 10 g per g of cellulose. In another aspect, an effective amount of the dioxy compound to cellulose is about $10^{-6}$ to about 10 g per g of cellulose. In another aspect, an effective amount of the dioxy compound to cellulose is about $10^{-6}$ to about 7.5 g per g of cellulose. In another aspect, an effective amount of the dioxy compound to cellulose is about $10^{-6}$ to about 5 g per g of cellulose. In another aspect, an effective amount of the dioxy compound to cellulose is about $10^{-6}$ to about 2.5 g per g of cellulose. In another aspect, an effective amount of the dioxy compound to cellulose is about $10^{-6}$ to about 1 g per g of cellulose. In another aspect, an effective amount of the dioxy compound to cellulose is about $10^{-5}$ to about 1 g per g of cellulose. In another aspect, an effective amount of the dioxy compound to cellulose is about $10^{-5}$ to about $10^{-1}$ g per g of cellulose. In another aspect, an effective amount of the dioxy compound to cellulose is about $10^{-4}$ to about $10^{-1}$ g per g of cellulose. In another aspect, an effective amount of the dioxy compound to cellulose is about $10^{-3}$ to about $10^{-1}$ g per g of cellulose. In another aspect, an effective amount of the dioxy compound to cellulose is about $10^{-3}$ to about $10^{-2}$ g per g of cellulose.

In another aspect, an effective amount of the dioxy compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM. In another aspect, an effective amount of the dioxy compound is about 0.1 µM to about 1 M. In another aspect, an effective amount of the dioxy compound is about 0.5 µM to about 0.75 M. In another aspect, an effective amount of the dioxy compound is about 0.75 µM to about 0.5 M. In another aspect, an effective amount of the dioxy compound is about 1 µM to about 0.25 M. In another aspect, an effective amount of the dioxy compound is about 1 µM to about 0.1 M. In another aspect, an effective amount of the dioxy compound is about 5 µM to about 50 mM. In another aspect, an effective amount of the dioxy compound is about 10 µM to about 25 mM. In another aspect, an effective amount of the dioxy compound is about 50 µM to about 25 mM. In another aspect, an effective amount of the dioxy compound is about 10 μM to about 10 mM. In another aspect, an effective amount of the dioxy compound is about 5 μM to about 5 mM. In another aspect, an effective amount of the dioxy compound is about 0.1 mM to about 1 mM.

In another aspect, one or more (e.g., several) dioxy compounds are used in any of the methods of the present invention.

In another aspect of the present invention, the dioxy compound(s) may be recycled from a completed saccharification or completed saccharification and fermentation to a new saccharification. The dioxy compound(s) can be recovered using standard methods in the art, e.g., filtration/centrifugation pre- or post-distillation, to remove residual solids, cellular debris, etc. and then recirculated to the new saccharification.

Polypeptides Having Cellulolytic Enhancing Activity and Polynucleotides Thereof

In the methods of the present invention, any GH61 polypeptide having cellulolytic enhancing activity can be used.

In a first aspect, the polypeptide having cellulolytic enhancing activity comprises the following motifs:

```
                              (SEQ ID NO: 131 or SEQ ID NO: 132)
[ILMV]-P-X(4,5)-G-X-Y-[ILMV]-X-R-X-[EQ]-X(4)-
[HNQ]
and

[FW]-[TF]-K-[AIV],
``` wherein X is any amino acid, X(4,5) is any amino acid at 4 or 5 contiguous positions, and X(4) is any amino acid at 4 contiguous positions.

The isolated polypeptide comprising the above-noted motifs may further comprise:

```
                              (SEQ ID NO: 133 or SEQ ID NO: 134)
H-X(1,2)-G-P-X(3)-[YW]-[AILMV], (SEQ ID NO: 135)
[EQ]-X-Y-X(2)-C-X-[EHQN]-[FILV]-X-[ILV],
or (SEQ ID NO: 136 or SEQ ID NO: 137)
H-X(1,2)-G-P-X(3)-[YW]-[AILMV]
and (SEQ ID NO: 138)
[EQ]-X-Y-X(2)-C-X-[EHQN]-[FILV]-X-[ILV],
``` wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred embodiment, the isolated GH61 polypeptide having cellulolytic enhancing activity further comprises H-X(1,2)-G-P-X(3)-[YW]-[AILMV] (SEQ ID NO: 139 or SEQ ID NO: 140). In another preferred embodiment, the isolated GH61 polypeptide having cellulolytic enhancing activity further comprises [EQ]X-Y-X(2)-C-X-[EHQN]-[FILV]-X-[ILV] (SEQ ID NO: 141). In another preferred embodiment, the isolated GH61 polypeptide having cellulolytic enhancing activity further comprises H-X(1,2)-G-P-X(3)-[YW]-[AILMV] (SEQ ID NO: 142 or SEQ ID NO: 143) and [EQ]-X-Y-X(2)-C-X-[EHQN]-[FILV]-X-[ILV] (SEQ ID NO: 144).

In a second aspect, isolated polypeptides having cellulolytic enhancing activity, comprise the following motif:

```
                              (SEQ ID NO: 145 or SEQ ID NO: 146)
[ILMV]-P-X(4,5)-G-X-Y-[ILMV]-X-R-X-[EQ]-X(3)-A-

[HNQ],
``` wherein X is any amino acid, X(4,5) is any amino acid at 4 or 5 contiguous positions, and X(3) is any amino acid at 3 contiguous positions. In the above motif, the accepted IUPAC single letter amino acid abbreviation is employed.

In a third aspect, the polypeptide having cellulolytic enhancing activity comprises an amino acid sequence that has a degree of identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, or SEQ ID NO: 170 of preferably at least 60%, more preferably at least 65%, more preferably at least 70%, more preferably at least 75%, more preferably at least 80%, more preferably at least 85%, even more preferably at least 90%, most preferably at least 91%, at least 92%, at least 93%, at least 94%, or at least 95%, or at least 100% and even most preferably at least 96%, at least 97%, at least 98%, at least 99%, or at least 100%.

In a preferred aspect, the mature polypeptide is amino acids 20 to 326 of SEQ ID NO: 2, amino acids 18 to 239 of SEQ ID NO: 4, amino acids 20 to 258 of SEQ ID NO: 6, amino acids 19 to 226 of SEQ ID NO: 8, amino acids 20 to 304 of SEQ ID NO: 10, amino acids 23 to 250 of SEQ ID NO: 12, amino acids 22 to 249 of SEQ ID NO: 14, amino acids 20 to 249 of SEQ ID NO: 16, amino acids 18 to 232 of SEQ ID NO: 18, amino acids 16 to 235 of SEQ ID NO: 20, amino acids 19 to 323 of SEQ ID NO: 22, amino acids 16 to 310 of SEQ ID NO: 24, amino acids 20 to 246 of SEQ ID NO: 26, amino acids 22 to 354 of SEQ ID NO: 28, amino acids 22 to 250 of SEQ ID NO: 30, or amino acids 22 to 322 of SEQ ID NO: 32, amino acids 24 to 444 of SEQ ID NO: 34, amino acids 26 to 253 of SEQ ID NO: 36, amino acids 20 to 223 of SEQ ID NO: 38, amino acids 18 to 246 of SEQ ID NO: 40, amino acids 20 to 334 of SEQ ID NO: 42, amino acids 18 to 227 of SEQ ID NO: 44, amino acids 22 to 368 of SEQ ID NO: 46, amino acids 25 to 330 of SEQ ID NO: 48, amino acids 17 to 236 of SEQ ID NO: 50, amino acids 17 to 250 of SEQ ID NO: 52, amino acids 23 to 478 of SEQ ID NO: 54, amino acids 17 to 230 of SEQ ID NO: 56, amino acids 20 to 257 of SEQ ID NO: 58, amino acids 23 to 251 of SEQ ID NO: 60, amino acids 19 to 349 of SEQ ID NO: 62, amino acids 24 to 436 of SEQ ID NO: 64, amino acids 21 to 344 of SEQ ID NO: 148, amino acids 21 to 389 of SEQ ID NO: 150, amino acids 22 to 406 of SEQ ID NO: 152, amino acids 20 to 427 of SEQ ID NO: 154, amino acids 18 to 267 of SEQ ID NO: 156, amino acids 21 to 273 of SEQ ID NO: 158, amino acids 21 to 322 of SEQ ID NO: 160, amino acids 18 to 234 of SEQ ID NO: 162, amino acids 24 to 233 of SEQ ID NO: 164, amino acids 17 to 237 of SEQ ID NO: 166, amino acids 20 to 484 of SEQ ID NO: 168, or amino acids 22 to 320 of SEQ ID NO: 170.

A polypeptide having cellulolytic enhancing activity preferably comprises or consists of the amino acid sequence of SEQ ID NO: 2 or an allelic variant thereof; or a fragment thereof that has cellulolytic enhancing activity. In a preferred aspect, the polypeptide comprises or consists of the amino acid sequence of SEQ ID NO: 2. In another preferred aspect, the polypeptide comprises or consists of the mature polypeptide of SEQ ID NO: 2. In another preferred aspect, the polypeptide comprises or consists of amino acids 20 to 326 of SEQ ID NO: 2, or an allelic variant thereof; or a fragment thereof that has cellulolytic enhancing activity. In another preferred aspect, the polypeptide comprises or consists of amino acids 20 to 326 of SEQ ID NO: 2.

A polypeptide having cellulolytic enhancing activity preferably comprises or consists of the amino acid sequence of SEQ ID NO: 4 or an allelic variant thereof; or a fragment thereof that has cellulolytic enhancing activity. In a preferred aspect, the polypeptide comprises or consists of the amino acid sequence of SEQ ID NO: 4. In another preferred aspect, the polypeptide comprises or consists of the mature polypeptide of SEQ ID NO: 4. In another preferred aspect, the polypeptide comprises or consists of amino acids 18 to 239 of SEQ ID NO: 4, or an allelic variant thereof; or a fragment thereof that has cellulolytic enhancing activity. In another preferred aspect, the polypeptide comprises or consists of amino acids 18 to 239 of SEQ ID NO: 4.

A polypeptide having cellulolytic enhancing activity preferably comprises or consists of the amino acid sequence of SEQ ID NO: 6 or an allelic variant thereof; or a fragment thereof that has cellulolytic enhancing activity. In a preferred aspect, the polypeptide comprises or consists of the amino acid sequence of SEQ ID NO: 6. In another preferred aspect, the polypeptide comprises or consists of the mature polypeptide of SEQ ID NO: 6. In another preferred aspect, the polypeptide comprises or consists of amino acids 20 to 258 of SEQ ID NO: 6, or an allelic variant thereof; or a fragment thereof that has cellulolytic enhancing activity. In another preferred aspect, the polypeptide comprises or consists of amino acids 20 to 258 of SEQ ID NO: 6.

A polypeptide having cellulolytic enhancing activity preferably comprises or consists of the amino acid sequence of SEQ ID NO: 8 or an allelic variant thereof; or a fragment thereof that has cellulolytic enhancing activity. In a preferred aspect, the polypeptide comprises or consists of the amino acid sequence of SEQ ID NO: 8. In another preferred aspect, the polypeptide comprises or consists of the mature polypeptide of SEQ ID NO: 8. In another preferred aspect, the polypeptide comprises or consists of amino acids 19 to 226 of SEQ ID NO: 8, or an allelic variant thereof; or a fragment thereof that has cellulolytic enhancing activity. In another preferred aspect, the polypeptide comprises or consists of amino acids 19 to 226 of SEQ ID NO: 8.

A polypeptide having cellulolytic enhancing activity preferably comprises or consists of the amino acid sequence of SEQ ID NO: 10 or an allelic variant thereof; or a fragment thereof that has cellulolytic enhancing activity. In a preferred aspect, the polypeptide comprises or consists of the amino acid sequence of SEQ ID NO: 10. In another preferred aspect, the polypeptide comprises or consists of the mature polypeptide of SEQ ID NO: 10. In another preferred aspect, the polypeptide comprises or consists of amino acids 20 to 304 of SEQ ID NO: 10, or an allelic variant thereof; or a fragment thereof that has cellulolytic enhancing activity. In another preferred aspect, the polypeptide comprises or consists of amino acids 20 to 304 of SEQ ID NO: 10.

A polypeptide having cellulolytic enhancing activity preferably comprises or consists of the amino acid sequence of SEQ ID NO: 12 or an allelic variant thereof; or a fragment thereof having cellulolytic enhancing activity. In a preferred aspect, the polypeptide comprises or consists of the amino acid sequence of SEQ ID NO: 12. In another preferred aspect, the polypeptide comprises or consists of the mature polypeptide of SEQ ID NO: 12. In another preferred aspect, the polypeptide comprises or consists of amino acids 16 to 317 of SEQ ID NO: 12, or an allelic variant thereof; or a fragment thereof having cellulolytic enhancing activity. In another preferred aspect, the polypeptide comprises or consists of amino acids 16 to 317 of SEQ ID NO: 12.

A polypeptide having cellulolytic enhancing activity preferably comprises or consists of the amino acid sequence of SEQ ID NO: 14 or an allelic variant thereof; or a fragment thereof that has cellulolytic enhancing activity. In a preferred aspect, the polypeptide comprises or consists of the amino acid sequence of SEQ ID NO: 14. In another preferred aspect, the polypeptide comprises or consists of the mature polypeptide of SEQ ID NO: 14. In another preferred aspect, the polypeptide comprises or consists of amino acids 23 to 250 of SEQ ID NO: 14, or an allelic variant thereof; or a fragment thereof that has cellulolytic enhancing activity. In another preferred aspect, the polypeptide comprises or consists of amino acids 23 to 250 of SEQ ID NO: 14.

A polypeptide having cellulolytic enhancing activity preferably comprises or consists of the amino acid sequence of SEQ ID NO: 16 or an allelic variant thereof; or a fragment thereof that has cellulolytic enhancing activity. In a preferred aspect, the polypeptide comprises or consists of the amino acid sequence of SEQ ID NO: 16. In another preferred aspect, the polypeptide comprises or consists of the mature polypeptide of SEQ ID NO: 16. In another preferred aspect, the polypeptide comprises or consists of amino acids 20 to 249 of SEQ ID NO: 16, or an allelic variant thereof; or a fragment thereof that has cellulolytic enhancing activity. In another preferred aspect, the polypeptide comprises or consists of amino acids 20 to 249 of SEQ ID NO: 16.

A polypeptide having cellulolytic enhancing activity preferably comprises or consists of the amino acid sequence of SEQ ID NO: 18 or an allelic variant thereof; or a fragment thereof that has cellulolytic enhancing activity. In a preferred aspect, the polypeptide comprises or consists of the amino acid sequence of SEQ ID NO: 18. In another preferred aspect, the polypeptide comprises or consists of the mature polypeptide of SEQ ID NO: 18. In another preferred aspect, the polypeptide comprises or consists of amino acids 18 to 232 of SEQ ID NO: 18, or an allelic variant thereof; or a fragment thereof that has cellulolytic enhancing activity. In another preferred aspect, the polypeptide comprises or consists of amino acids 18 to 232 of SEQ ID NO: 18.

A polypeptide having cellulolytic enhancing activity preferably comprises or consists of the amino acid sequence of SEQ ID NO: 20 or an allelic variant thereof; or a fragment thereof that has cellulolytic enhancing activity. In a preferred aspect, the polypeptide comprises or consists of the amino acid sequence of SEQ ID NO: 20. In another preferred aspect, the polypeptide comprises or consists of the mature polypeptide of SEQ ID NO: 20. In another preferred aspect, the polypeptide comprises or consists of amino acids 16 to 235 of SEQ ID NO: 20, or an allelic variant thereof; or a fragment thereof that has cellulolytic enhancing activity. In another preferred aspect, the polypeptide comprises or consists of amino acids 16 to 235 of SEQ ID NO: 20.

A polypeptide having cellulolytic enhancing activity preferably comprises or consists of the amino acid sequence of SEQ ID NO: 22 or an allelic variant thereof; or a fragment thereof that has cellulolytic enhancing activity. In a preferred aspect, the polypeptide comprises or consists of the amino acid sequence of SEQ ID NO: 22. In another preferred aspect, the polypeptide comprises or consists of the mature polypeptide of SEQ ID NO: 22. In another preferred aspect, the polypeptide comprises or consists of amino acids 19 to 323 of SEQ ID NO: 22, or an allelic variant thereof; or a fragment thereof that has cellulolytic enhancing activity. In another preferred aspect, the polypeptide comprises or consists of amino acids 19 to 323 of SEQ ID NO: 22.

A polypeptide having cellulolytic enhancing activity preferably comprises or consists of the amino acid sequence of SEQ ID NO: 24 or an allelic variant thereof; or a fragment thereof that has cellulolytic enhancing activity. In a preferred aspect, the polypeptide comprises or consists of the amino acid sequence of SEQ ID NO: 24. In another preferred aspect, the polypeptide comprises or consists of the mature polypeptide of SEQ ID NO: 24. In another preferred aspect, the polypeptide comprises or consists of amino acids 16 to 310 of SEQ ID NO: 24, or an allelic variant thereof; or a fragment thereof that has cellulolytic enhancing activity. In another preferred aspect, the polypeptide comprises or consists of amino acids 16 to 310 of SEQ ID NO: 24.

A polypeptide having cellulolytic enhancing activity preferably comprises or consists of the amino acid sequence of SEQ ID NO: 26 or an allelic variant thereof; or a fragment thereof that has cellulolytic enhancing activity. In a preferred aspect, the polypeptide comprises or consists of the amino acid sequence of SEQ ID NO: 26. In another preferred aspect, the polypeptide comprises or consists of the mature polypeptide of SEQ ID NO: 26. In another preferred aspect, the polypeptide comprises or consists of amino acids 20 to 246 of SEQ ID NO: 26, or an allelic variant thereof; or a fragment thereof that has cellulolytic enhancing activity. In another preferred aspect, the polypeptide comprises or consists of amino acids 20 to 246 of SEQ ID NO: 26.

A polypeptide having cellulolytic enhancing activity preferably comprises or consists of the amino acid sequence of SEQ ID NO: 28 or an allelic variant thereof; or a fragment thereof that has cellulolytic enhancing activity. In a preferred aspect, the polypeptide comprises or consists of the amino acid sequence of SEQ ID NO: 28. In another preferred aspect, the polypeptide comprises or consists of the mature polypeptide of SEQ ID NO: 28. In another preferred aspect, the polypeptide comprises or consists of amino acids 22 to 354 of SEQ ID NO: 28, or an allelic variant thereof; or a fragment thereof that has cellulolytic enhancing activity. In another preferred aspect, the polypeptide comprises or consists of amino acids 22 to 354 of SEQ ID NO: 28.

A polypeptide having cellulolytic enhancing activity preferably comprises or consists of the amino acid sequence of SEQ ID NO: 30 or an allelic variant thereof; or a fragment thereof that has cellulolytic enhancing activity. In a preferred aspect, the polypeptide comprises or consists of the amino acid sequence of SEQ ID NO: 30. In another preferred aspect, the polypeptide comprises or consists of the mature polypeptide of SEQ ID NO: 30. In another preferred aspect, the polypeptide comprises or consists of amino acids 22 to 250 of SEQ ID NO: 30, or an allelic variant thereof; or a fragment thereof that has cellulolytic enhancing activity. In another preferred aspect, the polypeptide comprises or consists of amino acids 22 to 250 of SEQ ID NO: 30.

A polypeptide having cellulolytic enhancing activity preferably comprises or consists of the amino acid sequence of SEQ ID NO: 32 or an allelic variant thereof; or a fragment thereof that has cellulolytic enhancing activity. In a preferred aspect, the polypeptide comprises or consists of the amino acid sequence of SEQ ID NO: 32. In another preferred aspect, the polypeptide comprises or consists of the mature polypeptide of SEQ ID NO: 32. In another preferred aspect, the polypeptide comprises or consists of amino acids 22 to 322 of SEQ ID NO: 32, or an allelic variant thereof; or a fragment thereof that has cellulolytic enhancing activity. In another preferred aspect, the polypeptide comprises or consists of amino acids 22 to 322 of SEQ ID NO: 32.

A polypeptide having cellulolytic enhancing activity preferably comprises or consists of the amino acid sequence of SEQ ID NO: 34 or an allelic variant thereof; or a fragment thereof that has cellulolytic enhancing activity. In a preferred aspect, the polypeptide comprises or consists of the amino acid sequence of SEQ ID NO: 34. In another preferred aspect, the polypeptide comprises or consists of the mature polypeptide of SEQ ID NO: 34. In another preferred aspect, the polypeptide comprises or consists of amino acids 24 to 444 of SEQ ID NO: 34, or an allelic variant thereof; or a fragment thereof that has cellulolytic enhancing activity. In another preferred aspect, the polypeptide comprises or consists of amino acids 24 to 444 of SEQ ID NO: 34.

A polypeptide having cellulolytic enhancing activity preferably comprises or consists of the amino acid sequence of SEQ ID NO: 36 or an allelic variant thereof; or a fragment thereof that has cellulolytic enhancing activity. In a preferred aspect, the polypeptide comprises or consists of the amino acid sequence of SEQ ID NO: 36. In another preferred aspect, the polypeptide comprises or consists of the mature polypeptide of SEQ ID NO: 36. In another preferred aspect, the polypeptide comprises or consists of amino acids 26 to 253 of SEQ ID NO: 36, or an allelic variant thereof; or a fragment thereof that has cellulolytic enhancing activity. In another preferred aspect, the polypeptide comprises or consists of amino acids 26 to 253 of SEQ ID NO: 36.

A polypeptide having cellulolytic enhancing activity preferably comprises or consists of the amino acid sequence of SEQ ID NO: 38 or an allelic variant thereof; or a fragment thereof that has cellulolytic enhancing activity. In a preferred aspect, the polypeptide comprises or consists of the amino acid sequence of SEQ ID NO: 38. In another preferred aspect, the polypeptide comprises or consists of the mature polypeptide of SEQ ID NO: 38. In another preferred aspect, the polypeptide comprises or consists of amino acids 20 to 223 of SEQ ID NO: 38, or an allelic variant thereof; or a fragment thereof that has cellulolytic enhancing activity. In another preferred aspect, the polypeptide comprises or consists of amino acids 20 to 223 of SEQ ID NO: 38.

A polypeptide having cellulolytic enhancing activity preferably comprises or consists of the amino acid sequence of SEQ ID NO: 40 or an allelic variant thereof; or a fragment thereof that has cellulolytic enhancing activity. In a preferred aspect, the polypeptide comprises or consists of the amino acid sequence of SEQ ID NO: 40. In another preferred aspect, the polypeptide comprises or consists of the mature polypeptide of SEQ ID NO: 40. In another preferred aspect, the polypeptide comprises or consists of amino acids 18 to 246 of SEQ ID NO: 40, or an allelic variant thereof; or a fragment thereof that has cellulolytic enhancing activity. In another preferred aspect, the polypeptide comprises or consists of amino acids 18 to 246 of SEQ ID NO: 40.

A polypeptide having cellulolytic enhancing activity preferably comprises or consists of the amino acid sequence of SEQ ID NO: 42 or an allelic variant thereof; or a fragment thereof that has cellulolytic enhancing activity. In a preferred aspect, the polypeptide comprises or consists of the amino acid sequence of SEQ ID NO: 42. In another preferred aspect, the polypeptide comprises or consists of the mature polypeptide of SEQ ID NO: 42. In another preferred aspect, the polypeptide comprises or consists of amino acids 20 to 334 of SEQ ID NO: 42, or an allelic variant thereof; or a fragment thereof that has cellulolytic enhancing activity. In another preferred aspect, the polypeptide comprises or consists of amino acids 20 to 334 of SEQ ID NO: 42.

A polypeptide having cellulolytic enhancing activity preferably comprises or consists of the amino acid sequence of SEQ ID NO: 44 or an allelic variant thereof; or a fragment thereof that has cellulolytic enhancing activity. In a preferred aspect, the polypeptide comprises or consists of the amino acid sequence of SEQ ID NO: 44. In another preferred aspect, the polypeptide comprises or consists of the mature polypeptide of SEQ ID NO: 44. In another preferred aspect, the polypeptide comprises or consists of amino acids 18 to 227 of SEQ ID NO: 44, or an allelic variant thereof; or a fragment thereof that has cellulolytic enhancing activity. In another preferred aspect, the polypeptide comprises or consists of amino acids 18 to 227 of SEQ ID NO: 44.

A polypeptide having cellulolytic enhancing activity preferably comprises or consists of the amino acid sequence of SEQ ID NO: 46 or an allelic variant thereof; or a fragment thereof that has cellulolytic enhancing activity. In a preferred aspect, the polypeptide comprises or consists of the amino acid sequence of SEQ ID NO: 46. In another preferred aspect, the polypeptide comprises or consists of the mature polypeptide of SEQ ID NO: 46. In another preferred aspect, the polypeptide comprises or consists of amino acids 22 to 368 of SEQ ID NO: 46, or an allelic variant thereof; or a fragment thereof that has cellulolytic enhancing activity. In another preferred aspect, the polypeptide comprises or consists of amino acids 22 to 368 of SEQ ID NO: 46.

A polypeptide having cellulolytic enhancing activity preferably comprises or consists of the amino acid sequence of SEQ ID NO: 48 or an allelic variant thereof; or a fragment thereof that has cellulolytic enhancing activity. In a preferred aspect, the polypeptide comprises or consists of the amino acid sequence of SEQ ID NO: 48. In another preferred aspect, the polypeptide comprises or consists of the mature polypeptide of SEQ ID NO: 48. In another preferred aspect, the polypeptide comprises or consists of amino acids 25 to 330 of SEQ ID NO: 48, or an allelic variant thereof; or a fragment thereof that has cellulolytic enhancing activity. In another preferred aspect, the polypeptide comprises or consists of amino acids 25 to 330 of SEQ ID NO: 48.

A polypeptide having cellulolytic enhancing activity preferably comprises or consists of the amino acid sequence of SEQ ID NO: 50 or an allelic variant thereof; or a fragment thereof that has cellulolytic enhancing activity. In a preferred aspect, the polypeptide comprises or consists of the amino acid sequence of SEQ ID NO: 50. In another preferred aspect, the polypeptide comprises or consists of the mature polypeptide of SEQ ID NO: 50. In another preferred aspect, the polypeptide comprises or consists of amino acids 17 to 236 of SEQ ID NO: 50, or an allelic variant thereof; or a fragment thereof that has cellulolytic enhancing activity. In another preferred aspect, the polypeptide comprises or consists of amino acids 17 to 236 of SEQ ID NO: 50.

A polypeptide having cellulolytic enhancing activity preferably comprises or consists of the amino acid sequence of SEQ ID NO: 52 or an allelic variant thereof; or a fragment thereof that has cellulolytic enhancing activity. In a preferred aspect, the polypeptide comprises or consists of the amino acid sequence of SEQ ID NO: 52. In another preferred aspect, the polypeptide comprises or consists of the mature polypeptide of SEQ ID NO: 52. In another preferred aspect, the polypeptide comprises or consists of amino acids 19 to 250 of SEQ ID NO: 52, or an allelic variant thereof; or a fragment thereof that has cellulolytic enhancing activity. In another preferred aspect, the polypeptide comprises or consists of amino acids 19 to 250 of SEQ ID NO: 52.

A polypeptide having cellulolytic enhancing activity preferably comprises or consists of the amino acid sequence of SEQ ID NO: 54 or an allelic variant thereof; or a fragment thereof that has cellulolytic enhancing activity. In a preferred aspect, the polypeptide comprises or consists of the amino acid sequence of SEQ ID NO: 54. In another preferred aspect, the polypeptide comprises or consists of the mature polypeptide of SEQ ID NO: 54. In another preferred aspect, the polypeptide comprises or consists of amino acids 23 to 478 of SEQ ID NO: 54, or an allelic variant thereof; or a fragment thereof that has cellulolytic enhancing activity. In another preferred aspect, the polypeptide comprises or consists of amino acids 23 to 478 of SEQ ID NO: 54.

A polypeptide having cellulolytic enhancing activity preferably comprises or consists of the amino acid sequence of SEQ ID NO: 56 or an allelic variant thereof; or a fragment thereof that has cellulolytic enhancing activity. In a preferred aspect, the polypeptide comprises or consists of the amino acid sequence of SEQ ID NO: 56. In another preferred aspect, the polypeptide comprises or consists of the mature polypeptide of SEQ ID NO: 56. In another preferred aspect, the polypeptide comprises or consists of amino acids 17 to 230 of SEQ ID NO: 56, or an allelic variant thereof; or a fragment thereof that has cellulolytic enhancing activity. In another preferred aspect, the polypeptide comprises or consists of amino acids 17 to 230 of SEQ ID NO: 56.

A polypeptide having cellulolytic enhancing activity preferably comprises or consists of the amino acid sequence of SEQ ID NO: 58 or an allelic variant thereof; or a fragment thereof that has cellulolytic enhancing activity. In a preferred aspect, the polypeptide comprises or consists of the amino acid sequence of SEQ ID NO: 58. In another preferred aspect, the polypeptide comprises or consists of the mature polypeptide of SEQ ID NO: 58. In another preferred aspect, the polypeptide comprises or consists of amino acids 20 to 257 of SEQ ID NO: 58, or an allelic variant thereof; or a fragment thereof that has cellulolytic enhancing activity. In another preferred aspect, the polypeptide comprises or consists of amino acids 20 to 257 of SEQ ID NO: 58.

A polypeptide having cellulolytic enhancing activity preferably comprises or consists of the amino acid sequence of SEQ ID NO: 60 or an allelic variant thereof; or a fragment thereof that has cellulolytic enhancing activity. In a preferred aspect, the polypeptide comprises or consists of the amino acid sequence of SEQ ID NO: 60. In another preferred aspect, the polypeptide comprises or consists of the mature polypeptide of SEQ ID NO: 60. In another preferred aspect, the polypeptide comprises or consists of amino acids 23 to 251 of SEQ ID NO: 60, or an allelic variant thereof; or a fragment thereof that has cellulolytic enhancing activity. In another preferred aspect, the polypeptide comprises or consists of amino acids 23 to 251 of SEQ ID NO: 60.

A polypeptide having cellulolytic enhancing activity preferably comprises or consists of the amino acid sequence of SEQ ID NO: 62 or an allelic variant thereof; or a fragment thereof that has cellulolytic enhancing activity. In a preferred aspect, the polypeptide comprises or consists of the amino acid sequence of SEQ ID NO: 62. In another preferred aspect, the polypeptide comprises or consists of the mature polypeptide of SEQ ID NO: 62. In another preferred aspect, the polypeptide comprises or consists of amino acids 19 to 349 of SEQ ID NO: 62, or an allelic variant thereof; or a fragment thereof that has cellulolytic enhancing activity. In another preferred aspect, the polypeptide comprises or consists of amino acids 19 to 349 of SEQ ID NO: 62.

A polypeptide having cellulolytic enhancing activity preferably comprises or consists of the amino acid sequence of SEQ ID NO: 64 or an allelic variant thereof; or a fragment thereof that has cellulolytic enhancing activity. In a preferred aspect, the polypeptide comprises or consists of the amino acid sequence of SEQ ID NO: 64. In another preferred aspect, the polypeptide comprises or consists of the mature polypeptide of SEQ ID NO: 64. In another preferred aspect, the polypeptide comprises or consists of amino acids 24 to 436 of SEQ ID NO: 64, or an allelic variant thereof; or a fragment thereof that has cellulolytic enhancing activity. In another preferred aspect, the polypeptide comprises or consists of amino acids 24 to 436 of SEQ ID NO: 64.

A polypeptide having cellulolytic enhancing activity preferably comprises or consists of the amino acid sequence of SEQ ID NO: 148 or an allelic variant thereof; or a fragment thereof that has cellulolytic enhancing activity. In a preferred aspect, the polypeptide comprises or consists of the amino acid sequence of SEQ ID NO: 148. In another preferred aspect, the polypeptide comprises or consists of the mature polypeptide of SEQ ID NO: 148. In another preferred aspect, the polypeptide comprises or consists of amino acids 21 to 344 of SEQ ID NO: 148, or an allelic variant thereof; or a fragment thereof that has cellulolytic enhancing activity. In another preferred aspect, the polypeptide comprises or consists of amino acids 21 to 344 of SEQ ID NO: 148.

A polypeptide having cellulolytic enhancing activity preferably comprises or consists of the amino acid sequence of SEQ ID NO: 150 or an allelic variant thereof; or a fragment thereof that has cellulolytic enhancing activity. In a preferred aspect, the polypeptide comprises or consists of the amino acid sequence of SEQ ID NO: 150. In another preferred aspect, the polypeptide comprises or consists of the mature polypeptide of SEQ ID NO: 150. In another preferred aspect, the polypeptide comprises or consists of amino acids 21 to 389 of SEQ ID NO: 150, or an allelic variant thereof; or a fragment thereof that has cellulolytic enhancing activity. In another preferred aspect, the polypeptide comprises or consists of amino acids 21 to 389 of SEQ ID NO: 150.

A polypeptide having cellulolytic enhancing activity preferably comprises or consists of the amino acid sequence of SEQ ID NO: 152 or an allelic variant thereof; or a fragment thereof that has cellulolytic enhancing activity. In a preferred aspect, the polypeptide comprises or consists of the amino acid sequence of SEQ ID NO: 152. In another preferred aspect, the polypeptide comprises or consists of the mature polypeptide of SEQ ID NO: 152. In another preferred aspect, the polypeptide comprises or consists of amino acids 22 to 406 of SEQ ID NO: 152, or an allelic variant thereof; or a fragment thereof that has cellulolytic enhancing activity. In another preferred aspect, the polypeptide comprises or consists of amino acids 22 to 406 of SEQ ID NO: 152.

A polypeptide having cellulolytic enhancing activity preferably comprises or consists of the amino acid sequence of SEQ ID NO: 154 or an allelic variant thereof; or a fragment thereof that has cellulolytic enhancing activity. In a preferred aspect, the polypeptide comprises or consists of the amino acid sequence of SEQ ID NO: 154. In another preferred aspect, the polypeptide comprises or consists of the mature polypeptide of SEQ ID NO: 154. In another preferred aspect, the polypeptide comprises or consists of amino acids 20 to 427 of SEQ ID NO: 154, or an allelic variant thereof; or a fragment thereof that has cellulolytic enhancing activity. In another preferred aspect, the polypeptide comprises or consists of amino acids 20 to 427 of SEQ ID NO: 154.

A polypeptide having cellulolytic enhancing activity preferably comprises or consists of the amino acid sequence of SEQ ID NO: 156 or an allelic variant thereof; or a fragment thereof that has cellulolytic enhancing activity. In a preferred aspect, the polypeptide comprises or consists of the amino acid sequence of SEQ ID NO: 156. In another preferred aspect, the polypeptide comprises or consists of the mature polypeptide of SEQ ID NO: 156. In another preferred aspect, the polypeptide comprises or consists of amino acids 18 to 267 of SEQ ID NO: 156, or an allelic variant thereof; or a fragment thereof that has cellulolytic enhancing activity. In another preferred aspect, the polypeptide comprises or consists of amino acids 18 to 267 of SEQ ID NO: 156.

A polypeptide having cellulolytic enhancing activity preferably comprises or consists of the amino acid sequence of SEQ ID NO: 158 or an allelic variant thereof; or a fragment thereof that has cellulolytic enhancing activity. In a preferred aspect, the polypeptide comprises or consists of the amino acid sequence of SEQ ID NO: 158. In another preferred aspect, the polypeptide comprises or consists of the mature polypeptide of SEQ ID NO: 158. In another preferred aspect, the polypeptide comprises or consists of amino acids 21 to 273 of SEQ ID NO: 158, or an allelic variant thereof; or a fragment thereof that has cellulolytic enhancing activity. In another preferred aspect, the polypeptide comprises or consists of amino acids 21 to 273 of SEQ ID NO: 158.

A polypeptide having cellulolytic enhancing activity preferably comprises or consists of the amino acid sequence of SEQ ID NO: 160 or an allelic variant thereof; or a fragment thereof that has cellulolytic enhancing activity. In a preferred aspect, the polypeptide comprises or consists of the amino acid sequence of SEQ ID NO: 160. In another preferred aspect, the polypeptide comprises or consists of the mature polypeptide of SEQ ID NO: 160. In another preferred aspect, the polypeptide comprises or consists of amino acids 21 to 322 of SEQ ID NO: 160, or an allelic variant thereof; or a fragment thereof that has cellulolytic enhancing activity. In another preferred aspect, the polypeptide comprises or consists of amino acids 21 to 322 of SEQ ID NO: 160.

A polypeptide having cellulolytic enhancing activity preferably comprises or consists of the amino acid sequence of SEQ ID NO: 162 or an allelic variant thereof; or a fragment thereof that has cellulolytic enhancing activity. In a preferred aspect, the polypeptide comprises or consists of the amino acid sequence of SEQ ID NO: 162. In another preferred aspect, the polypeptide comprises or consists of the mature polypeptide of SEQ ID NO: 162. In another preferred aspect, the polypeptide comprises or consists of amino acids 18 to 234 of SEQ ID NO: 162, or an allelic variant thereof; or a fragment thereof that has cellulolytic enhancing activity. In another preferred aspect, the polypeptide comprises or consists of amino acids 18 to 234 of SEQ ID NO: 162.

A polypeptide having cellulolytic enhancing activity preferably comprises or consists of the amino acid sequence of SEQ ID NO: 164 or an allelic variant thereof; or a fragment thereof that has cellulolytic enhancing activity. In a preferred aspect, the polypeptide comprises or consists of the amino acid sequence of SEQ ID NO: 164. In another preferred aspect, the polypeptide comprises or consists of the mature polypeptide of SEQ ID NO: 164. In another preferred aspect, the polypeptide comprises or consists of amino acids 24 to 233 of SEQ ID NO: 164, or an allelic variant thereof; or a fragment thereof that has cellulolytic enhancing activity. In another preferred aspect, the polypeptide comprises or consists of amino acids 24 to 233 of SEQ ID NO: 164.

A polypeptide having cellulolytic enhancing activity preferably comprises or consists of the amino acid sequence of SEQ ID NO: 166 or an allelic variant thereof; or a fragment thereof that has cellulolytic enhancing activity. In a preferred aspect, the polypeptide comprises or consists of the amino acid sequence of SEQ ID NO: 166. In another preferred aspect, the polypeptide comprises or consists of the mature polypeptide of SEQ ID NO: 166. In another preferred aspect, the polypeptide comprises or consists of amino acids 17 to 237 of SEQ ID NO: 166, or an allelic variant thereof; or a fragment thereof that has cellulolytic enhancing activity. In another preferred aspect, the polypeptide comprises or consists of amino acids 17 to 237 of SEQ ID NO: 166.

A polypeptide having cellulolytic enhancing activity preferably comprises or consists of the amino acid sequence of SEQ ID NO: 168 or an allelic variant thereof; or a fragment thereof that has cellulolytic enhancing activity. In a preferred aspect, the polypeptide comprises or consists of the amino acid sequence of SEQ ID NO: 168. In another preferred aspect, the polypeptide comprises or consists of the mature polypeptide of SEQ ID NO: 168. In another preferred aspect, the polypeptide comprises or consists of amino acids 20 to 484 of SEQ ID NO: 168, or an allelic variant thereof; or a fragment thereof that has cellulolytic enhancing activity. In another preferred aspect, the polypeptide comprises or consists of amino acids 20 to 484 of SEQ ID NO: 168.

A polypeptide having cellulolytic enhancing activity preferably comprises or consists of the amino acid sequence of SEQ ID NO: 170 or an allelic variant thereof; or a fragment thereof that has cellulolytic enhancing activity. In a preferred aspect, the polypeptide comprises or consists of the amino acid sequence of SEQ ID NO: 170. In another preferred aspect, the polypeptide comprises or consists of the mature polypeptide of SEQ ID NO: 170. In another preferred aspect, the polypeptide comprises or consists of amino acids 22 to 320 of SEQ ID NO: 170, or an allelic variant thereof; or a fragment thereof that has cellulolytic enhancing activity. In another preferred aspect, the polypeptide comprises or consists of amino acids 22 to 320 of SEQ ID NO: 170.

Preferably, a fragment of the mature polypeptide of SEQ ID NO: 2 contains at least 277 amino acid residues, more preferably at least 287 amino acid residues, and most preferably at least 297 amino acid residues. Preferably, a fragment of the mature polypeptide of SEQ ID NO: 4 contains at least 185 amino acid residues, more preferably at least 195 amino acid residues, and most preferably at least 205 amino acid residues. Preferably, a fragment of the mature polypeptide of SEQ ID NO: 6 contains at least 200 amino acid residues, more preferably at least 212 amino acid residues, and most preferably at least 224 amino acid residues. Preferably, a fragment of the mature polypeptide of SEQ ID NO: 8 contains at least 175 amino acid residues, more preferably at least 185 amino acid residues, and most preferably at least 195 amino acid residues. Preferably, a fragment of the mature polypeptide of SEQ ID NO: 10 contains at least 240 amino acid residues, more preferably at least 255 amino acid residues, and most preferably at least 270 amino acid residues. Preferably, a fragment of the mature polypeptide of SEQ ID NO: 12 contains at least 255 amino acid residues, more preferably at least 270 amino acid residues, and most preferably at least 285 amino acid residues. Preferably, a fragment of the mature polypeptide of SEQ ID NO: 14 contains at least 175 amino acid residues, more preferably at least 190 amino acid residues, and most preferably at least 205 amino acid residues. Preferably, a fragment of the mature polypeptide of SEQ ID NO: 16 contains at least 200 amino acid residues, more preferably at least 210 amino acid residues, and most preferably at least 220 amino acid residues. Preferably, a fragment of the mature polypeptide of SEQ ID NO: 18 contains at least 185 amino acid residues, more preferably at least 195 amino acid residues, and most preferably at least 205 amino acid residues. Preferably, a fragment of the mature polypeptide of SEQ ID NO: 20 contains at least 190 amino acid residues, more preferably at least 200 amino acid residues, and most preferably at least 210 amino acid residues. Preferably, a fragment of the mature polypeptide of SEQ ID NO: 22 contains at least 260 amino acid residues, more preferably at least 275 amino acid residues, and most preferably at least 290 amino acid residues. Preferably, a fragment of the mature polypeptide of SEQ ID NO: 24 contains at least 250 amino acid residues, more preferably at least 265 amino acid residues, and most preferably at least 280 amino acid residues. Preferably, a fragment of the mature polypeptide of SEQ ID NO: 26 contains at least 195 amino acid residues, more preferably at least 205 amino acid residues, and most preferably at least 214 amino acid residues. Preferably, a fragment of the mature polypeptide of SEQ ID NO: 28 contains at least 285 amino acid residues, more preferably at least 300 amino acid residues, and most preferably at least 315 amino acid residues. Preferably, a fragment of the mature polypeptide of SEQ ID NO: 30 contains at least 200 amino acid residues, more preferably at least 210 amino acid residues, and most preferably at least 220 amino acid residues. Preferably, a fragment of the mature polypeptide of SEQ ID NO: 32 contains at least 255 amino acid residues, more preferably at least 270 amino acid residues, and most preferably at least 285 amino acid residues. Preferably, a fragment of the mature polypeptide of SEQ ID NO: 34 contains at least 360 amino acid residues, more preferably at least 380 amino acid residues, and most preferably at least 400 amino acid residues. Preferably, a fragment of the mature polypeptide of SEQ ID NO: 36 contains at least 200 amino acid residues, more preferably at least 210 amino acid residues, and most preferably at least 220 amino acid residues. Preferably, a fragment of the mature polypeptide of SEQ ID NO: 38 contains at least 170 amino acid residues, more preferably at least 180 amino acid residues, and most preferably at least 190 amino acid residues. Preferably, a fragment of the mature polypeptide of SEQ ID NO: 40 contains at least 190 amino acid residues, more preferably at least 200 amino acid residues, and most preferably at least 210 amino acid residues. Preferably, a fragment of the mature polypeptide of SEQ ID NO: 42 contains at least 265 amino acid residues, more preferably at least 280 amino acid residues, and most preferably at least 295 amino acid residues. Preferably, a fragment of the mature polypeptide of SEQ ID NO: 44 contains at least 180 amino acid residues, more preferably at least 190 amino acid residues, and most preferably at least 200 amino acid residues. Preferably, a fragment of the mature polypeptide of SEQ ID NO: 46 contains at least 320 amino acid residues, more preferably at least 335 amino acid residues, and most preferably at least 350 amino acid residues. Preferably, a fragment of the mature polypeptide of SEQ ID NO: 48 contains at least 255 amino acid residues, more preferably at least 270 amino acid residues, and most preferably at least 285 amino acid residues. Preferably, a fragment of the mature polypeptide of SEQ ID NO: 50 contains at least 190 amino acid residues, more preferably at least 200 amino acid residues, and most preferably at least 210 amino acid residues. Preferably, a fragment of the mature polypeptide of SEQ ID NO: 52 contains at least 200 amino acid residues, more preferably at least 210 amino acid residues, and most preferably at least 220 amino acid residues. Preferably, a fragment of the mature polypeptide of SEQ ID NO: 54 contains at least 380 amino acid residues, more preferably at least 400 amino acid residues, and most preferably at least 420 amino acid residues.

Preferably, a fragment of the mature polypeptide of SEQ ID NO: 56 contains at least 180 amino acid residues, more preferably at least 190 amino acid residues, and most preferably at least 200 amino acid residues. Preferably, a fragment of the mature polypeptide of SEQ ID NO: 58 contains at least 210 amino acid residues, more preferably at least 220 amino acid residues, and most preferably at least 230 amino acid residues. Preferably, a fragment of the mature polypeptide of SEQ ID NO: 60 contains at least 190 amino acid residues, more preferably at least 200 amino acid residues, and most preferably at least 210 amino acid residues. Preferably, a fragment of the mature polypeptide of SEQ ID NO: 62 contains at least 270 amino acid residues, more preferably at least 290 amino acid residues, and most preferably at least 310 amino acid residues. Preferably, a fragment of the mature polypeptide of SEQ ID NO: 64 contains at least 340 amino acid residues, more preferably at least 360 amino acid residues, and most preferably at least 380 amino acid residues. Preferably, a fragment of the mature polypeptide of SEQ ID NO: 148 contains at least 280 amino acid residues, more preferably at least 295 amino acid residues, and most preferably at least 310 amino acid residues. Preferably, a fragment of the mature polypeptide of SEQ ID NO: 150 contains at least 310 amino acid residues, more preferably at least 330 amino acid residues, and most preferably at least 350 amino acid residues. Preferably, a fragment of the mature polypeptide of SEQ ID NO: 152 contains at least 320 amino acid residues, more preferably at least 340 amino acid residues, and most preferably at least 360 amino acid residues. Preferably, a fragment of the mature polypeptide of SEQ ID NO: 154 contains at least 350 amino acid residues, more preferably at least 370 amino acid residues, and most preferably at least 390 amino acid residues. Preferably, a fragment of the mature polypeptide of SEQ ID NO: 156 contains at least 220 amino acid residues, more preferably at least 230 amino acid residues, and most preferably at least 240 amino acid residues. Preferably, a fragment of the mature polypeptide of SEQ ID NO: 158 contains at least 220 amino acid residues, more preferably at least 230 amino acid residues, and most preferably at least 240 amino acid residues. Preferably, a fragment of the mature polypeptide of SEQ ID NO: 160 contains at least 255 amino acid residues, more preferably at least 270 amino acid residues, and most preferably at least 285 amino acid residues. Preferably, a fragment of the mature polypeptide of SEQ ID NO: 162 contains at least 185 amino acid residues, more preferably at least 195 amino acid residues, and most preferably at least 205 amino acid residues. Preferably, a fragment of the mature polypeptide of SEQ ID NO: 164 contains at least 180 amino acid residues, more preferably at least 190 amino acid residues, and most preferably at least 200 amino acid residues. Preferably, a fragment of the mature polypeptide of SEQ ID NO: 166 contains at least 190 amino acid residues, more preferably at least 200 amino acid residues, and most preferably at least 210 amino acid residues. Preferably, a fragment of the mature polypeptide of SEQ ID NO: 168 contains at least 385 amino acid residues, more preferably at least 410 amino acid residues, and most preferably at least 435 amino acid residues. Preferably, a fragment of the mature polypeptide of SEQ ID NO: 170 contains at least 255 amino acid residues, more preferably at least 270 amino acid residues, and most preferably at least 285 amino acid residues.

Preferably, a subsequence of the mature polypeptide coding sequence of SEQ ID NO: 1 contains at least 831 nucleotides, more preferably at least 861 nucleotides, and most preferably at least 891 nucleotides. Preferably, a subsequence of the mature polypeptide coding sequence of SEQ ID NO: 3 contains at least 555 nucleotides, more preferably at least 585 nucleotides, and most preferably at least 615 nucleotides. Preferably, a subsequence of the mature polypeptide coding sequence of SEQ ID NO: 5 contains at least 600 nucleotides, more preferably at least 636 nucleotides, and most preferably at least 672 nucleotides. Preferably, a subsequence of the mature polypeptide coding sequence of SEQ ID NO: 7 contains at least 525 nucleotides, more preferably at least 555 nucleotides, and most preferably at least 585 nucleotides. Preferably, a subsequence of the mature polypeptide coding sequence of SEQ ID NO: 9 contains at least 720 nucleotides, more preferably at least 765 nucleotides, and most preferably at least 810 nucleotides. Preferably, a subsequence of the mature polypeptide coding sequence of SEQ ID NO: 11 contains at least 765 nucleotides, more preferably at least 810 nucleotides, and most preferably at least 855 nucleotides. Preferably, a subsequence of the mature polypeptide coding sequence of nucleotides 67 to 796 of SEQ ID NO: 13 contains at least 525 nucleotides, more preferably at least 570 nucleotides, and most preferably at least 615 nucleotides. Preferably, a subsequence of the mature polypeptide coding sequence of SEQ ID NO: 15 contains at least 600 nucleotides, more preferably at least 630 nucleotides, and most preferably at least 660 nucleotides. Preferably, a subsequence of the mature polypeptide coding sequence of SEQ ID NO: 17 contains at least 555 nucleotides, more preferably at least 585 nucleotides, and most preferably at least 615 nucleotides. Preferably, a subsequence of the mature polypeptide coding sequence of SEQ ID NO: 19 contains at least 570 nucleotides, more preferably at least 600 nucleotides, and most preferably at least 630 nucleotides. Preferably, a subsequence of the mature polypeptide coding sequence of SEQ ID NO: 21 contains at least 780 nucleotides, more preferably at least 825 nucleotides, and most preferably at least 870 nucleotides. Preferably, a subsequence of the mature polypeptide coding sequence of SEQ ID NO: 23 contains at least 750 nucleotides, more preferably at least 795 nucleotides, and most preferably at least 840 nucleotides. Preferably, a subsequence of the mature polypeptide coding sequence of SEQ ID NO: 25 contains at least 585 nucleotides, more preferably at least 615 nucleotides, and most preferably at least 645 nucleotides. Preferably, a subsequence of the mature polypeptide coding sequence of SEQ ID NO: 27 contains at least 855 nucleotides, more preferably at least 900 nucleotides, and most preferably at least 945 nucleotides. Preferably, a subsequence of the mature polypeptide coding sequence of SEQ ID NO: 29 contains at least 600 nucleotides, more preferably at least 630 nucleotides, and most preferably at least 660 nucleotides. Preferably, a subsequence of the mature polypeptide coding sequence of SEQ ID NO: 31 contains at least 765 nucleotides, more preferably at least 810 nucleotides, and most preferably at least 855 nucleotides. Preferably, a subsequence of the mature polypeptide coding sequence of SEQ ID NO: 33 contains at least 1180 nucleotides, more preferably at least 1140 nucleotides, and most preferably at least 1200 nucleotides. Preferably, a subsequence of the mature polypeptide coding sequence of SEQ ID NO: 35 contains at least 600 nucleotides, more preferably at least 630 nucleotides, and most preferably at least 660 nucleotides. Preferably, a subsequence of the mature polypeptide coding sequence of SEQ ID NO: 37 contains at least 170 amino acid residues, more preferably at least 180 amino acid residues, and most preferably at least 190 nucleotides. Preferably, a subsequence of the mature polypeptide coding sequence of SEQ ID NO: 39 contains at least 570 nucleotides, more preferably at least 600 nucleotides, and most preferably at least 630 nucleotides. Preferably, a subsequence of the mature polypeptide coding sequence of SEQ ID NO: 41 contains at least 795 nucleotides, more preferably at least 840 nucleotides, and most preferably at least 885 nucleotides. Preferably, a subsequence of the mature polypeptide coding sequence of SEQ ID NO: 43 contains at least 540 nucleotides, more preferably at least 570 nucleotides, and most preferably at least 600 nucleotides. Preferably, a subsequence of the mature polypeptide coding sequence of SEQ ID NO: 45 contains at least 960 nucleotides, more preferably at least 1005 nucleotides, and most preferably at least 1050 nucleotides. Preferably, a subsequence of the mature polypeptide coding sequence of SEQ ID NO: 47 contains at least 765 nucleotides, more preferably at least 810 nucleotides, and most preferably at least 855 nucleotides. Preferably, a subsequence of the mature polypeptide coding sequence of SEQ ID NO: 49 contains at least 570 nucleotides, more preferably at least 600 nucleotides, and most preferably at least 630 nucleotides. Preferably, a subsequence of the mature polypeptide coding sequence of SEQ ID NO: 51 contains at least 600 nucleotides, more preferably at least 630 nucleotides, and most preferably at least 660 nucleotides. Preferably, a subsequence of the mature polypeptide coding sequence of SEQ ID NO: 53 contains at least 1140 nucleotides, more preferably at least 1200 nucleotides, and most preferably at least 1260 nucleotides. Preferably, a subsequence of the mature polypeptide coding sequence of SEQ ID NO: 55 contains at least 540 nucleotides, more preferably at least 570 nucleotides, and most preferably at least 600 nucleotides. Preferably, a subsequence of the mature polypeptide coding sequence of SEQ ID NO: 57 contains at least 630 nucleotides, more preferably at least 690 nucleotides, and most preferably at least 720 nucleotides. Preferably, a subsequence of the mature polypeptide coding sequence of SEQ ID NO: 59 contains at least 570 nucleotides, more preferably at least 600 nucleotides, and most preferably at least 630 nucleotides. Preferably, a subsequence of the mature polypeptide coding sequence of SEQ ID NO: 61 contains at least 810 nucleotides, more preferably at least 870 nucleotides, and most preferably at least 930 nucleotides. Preferably, a subsequence of the mature polypeptide coding sequence of SEQ ID NO: 63 contains at least 1020 nucleotides, more preferably at least 1080 nucleotides, and most preferably at least 1140 nucleotides. Preferably, a subsequence of the mature polypeptide coding sequence of SEQ ID NO: 147 contains at least 840 nucleotides, more preferably at least 885 nucleotides, and most preferably at least 930 nucleotides. Preferably, a subsequence of the mature polypeptide coding sequence of SEQ ID NO: 149 contains at least 930 nucleotides, more preferably at least 960 nucleotides, and most preferably at least 1050 nucleotides. Preferably, a subsequence of the mature polypeptide coding sequence of SEQ ID NO: 151 contains at least 960 nucleotides, more preferably at least 1020 nucleotides, and most preferably at least 1080 nucleotides. Preferably, a subsequence of the mature polypeptide coding sequence of SEQ ID NO: 153 contains at least 1050 nucleotides, more preferably at least 1110 nucleotides, and most preferably at least 1170 nucleotides. Preferably, a subsequence of the mature polypeptide coding sequence of SEQ ID NO: 155 contains at least 660 nucleotides, more preferably at least 690 nucleotides, and most preferably at least 720 nucleotides. Preferably, a subsequence of the mature polypeptide coding sequence of SEQ ID NO: 157 contains at least 660 nucleotides, more preferably at least 690 nucleotides, and most preferably at least 720 nucleotides. Preferably, a subsequence of the mature polypeptide coding sequence of SEQ ID NO: 159 contains at least 765 nucleotides, more preferably at least 810 nucleotides, and most preferably at least 855 nucleotides. Preferably, a subsequence of the mature polypeptide coding sequence of SEQ ID NO: 161 contains at least 555 nucleotides, more preferably at least 585 nucleotides, and most preferably at least 615 nucleotides. Preferably, a subsequence of the mature polypeptide coding sequence of SEQ ID NO: 163 contains at least 540 nucleotides, more preferably at least 570 nucleotides, and most preferably at least 600 nucleotides. Preferably, a subsequence of the mature polypeptide coding sequence of SEQ ID NO: 165 contains at least 570 nucleotides, more preferably at least 600 nucleotides, and most preferably at least 630 nucleotides. Preferably, a subsequence of the mature polypeptide coding sequence of SEQ ID NO: 167 contains at least 1155 nucleotides, more preferably at least 1230 nucleotides, and most preferably at least 1305 nucleotides. Preferably, a subsequence of the mature polypeptide coding sequence of SEQ ID NO: 169 contains at least 765 nucleotides, more preferably at least 810 nucleotides, and most preferably at least 855 nucleotides.

In a fourth aspect, the polypeptide having cellulolytic enhancing activity is encoded by a polynucleotide that hybridizes under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169, (ii) the genomic DNA sequence of the mature polypeptide coding sequence of SEQ ID NO: 7, SEQ ID NO: 9, SEQ ID NO: 11, SEQ ID NO: 15, SEQ ID NO: 161, SEQ ID NO: 163, or SEQ ID NO: 165, or the cDNA sequence of the mature polypeptide coding sequence of SEQ ID NO: 1, SEQ ID NO: 3, SEQ ID NO: 5, SEQ ID NO: 13, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 167, or SEQ ID NO: 169, (iii) a subsequence of (i) or (ii), or (iv) a full-length complementary strand of (i), (ii), or (iii) (J. Sambrook, E. F. Fritsch, and *T. Maniatus*, 1989, supra). A subsequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169 contains at least 100 contiguous nucleotides or preferably at least 200 contiguous nucleotides. Moreover, the subsequence may encode a polypeptide fragment that has cellulolytic enhancing activity. In a preferred aspect, the mature polypeptide coding sequence is nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, nucleotides 58 to 912 of SEQ ID NO: 9, nucleotides 46 to 951 of SEQ ID NO: 11, nucleotides 67 to 796 of SEQ ID NO: 13, nucleotides 77 to 766 of SEQ ID NO: 15, nucleotides 52 to 921 of SEQ ID NO: 17, nucleotides 46 to 851 of SEQ ID NO: 19, nucleotides 55 to 1239 of SEQ ID NO: 21, nucleotides 46 to 1250 of SEQ ID NO: 23, nucleotides 58 to 811 of SEQ ID NO: 25, nucleotides 64 to 1112 of SEQ ID NO: 27, nucleotides 64 to 859 of SEQ ID NO: 29, nucleotides 64 to 1018 of SEQ ID NO: 31, nucleotides 70 to 1483 of SEQ ID NO: 33, nucleotides 76 to 832 of SEQ ID NO: 35, nucleotides 58 to 974 of SEQ ID NO: 37, nucleotides 52 to 875 of SEQ ID NO: 39, nucleotides 58 to 1250 of SEQ ID NO: 41, nucleotides 52 to 795 of SEQ ID NO: 43, nucleotides 64 to 1104 of SEQ ID NO: 45, nucleotides 73 to 990 of SEQ ID NO: 47, nucleotides 49 to 1218 of SEQ ID NO: 49, nucleotides 55 to 930 of SEQ ID NO: 51, nucleotides 67 to 1581 of SEQ ID NO: 53, nucleotides 49 to 865 of SEQ ID NO: 55, nucleotides 58 to 1065 of SEQ ID NO: 57, nucleotides 67 to 868 of SEQ ID NO: 59, nucleotides 55 to 1099 of SEQ ID NO: 61, nucleotides 70 to 1483 of SEQ ID NO: 63, nucleotides 61 to 1032 of SEQ ID NO: 147, nucleotides 61 to 1167 of SEQ ID NO: 149, nucleotides 64 to 1218 of SEQ ID NO: 151, nucleotides 58 to 1281 of SEQ ID NO: 153, nucleotides 52 to 801 of SEQ ID NO: 155, nucleotides 61 to 819 of SEQ ID NO: 157, nucleotides 61 to 966 of SEQ ID NO: 159, nucleotides 52 to 702 of SEQ ID NO: 161, nucleotides 70 to 699 of SEQ ID NO: 163, nucleotides 49 to 711 of SEQ ID NO: 165, nucleotides 76 to 1452 of SEQ ID NO: 167, or nucleotides 64 to 1018 of SEQ ID NO: 169.

The nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169, or a subsequence thereof; as well as the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, or SEQ ID NO: 170, or a fragment thereof, may be used to design a nucleic acid probe to identify and clone DNA encoding polypeptides having cellulolytic enhancing activity from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169; the genomic DNA sequence of the mature polypeptide coding sequence of SEQ ID NO: 7, SEQ ID NO: 9, SEQ ID NO: 11, SEQ ID NO: 15, SEQ ID NO: 161, SEQ ID NO: 163, or SEQ ID NO: 165, or the cDNA sequence of the mature polypeptide coding sequence of SEQ ID NO: 1, SEQ ID NO: 3, SEQ ID NO: 5, SEQ ID NO: 13, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 167, or SEQ ID NO: 169; the full-length complementary strand thereof; or a subsequence thereof, under very low to very high stringency conditions, as described supra.

In a preferred aspect, the nucleic acid probe is the mature polypeptide coding sequence of SEQ ID NO: 1. In another preferred aspect, the nucleic acid probe is nucleotides 388 to 1332 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pEJG120 which is contained in *E. coli* NRRL B-30699, wherein the polynucleotide sequence thereof encodes a polypeptide having cellulolytic enhancing activity. In another preferred aspect, the nucleic acid probe is the mature polypeptide coding sequence contained in plasmid pEJG120 which is contained in *E. coli* NRRL B-30699.

In another preferred aspect, the nucleic acid probe is the mature polypeptide coding sequence of SEQ ID NO: 3. In another preferred aspect, the nucleic acid probe is nucleotides 98 to 821 of SEQ ID NO: 3. In another preferred aspect, the nucleic acid probe is a polynucleotide sequence that encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pTter61C which is contained in *E. coli* NRRL B-30813, wherein the polynucleotide sequence thereof encodes a polypeptide having cellulolytic enhancing activity. In another preferred aspect, the nucleic acid probe is the mature polypeptide coding sequence contained in plasmid pTter61C which is contained in *E. coli* NRRL B-30813.

In another preferred aspect, the nucleic acid probe is the mature polypeptide coding sequence of SEQ ID NO: 5. In another preferred aspect, the nucleic acid probe is nucleotides 126 to 978 of SEQ ID NO: 5. In another preferred aspect, the nucleic acid probe is a polynucleotide sequence that encodes the polypeptide of SEQ ID NO: 6, or a subsequence thereof. In another preferred aspect, the nucleic acid probe is SEQ ID NO: 5. In another preferred aspect, the nucleic acid probe is the polynucleotide sequence contained in plasmid pTter61D which is contained in *E. coli* NRRL B-30812, wherein the polynucleotide sequence thereof encodes a polypeptide having cellulolytic enhancing activity. In another preferred aspect, the nucleic acid probe is the mature polypeptide coding sequence contained in plasmid pTter61 D which is contained in *E. coli* NRRL B-30812.

In another preferred aspect, the nucleic acid probe is the mature polypeptide coding sequence of SEQ ID NO: 7. In another preferred aspect, the nucleic acid probe is nucleotides 55 to 678 of SEQ ID NO: 7. In another preferred aspect, the nucleic acid probe is a polynucleotide sequence that encodes the polypeptide of SEQ ID NO: 8, or a subsequence thereof. In another preferred aspect, the nucleic acid probe is SEQ ID NO: 7. In another preferred aspect, the nucleic acid probe is the polynucleotide sequence contained in plasmid pTter61E which is contained in *E. coli* NRRL B-30814, wherein the polynucleotide sequence thereof encodes a polypeptide having cellulolytic enhancing activity. In another preferred aspect, the nucleic acid probe is the mature polypeptide coding sequence contained in plasmid pTter61E which is contained in *E. coli* NRRL B-30814.

In another preferred aspect, the nucleic acid probe is the mature polypeptide coding sequence of SEQ ID NO: 9. In another preferred aspect, the nucleic acid probe is nucleotides 58 to 912 of SEQ ID NO: 9 In another preferred aspect, the nucleic acid probe is a polynucleotide sequence that encodes the polypeptide of SEQ ID NO: 10, or a subsequence thereof. In another preferred aspect, the nucleic acid probe is SEQ ID NO: 9. In another preferred aspect, the nucleic acid probe is the polynucleotide sequence contained in plasmid pTter61 G which is contained in *E. coli* NRRL B-30811, wherein the polynucleotide sequence thereof encodes a polypeptide having cellulolytic enhancing activity. In another preferred aspect, the nucleic acid probe is the mature polypeptide coding sequence contained in plasmid pTter61 G which is contained in *E. coli* NRRL B-30811.

In another preferred aspect, the nucleic acid probe is the mature polypeptide coding sequence of SEQ ID NO: 11. In another preferred aspect, the nucleic acid probe is nucleotides 46 to 951 of SEQ ID NO: 11. In another preferred aspect, the nucleic acid probe is a polynucleotide sequence that encodes the polypeptide of SEQ ID NO: 12, or a subsequence thereof. In another preferred aspect, the nucleic acid probe is SEQ ID NO: 11. In another preferred aspect, the nucleic acid probe is the polynucleotide sequence contained in plasmid pTter61F which is contained in *E. coli* NRRL B-50044, wherein the polynucleotide sequence thereof encodes a polypeptide having cellulolytic enhancing activity. In another preferred aspect, the nucleic acid probe is the mature polypeptide coding region contained in plasmid pTter61F which is contained in *E. coli* NRRL B-50044.

In another preferred aspect, the nucleic acid probe is the mature polypeptide coding sequence of SEQ ID NO: 13. In another preferred aspect, the nucleic acid probe is nucleotides 67 to 796 of SEQ ID NO: 13. In another preferred aspect, the nucleic acid probe is a polynucleotide sequence that encodes the polypeptide of SEQ ID NO: 14, or a subsequence thereof. In another preferred aspect, the nucleic acid probe is SEQ ID NO: 13. In another preferred aspect, the nucleic acid probe is the polynucleotide sequence contained in plasmid pDZA2-7 which is contained in *E. coli* NRRL B-30704, wherein the polynucleotide sequence thereof encodes a polypeptide having cellulolytic enhancing activity. In another preferred aspect, the nucleic acid probe is the mature polypeptide coding sequence contained in plasmid pDZA2-7 which is contained in *E. coli* NRRL B-30704.

In another preferred aspect, the nucleic acid probe is the mature polypeptide coding sequence of SEQ ID NO: 15. In another preferred aspect, the nucleic acid probe is nucleotides 77 to 766 of SEQ ID NO: 15. In another preferred aspect, the nucleic acid probe is a polynucleotide sequence that encodes the polypeptide of SEQ ID NO: 16, or a subsequence thereof. In another preferred aspect, the nucleic acid probe is SEQ ID NO: 15. In another preferred aspect, the nucleic acid probe is the polynucleotide sequence contained in plasmid pTr3337 which is contained in *E. coli* NRRL B-30878, wherein the polynucleotide sequence thereof encodes a polypeptide having cellulolytic enhancing activity. In another preferred aspect, the nucleic acid probe is the mature polypeptide coding sequence contained in plasmid pTr3337 which is contained in *E. coli* NRRL B-30878.

In another preferred aspect, the nucleic acid probe is the mature polypeptide coding sequence of SEQ ID NO: 17. In another preferred aspect, the nucleic acid probe is nucleotides 52 to 921 of SEQ ID NO: 17. In another preferred aspect, the nucleic acid probe is a polynucleotide sequence that encodes the polypeptide of SEQ ID NO: 18, or a subsequence thereof. In another preferred aspect, the nucleic acid probe is SEQ ID NO: 17. In another preferred aspect, the nucleic acid probe is the polynucleotide sequence contained in plasmid pSMai190 which is contained in *E. coli* NRRL B-50084, wherein the polynucleotide sequence thereof encodes a polypeptide having cellulolytic enhancing activity. In another preferred aspect, the nucleic acid probe is the mature polypeptide coding sequence contained in plasmid pSMai190 which is contained in *E. coli* NRRL B-50084.

In another preferred aspect, the nucleic acid probe is the mature polypeptide coding sequence of SEQ ID NO: 19. In another preferred aspect, the nucleic acid probe is nucleotides 46 to 851 of SEQ ID NO: 19. In another preferred aspect, the nucleic acid probe is a polynucleotide sequence that encodes the polypeptide of SEQ ID NO: 20, or a subsequence thereof. In another preferred aspect, the nucleic acid probe is SEQ ID NO: 19. In another preferred aspect, the nucleic acid probe is the polynucleotide sequence contained in plasmid pSMai192 which is contained in *E. coli* NRRL B-50086, wherein the polynucleotide sequence thereof encodes a polypeptide having cellulolytic enhancing activity. In another preferred aspect, the nucleic acid probe is the mature polypeptide coding sequence contained in plasmid pSMai192 which is contained in *E. coli* NRRL B-50086.

In another preferred aspect, the nucleic acid probe is the mature polypeptide coding sequence of SEQ ID NO: 21. In another preferred aspect, the nucleic acid probe is nucleotides 55 to 1239 of SEQ ID NO: 21. In another preferred aspect, the nucleic acid probe is a polynucleotide sequence that encodes the polypeptide of SEQ ID NO: 22, or a subsequence thereof. In another preferred aspect, the nucleic acid probe is SEQ ID NO: 21. In another preferred aspect, the nucleic acid probe is the polynucleotide sequence contained in plasmid pSMai191 which is contained in *E. coli* NRRL B-50085, wherein the polynucleotide sequence thereof encodes a polypeptide having cellulolytic enhancing activity. In another preferred aspect, the nucleic acid probe is the mature polypeptide coding sequence contained in plasmid pSMai191 which is contained in *E. coli* NRRL B-50085.

In another preferred aspect, the nucleic acid probe is the mature polypeptide coding sequence of SEQ ID NO: 23. In another preferred aspect, the nucleic acid probe is nucleotides 46 to 1250 of SEQ ID NO: 23. In another preferred aspect, the nucleic acid probe is a polynucleotide sequence that encodes the polypeptide of SEQ ID NO: 24, or a subsequence thereof. In another preferred aspect, the nucleic acid probe is SEQ ID NO: 23. In another preferred aspect, the nucleic acid probe is the polynucleotide sequence contained in plasmid pSMai193 which is contained in *E. coli* NRRL B-50087, wherein the polynucleotide sequence thereof encodes a polypeptide having cellulolytic enhancing activity. In another preferred aspect, the nucleic acid probe is the mature polypeptide coding sequence contained in plasmid pSMai193 which is contained in *E. coli* NRRL B-50087.

In another preferred aspect, the nucleic acid probe is the mature polypeptide coding sequence of SEQ ID NO: 25. In another preferred aspect, the nucleic acid probe is nucleotides 58 to 811 of SEQ ID NO: 25. In another preferred aspect, the nucleic acid probe is a polynucleotide sequence that encodes the polypeptide of SEQ ID NO: 26, or a subsequence thereof. In another preferred aspect, the nucleic acid probe is SEQ ID NO: 25. In another preferred aspect, the nucleic acid probe is the polynucleotide sequence contained in plasmid pSMai187 which is contained in *E. coli* NRRL B-50083, wherein the polynucleotide sequence thereof encodes a polypeptide having cellulolytic enhancing activity. In another preferred aspect, the nucleic acid probe is the mature polypeptide coding sequence contained in plasmid pSMai187 which is contained in *E. coli* NRRL B-50083.

In another preferred aspect, the nucleic acid probe is the mature polypeptide coding sequence of SEQ ID NO: 27. In another preferred aspect, the nucleic acid probe is nucleotides 64 to 1112 of SEQ ID NO: 27. In another preferred aspect, the nucleic acid probe is a polynucleotide sequence that encodes the polypeptide of SEQ ID NO: 28, or a subsequence thereof. In another preferred aspect, the nucleic acid probe is SEQ ID NO: 27. In another preferred aspect, the nucleic acid probe is the polynucleotide sequence contained in plasmid pXYZ1473 which is contained in *E. coli* DSM 22075, wherein the polynucleotide sequence thereof encodes a polypeptide having cellulolytic enhancing activity. In another preferred aspect, the nucleic acid probe is the mature polypeptide coding sequence contained in plasmid pXYZ1473 which is contained in *E. coli* DSM 22075.

In another preferred aspect, the nucleic acid probe is the mature polypeptide coding sequence of SEQ ID NO: 29. In another preferred aspect, the nucleic acid probe is nucleotides 64 to 859 of SEQ ID NO: 29. In another preferred aspect, the nucleic acid probe is a polynucleotide sequence that encodes the polypeptide of SEQ ID NO: 30, or a subsequence thereof. In another preferred aspect, the nucleic acid probe is SEQ ID NO: 29.

In another preferred aspect, the nucleic acid probe is the mature polypeptide coding sequence of SEQ ID NO: 31. In another preferred aspect, the nucleic acid probe is nucleotides 64 to 1018 of SEQ ID NO: 31. In another preferred aspect, the nucleic acid probe is a polynucleotide sequence that encodes the polypeptide of SEQ ID NO: 32, or a subsequence thereof. In another preferred aspect, the nucleic acid probe is SEQ ID NO: 31. In another preferred aspect, the nucleic acid probe is the polynucleotide sequence contained in plasmid pGEM-T-Ppin7 which is contained in *E. coli* DSM 22711, wherein the polynucleotide sequence thereof encodes a polypeptide having cellulolytic enhancing activity. In another preferred aspect, the nucleic acid probe is the mature polypeptide coding sequence contained in plasmid pGEM-T-Ppin7 which is contained in *E. coli* DSM 22711.

In another preferred aspect, the nucleic acid probe is the mature polypeptide coding sequence of SEQ ID NO: 33. In another preferred aspect, the nucleic acid probe is nucleotides 70 to 1483 of SEQ ID NO: 33. In another preferred aspect, the nucleic acid probe is a polynucleotide sequence that encodes the polypeptide of SEQ ID NO: 34, or a subsequence thereof. In another preferred aspect, the nucleic acid probe is SEQ ID NO: 33. In another preferred aspect, the nucleic acid probe is the polynucleotide sequence contained in plasmid pXYZ1483 which is contained in *E. coli* DSM 22600, wherein the polynucleotide sequence thereof encodes a polypeptide having cellulolytic enhancing activity. In another preferred aspect, the nucleic acid probe is the mature polypeptide coding sequence contained in plasmid pXYZ1483 which is contained in *E. coli* DSM 22600.

In another preferred aspect, the nucleic acid probe is the mature polypeptide coding sequence of SEQ ID NO: 35. In another preferred aspect, the nucleic acid probe is nucleotides 76 to 832 of SEQ ID NO: 35. In another preferred aspect, the nucleic acid probe is a polynucleotide sequence that encodes the polypeptide of SEQ ID NO: 36, or a subsequence thereof.

In another preferred aspect, the nucleic acid probe is SEQ ID NO: 35. In another preferred aspect, the nucleic acid probe is the polynucleotide sequence contained in plasmid pGEM-T-GH61D23Y4 which is contained in *E. coli* DSM 22882, wherein the polynucleotide sequence thereof encodes a polypeptide having cellulolytic enhancing activity. In another preferred aspect, the nucleic acid probe is the mature polypeptide coding sequence contained in plasmid pGEM-T-GH61D23Y4 which is contained in *E. coli* DSM 22882.

In another preferred aspect, the nucleic acid probe is the mature polypeptide coding sequence of SEQ ID NO: 37. In another preferred aspect, the nucleic acid probe is nucleotides 58 to 974 of SEQ ID NO: 37. In another preferred aspect, the nucleic acid probe is a polynucleotide sequence that encodes the polypeptide of SEQ ID NO: 38, or a subsequence thereof. In another preferred aspect, the nucleic acid probe is SEQ ID NO: 37. In another preferred aspect, the nucleic acid probe is the polynucleotide sequence contained in plasmid pSMai213 which is contained in *E. coli* NRRL B-50300, wherein the polynucleotide sequence thereof encodes a polypeptide having cellulolytic enhancing activity. In another preferred aspect, the nucleic acid probe is the mature polypeptide coding sequence contained in plasmid pSMai213 which is contained in *E. coli* NRRL B-50300.

In another preferred aspect, the nucleic acid probe is the mature polypeptide coding sequence of SEQ ID NO: 39. In another preferred aspect, the nucleic acid probe is nucleotides 52 to 875 of SEQ ID NO: 39. In another preferred aspect, the nucleic acid probe is a polynucleotide sequence that encodes the polypeptide of SEQ ID NO: 40, or a subsequence thereof. In another preferred aspect, the nucleic acid probe is SEQ ID NO: 39. In another preferred aspect, the nucleic acid probe is the polynucleotide sequence contained in plasmid pSMai216 which is contained in *E. coli* NRRL B-50301, wherein the polynucleotide sequence thereof encodes a polypeptide having cellulolytic enhancing activity. In another preferred aspect, the nucleic acid probe is the mature polypeptide coding sequence contained in plasmid pSMai216 which is contained in *E. coli* NRRL B-50301.

In another preferred aspect, the nucleic acid probe is the mature polypeptide coding sequence of SEQ ID NO: 41. In another preferred aspect, the nucleic acid probe is nucleotides 58 to 1250 of SEQ ID NO: 41. In another preferred aspect, the nucleic acid probe is a polynucleotide sequence that encodes the polypeptide of SEQ ID NO: 42, or a subsequence thereof. In another preferred aspect, the nucleic acid probe is SEQ ID NO: 41. In another preferred aspect, the nucleic acid probe is the polynucleotide sequence contained in plasmid p pSMai217 which is contained in *E. coli* NRRL B-50302, wherein the polynucleotide sequence thereof encodes a polypeptide having cellulolytic enhancing activity. In another preferred aspect, the nucleic acid probe is the mature polypeptide coding sequence contained in plasmid pSMai217 which is contained in *E. coli* NRRL B-50302.

In another preferred aspect, the nucleic acid probe is the mature polypeptide coding sequence of SEQ ID NO: 43. In another preferred aspect, the nucleic acid probe is nucleotides 52 to 795 of SEQ ID NO: 43. In another preferred aspect, the nucleic acid probe is a polynucleotide sequence that encodes the polypeptide of SEQ ID NO: 44, or a subsequence thereof. In another preferred aspect, the nucleic acid probe is SEQ ID NO: 43. In another preferred aspect, the nucleic acid probe is the polynucleotide sequence contained in plasmid pSMai218 which is contained in *E. coli* NRRL B-50303, wherein the polynucleotide sequence thereof encodes a polypeptide having cellulolytic enhancing activity. In another preferred aspect, the nucleic acid probe is the mature polypeptide coding sequence contained in plasmid pSMai218 which is contained in *E. coli* NRRL B-50303.

In another preferred aspect, the nucleic acid probe is the mature polypeptide coding sequence of SEQ ID NO: 45. In another preferred aspect, the nucleic acid probe is nucleotides 64 to 1104 of SEQ ID NO: 45. In another preferred aspect, the nucleic acid probe is a polynucleotide sequence that encodes the polypeptide of SEQ ID NO: 46, or a subsequence thereof. In another preferred aspect, the nucleic acid probe is SEQ ID NO: 45. In another preferred aspect, the nucleic acid probe is the polynucleotide sequence contained in plasmid pAG68 which is contained in *E. coli* NRRL B-50320, wherein the polynucleotide sequence thereof encodes a polypeptide having cellulolytic enhancing activity. In another preferred aspect, the nucleic acid probe is the mature polypeptide coding sequence contained in plasmid pAG68 which is contained in *E. coli* NRRL B-50320.

In another preferred aspect, the nucleic acid probe is the mature polypeptide coding sequence of SEQ ID NO: 47. In another preferred aspect, the nucleic acid probe is nucleotides 73 to 990 of SEQ ID NO: 47. In another preferred aspect, the nucleic acid probe is a polynucleotide sequence that encodes the polypeptide of SEQ ID NO: 48, or a subsequence thereof. In another preferred aspect, the nucleic acid probe is SEQ ID NO: 47. In another preferred aspect, the nucleic acid probe is the polynucleotide sequence contained in plasmid pAG69 which is contained in *E. coli* NRRL B-50321, wherein the polynucleotide sequence thereof encodes a polypeptide having cellulolytic enhancing activity. In another preferred aspect, the nucleic acid probe is the mature polypeptide coding sequence contained in plasmid pAG69 which is contained in *E. coli* NRRL B-50321.

In another preferred aspect, the nucleic acid probe is the mature polypeptide coding sequence of SEQ ID NO: 49. In another preferred aspect, the nucleic acid probe is nucleotides 49 to 1218 of SEQ ID NO: 49. In another preferred aspect, the nucleic acid probe is a polynucleotide sequence that encodes the polypeptide of SEQ ID NO: 50, or a subsequence thereof. In another preferred aspect, the nucleic acid probe is SEQ ID NO: 49. In another preferred aspect, the nucleic acid probe is the polynucleotide sequence contained in plasmid pAG75 which is contained in *E. coli* NRRL B-50322, wherein the polynucleotide sequence thereof encodes a polypeptide having cellulolytic enhancing activity. In another preferred aspect, the nucleic acid probe is the mature polypeptide coding sequence contained in plasmid pAG75 which is contained in *E. coli* NRRL B-50322.

In another preferred aspect, the nucleic acid probe is the mature polypeptide coding sequence of SEQ ID NO: 51. In another preferred aspect, the nucleic acid probe is nucleotides 55 to 930 of SEQ ID NO: 51. In another preferred aspect, the nucleic acid probe is a polynucleotide sequence that encodes the polypeptide of SEQ ID NO: 52, or a subsequence thereof. In another preferred aspect, the nucleic acid probe is SEQ ID NO: 51. In another preferred aspect, the nucleic acid probe is the polynucleotide sequence contained in plasmid pAG76 which is contained in *E. coli* NRRL B-50323, wherein the polynucleotide sequence thereof encodes a polypeptide having cellulolytic enhancing activity. In another preferred aspect, the nucleic acid probe is the mature polypeptide coding sequence contained in plasmid pAG76 which is contained in *E. coli* NRRL B-50323.

In another preferred aspect, the nucleic acid probe is the mature polypeptide coding sequence of SEQ ID NO: 53. In another preferred aspect, the nucleic acid probe is nucleotides 67 to 1581 of SEQ ID NO: 53. In another preferred aspect, the nucleic acid probe is a polynucleotide sequence that encodes the polypeptide of SEQ ID NO: 54, or a subsequence thereof. In another preferred aspect, the nucleic acid probe is SEQ ID NO: 53. In another preferred aspect, the nucleic acid probe is the polynucleotide sequence contained in plasmid pAG77 which is contained in *E. coli* NRRL B-50324, wherein the polynucleotide sequence thereof encodes a polypeptide having cellulolytic enhancing activity. In another preferred aspect, the nucleic acid probe is the mature polypeptide coding sequence contained in plasmid pAG77 which is contained in *E. coli* NRRL B-50324.

In another preferred aspect, the nucleic acid probe is the mature polypeptide coding sequence of SEQ ID NO: 55. In another preferred aspect, the nucleic acid probe is nucleotides 49 to 865 of SEQ ID NO: 55. In another preferred aspect, the nucleic acid probe is a polynucleotide sequence that encodes the polypeptide of SEQ ID NO: 56, or a subsequence thereof. In another preferred aspect, the nucleic acid probe is SEQ ID NO: 55. In another preferred aspect, the nucleic acid probe is the polynucleotide sequence contained in plasmid pAG78 which is contained in *E. coli* NRRL B-50325, wherein the polynucleotide sequence thereof encodes a polypeptide having cellulolytic enhancing activity. In another preferred aspect, the nucleic acid probe is the mature polypeptide coding sequence contained in plasmid pAG78 which is contained in *E. coli* NRRL B-50325.

In another preferred aspect, the nucleic acid probe is the mature polypeptide coding sequence of SEQ ID NO: 57. In another preferred aspect, the nucleic acid probe is nucleotides 58 to 1065 of SEQ ID NO: 57. In another preferred aspect, the nucleic acid probe is a polynucleotide sequence that encodes the polypeptide of SEQ ID NO: 58, or a subsequence thereof. In another preferred aspect, the nucleic acid probe is SEQ ID NO: 57. In another preferred aspect, the nucleic acid probe is the polynucleotide sequence contained in plasmid p pAG79 which is contained in *E. coli* NRRL B-50326, wherein the polynucleotide sequence thereof encodes a polypeptide having cellulolytic enhancing activity. In another preferred aspect, the nucleic acid probe is the mature polypeptide coding sequence contained in plasmid pAG79 which is contained in *E. coli* NRRL B-50326.

In another preferred aspect, the nucleic acid probe is the mature polypeptide coding sequence of SEQ ID NO: 59. In another preferred aspect, the nucleic acid probe is nucleotides 67 to 868 of SEQ ID NO: 59. In another preferred aspect, the nucleic acid probe is a polynucleotide sequence that encodes the polypeptide of SEQ ID NO: 60, or a subsequence thereof. In another preferred aspect, the nucleic acid probe is SEQ ID NO: 59. In another preferred aspect, the nucleic acid probe is the polynucleotide sequence contained in plasmid plasmid pGEM-T-GH61a51486 which is contained in *E. coli* DSM 22656, wherein the polynucleotide sequence thereof encodes a polypeptide having cellulolytic enhancing activity. In another preferred aspect, the nucleic acid probe is the mature polypeptide coding sequence contained in plasmid plasmid pGEM-T-GH61a51486 which is contained in *E. coli* DSM 22656.

In another preferred aspect, the nucleic acid probe is the mature polypeptide coding sequence of SEQ ID NO: 61. In another preferred aspect, the nucleic acid probe is nucleotides 55 to 1099 of SEQ ID NO: 61. In another preferred aspect, the nucleic acid probe is a polynucleotide sequence that encodes the polypeptide of SEQ ID NO: 62, or a subsequence thereof. In another preferred aspect, the nucleic acid probe is SEQ ID NO: 61. In another preferred aspect, the nucleic acid probe is the polynucleotide sequence contained in plasmid pGEM-T-GH61DYF which is contained in *E. coli* DSM 22654, wherein the polynucleotide sequence thereof encodes a polypeptide having cellulolytic enhancing activity. In another preferred aspect, the nucleic acid probe is the mature polypeptide coding sequence contained in plasmid pGEM-T-GH61DYF which is contained in *E. coli* DSM 22654.

In another preferred aspect, the nucleic acid probe is the mature polypeptide coding sequence of SEQ ID NO: 63. In another preferred aspect, the nucleic acid probe is nucleotides 70 to 1483 of SEQ ID NO: 63. In another preferred aspect, the nucleic acid probe is a polynucleotide sequence that encodes the polypeptide of SEQ ID NO: 64, or a subsequence thereof. In another preferred aspect, the nucleic acid probe is SEQ ID NO: 63. In another preferred aspect, the nucleic acid probe is the polynucleotide sequence contained in plasmid pGEM-T-GH61D14YH which is contained in *E. coli* DSM 22657, wherein the polynucleotide sequence thereof encodes a polypeptide having cellulolytic enhancing activity. In another preferred aspect, the nucleic acid probe is the mature polypeptide coding sequence contained in plasmid pGEM-T-GH61D14YH which is contained in *E. coli* DSM 22657.

In another preferred aspect, the nucleic acid probe is the mature polypeptide coding sequence of SEQ ID NO: 147. In another preferred aspect, the nucleic acid probe is nucleotides 61 to 1032 of SEQ ID NO: 147. In another preferred aspect, the nucleic acid probe is a polynucleotide sequence that encodes the polypeptide of SEQ ID NO: 147, or a subsequence thereof. In another preferred aspect, the nucleic acid probe is SEQ ID NO: 147.

In another preferred aspect, the nucleic acid probe is the mature polypeptide coding sequence of SEQ ID NO: 149. In another preferred aspect, the nucleic acid probe is nucleotides 61 to 1167 of SEQ ID NO: 149. In another preferred aspect, the nucleic acid probe is a polynucleotide sequence that encodes the polypeptide of SEQ ID NO: 149, or a subsequence thereof. In another preferred aspect, the nucleic acid probe is SEQ ID NO: 149.

In another preferred aspect, the nucleic acid probe is the mature polypeptide coding sequence of SEQ ID NO: 151. In another preferred aspect, the nucleic acid probe is nucleotides 64 to 1218 of SEQ ID NO: 151. In another preferred aspect, the nucleic acid probe is a polynucleotide sequence that encodes the polypeptide of SEQ ID NO: 151, or a subsequence thereof. In another preferred aspect, the nucleic acid probe is SEQ ID NO: 151.

In another preferred aspect, the nucleic acid probe is the mature polypeptide coding sequence of SEQ ID NO: 153. In another preferred aspect, the nucleic acid probe is nucleotides 58 to 1281 of SEQ ID NO: 153. In another preferred aspect, the nucleic acid probe is a polynucleotide sequence that encodes the polypeptide of SEQ ID NO: 153, or a subsequence thereof. In another preferred aspect, the nucleic acid probe is SEQ ID NO: 153.

In another preferred aspect, the nucleic acid probe is the mature polypeptide coding sequence of SEQ ID NO: 155. In another preferred aspect, the nucleic acid probe is nucleotides 52 to 801 of SEQ ID NO: 155. In another preferred aspect, the nucleic acid probe is a polynucleotide sequence that encodes the polypeptide of SEQ ID NO: 155, or a subsequence thereof. In another preferred aspect, the nucleic acid probe is SEQ ID NO: 155.

In another preferred aspect, the nucleic acid probe is the mature polypeptide coding sequence of SEQ ID NO: 157. In another preferred aspect, the nucleic acid probe is nucleotides 61 to 819 of SEQ ID NO: 157. In another preferred aspect, the nucleic acid probe is a polynucleotide sequence that encodes the polypeptide of SEQ ID NO: 157, or a subsequence thereof. In another preferred aspect, the nucleic acid probe is SEQ ID NO: 157.

In another preferred aspect, the nucleic acid probe is the mature polypeptide coding sequence of SEQ ID NO: 159. In another preferred aspect, the nucleic acid probe is nucleotides 61 to 966 of SEQ ID NO: 159. In another preferred aspect, the nucleic acid probe is a polynucleotide sequence that encodes the polypeptide of SEQ ID NO: 159, or a subsequence thereof. In another preferred aspect, the nucleic acid probe is SEQ ID NO: 159.

In another preferred aspect, the nucleic acid probe is the mature polypeptide coding sequence of SEQ ID NO: 161. In another preferred aspect, the nucleic acid probe is nucleotides 52 to 702 of SEQ ID NO: 161. In another preferred aspect, the nucleic acid probe is a polynucleotide sequence that encodes the polypeptide of SEQ ID NO: 161, or a subsequence thereof. In another preferred aspect, the nucleic acid probe is SEQ ID NO: 161.

In another preferred aspect, the nucleic acid probe is the mature polypeptide coding sequence of SEQ ID NO: 163. In another preferred aspect, the nucleic acid probe is nucleotides 70 to 699 of SEQ ID NO: 163. In another preferred aspect, the nucleic acid probe is a polynucleotide sequence that encodes the polypeptide of SEQ ID NO: 163, or a subsequence thereof. In another preferred aspect, the nucleic acid probe is SEQ ID NO: 163.

In another preferred aspect, the nucleic acid probe is the mature polypeptide coding sequence of SEQ ID NO: 165. In another preferred aspect, the nucleic acid probe is nucleotides 49 to 711 of SEQ ID NO: 165. In another preferred aspect, the nucleic acid probe is a polynucleotide sequence that encodes the polypeptide of SEQ ID NO: 165, or a subsequence thereof. In another preferred aspect, the nucleic acid probe is SEQ ID NO: 165.

In another preferred aspect, the nucleic acid probe is the mature polypeptide coding sequence of SEQ ID NO: 167. In another preferred aspect, the nucleic acid probe is nucleotides 76 to 1452 of SEQ ID NO: 167. In another preferred aspect, the nucleic acid probe is a polynucleotide sequence that encodes the polypeptide of SEQ ID NO: 167, or a subsequence thereof. In another preferred aspect, the nucleic acid probe is SEQ ID NO: 167.

In another preferred aspect, the nucleic acid probe is the mature polypeptide coding sequence of SEQ ID NO: 169. In another preferred aspect, the nucleic acid probe is nucleotides 64 to 1018 of SEQ ID NO: 169. In another preferred aspect, the nucleic acid probe is a polynucleotide sequence that encodes the polypeptide of SEQ ID NO: 169, or a subsequence thereof. In another preferred aspect, the nucleic acid probe is SEQ ID NO: 169.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, Proc. Natl. Acad. Sci. USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a fifth aspect, the polypeptide having cellulolytic enhancing activity is encoded by a polynucleotide comprising or consisting of a nucleotide sequence that has a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169 of preferably at least 60%, more preferably at least 65%, more preferably at least 70%, more preferably at least 75%, more preferably at least 80%, more preferably at least 85%, even more preferably at least 90%, most preferably at least 91%, at least 92%, at least 93%, at least 94%, or at least 95%, and even most preferably at least 96%, at least 97%, at least 98%, at least 99%, or at least 100%.

In a sixth aspect, the polypeptide having cellulolytic enhancing activity is an artificial variant comprising a substitution, deletion, and/or insertion of one or more (e.g., several) amino acids of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, or SEQ ID NO: 170; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, or SEQ ID NO: 170, is not more than 10, e.g., 1, 2, 3, 4, 5, 6, 7, 8 or 9.

A polypeptide having cellulolytic enhancing activity may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

A polypeptide having cellulolytic enhancing activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having cellulolytic enhancing activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having cellulolytic enhancing activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having cellulolytic enhancing activity.

In another aspect, the polypeptide is a *Streptococcus equisimilis, Streptococcus pyogenes, Streptococcus uberis,* or *Streptococcus equi* subsp. *Zooepidemicus* polypeptide having cellulolytic enhancing activity.

In another aspect, the polypeptide is a *Streptomyces achromogenes, Streptomyces avermitilis, Streptomyces coelicolor, Streptomyces griseus,* or *Streptomyces lividans* polypeptide having cellulolytic enhancing activity.

The polypeptide having cellulolytic enhancing activity may also be a fungal polypeptide, and more preferably a yeast polypeptide such as a *Candida, Kluyveromyces, Pichia, Saccharomyces, Schizosaccharomyces,* or *Yarrowia* polypeptide having cellulolytic enhancing activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having cellulolytic enhancing activity.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellulolytic enhancing activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crook-* wellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium pinophilum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride, or Trichophaea saccata polypeptide having cellulolytic enhancing activity.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, polypeptides having cellulolytic enhancing activity may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic DNA or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra)

Polynucleotides comprising nucleotide sequences that encode polypeptide having cellulolytic enhancing activity can be isolated and utilized to express the polypeptide having cellulolytic enhancing activity for evaluation in the methods of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain or a related organism and thus, for example, may be an allelic or species variant of the polypeptide encoding region of the polynucleotide.

The polynucleotides comprise nucleotide sequences that have a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169 of preferably at least 60%, more preferably at least 65%, more preferably at least 70%, more preferably at least 75%, more preferably at least 80%, more preferably at least 85%, even more preferably at least 90%, most preferably at least 91%, at least 92%, at least 93%, at least 94%, or at least 95%, and even most preferably at least 96%, at least 97%, at least 98%, or at least 99%, which encode a polypeptide having cellulolytic enhancing activity.

The polynucleotide may also be a polynucleotide encoding a polypeptide having cellulolytic enhancing activity that hybridizes under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, or SEQ ID NO: 169, (ii) the genomic DNA sequence of the mature polypeptide coding sequence of SEQ ID NO: 7, SEQ ID NO: 9, SEQ ID NO: 11, SEQ ID NO: 15, SEQ ID NO: 161, SEQ ID NO: 163, or SEQ ID NO: 165 or the cDNA sequence of the mature polypeptide coding sequence of SEQ ID NO: 1, SEQ ID NO: 3, SEQ ID NO: 5, SEQ ID NO: 13, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 167, or SEQ ID NO: 169, or (iii) a full-length complementary strand of (i) or (ii); or allelic variants and subsequences thereof (Sambrook et al., 1989, supra), as defined herein.

As described earlier, the techniques used to isolate or clone a polynucleotide encoding a polypeptide are known in the art and include isolation from genomic DNA, preparation from cDNA, or a combination thereof.

Enzyme Compositions

The enzyme compositions can comprise any protein that is useful in degrading or converting a cellulosic material.

In one aspect, the enzyme composition comprises or further comprises one or more (e.g., several) proteins selected from the group consisting of a cellulase, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a beta-glucosidase.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the methods of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The enzymes can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another preferred aspect, the polypeptide is a *Streptococcus equisimilis*, *Streptococcus pyogenes*, *Streptococcus uberis*, or *Streptococcus* equi subsp. *Zooepidemicus* polypeptide having enzyme activity.

In another preferred aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In a preferred aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another preferred aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, *Trichoderma viride*, or *Trichophaea saccata* polypeptide having enzyme activity.

Chemically modified or protein engineered mutants of the polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic enzymes may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLIC™ CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids. The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention include, but are not limited to, a *Trichoderma reesei* endoglucanase I (Penttila et al., 1986, *Gene* 45: 253-263; *Trichoderma reesei* Cel7B endoglucanase I; GENBANK™ accession no. M15665; SEQ ID NO: 66); *Trichoderma reesei* endoglucanase II (Saloheimo, et al., 1988, *Gene* 63:11-22; *Trichoderma reesei* Cel5A endoglucanase II; GENBANK™ accession no. M19373; SEQ ID NO: 68); *Trichoderma reesei* endoglucanase III (Okada et al., 1988, *Appl. Environ. Microbiol.* 64: 555-563; GENBANK™ accession no. AB003694; SEQ ID NO: 70); *Trichoderma reesei* endoglucanase V (Saloheimo et al., 1994, *Molecular Microbiology* 13: 219-228; GENBANK™ accession no. Z33381; SEQ ID NO: 72); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V (SEQ ID NO: 74); *Myceliophthora thermophila* CBS117.65 endoglucanase (SEQ ID NO: 76); basidiomycete CBS 495.95 endoglucanase (SEQ ID NO: 78); basidiomycete CBS 494.95 endoglucanase (SEQ ID NO: 80); *Thielavia terrestris* NRRL 8126 CEL6B endoglucanase (SEQ ID NO: 82); *Thielavia terrestris* NRRL 8126 CEL6C endoglucanase (SEQ ID NO: 84); *Thielavia terrestris* NRRL 8126 CEL7C endoglucanase (SEQ ID NO: 86); *Thielavia terrestris* NRRL 8126 CEL7E endoglucanase (SEQ ID NO: 88); *Thielavia terrestris* NRRL 8126 CEL7F endoglucanase (SEQ ID NO: 90); *Cladorrhinum foecundissimum* ATCC 62373 CEL7A endoglucanase (SEQ ID NO: 92); and *Trichoderma reesei* strain No. VTT-D-80133 endoglucanase (SEQ ID NO: 94; GENBANK™ accession no. M15665). The endoglucanases of SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, and SEQ ID NO: 94 described above are encoded by the mature polypeptide coding sequence of SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, and SEQ ID NO: 93, respectively.

Examples of cellobiohydrolases useful in the present invention include, but are not limited to, *Trichoderma reesei* cellobiohydrolase I (SEQ ID NO: 96); *Trichoderma reesei* cellobiohydrolase II (SEQ ID NO: 98); *Humicola insolens* cellobiohydrolase I (SEQ ID NO: 100); *Myceliophthora thermophila* cellobiohydrolase II (SEQ ID NO: 102 and SEQ ID NO: 104); *Thielavia terrestris* cellobiohydrolase II (CEL6A) (SEQ ID NO: 106); *Chaetomium thermophilum* cellobiohydrolase I (SEQ ID NO: 108); and *Chaetomium thermophilum* cellobiohydrolase II (SEQ ID NO: 110). The cellobiohydrolases of SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, and SEQ ID NO: 112 described above are encoded by the mature polypeptide coding sequence of SEQ ID NO: 97, SEQ ID NO: 99, SEQ ID NO: 101, SEQ ID NO: 103, SEQ ID NO: 105, SEQ ID NO: 107, and SEQ ID NO: 109, respectively.

Examples of beta-glucosidases useful in the present invention include, but are not limited to, *Aspergillus oryzae* beta-glucosidase (SEQ ID NO: 112); *Aspergillus fumigatus* beta-glucosidase (SEQ ID NO: 114); *Penicillium brasilianum* IBT 20888 beta-glucosidase (SEQ ID NO: 116); *Aspergillus niger* beta-glucosidase (SEQ ID NO: 118); and *Aspergillus aculeatus* beta-glucosidase (SEQ ID NO: 120). The beta-glucosidases of SEQ ID NO: 112, SEQ ID NO: 114, SEQ ID NO: 116, SEQ ID NO: 118, and SEQ ID NO: 120 described above are encoded by the mature polypeptide coding sequence of SEQ ID NO: 111, SEQ ID NO: 113, SEQ ID NO: 115, SEQ ID NO: 117, and SEQ ID NO: 119, respectively.

Examples of other beta-glucosidases useful in the present invention include a *Aspergillus oryzae* beta-glucosidase variant fusion protein of SEQ ID NO: 122 or the *Aspergillus oryzae* beta-glucosidase fusion protein of SEQ ID NO: 124. The beta-glucosidase fusion proteins of SEQ ID NO: 122 and SEQ ID NO: 124 are encoded by SEQ ID NO: 121 and SEQ ID NO: 123, respectively.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be useful in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, and U.S. Pat. No. 5,776,757.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740 L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8X212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number QOUHJ1), and *Humicola insolens* DSM 1800 acetylxylan esterase (WO 2009/073709).

Examples of ferulic acid esterases useful in the methods of the present invention include, but are not limited to, *Humicola*

*insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8X211), *Aspergillus niger* alpha-glucuronidase (Uniprot accession number Q96WX9), *Aspergillus terreus* alpha-glucuronidase (SwissProt accession number Q0CJP9), and *Aspergillus fumigatus* alpha-glucuronidase (SwissProt accession number Q4WW45).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Nucleic Acid Constructs

An isolated polynucleotide encoding a polypeptide, e.g., a polypeptide having cellulolytic enhancing activity, a cellulolytic enzyme, a hemicellulolytic enzyme, etc., may be manipulated in a variety of ways to provide for expression of the polypeptide by constructing a nucleic acid construct comprising an isolated polynucleotide encoding the polypeptide operably linked to one or more (e.g., several) control sequences that direct the expression of the coding sequence in a suitable host cell under conditions compatible with the control sequences. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be a promoter sequence, a polynucleotide that is recognized by a host cell for expression of a polynucleotide encoding a polypeptide. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs in the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs in the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in *Aspergilli* in which the untranslated leader has been replaced by an untranslated leader from a gene encoding triose phosphate isomerase in *Aspergilli*; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The various nucleotide and control sequences may be joined together to produce a recombinant expression vector that may include one or more (e.g., several) convenient restriction sites to allow for insertion or substitution of a polynucleotide encoding a polypeptide, e.g., a polypeptide having cellulolytic enhancing activity, a cellulolytic enzyme, a hemicellulolytic enzyme, etc., at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

Recombinant host cells comprising a polynucleotide encoding a polypeptide, e.g., a polypeptide having cellulolytic enhancing activity, a cellulolytic enzyme, a hemicellulolytic enzyme, etc., can be advantageously used in the recombinant production of the polypeptide. A construct or vector comprising such a polynucleotide is introduced into a host cell so that the vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide, e.g., a prokaryote or a eukaryote.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes*,

*Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

Methods for producing a polypeptide, e.g., a polypeptide having cellulolytic enhancing activity, a cellulolytic enzyme, a hemicellulolytic enzyme, etc., comprise (a) cultivating a cell, which in its wild-type form is capable of producing the polypeptide, under conditions conducive for production of the polypeptide; and (b) recovering the polypeptide.

Alternatively, methods for producing a polypeptide, e.g., a polypeptide having cellulolytic enhancing activity, a cellulolytic enzyme, a hemicellulolytic enzyme, etc., comprise (a) cultivating a recombinant host cell under conditions conducive for production of the polypeptide; and (b) recovering the polypeptide.

In the production methods, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. The polypeptides having cellulolytic enhancing activity are detected using the methods described herein.

The resulting broth may be used as is or the polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell expressing a polypeptide is used as a source of the polypeptide.

Methods for Processing Cellulosic Material

The compositions and methods of the present invention can be used to saccharify a cellulosic material to fermentable sugars and convert the fermentable sugars to many useful substances, e.g., fuel, potable ethanol, and/or fermentation products (e.g., acids, alcohols, ketones, gases, and the like). The production of a desired fermentation product from cellulosic material typically involves pretreatment, enzymatic hydrolysis (saccharification), and fermentation.

The present invention also relates to methods for degrading or converting a cellulosic material, comprising: treating the cellulosic material with an enzyme composition in the presence of a polypeptide having cellulolytic enhancing activity and a dioxy compound. In one aspect, the method above further comprises recovering the degraded or converted cellulosic material. Soluble products of degradation or conversion of the cellulosic material can be separated from the insoluble cellulosic material using technology well known in the art such as, for example, centrifugation, filtration, and gravity settling.

The present invention also relates to methods for producing a fermentation product, comprising: (a) saccharifying a cellulosic material with an enzyme composition in the presence of a polypeptide having cellulolytic enhancing activity and a dioxy compound; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity and a dioxy compound. In one aspect, the fermenting of the cellulosic material produces a fermentation product. In another aspect, the method further comprises recovering the fermentation product from the fermentation.

In one aspect, the dioxy compound is recovered following saccharification or fermentation and recycled back to a new saccharification reaction. Recycling of the dioxy compound can be accomplished using processes conventional in the art.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze cellulosic material to fermentable sugars, e.g., glucose, cellobiose, cellotriose, and pentose monomers, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flavio Fária de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment.

In practicing the methods of the present invention, any pretreatment process known in the art can be used to disrupt plant cell wall components of cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment: In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: Cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having cellulolytic enhancing activity and a dioxy compound. The enzyme and protein components of the compositions can be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The optimum amounts of the enzymes and polypeptides having cellulolytic enhancing activity depend on several factors including, but not limited to, the mixture of component cellulolytic enzymes, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In one aspect, an effective amount of cellulolytic or hemicellulolytic enzyme protein to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another aspect, an effective amount of a polypeptide having cellulolytic enhancing activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another aspect, an effective amount of a polypeptide having cellulolytic enhancing activity to cellulolytic enzyme protein is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic enzyme protein.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as some yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; *E. coli*, especially *E. coli* strains that have been genetically modified to improve the yield of ethanol; *Clostridium*, such as *Clostridium acetobutylicum*, *Chlostridium thermocellum*, and *Chlostridium phytofermentans*; *Geobacillus* sp.; *Thermoanaerobacter*, such as *Thermoanaerobacter saccharolyticum*; and *Bacillus*, such as *Bacillus coagulans*.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida*

*pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis, Clostridium acetobutylicum, Clostridium thermocellum, Chlostridium phytofermentans, Geobacillus* sp., *Thermoanaerobacter saccharolyticum*, and *Bacillus coagulans* (Philippidis, 1996, supra).

In a preferred aspect, the bacterium is a *Zymomonas*. In a more preferred aspect, the bacterium is *Zymomonas* mobilis. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRANDT™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol*. 39-40: 135-147; Ho et al., 1998, Genetically engineered *Saccharomyces* yeast capable of effectively cofermenting glucose and xylose, *Appl. Environ. Microbiol*. 64: 1852-1859; Kotter and Ciriacy, 1993, Xylose fermentation by *Saccharomyces cerevisiae, Appl. Microbiol. Biotechnol*. 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol*. 61: 4184-4190; Kuyper et al., 2004, Minimal metabolic engineering of *Saccharomyces cerevisiae* for efficient anaerobic xylose fermentation: a proof of principle, FEMS Yeast Research 4: 655-664; Beall et al., 1991, Parametric studies of ethanol production from xylose and other sugars by recombinant *Escherichia coli, Biotech. Bioeng*. 38: 296-303; Ingram et al., 1998, Metabolic engineering of bacteria for ethanol production, *Biotechnol. Bioeng*. 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol*. 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another more preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Media

SY50 medium was composed of 50 g of sucrose, 2 g of $MgSO_4 \cdot 7H_2O$, 10 g of $KH_2PO_4$, anhydrous, 2 g of $K_2SO_4$, 2 g of citric acid, 10 g of yeast extract, 2 g of urea, 0.5 g of $CaCl_2 \cdot 2H_2O$, and 0.5 g of 200×AMG trace metals solution, and deionized water to 1 liter (pH 6.0).

200×AMG trace metals solution was composed of 3 g of citric acid, 14.3 g of $ZnSO_4 \cdot 7H_2O$, 2.5 g of $CuSO_4 \cdot 5H_2O$, 13.8 g of $FeSO_4 \cdot 7H_2O$, and 8.5 g of $MnSO_4 \cdot H_2O$, and deionized water to 1 liter.

Example 1

Preparation of *Thermoascus aurantiacus* GH61A polypeptide Having Cellulolytic Enhancing Activity

*T. aurantiacus* GH61A polypeptide (SEQ ID NO: 13 [DNA sequence] and SEQ ID NO: 14 [deduced amino acid sequence]) was recombinantly produced in *Aspergillus oryzae* JaL250 according to WO 2005/074656. The recombinantly produced *T. aurantiacus* GH61A polypeptide was first concentrated by ultrafiltration using a 10 kDa membrane, buffer exchanged into 20 mM Tris-HCl pH 8.0, and then purified using a 20 ml MONO Q® column (GE Healthcare, Piscataway, N.J., USA) with a 500 ml 0-600 mM NaCl linear gradient in 20 mM Tris-HCl pH 8.0. Fractions were collected and pooled based on SDS-PAGE. The pooled fractions were concentrated by ultrafiltration using a 10 kDa membrane, and chromatographed using a 320 ml SUPERDEX® 75 SEC column (GE Healthcare, Piscataway, N.J., USA) with isocratic elution of approximately 1.3 liters of 150 mM NaCl-20 mM Tris-HCl pH 8.0. Fractions were collected and pooled based on SDS-PAGE. Pooled fractions were concentrated and desalted into 20 mM Tris-HCl pH 8.5 using a VIVASPIN® 20 10 kDa MWCO centrifugal concentration filter (GE Healthcare UK limited, Little Chalfont, Buckinghamshire, UK). The purified *T. aurantiacus* GH61A polypeptide was used in Examples 9-19 and 30.

Alternatively, the recombinantly produced *T. aurantiacus* GH61A polypeptide was first concentrated by ultrafiltration using a 10 kDa membrane, buffer exchanged into 20 mM Tris-HCl pH 8.0, and then purified using a 320 ml SUPERDEX® 75 SEC column (GE Healthcare, Piscataway, N.J., USA) with isocratic elution of approximately 1.3 liter of 150 mM NaCl-20 mM Tris-HCl pH 8.0. Fractions were collected and pooled based on SDS-PAGE. Pooled fractions were concentrated and desalted into 20 mM Tris-HCl pH 8.0 using a VIVASPIN 20® 10 kDa MWCO centrifugal concentration filter. The purified *T. aurantiacus* GH61A polypeptide was used in Examples 21 and 22.

Alternatively, the recombinantly produced *T. aurantiacus* GH61A polypeptide was first concentrated from 60 ml to 7 ml, by ultrafiltration using a VIVASPIN® 20 10 kDa MWCO centrifugal concentration filter, buffer exchanged into 20 mM Tris-HCl plus 150 mM NaCl pH 8.0, and then purified using a 320 ml SUPERDEX® 75 column (GE Healthcare, Piscataway, N.J., USA) equilibrated with 20 mM Tris-HCl plus 150 mM NaCl pH 8.0 at a flow rate of 1 ml per minute. Fractions of 20 ml were collected and pooled based on SDS-PAGE. The purified *T. aurantiacus* GH61A polypeptide was used in Examples 23-26, and 31.

Protein concentration was determined using a Microplate BCA™ Protein Assay Kit (Thermo Fisher Scientific Inc., Rockford, Ill., USA) in which bovine serum albumin was used as a protein standard.

Example 2

Preparation of *Thielavia terrestris* GH61E Polypeptide Having Cellulolytic Enhancing Activity

*T. terrestris* GH61E polypeptide (SEQ ID NO: 7 [DNA sequence] and SEQ ID NO: 8 [deduced amino acid sequence]) was recombinantly produced in *Aspergillus oryzae* JaL250 and purified as described in U.S. Pat. No. 7,361,495.

Example 3

Preparation of *Thermoascus aurantiacus* CEL5A Endoglucanase II

*T. aurantiacus* CGMCC 0670 cDNA encoding a Cel5A endoglucanase II (SEQ ID NO: 171 [DNA sequence] and SEQ ID NO: 172 [deduced amino acid sequence]) was cloned according to the following procedure. The *T. aurantiacus* strain was grown in 80 ml of CBH1 medium (2.5% AVICEL®, 0.5% glucose, 0.14% $(NH_4)_2SO_4$) in 500 ml Erlenmeyer baffled flasks at 45° C. for 3 days with shaking at 165 rpm. Mycelia were harvested by centrifugation at 7000 rpm for 30 minutes and stored at −80° C. before use for RNA extraction. RNA was isolated from 100 mg of mycelia using a RNEASY® Plant Mini Kit.

The cDNA for the *T. aurantiacus* endoglucanase was isolated by RT PCR using a 3' RACE System and a 5' RACE System (Invitrogen, Carlsbad, Calif., USA) and primers BG025-1, BG025-2, BG025-3, and BG025-4 shown below to the N-terminal amino acids.

```
Primer BG025-1:
                                   (SEQ ID NO: 125)
5'-AA(T/C)GA(A/G)TC(T/C/A/G)GG(T/C/A/G)GC (T/C/A/G)GAATT-3'

Primer BG025-2:
                                   (SEQ ID NO: 126)
5'-AA(T/C)GA(A/G)TC(T/C/A/G)GG(T/C/A/G)GC (T/C/A/G)GAGTT-3'

Primer BG025-3:
                                   (SEQ ID NO: 127)
5'-AA(T/C)GA(A/G)AG(T/C)GG(T/C/A/G)GC(T/C/A/G)

GAATT-3'

Primer BG025-4:
                                   (SEQ ID NO: 128)
5'-AA(T/C)GA(A/G)AG(T/C)GG(T/C/A/G)GC(T/C/A/G)

GAGTT-3'
```

The RT PCR products were ligated into plasmid pGEM-T using a pGEM-T Vector System (Promega, Madison, Wis., USA) and transformed into *E. coli* strain JM109 (Promega, Madison, Wis., USA). A single clone harboring a plasmid named pBGC1009 containing the endoglucanase cDNA was isolated.

PCR primers were designed to amplify the cDNA encoding the *T. aurantiacus* endoglucanase from plasmid pBGC1009. Restriction enzyme sites Bsp HI and Pac I were incorporated for in-frame cloning into *Aspergillus oryzae* expression plasmid pBM120a (WO 2006/039541).

```
Primer 996261:
                                       (SEQ ID NO: 129)
5'-GATCTCATGAAGCTCGGCTCTCTCGT-3'
    Bsp HI Primer 996167:
                                       (SEQ ID NO: 130)
5'-TTAATTAATCAAAGATACGGAGTCAAAATAGG-3'
    PacI
```

The fragment of interest was amplified by PCR using an EXPAND™ High Fidelity PCR System (Roche Diagnostics Corporation, Indianapolis, Ind., USA). The PCR amplification reaction mixture contained 1 µl of 0.09 µg/µl pBGC1009, 1 µl of primer 996261 (50 pmol/µl), 1 µl of primer 996167 (50 pmol/µl), 5 µl of 10×PCR buffer with 15 mM MgCl$_2$, 1 µl of dNTP mix (10 mM each), 37.25 µl of water, and 0.75 µl (3.5 U/µl) of DNA polymerase mix. An EPPENDORF® MASTERCYCLER® thermocycler (Eppendorf Scientific, Inc., Westbury, N.Y., USA) was used to amplify the fragment programmed for 1 cycle at 94° C. for 2 minutes; 10 cycles each at 94° C. for 15 seconds, 55° C. for 30 seconds, 72° C. for 1.5 minutes; 15 cycles each at 94° C. for 15 seconds, 55° C. for 30 seconds, and 72° C. for 1.5 minutes plus 5 second elongation at each successive cycle; 1 cycle at 72° C. for 7 minutes; and a 4° C. hold.

The 1008 bp PCR product was purified by 1% agarose gel electrophoresis using 40 mM Tris base, 20 mM sodium acetate, 1 mM disodium EDTA (TAE) buffer, excised from the gel, and purified using a QIAQUICK® Gel Purification Kit (QIAGEN Inc., Valencia, Calif., USA). The purified product was ligated directly into pCR®2.1-TOPO® (Invitrogen, Carlsbad, Calif., USA) according to the manufacturer's instructions. The resulting plasmid was named pBM124a.

Plasmid pBM124a was digested with Bsp HI and Pac I, purified by 1% agarose gel electrophoresis using TAE buffer, excised from the gel, and purified using a QIAQUICK® Gel Purification Kit. The plasmid fragment was ligated to the vector pBM120a, which was digested with Nco I and Pac I. The resulting expression plasmid was designated pBM123a. Plasmid pBM123a contains a duplicate NA2-TPI promoter driving expression of the *T. aurantiacus* endoglucanase cDNA clone, the AMG terminator, and amdS as a selectable marker.

*Aspergillus oryzae* BECh2 (WO 2000/139322) protoplasts were prepared according to the method of Christensen et al., 1988, supra. Six µg of pBM123a were used to transform *A. oryzae* BECh2. Primary transformants were selected on COVE plates for 5 days. Transformants were spore purified twice prior to shake flask analysis.

Spores of the transformants were inoculated into 25 ml of MY25 medium in 125 ml shake flasks. The cultures were incubated at 34° C., 200 rpm on a platform shaker for five days. On day 3 and day 5, culture supernatants were harvested and clarified by centrifugation to remove mycelia. Twenty microliters of supernatant from three transformants were analyzed using a CRITERION® stain-free, 10-20% gradient SDS-PAGE gel (Bio-Rad Laboratories, Inc., Hercules, Calif., USA) according to the manufacturer's instructions. SDS-PAGE profiles of the cultures showed that all transformants had a new major band of approximately 32 kDa. One transformant was chosen and named EXP00858.

Plastic, non-baffled 500 ml shake flasks containing 100 ml of SY50 medium were inoculated with 0.1 ml of a spore stock of EXP00858, and incubated at 34° C., 200 rpm for 24 hours to produce a seed culture. Fifty ml of the seed culture was inoculated into a 2 liter fermentation tank containing 2 liters of medium composed per liter of 0.5 g of pluronic acid, 30 g of sucrose, 2 g of MgSO$_4$.7H$_2$O, 2 g of anhydrous KH$_2$PO$_4$, 1 g of citric acid, 2 g of (NH$_4$)$_2$SO$_4$, 1 g of K$_2$SO$_4$, 20 g of yeast extract, and 0.5 g of 200×AMG trace metals solution, pH 5.0. The fermentation was fed with a maltose feed. The pH was controlled using 5N H$_3$PO$_4$ and 15% NH$_4$OH and maintained at 5.0 and then raised to 5.25. Temperature was maintained 34.0° C.+/−1.0° C. Agitation was 1000 rpm. Airflow was 1.0 vvm.

A 200 ml volume of cell-free supernatant was diluted to 1 liter with deionized water. The pH was adjusted to 8 and the sample filter sterilized using a 0.22 µm polyethersulphone (PES) filter. The filter sterilized sample was loaded onto a 250 ml Q SEPHAROSE™ Fast Flow column (GE Healthcare, Piscataway, N.J., USA) pre-equilibrated with 25 mM Tris pH 8. The enzyme was eluted from the column with a 0 to 1 M NaCl gradient in the same buffer. The fractions containing endoglucanase activity were pooled (400 ml) and the enzyme concentration calculated from the theoretic extinction coefficient and the absorbance of the sample at 280 nm.

Example 4

Preparation of *Aspergillus oryzae* CEL3A Beta-Glucosidase

*A. oryzae* CEL3A beta-glucosidase (SEQ ID NO: 111 [DNA sequence] and SEQ ID NO: 112 [deduced amino acid sequence]) was recombinantly prepared as described in WO 2004/099228, and purified as described by Langston et al., 2006, *Biochim. Biophys. Acta Proteins Proteomics* 1764: 972-978. Protein concentration was determined using a Microplate BCA™ Protein Assay Kit.

Example 5

Preparation of *Penicillium brasilianum* CEL3A Beta-Glucosidase

*P. brasilianum* IBT 20888 Cel3A beta-glucosidase (SEQ ID NO: 115 [DNA sequence] and SEQ ID NO: 116 [deduced amino acid sequence]) was recombinantly prepared according to WO 2007/019442 using *Aspergillus oryzae* as a host. Filtered broth was concentrated and buffer exchanged using a tangential flow concentrator equipped with a 10 kDa polyethersulfone membrane with 20 mM Tris-HCl pH 8.0. The sample was loaded onto a Q SEPHAROSE® High Performance column (GE Healthcare, Piscataway, N.J., USA) equilibrated in 20 mM Tris pH 8.0, and bound proteins were eluted with a linear gradient from 0-600 mM sodium chloride. The fractions were concentrated and desalted into 20 mM Tris pH 8.0 using a VIVASPIN® 20 10 kDa MWCO centrifugal concentration filter. Protein concentration was determined using a Microplate BCA™ Protein Assay Kit in which bovine serum albumin was used as a protein standard.

Example 6

Preparation of *Trichoderma reesei* CEL7A Cellobiohydrolase I

*T. reesei* CEL7A cellobiohydrolase I (SEQ ID NO: 95 [DNA sequence] and SEQ ID NO: 96 [deduced amino acid sequence]) was prepared as described by Ding and Xu, 2004, "Productive cellulase adsorption on cellulose" in Lignocellulose Biodegradation (Saha, B. C. ed.), Symposium Series 889, pp. 154-169, American Chemical Society, Washington, D.C. Protein concentration was determined using a Microplate BCA™ Protein Assay Kit.

Example 7

Preparation of *Trichoderma reesei* CEL7B Endoglucanase I

*T. reesei* CEL7B endoglucanase I (EGI) (SEQ ID NO: 65 [DNA sequence] and SEQ ID NO: 66 [deduced amino acid sequence]) was cloned and expressed in *Aspergillus oryzae* JaL250 as described in WO 2005/067531. Filtered broth was concentrated and buffer exchanged using a tangential flow concentrator equipped with a 10 kDa polyethersulfone membrane with 20 mM Tris-HCl pH 8.5. The sample was loaded onto a Q SEPHAROSE® High Performance column (GE Healthcare, Piscataway, N.J., USA) equilibrated in 20 mM Tris pH 8.5, and bound proteins were eluted with a linear gradient from 0-600 mM sodium chloride. The fractions were concentrated and desalted into 20 mM Tris pH 8.0, 150 mM NaCl using VIVASPIN® 20 10 kDa MWCO centrifugal concentration filter. Protein concentration was determined using a Microplate BCA™ Protein Assay Kit in which bovine serum albumin was used as a protein standard.

Example 8

Microcrystalline Cellulose Conversion Assay I

A 5% microcrystalline cellulose slurry was prepared by addition of 2.5 g of AVICEL®PH101 (Sigma-Aldrich, St. Louis, Mo., USA) to a graduated 50 ml screw-cap conical tube followed by 15 ml of 1 M sodium acetate pH 5 and 1 ml of 100 mM $MnSO_4$ and approximately 20 ml of deionizer water. Each conical tube was then mixed thoroughly by shaking/vortexing, and adjusted to 50 ml total with deionized water and mixed again. Contents of the tube were then quickly transferred to a 100 ml beaker and stirred rapidly with a magnetic stirrer. Five hundred μl aliquots of the 5% AVICEL® slurry were pipetted into wells of a 2.0 ml 96-deepwell plate (Axygen, Union City, Calif., USA) using a 1000 μl micropipette with a wide aperture tip (end of tip cut off about 2 mm from the base). Three hundred μl of either deionized water or a 1% dioxy compound solution (dissolved in deionized water) was added to each well.

The dioxy compounds assayed include caffeic acid (Sigma-Aldrich, St. Louis, Mo., USA), dichlorophenolindophenol (DCPIP; Sigma-Aldrich, St. Louis, Mo., USA), ethyl gallate (Sigma-Aldrich, St. Louis, Mo., USA), gallic acid (Sigma-Aldrich, St. Louis, Mo., USA), 3,4-dihydroxybenzoic acid (Sigma-Aldrich, St. Louis, Mo., USA), pyrocatechol (Sigma-Aldrich, St. Louis, Mo., USA), pyrogallol (Sigma-Aldrich, St. Louis, Mo., USA), sinapinic acid (3,5 dimethoxy-4-hydroxy cinnamic acid; Apin Chemicals LTD, Abingdon, UK), and tannic acid (Sigma-Aldrich, St. Louis, Mo., USA).

Enzyme mixtures were prepared and then added simultaneously to all wells in a volume of 200 μl, for a total of 1 ml in each reaction. The plate was then sealed using an ALPS-300™ plate heat sealer (Abgene, Epsom, United Kingdom), mixed thoroughly, and incubated at either 50° C. or 60° C. for approximately 4 days. All experiments reported were performed in triplicate.

Primary analysis of the hydrolysis reactions was performed using an AGILENT® 1100 HPLC with CHEMSTATION® software (Agilent Technologies, Santa Clara, Calif., USA) equipped with an AMINEX™ HPX-87H column (Bio-Rad Laboratories, Inc., Hercules, Calif., USA). After approximately 4 days, the deep-well plate was removed from the incubator and chilled overnight to 4° C. The plate was then mixed well by inversion and briefly centrifuged at 52×g in a SORVALL® RT7 centrifuge (Thermo Fisher Scientific, Waltham, Mass., USA) for 10 seconds. Samples were then mixed by pipetting, and 200 μl from each well were transferred to a MULTISCREEN® HV centrifuge filter plate assembly (Millipore, Bedford, Mass., USA). The centrifuge filter plate assembly was centrifuged at 2000 rpm in a SORVALL® RT7 centrifuge for 20 minutes. The filtrates were transferred to a 96 well autosampler plate (Nunc, Roskilde, Denmark) and diluted 1:1 with 5 mM $H_2SO_4$, sealed with a silicon sealing mat (Thermo Scientific, Rochester, N.Y., USA), and inserted into an HPLC injector module (set to 4° C.) for injection of 20 μl onto a CATION H™ guard column (Bio-Rad Laboratories, Inc., Hercules, Calif., USA) connected to a 4.6×250 mm AMINEX® HPX-87H column followed by elution with 0.05% w/w benzoic acid in 5 mM $H_2SO_4$. Sugars were detected using a refractive index detector (Agilent Technologies, Inc., Santa Clara, Calif., USA) with quantification by integration compared to purified sugar standards.

All HPLC data processing was performed using MICROSOFT EXCEL™ software (Microsoft, Richland, Wash., USA). Measured glucose concentrations were adjusted for the appropriate dilution factor. In this assay only glucose was measured since beta-glucosidase was at high levels in all samples but the controls. The degree of cellulose conversion was calculated using the following equation:

$$\% \ conversion = \frac{[glucose](mg/ml)}{[glucose \ in \ limit \ digest](mg/ml)} \times 100 \quad \text{(Equation 1)}$$

A limit digest was performed to determine the total concentration accessible glucose equivalents using 100 mg of *T. reesei* cellulase (CELLIC™ CTec, Novozymes A/S, Bagsvaerd, Denmark) per gram cellulose, Triplicate data points were averaged and standard deviation was calculated.

Example 9

Effect of Combinations of *Thermoascus aurantiacus* GH61A or *Thielavia terrestris* GH61E Polypeptide with Dioxy Compounds, *Penicillium brasilianum* CEL3A Beta-Glucosidase, and *Thermoascus aurantiacus* CEL5A Endoglucanase II on the Conversion of Microcrystalline Cellulose

*T. aurantiacus* GH61A or *T. terrestris* GH61E polypeptide and tannic acid, gallic acid, ethyl gallate, pyrogallol, pyrocatechol, caffeic acid, or sinapinic acid were evaluated for their ability to enhance the hydrolysis of microcrystalline cellulose by the combination of *T. aurantiacus* CEL5A endoglucanase II and *P. brasilianum* CEL3A beta-glucosidase. The microcrystalline cellulose hydrolysis assay was performed as described in Example 8.

The conversion of microcrystalline cellulose by the combination of *T. aurantiacus* CEL5A endoglucanase II (5 mg protein per g cellulose) and *P. brasilianum* CEL3A beta-glucosidase (5 mg protein per g cellulose); the combination of

Figure 1B:
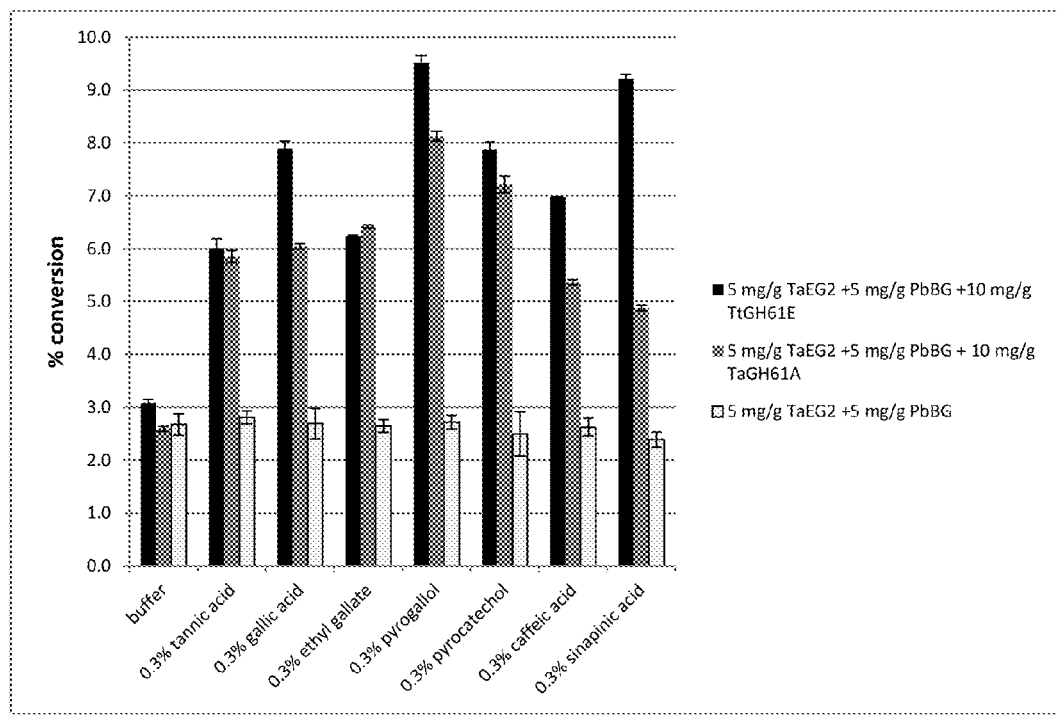

*T. aurantiacus* CEL5A endoglucanase II (5 mg protein per g cellulose) and *P. brasilianum* CEL3A beta-glucosidase (5 mg protein per g cellulose) with either *T. aurantiacus* GH61A polypeptide (10 mg protein per g cellulose) or *T. terrestris* GH61E (10 mg protein per g cellulose); the combination of *T. aurantiacus* CEL5A endoglucanase II (5 mg protein per g cellulose) and *P. brasilianum* CEL3A beta-glucosidase (5 mg protein per g cellulose) with the each of the dioxy compounds tannic acid, gallic acid, ethyl gallate, pyrogallol, pyrocatechol, caffeic acid, and sinapinic acid (0.3% w/w in each case); and the combination of *T. aurantiacus* CEL5A endoglucanase II (5 mg protein per g cellulose) and *P. brasilianum* CEL3A beta-glucosidase (5 mg protein per g cellulose) with the each of the dioxy compounds tannic acid, gallic acid, ethyl gallate, pyrogallol, pyrocatechol, caffeic acid, and sinapinic acid (0.3% w/w in each case), with either *T. aurantiacus* GH61A polypeptide (10 mg protein per g cellulose) or *T. terrestris* GH61E (10 mg protein per g cellulose) was assayed as described in Example 8. Data were collected and analyzed, as described in Example 8, after 96 hours of incubation at either 50° C. or 60° C. The results of the 50° C. incubations are shown in FIG. 1A and results of the 60° C. incubations are shown in FIG. 1B.

The combination of *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 2.4±0.2% and 2.7±0.2% at 50° C. and 60° C., respectively. Addition of *T. aurantiacus* GH61A polypeptide (10 mg protein per g cellulose) to the combination of *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 2.2±0.1% and 2.6±0.1% at 50° C. and 60° C., respectively. Addition of *T. terrestris* GH61E polypeptide (10 mg protein per g cellulose) to the combination of *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 2.8±0.1% and 3.1±0.1% at 50° C. and 60° C., respectively.

The combination of tannic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in no significant change in conversion of microcrystalline cellulose at either 50° C. or 60° C. compared to the combination of *T. aurantiacus* CEL5A endoglucanase II (5 mg protein per g cellulose) and *P. brasilianum* CEL3A beta-glucosidase (5 mg protein per g cellulose) in the absence of tannic acid. Addition of *T. aurantiacus* GH61A polypeptide (10 mg protein per g cellulose) to the combination of tannic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 7.2±0.1% and 5.9±0.1% at 50° C. and 60° C., respectively. Addition of *T. terrestris* GH61E polypeptide (10 mg protein per g cellulose) to the combination of tannic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 5.7±0.1% and 6.0±0.2% at 50° C. and 60° C., respectively.

The combination of gallic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in no significant change in conversion of microcrystalline cellulose at either 50° C. or 60° C. compared to the combination of *T. aurantiacus* CEL5A endoglucanase II (5 mg protein per g cellulose) and *P. brasilianum* CEL3A beta-glucosidase (5 mg protein per g cellulose) in the absence of gallic acid. Addition of *T. aurantiacus* GH61A polypeptide (10 mg protein per g cellulose) to the combination of gallic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 6.4±0.1% and 6.0±0.1% at 50° C. and 60° C., respectively. Addition of *T. terrestris* GH61E polypeptide (10 mg protein per g cellulose) to the combination of gallic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 9.3±0.1% and 7.9±0.1% at 50° C. and 60° C., respectively.

The combination of ethyl gallate (0.3% w/w) with *T. aurantiacus* CEL5A endoglucanase II (5 mg protein per g cellulose) and *P. brasilianum* CEL3A beta-glucosidase (5 mg protein per g cellulose) resulted in no significant change in conversion of microcrystalline cellulose at either 50° C. or 60° C. compared to the combination of *T. aurantiacus* CEL5A endoglucanase II (5 mg protein per g cellulose) and *P. brasilianum* CEL3A beta-glucosidase (5 mg protein per g cellulose) in the absence of ethyl gallate. Addition of *T. aurantiacus* GH61A polypeptide (10 mg protein per g cellulose) to the combination of ethyl gallate (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 5.3±0.1% and 6.4±0.1% at 50° C. and 60° C., respectively. Addition of *T. terrestris* GH61E polypeptide (10 mg protein per g cellulose) to the combination of ethyl gallate (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 6.0±0.3% and 6.2±0.1% at 50° C. and 60° C., respectively.

The combination of pyrogallol (0.3% w/w) with *T. aurantiacus* CEL5A endoglucanase II (5 mg protein per g cellulose) and *P. brasilianum* CEL3A beta-glucosidase (5 mg protein per g cellulose) resulted in no significant change in conversion of microcrystalline cellulose at either 50° C. or 60° C. compared to the combination of *T. aurantiacus* CEL5A endoglucanase II (5 mg protein per g cellulose) and *P. brasilianum* CEL3A beta-glucosidase (5 mg protein per g cellulose) in the absence of pyrogallol. Addition of *T. aurantiacus* GH61A polypeptide (10 mg protein per g cellulose) to the combination of pyrogallol (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 6.2±0.1% and 8.1±0.1% at 50° C. and 60° C., respectively. Addition of *T. terrestris* GH61E polypeptide (10 mg protein per g cellulose) to the combination of pyrogallol (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 7.1±0.5% and 9.5±0.1% at 50° C. and 60° C., respectively.

The combination of pyrocatechol (0.3% w/w) with *T. aurantiacus* CEL5A endoglucanase II (5 mg protein per g cellulose) and *P. brasilianum* CEL3A beta-glucosidase (5 mg protein per g cellulose) resulted in no significant change in conversion of microcrystalline cellulose at either 50° C. or 60° C. compared to the combination of *T. aurantiacus*

CEL5A endoglucanase II (5 mg protein per g cellulose) and *P. brasilianum* CEL3A beta-glucosidase (5 mg protein per g cellulose) in the absence of pyrocatechol. Addition of *T. aurantiacus* GH61A polypeptide (10 mg protein per g cellulose) to the combination of pyrocatechol (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 8.4±0.1% and 7.2±0.2% at 50° C. and 60° C., respectively. Addition of *T. terrestris* GH61E polypeptide (10 mg protein per g cellulose) to the combination of pyrocatechol (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 7.4±0.2% and 7.9±0.1% at 50° C. and 60° C., respectively.

The combination of caffeic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in no significant change in conversion of microcrystalline cellulose at either 50° C. or 60° C. compared to the combination of *T. aurantiacus* CEL5A endoglucanase II (5 mg protein per g cellulose) and *P. brasilianum* CEL3A beta-glucosidase (5 mg protein per g cellulose) in the absence of caffeic acid. Addition of *T. aurantiacus* GH61A polypeptide (10 mg protein per g cellulose) to the combination of caffeic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 3.9±0.1% and 5.4±0.1% at 50° C. and 60° C., respectively. Addition of *T. terrestris* GH61E polypeptide (10 mg protein per g cellulose) to the combination of caffeic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 4.4±0.1% and 7.0±0.1% at 50° C. and 60° C., respectively.

The combination of sinapinic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in no significant change in conversion of microcrystalline cellulose at either 50° C. or 60° C. compared to the combination of *T. aurantiacus* CEL5A endoglucanase II (5 mg protein per g cellulose) and *P. brasilianum* CEL3A beta-glucosidase (5 mg protein per g cellulose) in the absence of sinapinic acid. Addition of *T. aurantiacus* GH61A polypeptide (10 mg protein per g cellulose) to the combination of sinapinic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 4.4±0.3% and 4.9±0.1% at 50° C. and 60° C., respectively. Addition of *T. terrestris* GH61E polypeptide (10 mg protein per g cellulose) to the combination of sinapinic acid (0.3% w/w) with *T. aurantiacus* CEL5A endoglucanase II (5 mg protein per g cellulose) and *P. brasilianum* CEL3A beta-glucosidase (5 mg protein per g cellulose) resulted in conversion of microcrystalline cellulose of 6.3±0.1% and 9.2±0.1% at 50° C. and 60° C., respectively.

Example 10

Microcrystalline Cellulose Conversion Assay II

A 5% microcrystalline cellulose slurry was prepared by addition of 2.5 g of AVICEL® PH101 to a graduated 50 ml screw-cap conical tube followed by approximately 40 ml of deionized water. Each conical tube was then mixed thoroughly by shaking/vortexing, and adjusted to 50 ml total with deionized water and mixed again. For samples containing dioxy compounds, a similar slurry was prepared by the addition of 100 mg of solid dioxy compound and 2.5 g of AVICEL® PH101 to a graduated 50 ml screw-cap conical tube followed by approximately 40 ml of deionized water. Each conical tube was then mixed thoroughly by shaking/vortexing, and adjusted to 50 ml total with deionized water and mixed again.

The dioxy compounds assayed include caffeic acid, dichlorophenolindophenol (DCPIP), ethyl gallate, gallic acid, 3,4-dihydroxybenzoic acid, pyrocatechol, pyrogallol, sinapinic acid (3,5 dimethoxy-4-hydroxy cinnamic acid), and tannic acid.

In all cases, the contents of the tube (5% microcrystalline cellulose slurry with or without 0.2% dioxy compound) were then quickly transferred to a 100 ml beaker and stirred rapidly with a magnetic stirrer. Five hundred µl aliquots of the 5% AVICEL® slurry were pipetted into wells of a 2.0 ml 96-deepwell plate (Axygen, Union City, Calif.) using a 1000 µl micropipette with a wide aperture tip (end of tip cut off about 2 mm from the base). One hundred µl of deionized water and 300 µl of 3.33 mM $MnSO_4$-500 mM sodium acetate pH 5 were then added to each well. Enzyme mixtures were prepared and then added simultaneously to all wells in a volume of 100 µl, for a total of 1 ml in each reaction. The plate was then sealed using an ALPS-300™ plate heat sealer, mixed thoroughly, and incubated at 50° C. for approximately 5 days. All experiments reported were performed in triplicate.

Primary analysis of the hydrolysis reactions was performed using an AGILENT® 1100 HPLC with CHEMSTATION® software equipped with an AMINEX™ HPX-87H column. After approximately 4 days, the deep-well plate was removed from the incubator and chilled overnight to 4° C. The plate was then mixed well by inversion and briefly centrifuged at 52×g in a SORVALL® RT7 centrifuge for 10 seconds. Samples were then mixed by pipetting, and 200 µl from each well were transferred to a MULTISCREEN® HV centrifuge filter plate assembly. The centrifuge filter plate assembly was centrifuged at 2000 rpm in a SORVALL® RT7 centrifuge for 20 minutes. The filtrates were transferred to a 96 well autosampler plate and diluted 1:1 with 5 mM $H_2SO_4$, sealed with a silicon sealing mat, and inserted into an HPLC injector module (set to 4° C.) for injection of 20 µl onto a CATION H™ guard column connected to a 4.6×250 mm AMINEX® HPX-87H column with elution by 0.05% w/w benzoic acid in 5 mM $H_2SO_4$. Sugars were detected using a refractive index detector with quantification by integration compared to purified sugar standards.

All HPLC data processing was performed using MICROSOFT EXCEL™ software. Measured glucose concentrations were adjusted for the appropriate dilution factor. In this assay only glucose was measured since beta-glucosidase was at high levels in all samples but the controls. The degree of cellulose conversion was calculated using Equation 1. Triplicate data points were averaged and standard deviation was calculated.

Example 11

Effect of the Addition of Dioxy Compounds to the Combination of *Thermoascus aurantiacus* GH61A Polypeptide, *Aspergillus oryzae* CEL3A Beta-Glucosidase, and *Trichoderma reesei* CEL7A Cellobiohydrolase I on the Conversion of Microcrystalline Cellulose

*T. aurantiacus* GH61A polypeptide and various dioxy compounds were tested for their ability to enhance the hydrolysis of microcrystalline cellulose by the combination of *T. reesei* CEL7A cellobiohydrolase I and *A. oryzae* CEL3A beta-glucosidase. The microcrystalline cellulose hydrolysis assay was performed as described in Example 10.

Figure 2:
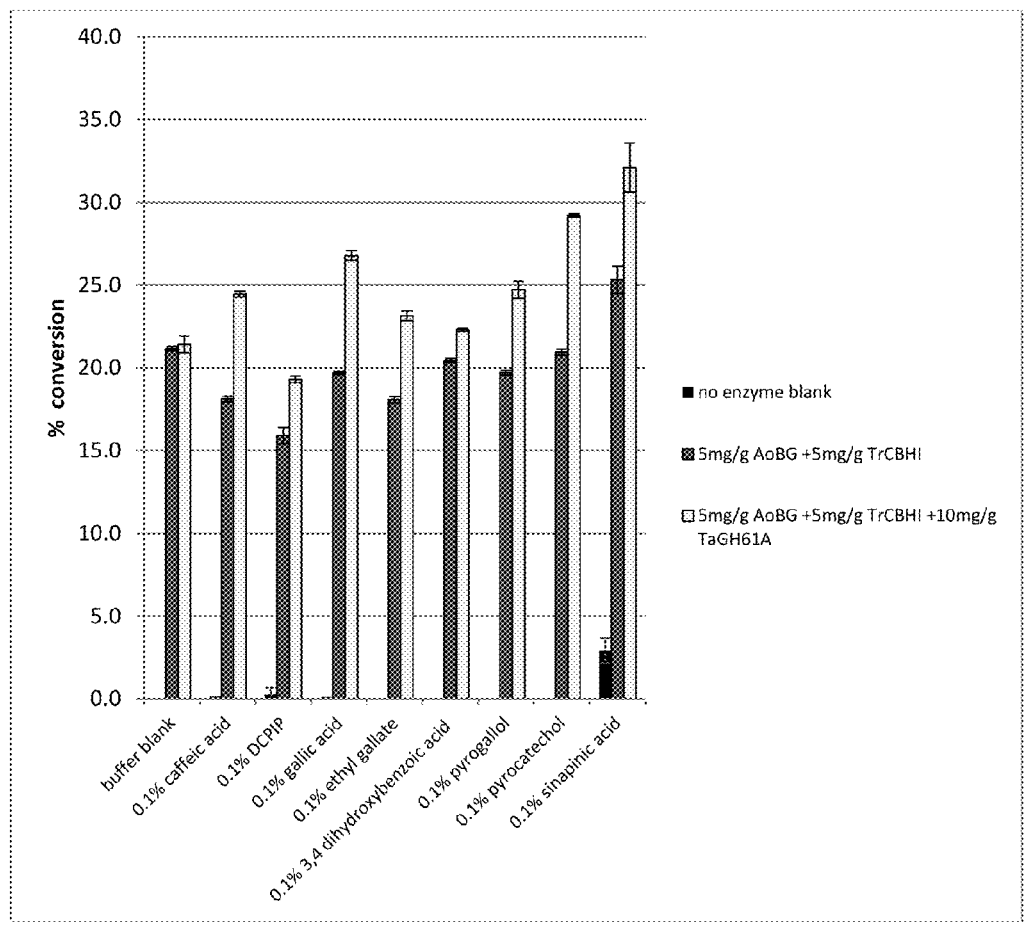
FIG. 2 shows the effect of the addition of dioxy compounds to the combination of *T. aurantiacus* GH61A polypeptide, *Aspergillus oryzae* CEL3A beta-glucosidase, and *Trichoderma reesei* CEL7A cellobiohydrolase I on the conversion of microcrystalline cellulose.

The conversion of microcrystalline cellulose by the combination of *T. reesei* CEL7A cellobiohydrolase I (5 mg protein per g cellulose) and *A. oryzae* CEL3A beta-glucosidase (5 mg protein per g cellulose); the combination of *T. reesei* CEL7A cellobiohydrolase I (5 mg protein per g cellulose) and *A. oryzae* CEL3A beta-glucosidase (5 mg protein per g cellulose) with each of the dioxy compounds listed (0.1% w/w); and the combination of *T. reesei* CEL7A cellobiohydrolase I (5 mg protein per g cellulose) and *A. oryzae* CEL3A beta-glucosidase (5 mg protein per g cellulose) with both *T. aurantiacus* GH61A polypeptide (10 mg protein per g cellulose) and each of a selection of the dioxy compounds (0.1% w/w) were assayed as described in Example 10. Data were collected and analyzed, as described in Example 10, after 72 hours of incubation at 50° C. The results are shown in FIG. 2.

The combination of *T. reesei* CEL7A cellobiohydrolase I (5 mg protein per g cellulose) and *A. oryzae* CEL3A beta-glucosidase (5 mg protein per g cellulose) resulted in 21.2±0.1% conversion of the microcrystalline cellulose. The addition of *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in no significant change in conversion (21.4±0.5% conversion) of the microcrystalline cellulose compared to the combination of *T. reesei* CEL7A cellobiohydrolase I (5 mg protein per g cellulose) and *A. oryzae* CEL3A beta-glucosidase (5 mg protein per g cellulose) in the absence of *T. aurantiacus* GH61A polypeptide.

The addition of caffeic acid (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 18.1±0.2%. The addition of both caffeic acid (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in an increase in conversion of microcrystalline cellulose of 24.5±0.2%. Addition of caffeic acid (0.1% w/w) alone resulted in no significant hydrolysis of the microcrystalline cellulose.

The addition of dichlorophenolindophenol (DCPIP) (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 15.9±0.5%. The addition of both DCPIP (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 19.3±0.2%. Addition of DCPIP (0.1% w/w) alone resulted in no significant hydrolysis of the microcrystalline cellulose.

The addition of gallic acid (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 19.7±0.1%. The addition of both gallic acid (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 26.8±0.3%. Addition of gallic acid (0.1% w/w) alone resulted in no significant hydrolysis of the microcrystalline cellulose.

The addition of ethyl gallate (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 18.1±0.2%. The addition of both ethyl gallate (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 23.1±0.3%. Addition of ethyl gallate (0.1% w/w) alone resulted in no significant hydrolysis of the microcrystalline cellulose.

The addition of 3,4-dihydroxybenzoic acid (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 20.4±0.1%. The addition of both 3,4-dihydroxybenzoic acid (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 22.3±0.1%. Addition of 3,4-dihydroxybenzoic acid (0.1% w/w) alone resulted in no significant hydrolysis of the microcrystalline cellulose.

The addition of pyrogallol (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 19.7±0.1%. The addition of both pyrogallol (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 24.7±0.5%. Addition of pyrogallol (0.1% w/w) alone resulted in no significant hydrolysis of the microcrystalline cellulose.

The addition of pyrocatechol (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in no significant change in conversion of the microcrystalline cellulose compared to the combination of *T. reesei* CEL7A cellobiohydrolase I (5 mg protein per g cellulose) and *A. oryzae* CEL3A beta-glucosidase (5 mg protein per g cellulose) in buffer. The addition of both pyrocatechol (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 29.2±0.1%. Addition of pyrocatechol (0.1% w/w) alone resulted in no significant hydrolysis of the microcrystalline cellulose.

The addition of sinapinic acid (0.1% w/w) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 25.3±0.8%. The addition of both sinapinic acid (0.1% w/w) and *T. aurantiacus* GH61A polypeptide (10 mg protein per g cellulose) to the combination of *T. reesei* CEL7A cellobiohydrolase I (5 mg protein per g cellulose) and *A. oryzae* CEL3A beta-glucosidase (5 mg protein per g cellulose) resulted in conversion of the microcrystalline cellulose of 32.1±1.5%. Addition of sinapinic acid (0.1% w/w) alone resulted in 2.9±0.8% conversion of the microcrystalline cellulose.

Example 12

Microcrystalline Cellulose Conversion Assay III

A 5% microcrystalline cellulose slurry was prepared by addition of 2.5 g of AVICEL® PH101 to a graduated 50 ml screw-cap conical tube followed by approximately 40 ml of deionized water. Each conical tube was then mixed thoroughly by shaking/vortexing, and adjusted to 50 ml total with deionized water and mixed again. Contents of the tube were then quickly transferred to a 100 ml beaker and stirred rapidly with a magnetic stirrer. Five hundred μl aliquots of the 5% AVICEL® slurry were pipetted into wells of a 2.0 ml 96-deepwell plate (Axygen, Union City, Calif., USA) using a 1000 μl micropipette with a wide aperture tip (end of tip cut off about 2 mm from the base). Two hundred μl of deionized water and 100 μl of 10 mM $MnSO_4$-500 mM sodium acetate pH 5 were then added to each well. One hundred μl of either deionized water, a 1% gallic acid solution dissolved in water, or a 1% gallic acid solution containing 50 mM EDTA was added to each well. Enzyme mixtures were prepared and then added simultaneously to all wells in a volume of 100 μl, for a total of 1 ml in each reaction. The plate was then sealed using an ALPS-300™ plate heat sealer, mixed thoroughly, and incubated at 50° C. for approximately 3 days. All experiments reported were performed in triplicate.

Primary analysis of the hydrolysis reactions was performed using an AGILENT® 1100 HPLC with CHEMSTATION® software equipped with an AMINEX™ HPX-87H column. After approximately 4 days, the deep-well plate was removed from the incubator and chilled overnight to 4° C. The plate was then mixed well by inversion and briefly centrifuged 52×g in a SORVALL® RT7 centrifuge for 10 seconds. Samples were then mixed by pipetting, and 200 μl from each well were transferred to a MULTISCREEN® HV centrifuge filter plate assembly. The centrifuge filter plate assembly was centrifuged at 2000 rpm in a SORVALL® RT7 centrifuge for 20 minutes. The filtrates were transferred to a 96 well autosampler plate and diluted 1:1 with 5 mM $H_2SO_4$, sealed with a silicon sealing mat, and inserted into an HPLC injector module (set to 4° C.) for injection of 20 μl onto a CATION H™ guard column connected to a 4.6×250 mm AMINEX® HPX-87H column followed by elution with 0.05% w/w benzoic acid in 5 mM $H_2SO_4$. Sugars were detected using a refractive index detector with quantification by integration compared to purified sugar standards.

All HPLC data processing was performed using MICROSOFT EXCEL™ software. Measured glucose concentrations were adjusted for the appropriate dilution factor. In this assay only glucose was measured since beta-glucosidase was at high levels in all samples but the controls. The degree of cellulose conversion was calculated using Equation 1. Triplicate data points were averaged and standard deviation was calculated.

Example 13

Effect of the Combination of Gallic Acid, *Thermoascus aurantiacus* GH61A Polypeptide, *Aspergillus oryzae* CEL3A Beta-Glucosidase, and *Trichoderma reesei* Cel7B Endoglucanase I on the Conversion of Microcrystalline Cellulose in the Absence and Presence of EDTA

*T. aurantiacus* GH61A polypeptide and gallic acid were tested for their ability to enhance the hydrolysis of microcrystalline cellulose by the combination of *T. reesei* Cel7B endoglucanase I and *A. oryzae* CEL3A beta-glucosidase. The microcrystalline cellulose hydrolysis assay was performed as described in Example 12.

Figure 3:
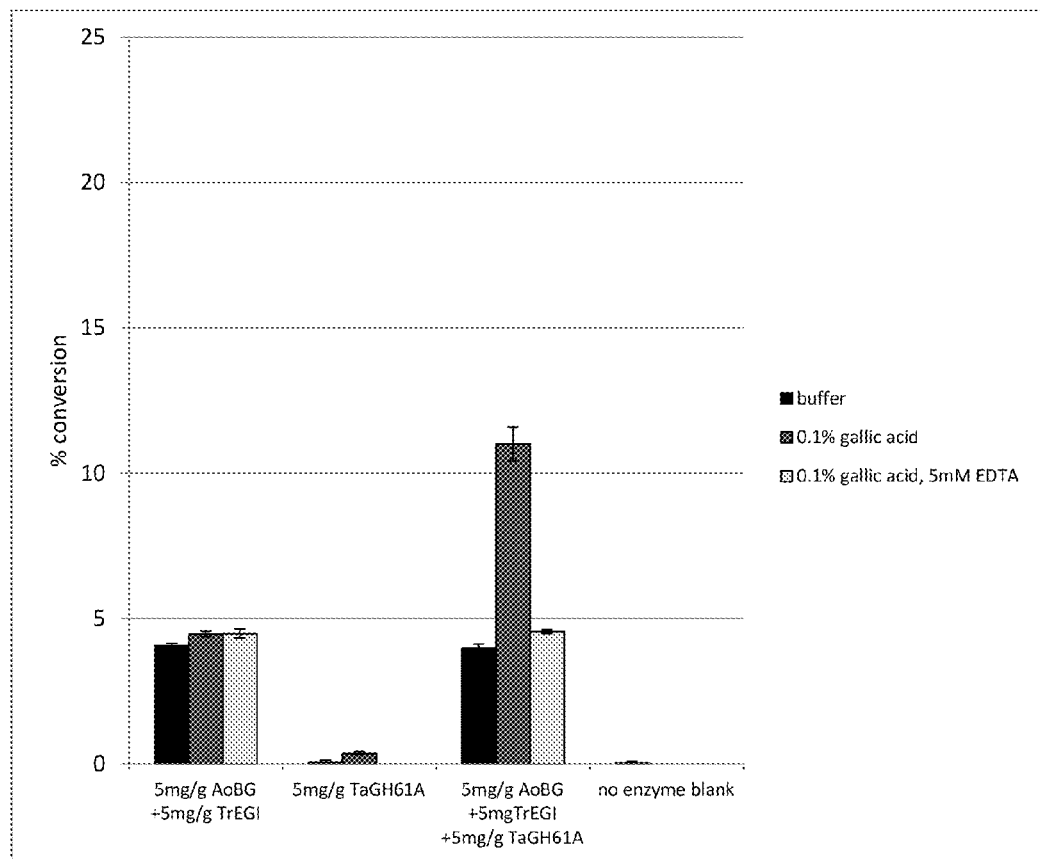
FIG. 3 shows the effect of the combination of gallic acid, *T. aurantiacus* GH61A polypeptide, *A. oryzae* CEL3A beta-glucosidase, and *Trichoderma reesei* Cel7B endoglucanase I on the conversion of microcrystalline cellulose in the absence and presence of EDTA.

The conversion of microcrystalline cellulose by of the combination of *T. reesei* Cel7B endoglucanase I (5 mg protein per g cellulose) and *A. oryzae* CEL3A beta-glucosidase (5 mg protein per g cellulose); the individual components *T. aurantiacus* GH61A polypeptide (5 mg protein per g cellulose) or gallic acid (0.1% w/w); the combination of *T. reesei* Cel7B endoglucanase I (5 mg protein per g cellulose) and *A. oryzae* CEL3A beta-glucosidase (5 mg protein per g cellulose) with *T. aurantiacus* GH61A polypeptide (5 mg protein per g cellulose); the combination of *T. reesei* Cel7B endoglucanase I (5 mg protein per g cellulose) and *A. oryzae* CEL3A beta-glucosidase (5 mg protein per g cellulose) with gallic acid (0.1% w/w); the combination of *T. reesei* Cel7B endoglucanase I (5 mg protein per g cellulose) and *A. oryzae* CEL3A beta-glucosidase (5 mg protein per g cellulose) with both *T. aurantiacus* GH61A polypeptide (5 mg protein per g cellulose) and gallic acid (0.1% w/w); and the combination of *T. reesei* Cel7B endoglucanase I (5 mg protein per g cellulose) and *A. oryzae* CEL3A beta-glucosidase (5 mg protein per g cellulose) with both *T. aurantiacus* GH61A polypeptide (5 mg protein per g cellulose) and gallic acid (0.1% w/w) and 5 mM EDTA were assayed as described in Example 12. Data were collected and analyzed, as described in Example 12, after 72 hours of incubation at 50° C. The results are shown in FIG. 3.

The combination of *T. reesei* Cel7B endoglucanase I (5 mg protein per g cellulose) and *A. oryzae* CEL3A beta-glucosidase (5 mg protein per g cellulose) resulted in 4.1±0.1% conversion of the microcrystalline cellulose. The addition of gallic acid (0.1% w/w) to the combination of *T. reesei* Cel7B endoglucanase I (5 mg protein per g cellulose) and *A. oryzae* CEL3A beta-glucosidase (5 mg protein per g cellulose) resulted in 4.5±0.1% conversion of the microcrystalline cellulose. The addition of the combination of gallic acid (0.1% w/w) and 5 mM EDTA to *A. oryzae* CEL3A beta-glucosidase (5 mg protein per g cellulose) to the cellulose resulted in 4.5±0.2% conversion of the microcrystalline cellulose.

*T. aurantiacus* GH61A polypeptide (5 mg protein per g cellulose) resulted in no significant conversion of microcrystalline cellulose hydrolysis. The mixture of *T. aurantiacus* GH61A polypeptide (5 mg protein per g cellulose) with gallic acid (0.1% w/w) resulted in 0.4±0.1% conversion of the microcrystalline cellulose. The mixture of *T. aurantiacus* GH61A polypeptide (5 mg protein per g cellulose) with gallic acid (0.1% w/w) and 5 mM EDTA produced no significant conversion of the microcrystalline cellulose.

The combination of *T. reesei* Cel7B endoglucanase I (5 mg protein per g cellulose) and *A. oryzae* CEL3A beta-glucosidase (5 mg protein per g cellulose) with *T. aurantiacus* GH61A polypeptide (5 mg protein per g cellulose) resulted in 4.0±0.2% conversion of the microcrystalline cellulose. The combination of *T. reesei* Cel7B endoglucanase I (5 mg protein per g cellulose) and *A. oryzae* CEL3A beta-glucosidase (5 mg protein per g cellulose) with both *T. aurantiacus* GH61A polypeptide (5 mg protein per g cellulose) and gallic acid (0.1% w/w) resulted in 11.0±0.6% conversion of the microcrystalline cellulose. The combination of *T. reesei* Cel7B endoglucanase I (5 mg protein per g cellulose) and *A. oryzae* CEL3A beta-glucosidase (5 mg protein per g cellulose) with *T. aurantiacus* GH61A polypeptide (5 mg protein per g cellulose), gallic acid (0.1% w/w), and 5 mM EDTA resulted in 4.6±0.1% conversion of the microcrystalline cellulose.

Gallic acid (0.1% w/w) alone resulted in no significant conversion of the microcrystalline cellulose. Gallic acid (0.1% w/w) and 5 mM EDTA resulted in no significant conversion of the microcrystalline cellulose.

Example 14

Preparation of Bacterial Cellulose

Bacterial cellulose was prepared from NATA DE COCO (Huerto International Trading, Lucena City, Philippines) by extensive rinsing of one 500 ml can of cubes with water followed by homogenation for 15 minutes in 0.25 M sodium hydroxide using a WARING BLENDER® (Waring Products, Torrington, Conn., USA). The resulting slurry was pelleted at 40,000×g in a SORVALL® RT7 centrifuge. The supernatant was discarded. The pellet was then resuspended in 0.25 M sodium hydroxide and stirred overnight at 4° C. This procedure was repeated four times. Following the first washing steps, the cellulose was washed six times under similar conditions, substituting water for 0.25 M sodium hydroxide. Following the water washing, the cellulose was again homogenized for 15 minutes in a WARING BLENDER®, and adjusted to a final volume of 250 ml.

Example 15

Bacterial Cellulose Conversion Assay

A 0.36% bacterial cellulose slurry was prepared as described in Example 14. This 0.36% slurry was thoroughly resuspended by shaking, and quickly transferred to a 100 ml beaker and stirred rapidly with a magnetic stirrer. Seven hundred µl aliquots of the bacterial cellulose slurry were pipetted into wells of a 2.0 ml 96-deepwell plate (Axygen, Union City, Calif.) using a 1000 µl micropipette with a wide aperture tip (end of tip cut off about 2 mm from the base). One hundred µl of 10 mM MnSO$_4$-500 mM sodium acetate pH 5 was then added to each well. One hundred µl of either deionized water, a 1% gallic acid solution dissolved in water, or a 1% gallic acid solution containing 50 mM EDTA were added to each well. Enzyme mixtures were prepared and then added simultaneously to all wells in a volume of 100 µl, for a total of 1 ml in each reaction. The plate was then sealed using an ALPS-300™ plate heat sealer, mixed thoroughly, and incubated at 50° C. for approximately 3 days. All experiments reported were performed in triplicate.

Primary analysis of the hydrolysis reactions was performed using an AGILENT® 1100 HPLC with CHEMSTATION® software equipped with an AMINEX™ HPX-87H column. After approximately 4 days, the deep-well plate was removed from the incubator and chilled overnight to 4° C. The plate was then mixed well by inversion and briefly centrifuged 52×g in a SORVALL® RT7 centrifuge for 10 seconds. Samples were then mixed by pipetting, and 200 µl from each well were transferred to a MULTISCREEN® HV centrifuge filter plate assembly. The centrifuge filter plate assembly was centrifuged at 2000 rpm in a SORVALL® RT7 centrifuge for 20 minutes. The filtrates were transferred to a 96 well autosampler plate and diluted 1:1 with 5 mM H$_2$SO$_4$, sealed with a silicon sealing mat, and inserted into an HPLC injector module (set to 4° C.) for injection of 20 µl onto a CATION H™ guard column connected to a 4.6×250 mm AMINEX® HPX-87H column followed by elution with 0.05% w/w benzoic acid in 5 mM H$_2$SO$_4$. Sugars were detected using a refractive index detector with quantification by integration compared to purified sugar standards.

All HPLC data processing was performed using MICROSOFT EXCEL™ software. Measured glucose concentrations were adjusted for the appropriate dilution factor. In this assay only glucose was measured since beta-glucosidase was at high levels in all samples but the controls. Percent conversion was determined using Equation 1. Triplicate data points were averaged and standard deviation was calculated.

Example 16

Effect of the Combination of Gallic Acid, *Thermoascus aurantiacus* GH61A Polypeptide, and *Aspergillus oryzae* CEL3A Beta-Glucosidase on Conversion of Bacterial Cellulose and Inhibition of this Effect by EDTA Addition

*T. aurantiacus* GH61A polypeptide and gallic acid were tested for their ability to enhance the conversion of bacterial cellulose by *A. oryzae* CEL3A beta-glucosidase. The bacterial cellulose hydrolysis assay was performed as described in Example 15.

Figure 4:
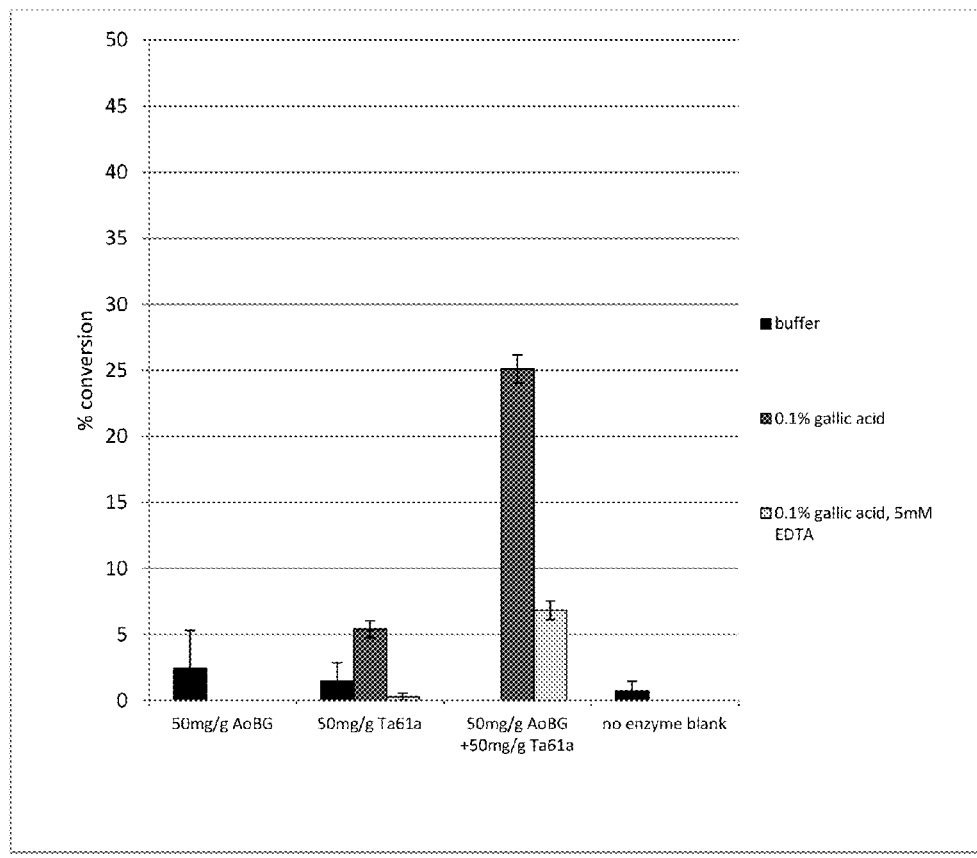
FIG. 4 shows the effect of the combination of gallic acid, *T. aurantiacus* GH61A polypeptide, and *A. oryzae* CEL3A beta-glucosidase on conversion of bacterial cellulose inhibition of this effect by EDTA addition.

The conversion of bacterial cellulose by *A. oryzae* CEL3A beta-glucosidase (50 mg protein per g cellulose); the individual components *T. aurantiacus* GH61A polypeptide (50 mg protein per g cellulose) or gallic acid (0.1% w/w); the combination of *A. oryzae* CEL3A beta-glucosidase (50 mg protein per g cellulose) with *T. aurantiacus* GH61A polypeptide (50 mg protein per g cellulose); the combination of *A. oryzae* CEL3A beta-glucosidase (50 mg protein per g cellulose) with gallic acid (0.1% w/w); the combination of *A. oryzae* CEL3A beta-glucosidase (50 mg protein per g cellulose) with both *T. aurantiacus* GH61A polypeptide (50 mg protein per g cellulose) and gallic acid (0.1% w/w); and the combination of *A. oryzae* CEL3A beta-glucosidase (50 mg protein per g cellulose) with both *T. aurantiacus* GH61A polypeptide (50 mg protein per g cellulose) and gallic acid (0.1% w/w) and 5 mM EDTA was assayed as described in Example 15. Data was collected and analyzed, as described in Example 15, after 72 hours of incubation at 50° C. The results are shown in FIG. 4.

*A. oryzae* CEL3A beta-glucosidase (50 mg protein per g cellulose) resulted in little or no conversion (2.4±2.9% conversion) of the bacterial cellulose. The addition of either gallic acid (0.1% w/w) alone or the combination of gallic acid (0.1% w/w) and 5 mM EDTA to *A. oryzae* CEL3A beta-glucosidase (50 mg protein per g cellulose) resulted in no significant hydrolysis of the bacterial cellulose.

*T. aurantiacus* GH61A polypeptide (50 mg protein per g cellulose) resulted in little or no conversion (1.5±1.4% conversion) of the bacterial cellulose. The combination of *T. aurantiacus* GH61A polypeptide (50 mg protein per g cellulose) with gallic acid (0.1% w/w) resulted in 5.4±0.6% conversion of the bacterial cellulose. The combination of *T. aurantiacus* GH61A polypeptide (50 mg protein per g cellulose) with gallic acid (0.1% w/w) and 5 mM EDTA resulted in no significant hydrolysis of the bacterial cellulose.

The combination of *A. oryzae* CEL3A beta-glucosidase (50 mg protein per g cellulose) with *T. aurantiacus* GH61A polypeptide (50 mg protein per g cellulose) resulted in no significant conversion of the bacterial cellulose. The combination of *A. oryzae* CEL3A beta-glucosidase (50 mg protein per g cellulose) with both *T. aurantiacus* GH61A polypeptide (50 mg protein per g cellulose) and gallic acid (0.1% w/w) resulted in 25.1±1.1% conversion of the bacterial cellulose. The combination of *A. oryzae* CEL3A beta-glucosidase (50 mg protein per g cellulose) with *T. aurantiacus* GH61A polypeptide (50 mg protein per g cellulose), gallic acid (0.1% w/w), and 5 mM EDTA resulted in 6.8±0.7% conversion of the bacterial cellulose.

Gallic acid (0.1% w/w) alone resulted in no significant conversion of the bacterial cellulose. Gallic acid (0.1% w/w) and 5 mM EDTA resulted in no significant conversion of the bacterial cellulose.

Example 17

Preparation of Phosphoric Acid Swollen Cellulose (PASC)

A 1% phosphoric acid swollen cellulose (PASC) slurry was prepared from AVICEL® PH101 using the protocol described by Zhang et al., 2006, *Biomacromolecules* 7: 644-648.

Example 18

Phosphoric Acid Swollen Cellulose (PASC) Hydrolysis Assay

The 1.0% PASC slurry prepared as described in Example 17 was thoroughly resuspended by shaking, and quickly transferred to a 100 ml beaker and stirred rapidly with a magnetic stirrer. Five hundred µl aliquots of the 1.0% PASC slurry were pipetted into wells of a 2.0 ml 96-deepwell plate (Axygen, Union City, Calif., USA) using a 1000 µl micropipette with a wide aperture tip (end of tip cut off about 2 mm from the base). One hundred µl of 10 mM $MnSO_4$-500 mM sodium acetate pH 5 were then added to each well. Three hundred µl of either deionized water or a gallic acid dilution in water were added to each well, with gallic acid dilutions ranging from 0%-1% gallic acid; final concentration (in a 1 ml final assay volume) of gallic acid ranges from 0% to 0.3% gallic acid. Enzyme mixtures were prepared and then added simultaneously to all wells in a volume of 100 µl, for a total of 1 ml in each reaction. The plate was then sealed using an ALPS-300™ plate heat sealer (Abgene, Epsom, United Kingdom), mixed thoroughly, and incubated at 50° C. for approximately 3 days. All experiments reported were performed in triplicate.

Primary analysis of the hydrolysis reactions was performed using an AGILENT® 1100 HPLC with CHEMSTATION® software equipped with an AMINEX™ HPX-87H column. After approximately 4 days, the deep-well plate was removed from the incubator and chilled overnight to 4° C. The plate was then mixed well by inversion and briefly centrifuged 52×g in a SORVALL® RT7 centrifuge for 10 seconds. Samples were then mixed by pipetting, and 200 µl from each well were transferred to a MULTISCREEN® HV centrifuge filter plate assembly. The centrifuge filter plate assembly was centrifuged at 2000 rpm in a SORVALL®RT7 centrifuge for 20 minutes. The filtrates were transferred to a 96 well autosampler plate and diluted 1:1 with 5 mM $H_2SO_4$, sealed with a silicon sealing mat, and inserted into an HPLC injector module (set to 4° C.) for injection of 20 µl onto a CATION H™ guard column connected to a 4.6×250 mm AMINEX® HPX-87H column followed by elution with 0.05% w/w benzoic acid in 5 mM $H_2SO_4$. Sugars were detected using a refractive index detector with quantification by integration compared to purified sugar standards.

All HPLC data processing was performed using MICROSOFT EXCEL™ software. Measured glucose concentrations were adjusted for the appropriate dilution factor. In this assay only glucose was measured since beta-glucosidase was at high levels in all samples but the controls. Percent conversion was calculated using Equation 1. Triplicate data points were averaged and standard deviation was calculated.

Example 19

Effect of Various Concentrations of Gallic Acid on the Combination of *Thermoascus Aurantiacus* GH61A Polypeptide and *Aspergillus oryzae* CEL3A Beta-Glucosidase on the Conversion of Phosphoric Acid Swollen Cellulose (PASC)

*T. aurantiacus* GH61A and gallic acid were tested for their ability to enhance conversion of PASC by *A. oryzae* CEL3A beta-glucosidase. The PASC hydrolysis assay was performed as described in Example 18.

Figure 5:
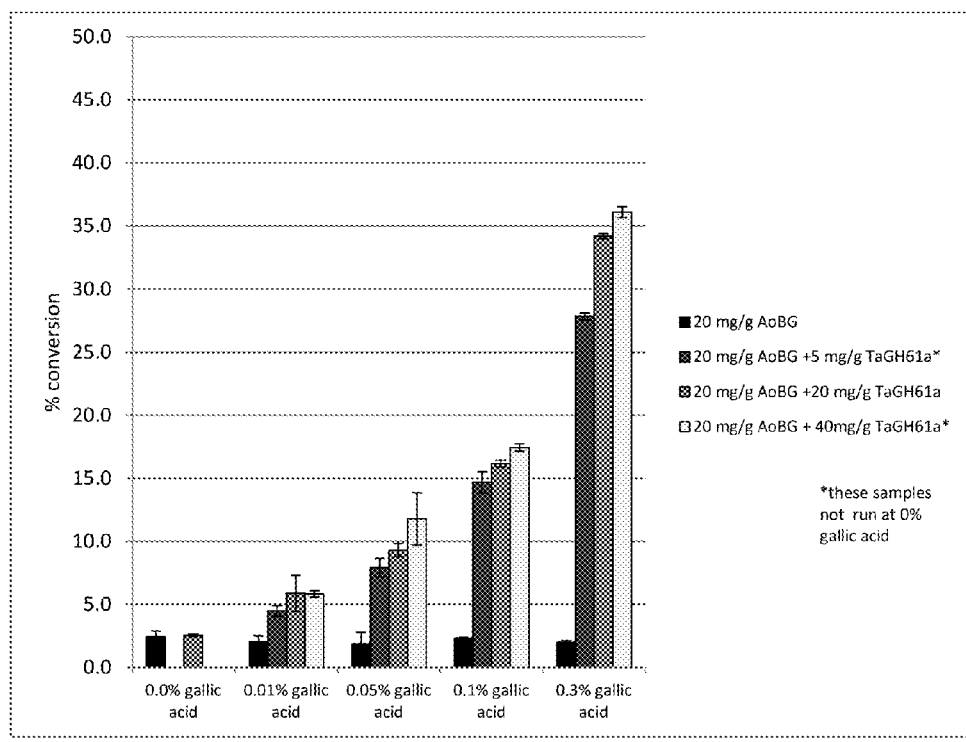
FIG. 5 shows the effect of the various concentrations of gallic acid on the combination of *T. aurantiacus* GH61A polypeptide and *A. oryzae* CEL3A beta-glucosidase on the conversion of phosphoric acid swollen cellulose (PASC).

The conversion of PASC by *A. oryzae* CEL3A beta-glucosidase (20 mg protein per g cellulose); the combination of *A. oryzae* CEL3A beta-glucosidase (20 mg protein per g cellulose) with gallic acid (0%-0.3% w/w); and the combination of *A. oryzae* CEL3A beta-glucosidase (20 mg protein per g cellulose) with both *T. aurantiacus* GH61A polypeptide (5-40 mg protein per g cellulose) and gallic acid (0.0%-0.3% w/w) were assayed as described in Example 18. Data were collected and analyzed, as described in Example 18, after 72 hours of incubation at 50° C. The results are shown in FIG. 5.

*A. oryzae* CEL3A beta-glucosidase (20 mg protein per g cellulose) resulted in 2.4±0.5% conversion of PASC. The addition of *T. aurantiacus* GH61A polypeptide (20 mg protein per g cellulose) to *A. oryzae* CEL3A beta-glucosidase (20 mg protein per g cellulose) resulted in no significant change in conversion of PASC (2.6±0.1%) compared to *A. oryzae* CEL3A beta-glucosidase (20 mg protein per g cellulose) in the absence of *T. aurantiacus* GH61A polypeptide.

The addition of gallic acid (0.01% w/w) to *A. oryzae* CEL3A beta-glucosidase (20 mg protein per g cellulose) resulted in 2.5±0.5% conversion of PASC. The addition of *T. aurantiacus* GH61A polypeptide (5 mg protein per g cellulose) to the combination of *A. oryzae* CEL3A beta-glucosidase (20 mg protein per g cellulose) and gallic acid (0.01% w/w) resulted in conversion of PASC of 4.5±0.4%. The addition of *T. aurantiacus* GH61A polypeptide (20 mg protein per g cellulose) to the combination of *A. oryzae* CEL3A beta-glucosidase (20 mg protein per g cellulose) and gallic acid (0.01% w/w) resulted in conversion of PASC of 5.9±1.4%. The addition of *T. aurantiacus* GH61A polypeptide (40 mg protein per g cellulose) to the combination of *A. oryzae* CEL3A beta-glucosidase (20 mg protein per g cellulose) and gallic acid (0.01% w/w) resulted in conversion of PASC of 5.8±0.3%.

The addition of gallic acid (0.05% w/w) to *A. oryzae* CEL3A beta-glucosidase (20 mg protein per g cellulose) resulted in 1.9±0.9% conversion of PASC. The addition of *T. aurantiacus* GH61A polypeptide (5 mg protein per g cellulose) to the combination of *A. oryzae* CEL3A beta-glucosidase (20 mg protein per g cellulose) and gallic acid (0.05% w/w) resulted in conversion of PASC of 7.9±0.7%. The addition of *T. aurantiacus* GH61A polypeptide (20 mg protein per g cellulose) to the combination of *A. oryzae* CEL3A beta-glucosidase (20 mg protein per g cellulose) and gallic acid (0.05% w/w) resulted in conversion of PASC of 9.3±0.5%. The addition of *T. aurantiacus* GH61A polypeptide (40 mg protein per g cellulose) to the combination of *A. oryzae* CEL3A beta-glucosidase (20 mg protein per g cellulose) and gallic acid (0.05% w/w) resulted in conversion of PASC of 11.8±2.1%.

The addition of gallic acid (0.1% w/w) to *A. oryzae* CEL3A beta-glucosidase (20 mg protein per g cellulose) resulted in 2.3±0.1% conversion of the PASC. The addition of *T. aurantiacus* GH61A polypeptide (5 mg protein per g cellulose) to the combination of *A. oryzae* CEL3A beta-glucosidase (20 mg protein per g cellulose) and gallic acid (0.1% w/w) resulted in conversion of PASC of 14.7±0.8%. The addition of *T. aurantiacus* GH61A polypeptide (20 mg protein per g cellulose) to the combination of *A. oryzae* CEL3A beta-glucosidase (20 mg protein per g cellulose) and gallic acid (0.1% w/w) resulted in conversion of PASC of 16.2±0.3%. The addition of *T. aurantiacus* GH61A polypeptide (40 mg protein per g cellulose) to the combination of *A. oryzae* CEL3A beta-glucosidase (20 mg protein per g cellulose) and gallic acid (0.1% w/w) resulted in conversion of PASC of 17.4±0.3%.

The addition of gallic acid (0.3% w/w) to *A. oryzae* CEL3A beta-glucosidase (20 mg protein per g cellulose) resulted in 2±0.1% conversion of PASC. The addition of *T. aurantiacus* GH61A polypeptide (5 mg protein per g cellulose) to the combination of *A. oryzae* CEL3A beta-glucosidase (20 mg protein per g cellulose) and gallic acid (0.3% w/w) resulted in an increase in conversion of PASC of 27.8±0.3%. The addition of *T. aurantiacus* GH61A polypeptide (20 mg protein per g cellulose) to the combination of *A. oryzae* CEL3A beta-glucosidase (20 mg protein per g cellulose) and gallic acid (0.3% w/w) resulted in conversion of PASC of 34.2±0.2%. The addition of *T. aurantiacus* GH61A polypeptide (40 mg protein per g cellulose) to the combination of *A. oryzae* CEL3A beta-glucosidase (20 mg protein per g cellulose) and gallic acid (0.3% w/w) resulted in conversion of PASC of 36.1±0.4%.

Example 20

Phosphoric Acid Swollen Cellulose (PASC) Conversion Assay

A 1.0% PASC slurry was prepared as described in Example 17. Ten ml of the 1.0% PASC slurry, 10 ml of $H_2O$, and 20 mg of dioxy compound were thoroughly mixed by shaking, Five hundred µl aliquots of the 0.50% phosphoric acid swollen cellulose/0.05% dioxy compound slurry were pipetted into wells of a 2.0 ml 96-deepwell plate (Axygen, Union City, Calif., USA) using a 1000 µl micropipette with a wide aperture tip (end of tip cut off about 2 mm from the base). One hundred µl of 10 mM $MnSO_4$-500 mM sodium acetate pH 5 were then added to each well. Two hundred µl of deionized water were added to each well. Enzyme mixtures were prepared and then added simultaneously to all wells in a volume of 200 µl, for a total of 1 ml in each reaction. The plate was then sealed using an ALPS-300™ plate heat sealer, mixed thoroughly, and incubated at 50° C. for approximately 3 days. All experiments reported were performed in triplicate.

Primary analysis of the hydrolysis reactions was performed using an AGILENT® 1100 HPLC with CHEMSTATION® software equipped with an AMINEX™ HPX-87H column. After approximately 4 days, the deep-well plate was removed from the incubator and chilled overnight to 4° C. The plate was then mixed well by inversion and briefly centrifuged 52×g in a SORVALL® RT7 centrifuge for 10 seconds. Samples were then mixed by pipetting, and 200 µl from each well were transferred to a MULTISCREEN® HV centrifuge filter plate assembly. The centrifuge filter plate assembly was centrifuged at 2000 rpm in a SORVALL® RT7 centrifuge for 20 minutes. The filtrates were transferred to a 96 well autosampler plate and diluted 1:1 with 5 mM $H_2SO_4$, sealed with a silicon sealing mat, and inserted into an HPLC injector module (set to 4° C.) for injection of 20 µl onto a CATION H™ guard column connected to a 4.6×250 mm AMINEX® HPX-87H column followed by elution with 0.05% w/w benzoic acid in 5 mM $H_2SO_4$. Sugars were detected using a refractive index detector with quantification by integration compared to purified sugar standards.

All HPLC data processing was performed using MICROSOFT EXCEL™ software. Measured glucose concentrations were adjusted for the appropriate dilution factor. In this assay only glucose was measured since beta-glucosidase was at high levels in all samples but the controls. Percent conversion was calculated using Equation 1. Triplicate data points were averaged and standard deviation was calculated.

Example 21

Effect of 4-tert-butyl-5-methoxy-1,2-benzenediol on the Combination of *Thermoascus Aurantiacus* GH61A Polypeptide and *Aspergillus oryzae* CEL3A Beta-Glucosidase on the Conversion of Phosphoric Acid Swollen Cellulose

*T. aurantiacus* GH61A polypeptide and 4-tert-butyl-5-methoxy-1,2-benzenediol were tested for their ability to enhance the conversion of phosphoric acid swollen cellulose by *Aspergillus oryzae* CEL3A beta-glucosidase. The PASC assay was performed as described in Example 20.

Figure 6:
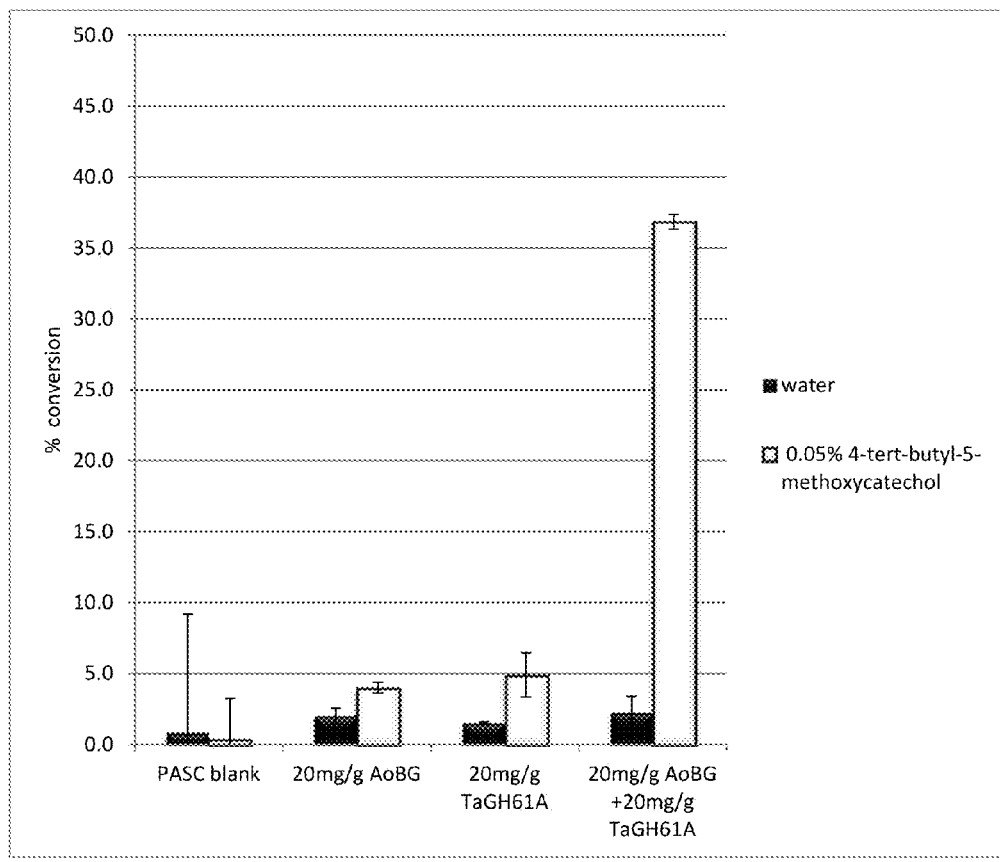
FIG. 6 shows the effect of 4-tert-butyl-5-methoxy-1,2-benzenediol on the combination of *T. aurantiacus* GH61A polypeptide and *A. oryzae* CEL3A beta-glucosidase on the conversion of PASC.

The conversion of PASC by *Aspergillus oryzae* CEL3A beta-glucosidase (20 mg protein per g cellulose); the combination of *Aspergillus oryzae* CEL3A beta-glucosidase (20 mg protein per g cellulose) with 4-tert-butyl-5-methoxy-1,2-benzenediol (0.05% w/w); and the combination of *Aspergillus oryzae* CEL3A beta-glucosidase (20 mg protein per g cellulose) with both *Thermoascus aurantiacus* GH61A polypeptide (20 mg protein per g cellulose) and 4-tert-butyl-5-methoxy-1,2-benzenediol (0.05% w/w) were assayed as described in Example 20. Data were collected and analyzed, as described in Example 20, after 72 hours of incubation at 50° C. The results are shown in FIG. 6.

*A. oryzae* CEL3A beta-glucosidase (20 mg protein per g cellulose) resulted in 2.0±0.1% conversion of the phosphoric acid swollen cellulose. The addition of *T. aurantiacus* GH61A polypeptide (20 mg protein per g cellulose) resulted in 1.5±1.1% conversion of PASC. The addition of *T. aurantiacus* GH61A polypeptide (20 mg protein per g cellulose) to *A. oryzae* CEL3A beta-glucosidase (20 mg protein per g cellulose) resulted in 2.3±0.6% conversion of phosphoric acid swollen cellulose.

The addition of 4-tert-butyl-5-methoxy-1,2-benzenediol (0.05% w/w) alone resulted in no significant (0.4±0.4%) conversion of PASC. The addition of 4-tert-butyl-5-methoxy-1, 2-benzenediol (0.05% w/w) to *A. oryzae* CEL3A beta-glucosidase (20 mg protein per g cellulose) resulted in 4.0±0.1% conversion of PASC. The addition of *T. aurantiacus* GH61A polypeptide (20 mg protein per g cellulose) and 4-tert-butyl-5-methoxy-1,2-benzenediol (0.05% w/w) resulted in 4.9±0.5% conversion of PASC. The addition of *T. aurantia*- cus GH61A polypeptide (20 mg protein per g cellulose) to the combination of *A. oryzae* CEL3A beta-glucosidase (20 mg protein per g cellulose) and 4-tert-butyl-5-methoxy-1,2-benzenediol (0.05% w/w) resulted in conversion of PASC of 36.9±2.9%.

Example 22

Evaluation of Dioxy Compounds on GH61 Polypeptides Having Cellulolytic Enhancing Activity The effect of various dioxy compounds on the cellulolytic enhancing activity of GH61 polypeptides was evaluated according to the procedures described below.

Microcrystalline cellulose, milled unwashed pretreated corn stover (milled unwashed PCS), and milled washed pretreated corn stover (milled washed PCS) were used as sources of the cellulosic material. Microcrystalline cellulose (AVICEL® PH101) was obtained from Sigma-Aldrich (St. Louis, Mo., USA). Milled washed and unwashed PCS were prepared according to the procedure described below.

Corn stover was pretreated at the U.S. Department of Energy National Renewable Energy Laboratory (NREL) using 1.4% (w/v) sulfuric acid at 165° C. and 107 psi for 8 minutes. The water-insoluble solids in the pretreated corn stover (PCS) contained 57.5% cellulose, 4.6% hemicellulose, and 28.4% lignin. The cellulose and hemicellulose composition were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. Whole slurry PCS was prepared by adjusting the pH to 5.0 by addition of 10 M NaOH with extensive mixing, and then autoclaving for 20 minutes at 120° C. The dry weight of the whole slurry PCS was 29% TS (total solids). Milled unwashed PCS (dry weight 32.35%) was prepared by milling whole slurry PCS in a Cosmos ICMG 40 wet multi-utility grinder (EssEmm Corporation, Tamil Nadu, India). Milled washed PCS (dry weight 32.35%) was prepared by milling whole slurry PCS in a Cosmos ICMG 40 wet multi-utility grinder, followed by washing with deionized water and decanting off the supernatant fraction repeatedly until the pH was greater than 4.

A *Trichoderma reesei* cellulase composition (CELLUCLAST® supplemented with *A. oryzae* beta-glucosidase, available from Novozymes A/S, Bagsvaerd, Denmark) was used as the cellulase preparation. The cellulase preparation is designated herein as "*Trichoderma reesei* cellulase composition" unless specified otherwise.

The hydrolysis of AVICEL® or milled washed PCS was conducted using 2.0 ml 96-deepwell plates (Axygen, Union City, Calif., USA) in a total reaction volume of 1.0 ml. Each hydrolysis was performed with 14 mg of AVICEL® (14 mg of cellulose) or 50 mg of PCS (total insoluble solids; 28.8 mg of cellulose) per ml of 50 mM sodium acetate pH 5.0 buffer containing 1 mM manganese sulfate and the *T. reesei* cellulase composition at 4 mg protein per gram of cellulose with and without a dioxy compound at a specified concentration and with and without GH61 polypeptide at 0.4 mg/g cellulose (unless otherwise specified). For the hydrolysis of milled unwashed PCS, the *T. reesei* cellulase composition was dosed at 2 mg protein per gram of cellulose with and without a dioxy compound at a specified concentration and with and without GH61 polypeptide having cellulolytic enhancing activity at 0.2 mg/g cellulose (unless otherwise specified). The plate was then sealed using an ALPS-300™ or an ALPS-3000™ plate heat sealer, mixed thoroughly, and incubated at 50° C. for 7 days with agitation at 150 rpm in an Innova 4080 incubation shaker (New Brunswick Scientific, Edison, N.J., USA). Later experiments were mixed thoroughly prior to incubation in an IsoTemp incubator (Fisher Scientific, Hampton, N.H., USA) and prior to sampling for analysis, but were not continuously mixed. All experiments were performed at least in duplicate.

Following hydrolysis, samples were filtered using a 0.45 μm MULTISCREEN® 96-well filter plate and filtrates analyzed for sugar content as described below. When not used immediately, filtered aliquots were frozen at −20° C. The sugar concentrations of samples, diluted to appropriate concentrations in 0.005 M $H_2SO_4$, were measured using a 4.6× 250 mm AMINEX® HPX-87H column by elution with 0.05% w/w benzoic acid-0.005 M $H_2SO_4$ at 65° C. at a flow rate of 0.6 ml per minute, and quantitation by integration of the glucose and cellobiose signals from refractive index detection calibrated by pure sugar samples. The resultant glucose and cellobiose equivalents were used to calculate the percentage of cellulose conversion for each reaction. Measured sugar concentrations were adjusted for the appropriate dilution factor. In case of milled washed PCS, the net concentrations of enzymatically-produced sugars were determined by adjusting the measured sugar concentrations for corresponding background sugar concentrations in milled washed PCS obtained from a control hydrolysis in which no enzymes (such as the *T. reesei* cellulase composition) were added. Data were processed using MICROSOFT EXCEL™ software.

The extent of cellulose conversion was calculated based on the mass ratio of solubilized glucosyl units to the initial mass of insoluble cellulose. In practice, only glucose and cellobiose were counted for soluble sugars, as cellodextrins longer than cellobiose were negligible (due to enzymatic hydrolysis). The extent of total cellulose conversion was calculated using the following equation:

$$\% \ conversion = \frac{(1.053 \times [cellobiose] \ (mg/ml) + ([glucose](mg/ml)/1.111)}{[cellulose] \ (mg/ml)} \times 100 \quad \text{(Equation 2)}$$

The 1.111 and 1.053 factors for glucose and cellobiose, respectively, take into account the increase in mass when the glucosyl units in cellulose (average molecular mass of 162 daltons) are converted to glucose (molecular mass of 180 daltons) or cellobiose glucosyl units (average molecular mass of 171 daltons).

The dioxy compounds evaluated included 4-chloro-1,2-benzenediol, 4-nitro-1,2-benzenediol, methyl-4-hydroxybenzoate, 3,5-dihydroxybenzoic acid, 4-hydroxybenzoic acid, 2,6-dimethoxyphenol, methyl-3,5-dimethoxy-4-hydroxybenzoate, methyl-3,4,5-trihydroxybenzoate, 3,4-dihydroxybenzoic acid, pyrocatechol, pyrocatechol violet, pyrogallol, 2,3,4-trihydroxybenzophenone, and 2,4,4'-trihydroxybenzophenone. The compounds were obtained from Sigma-Aldrich Co. (St. Louis, Mo., USA).

Example 23

Effect of *T. Aurantiacus* GH61 Polypeptide on Hydrolysis of Microcrystalline Cellulose or PCS by the *T. Reesei* Cellulase Composition The effect of the *T. aurantiacus* GH61A polypeptide on the hydrolysis of AVICEL® or milled washed PCS by the *T. reesei* cellulase composition was determined using the same experimental conditions and procedures described in Example 22 in the absence of a dioxy compound.

The presence of the *T. aurantiacus* GH61A polypeptide did not enhance hydrolysis of AVICEL® by the *T. reesei* cellulase composition. Percent conversion of AVICEL® was 16±1%, 31±4%, 42.7±0.9%, 45±3%, and 52.9±0.8% at 1, 3, 5, 7, and 8 days, respectively, in the absence of the *T. aurantiacus* GH61A polypeptide versus 16±1%, 30±4%, 41±1%, 45±4%, and 52±1%, at 1, 3, 5, 7, and 8 days, respectively, in the presence of the *T. aurantiacus* GH61A polypeptide.

Example 24

Effect of Dioxy Compounds on *T. Aurantiacus* GH61A Polypeptide During Hydrolysis of Microcrystalline Cellulose by the *T. Reesei* Cellulase Composition The effect of various dioxy compounds on the cellulolytic enhancing activity of the *T. aurantiacus* GH61A polypeptide during hydrolysis of AVICEL® by the *T. reesei* cellulase composition was determined using the experimental conditions and procedures described in Example 22. The concentration of each dioxy compound was 5 mM.

The effect of a dioxy compound on hydrolysis of a cellulosic material by the *T. reesei* cellulase composition in the absence of a GH61 polypeptide was quantified by determining the ratio of percent conversion of the cellulosic material in the presence of the dioxy compound to the percent conversion of the cellulosic material in the absence of the dioxy compound:

$$\text{Dioxy compound effect}_{(no\ GH61)} = \frac{\%\ conversion_{(no\ GH61+dioxy\ compound)}}{\%\ conversion_{(no\ GH61\ no\ dioxy\ compound)}} \quad \text{(Equation 3)}$$

Stimulation of hydrolysis by the dioxy compound yields a ratio>1; inhibition of hydrolysis yields a ratio<1, and no effect on hydrolysis yields a ratio=1 (FIG. 7, white bars).

The effect of a dioxy compound on hydrolysis of a cellulosic material by the *T. reesei* cellulase composition in the presence of a GH61 polypeptide was quantified by determining the ratio of percent conversion of the cellulosic material in the presence of the dioxy compound to the percent conversion of the cellulosic material in the absence of the dioxy compound:

$$\text{Dioxy compound effect}_{(+GH61)} = \frac{\%\ conversion_{(+GH61+dioxy\ compound)}}{\%\ conversion_{(+GH61\ no\ dioxy\ compound)}} \quad \text{(Equation 4)}$$

Stimulation of hydrolysis by the dioxy compound yields a ratio>1; inhibition of hydrolysis yields a ratio<1, and no effect on hydrolysis yields a ratio=1 (FIG. 7, grey bars).

The effect of a GH61 polypeptide on hydrolysis of a cellulosic material by the *T. reesei* cellulase composition in the presence of a dioxy compound was quantified by determining the ratio of percent conversion of the cellulosic material in the presence of the GH61 polypeptide to the percent conversion of the cellulosic material in the absence of the GH61 polypeptide:

$$GH61\ \text{effect} = \frac{\%\ conversion_{(+GH61+dioxy\ compound)}}{\%\ conversion_{(no\ GH61+dioxy\ compound)}} \quad \text{(Equation 5)}$$

Enhancement of hydrolysis by the GH61 polypeptide yields a ratio>1; inhibition of hydrolysis yields a ratio<1, and no effect on hydrolysis yields a ratio=1 (FIG. 7, black bars).

Figure 7A:
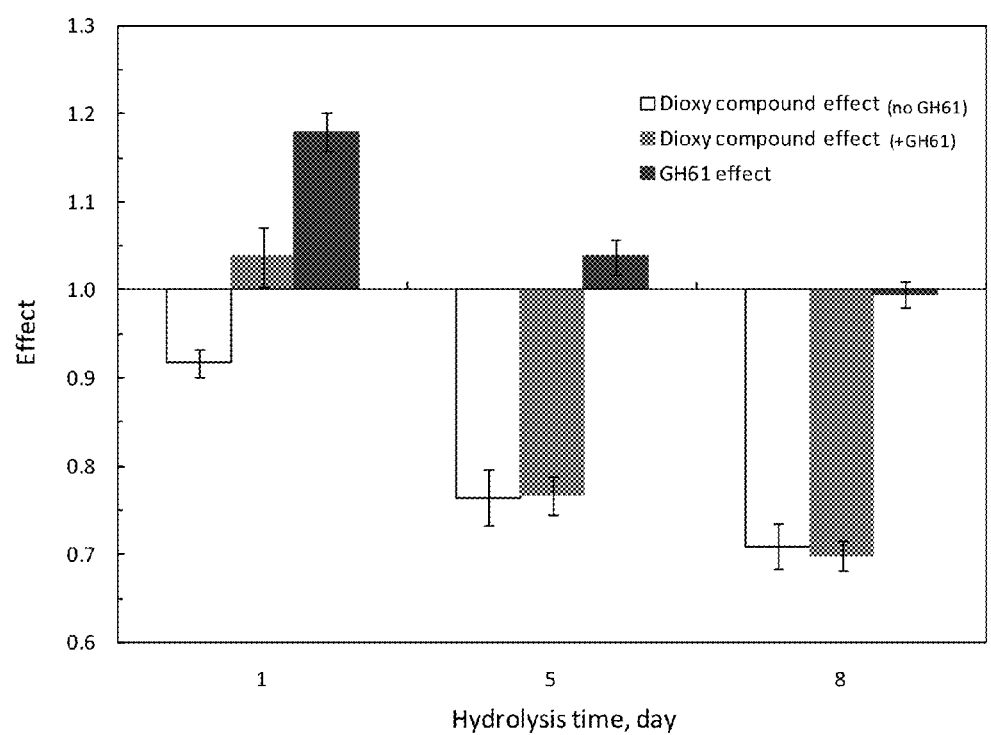
FIGS. 7A (4-chloro-1,2-benzenediol) and 7B (4-nitro-1,2-benzenediol) show (1) the effect of a dioxy compound on hydrolysis of AVICEL® by a *Trichoderma reesei* cellulase composition in the absence of a GH61A polypeptide (white bars), (2) the effect of a dioxy compound on hydrolysis of AVICEL® by the *T. reesei* cellulase composition in the presence of a GH61A polypeptide (grey bars), and (3) the effect of a GH61A polypeptide on hydrolysis of AVICEL® by the *T. reesei* cellulase composition in the presence of a dioxy compound (black bars) for 1, 5, and 8 days.

FIGS. 7A (4-chloro-1,2-benzenediol) and 7B (4-nitro-1,2-benzenediol) show (1) the effect of a dioxy compound on hydrolysis of AVICEL® by the *T. reesei* cellulase composition in the absence of a GH61A polypeptide (white bars), (2) the effect of a dioxy compound on hydrolysis of AVICEL® by the *T. reesei* cellulase composition in the presence of a GH61A polypeptide (grey bars), and (3) the effect of a GH61A polypeptide on hydrolysis of AVICEL® by the *T. reesei* cellulase composition in the presence of a dioxy compound (black bars) for 1, 5, and 8 days.

FIG. 7A demonstrates that hydrolysis of AVICEL® by the *T. reesei* cellulase composition was increasingly inhibited by the presence of 4-chloro-1,2-benzenediol from day 1 to day 8 as indicated by the dioxy compound effect$_{(no\ GH61)}$ (Equation 3) which was less than 1 (FIG. 7A, white bars). The effect of 4-chloro-1,2-benzenediol on hydrolysis of AVICEL® by the *T. reesei* cellulase composition in the presence of the *T. aurantiacus* GH61A polypeptide increased on day 1 but decreased on days 5 and 8 as indicated by the dioxy compound effect$_{(+GH61)}$ (Equation 4) which was less than 1 (FIG. 7A, grey bars). However, the effect of the *T. aurantiacus* GH61A polypeptide was greater than 1 (GH61 effect, Equation 5) at 1 and 5 days (FIG. 7A, black bars), indicating that the *T. aurantiacus* GH61A polypeptide enhanced hydrolysis when 4-chloro-1,2-benzenediol was present.

Figure 7B:
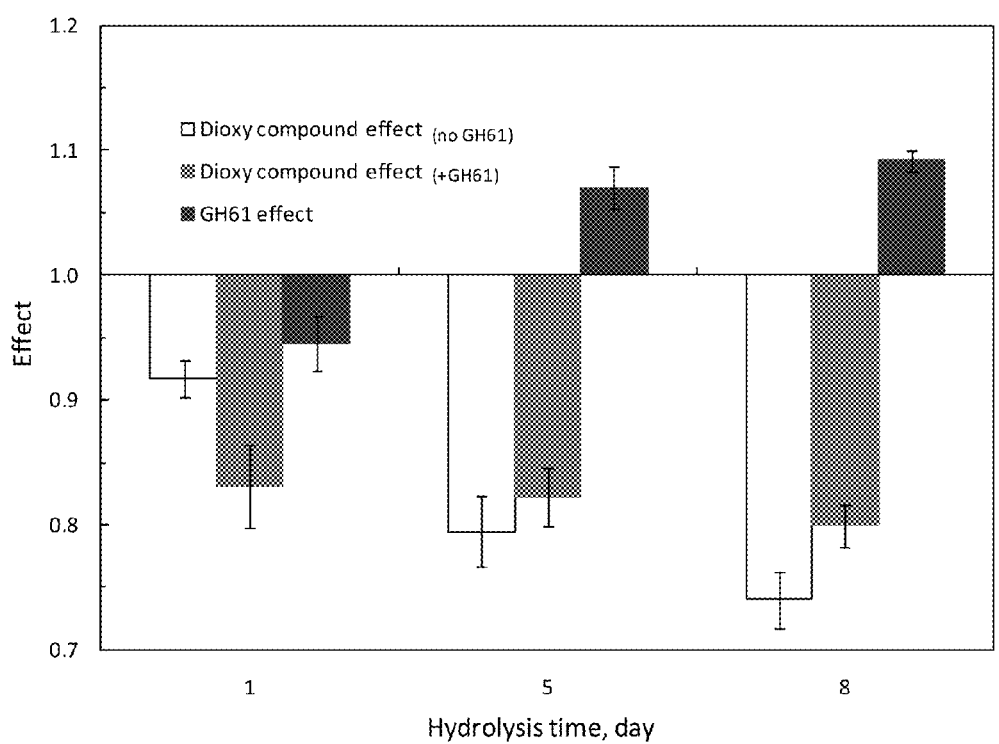

FIG. 7B demonstrates that hydrolysis of AVICEL® by the *T. reesei* cellulase composition was increasingly inhibited by the presence of 4-nitro-1,2-benzenediol from day 1 to day 8 as indicated by the dioxy compound effect$_{(no\ GH61)}$ (Equation 3), which was less than 1 (FIG. 7B, white bars). The effect of 4-nitro-1,2-benzenediol on hydrolysis of AVICEL® by the *T. reesei* cellulase composition in the presence of the *T. aurantiacus* GH61A polypeptide produced a dioxy compound effect$_{(+GH61)}$ (Equation 3) of less than 1 at 1, 5, and 8 days (FIG. 7B, grey bars). However, the effect of the *T. aurantiacus* GH61A polypeptide was greater than 1 (GH61 effect, Equation 5) at 5 and 8 days (FIG. 7B, black bars), indicating that the *T. aurantiacus* GH61A polypeptide enhanced hydrolysis when 4-nitro-1,2-benzenediol was present.

The overall results demonstrated that cellulolytic enhancing activity of the GH61 polypeptide was apparent in the presence of 4-chloro-1,2-benzenediol or 4-nitro-1,2-benzenediol during hydrolysis of AVICEL® by the *T. reesei* cellulase composition. However, the *T. aurantiacus* GH61A polypeptide had no detectable effect on hydrolysis of AVICEL® by the *T. reesei* cellulase composition in the absence of a dioxy compound.

Example 25

Effect of Dioxy Compounds on *Thermoascus aurantiacus aurantiacus* GH61A Polypeptide During Hydrolysis of Microcrystalline Cellulose by the *Trichoderma Reesei* Cellulase Composition The effect of various dioxy compounds on the cellulolytic enhancing activity of the *T. aurantiacus* GH61A polypeptide during hydrolysis of AVICEL® by the *T. reesei* cellulase composition was determined using the experimental conditions and procedures described in Example 22 and quantified as described in Example 22 with the following exceptions. The concentration of each dioxy compound was 1 mM, the concentration of the *T. aurantiacus* GH61A polypeptide was 2 mg per g cellulose, the concentration of cellulose was 29.5 mg per ml, and the extent of cellulolysis was determined at 3 and 7 days of hydrolysis. The dioxy compounds examined included methyl-4-hydroxybenzoate, 3,5-dihydroxybenzoic acid, 4-hydroxybenzoic acid, 2,6-dimethoxyphenol, methyl-3,5-dimethoxy-4-hydroxybenzoate, methyl-3,4,5-trihydroxybenzoate, 3,4-dihydroxybenzoic acid, pyrocatechol, pyrogallol, 2,3,4-trihydroxybenzophenone, 2,4,4'-trihydroxybenzophenone, acrolein diacetal, and pyrocatechol violet.

Figure 8A:
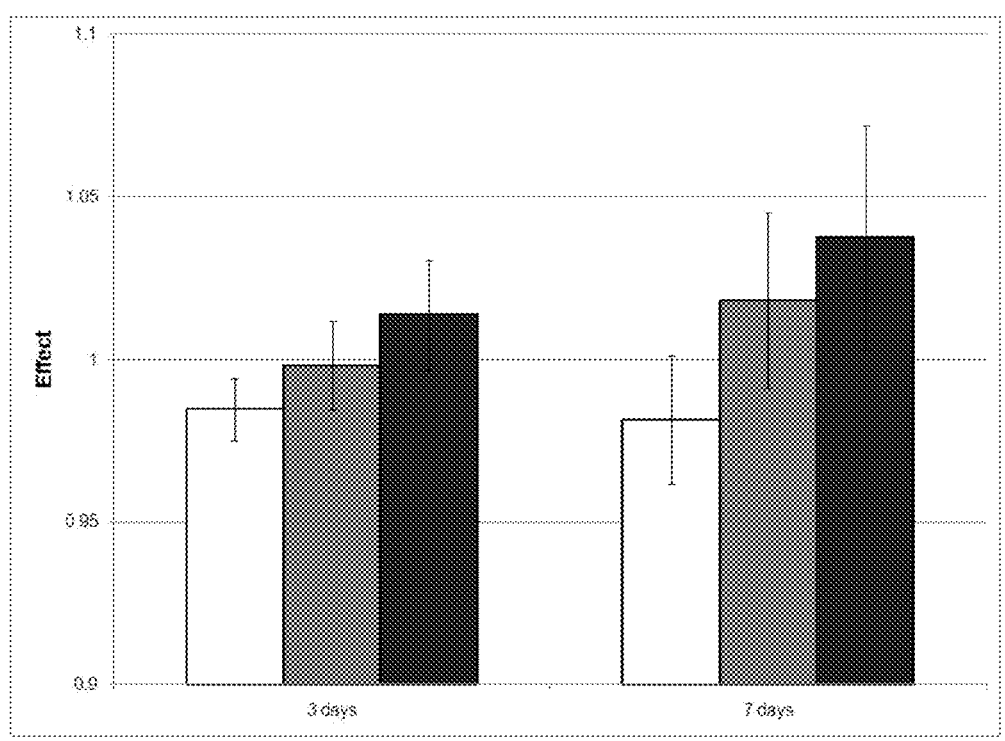
FIGS. 8A (methyl-4-hydroxybenzoate), 8B (3,5-dihydroxybenzoic acid), 8C (4-hydroxybenzoic acid), 8D (2,6-dimethoxyphenol), 8E (4-hydroxy-3-methoxycinnamic acid), 8F (methyl-3,4,5-trihydroxybenzoate), 8G (3,4-dihydroxybenzoic acid), 8H (pyrocatechol), 8I (pyrogallol), 8J (2,3,4-trihydroxybenzophenone), 8K (2,4,4'-trihydroxybenzophenone), 8L (acrolein diacetal), and 8M (pyrocatechol violet) show (1) the effect of a dioxy compound on hydrolysis of AVICEL® by a *T. reesei* cellulase composition in the absence of a GH61 polypeptide (white bars), (2) the effect of a dioxy compound on hydrolysis of AVICEL® by a *T. reesei* cellulase composition in the presence of a GH61 polypeptide (grey bars), and (3) the effect of a GH61 polypeptide on hydrolysis of AVICEL® by a *T. reesei* cellulase composition in the presence of a dioxy compound (black bars) at 3 and 7 days of hydrolysis (1, 3, and 7 days of hydrolysis for pyrocatechol violet).
Figure 8B:
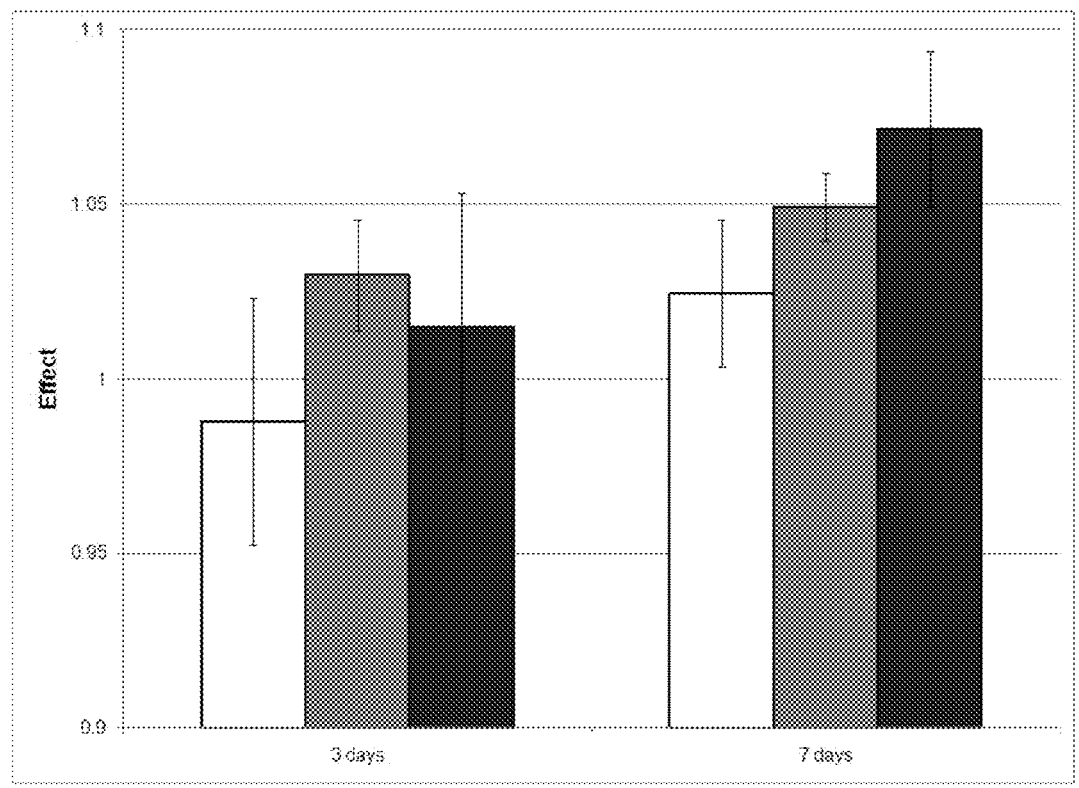
Figure 8C:
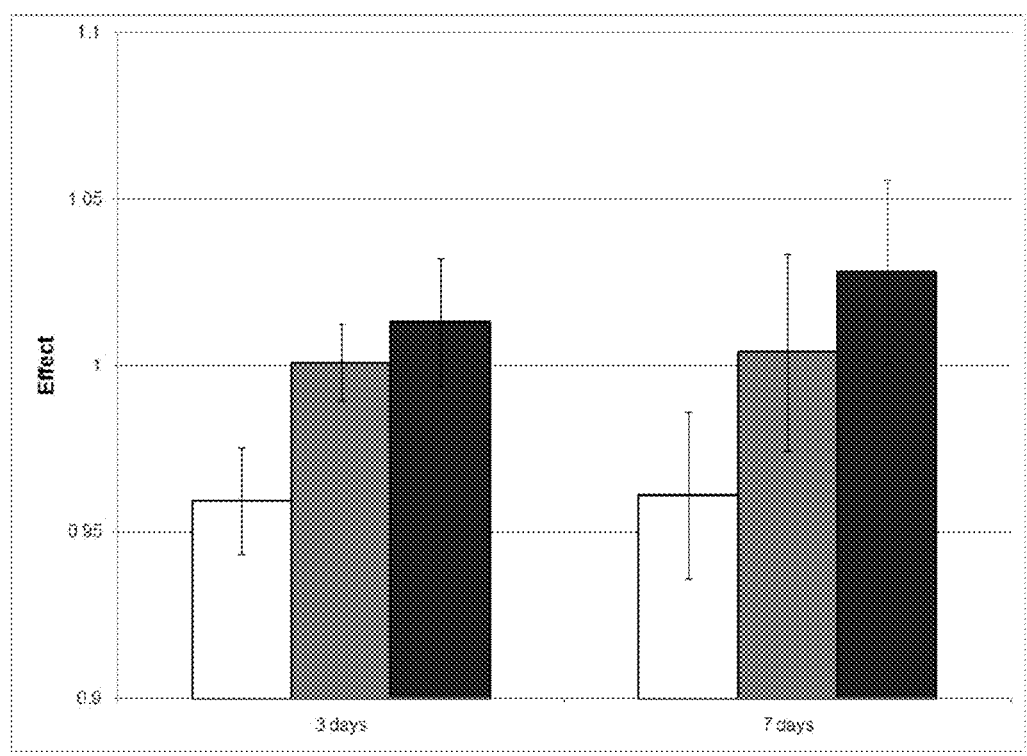

FIGS. 8A (methyl-4-hydroxybenzoate), 8B (3,5-dihydroxybenzoic acid), 8C (4-hydroxybenzoic acid), 8D (2,6-dimethoxyphenol), 8E (4-hydroxy-3-methoxycinnamic acid), 8F (methyl-3,4,5-trihydroxybenzoate), 8G (3,4-dihydroxybenzoic acid), 8H (pyrocatechol), 8I (pyrogallol), 8J (2,3,4-trihydroxybenzophenone), 8K (2,4,4'-trihydroxybenzophenone), 8L (acrolein diacetal), and 8M (pyrocatechol violet) show (1) the effect of a dioxy compound on hydrolysis of AVICEL® by the *T. reesei* cellulase composition in the absence of a GH61 polypeptide (white bars), (2) the effect of a dioxy compound on hydrolysis of AVICEL® by the *T. reesei* cellulase composition in the presence of a GH61 polypeptide (grey bars), and (3) the effect of a GH61 polypeptide on hydrolysis of AVICEL® by the *T. reesei* cellulase composition in the presence of a dioxy compound (black bars) at 3 and 7 days of hydrolysis (1, 3 and 7 days of hydrolysis for pyrocatechol violet).

FIGS. 8A-8M all have the following common characteristic. For all of the dioxy compounds shown in these figures, the 7 day saccharification time points show an enhancement of cellulose conversion by the *T. reesei* cellulase composition with *T. aurantiacus* GH61A polypeptide in the presence of the dioxy compound in comparison to the conversion by the *T. reesei* cellulase composition in the absence of the *T. aurantiacus* GH61A polypeptide. The dioxy compounds showed greater or lesser degrees of inhibition of the cellulase composition in the absence of the GH61A polypeptide (FIGS. 8A to 8M, white bars), and greater or lesser inhibition of the cellulase composition in the presence of the GH61A polypeptide (FIGS. 8A to 8M, gray bars). In each case, however, addition of the GH61A polypeptide to hydrolyses in the presence of the dioxy compound enhanced the hydrolysis, compared to hydrolyses performed in the presence of the dioxy compound without the GH61A polypeptide as indicated by a dioxy compound effect$_{(+GH61)}$ greater than the dioxy compound effect$_{(no\ GH61)}$, and a GH61 effect greater than 1, as defined by Equations 3, 4 and 5.

Figure 8D:
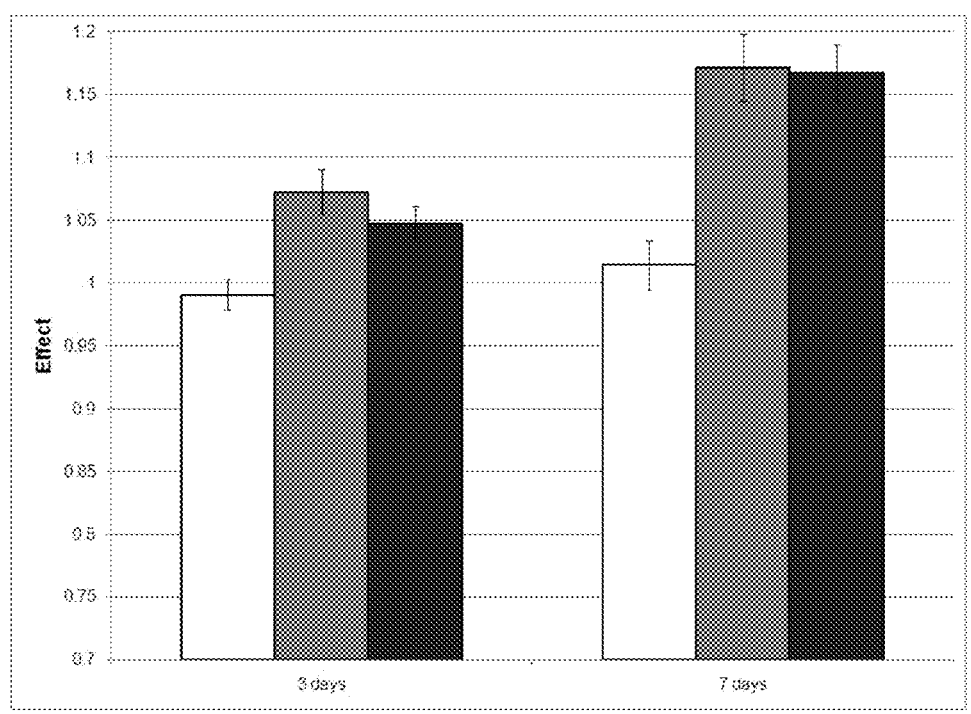
Figure 8E:
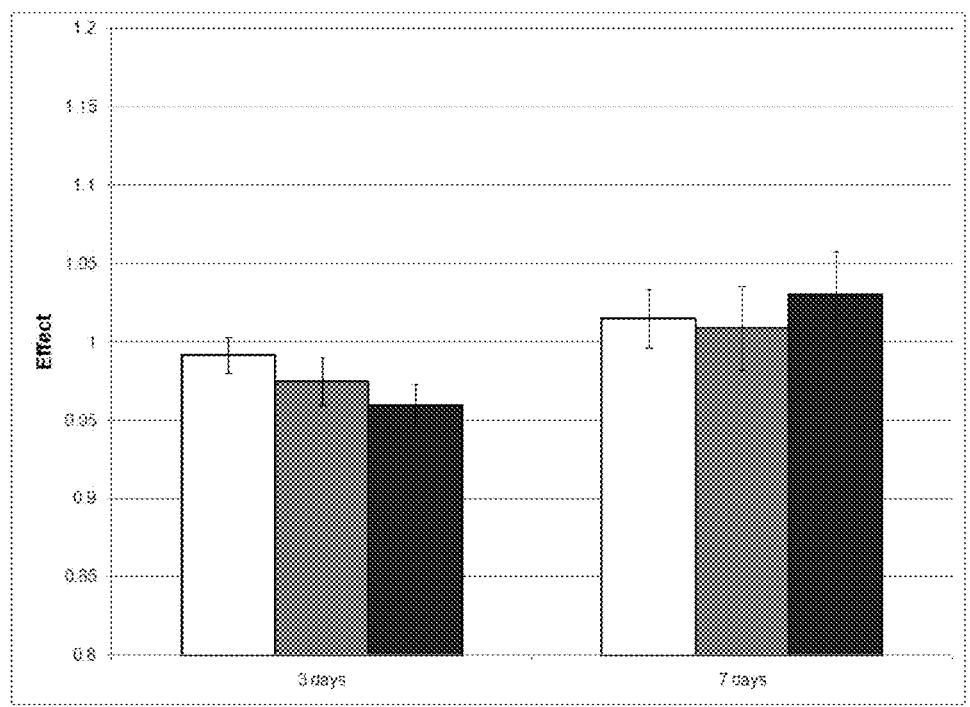
Figure 8F:
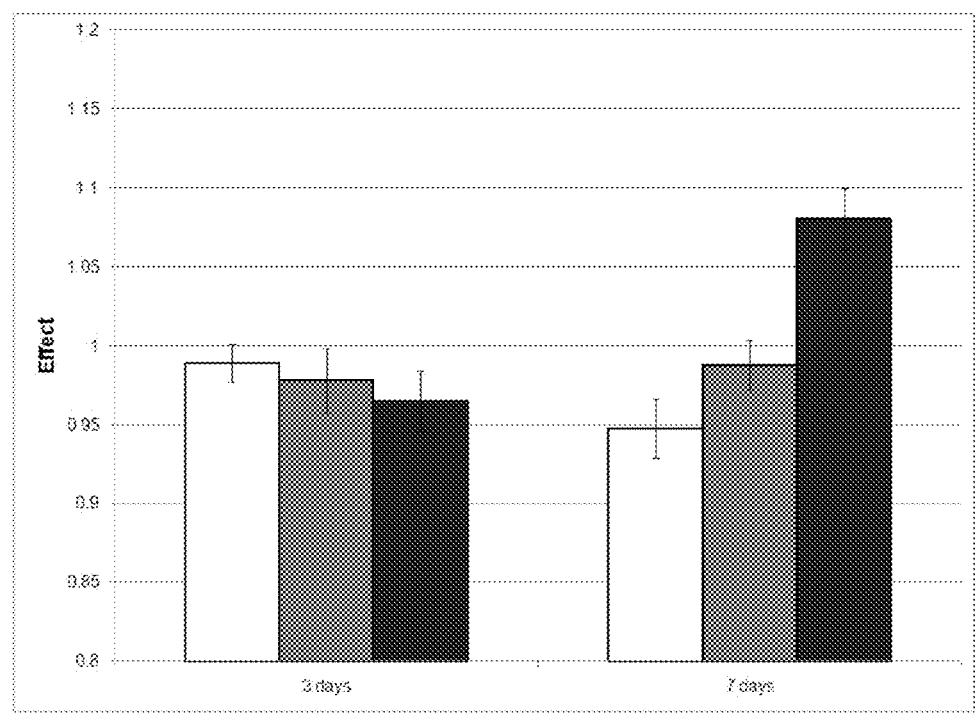
Figure 8G:
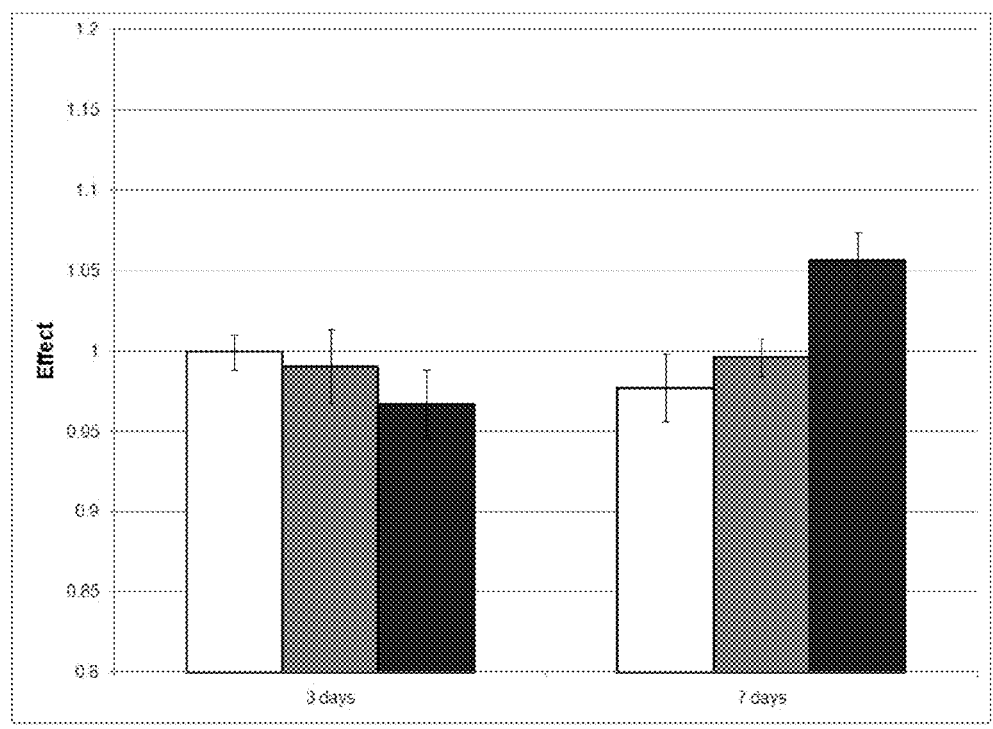
Figure 8H:
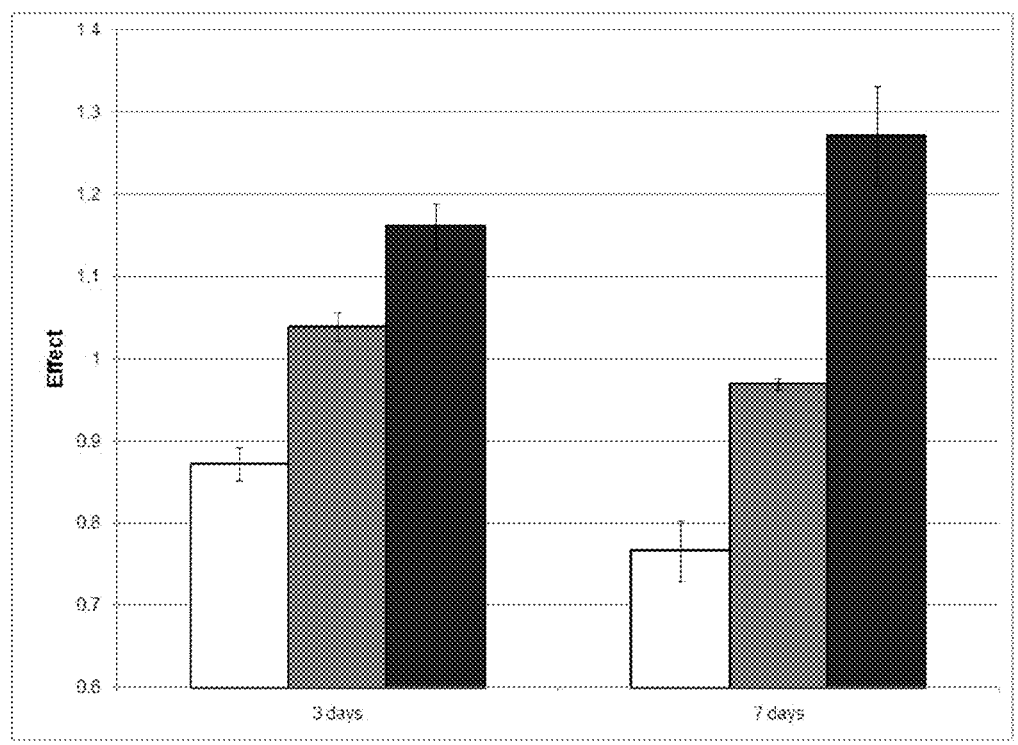
Figure 8I:
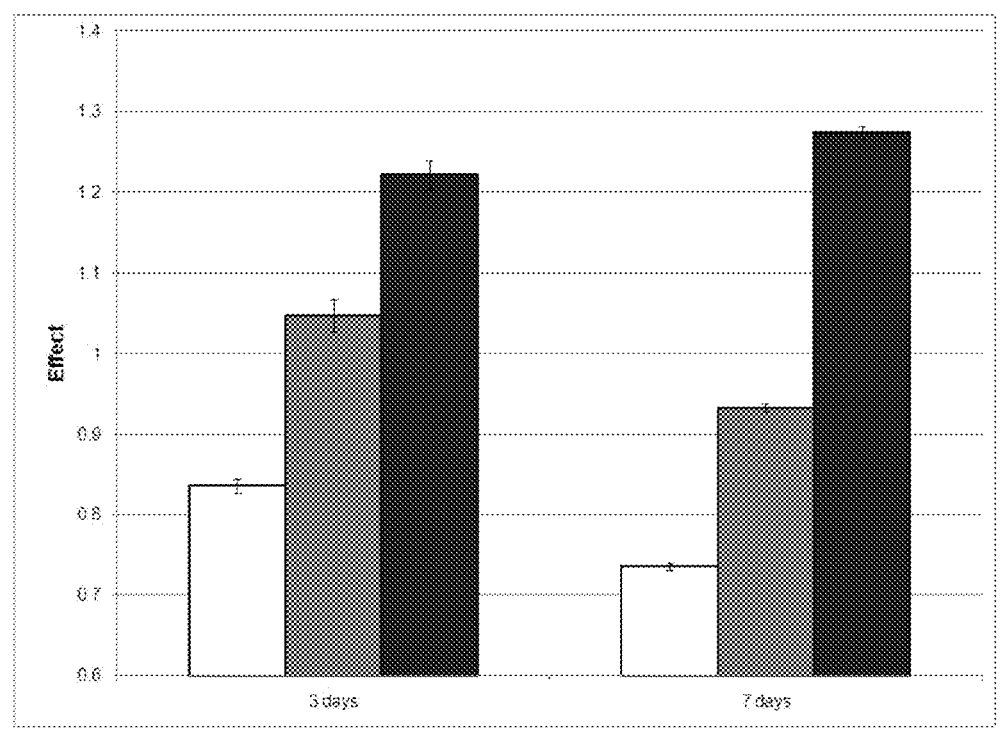
Figure 8J:
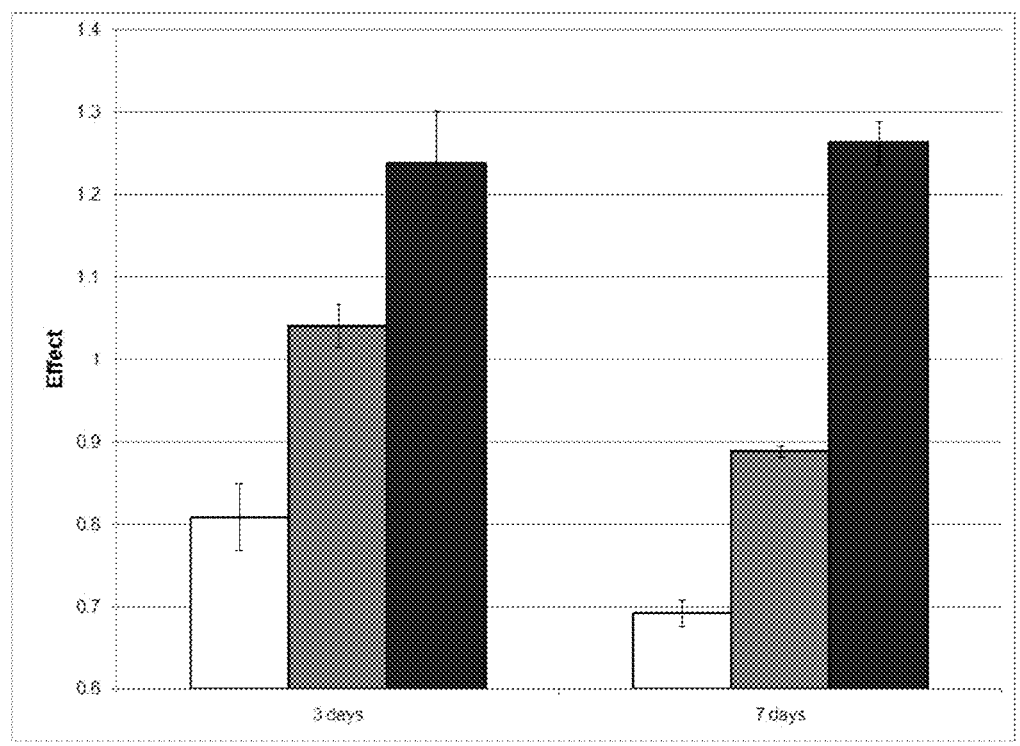
Figure 8K:
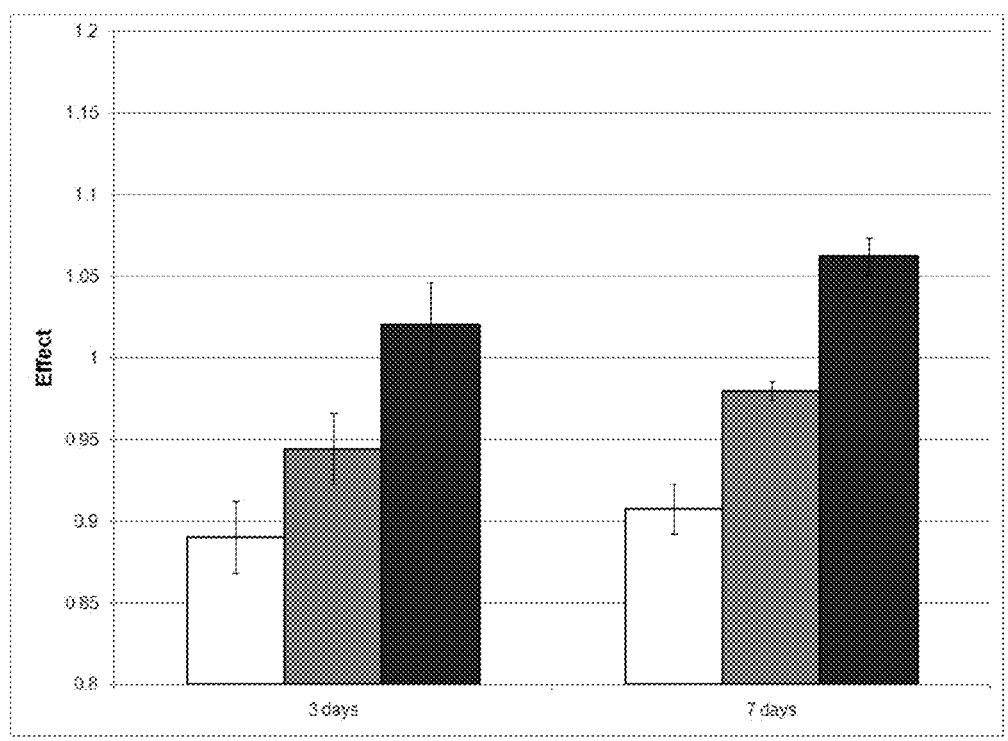
Figure 8L:
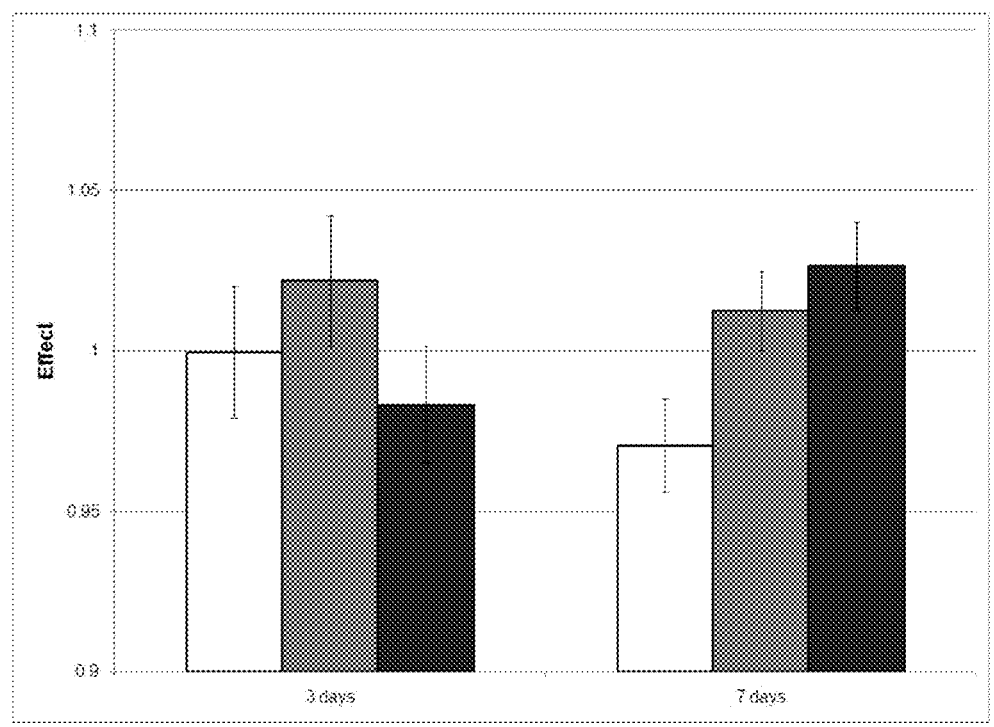
Figure 8M:
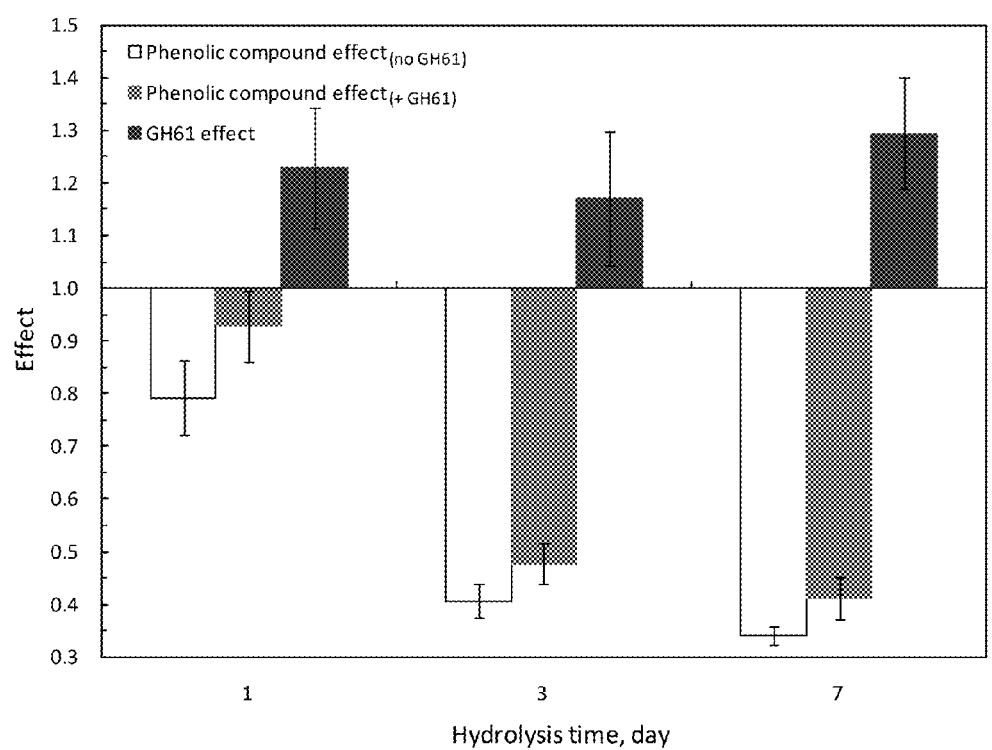

In the presence of many of these dioxy compounds, the hydrolysis of AVICEL® in the presence of both the *T. aurantiacus* GH61A polypeptide and the dioxy compound was greater than the inhibition by the dioxy compound, leading to an overall enhancement of cellulolysis. Examples of this include, but are not limited to, methyl-4-hydroxybenzoate (FIG. 8A) and 2,6-dimethoxyphenol (FIG. 8D).

These results demonstrated that cellulolytic enhancing activity of the GH61 polypeptide was apparent in the presence of these dioxy compounds during hydrolysis of AVICEL® by the *T. reesei* cellulase composition. However, the *T. aurantiacus* GH61A polypeptide had no detectable effect on hydrolysis of AVICEL® by the *T. reesei* cellulase composition in the absence of a dioxy compound (Example 23).

Example 26

Effect of Dioxy Compounds on *Thermoascus aurantiacus* GH61A Polypeptide During Hydrolysis of Microcrystalline Cellulose by the *Trichoderma reesei* Cellulase Composition The effect of 1,3-propanediol, 2,4-pentanediol, tartrate, and 3-ethoxy-1,2-propanediol on the cellulolytic enhancing activity of the *T. aurantiacus* GH61A polypeptide during hydrolysis of AVICEL® by the *T. reesei* cellulase composition was determined using the experimental conditions and procedures described in Example 22 with the following exceptions. The concentration of dioxy compounds was 5 mM, the concentration of the *T. aurantiacus* GH61A polypeptide was 0.4 mg per g cellulose, and the concentration of cellulose was 14 mg per ml for 1,3-propanediol and 2,4-pentanediol. The concentration of dioxy compounds was 1 mM, the concentration of the *T. aurantiacus* GH61A polypeptide was 2 mg per g cellulose and the concentration of cellulose was 29.5 mg per ml for tartrate and 3-ethoxy-1,2-propanediol.

Figure 9A:
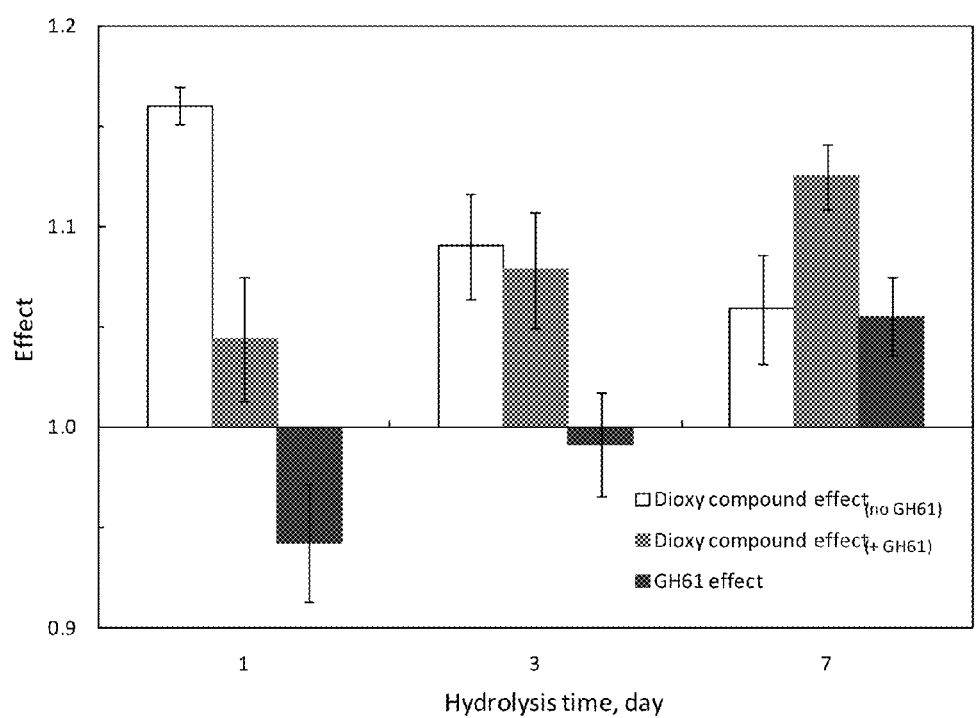
FIGS. 9A (1,3-propanediol), 9B (2,4-pentanediol), 9C (tartrate), and 9D (3-ethoxy-1,2-propanediol) show (1) the effect of a dioxy compound on hydrolysis of AVICEL® by a *T. reesei* cellulase composition in the absence of a GH61 polypeptide (dioxy compound effect$_{(no\ GH61)}$, white bars), (2) the effect of a dioxy compound on hydrolysis of AVICEL® by a *T. reesei* cellulase composition in the presence of a GH61 polypeptide (dioxy compound effect$_{(+GH61)}$, grey bars), and (3) the effect of a GH61 polypeptide on hydrolysis of AVICEL® by a *T. reesei* cellulase composition in the presence of a dioxy compound (GH61 effect, black bars) for 1, 3, and 7 days.

FIGS. 9A (1,3-propanediol), 9B (2,4-pentanediol), 9C (tartrate), and 9D (3-ethoxy-1,2-propanediol) show (1) the effect of a dioxy compound on hydrolysis of AVICEL® by the *T. reesei* cellulase composition in the absence of a GH61 polypeptide (dioxy compound effect$_{(no\ GH61)}$, white bars), (2) the effect of a dioxy compound on hydrolysis of AVICEL® by the *T. reesei* cellulase composition in the presence of a GH61 polypeptide (dioxy compound effect$_{(+GH61)}$, grey bars), and (3) the effect of a GH61 polypeptide on hydrolysis of AVICEL® by the *T. reesei* cellulase composition in the presence of a dioxy compound (GH61 effect, black bars) for 1, 3, and 7 days.

Hydrolysis of AVICEL® by the *T. reesei* cellulase composition was greater with 1,3-propanediol than without, especially at early stages of hydrolysis, as indicated by the dioxy compound effect$_{(no\ GH61)}$, which was greater than 1 (FIG. 9A, white bars) as defined by Equation 3. In the presence of the *T. aurantiacus* GH61A polypeptide, hydrolysis of AVICEL® by the *T. reesei* cellulase composition was also increased by the presence of 1,3-propanediol and, especially at later stages of hydrolysis, as indicated by the dioxy compound effect$_{(+GH61)}$, which was also greater than 1 (FIG. 9A, grey bars) as defined by Equation 4. The *T. aurantiacus* GH61A polypeptide did not enhance hydrolysis of microcrystalline cellulose in the absence of 1,3-propanediol (Example 23), however in the presence of 1,3-propanediol, hydrolysis was enhanced by addition of the *T. aurantiacus* GH61A polypeptide to the *T. reesei* cellulase composition. This was evident as the GH61 effect (Equation 5) was greater than 1, indicating enhancement of hydrolysis. Furthermore, with 1,3-propanediol present, the effect of the *T. aurantiacus* GH61A polypeptide increased as the hydrolysis progressed, indicating that the effects of *T. aurantiacus* GH61A polypeptide addition increased over this time period (FIG. 9A, black bars). 1,3-Propanediol was, therefore, beneficial for AVICEL® hydrolysis, and additionally, its presence in combination with the GH61 polypeptide demonstrated a GH61 polypeptide-dependent enhancement of cellulolysis by the *T. reesei* cellulase composition.

Figure 9B:
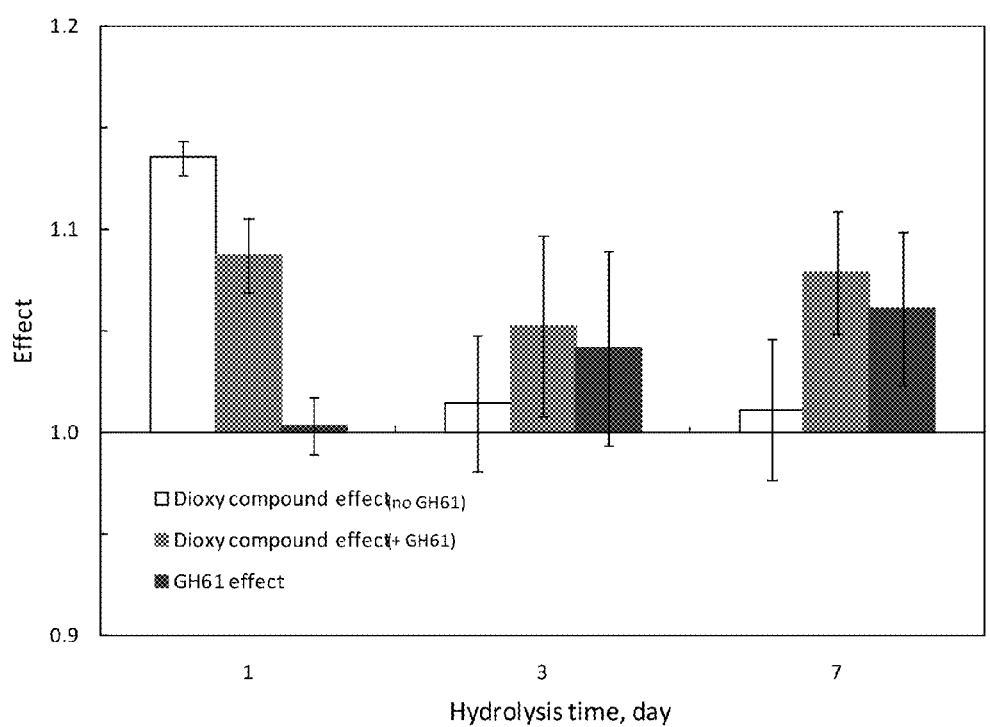

Similarly, hydrolysis of AVICEL® by the *T. reesei* cellulase composition was increased at day 1 by the presence of 2,4-pentanediol, producing a dioxy compound effect$_{(no\ GH61)}$ greater than 1 (FIG. 9B, day 1 white bar) as defined by Equation 3. Hydrolysis of AVICEL® by the *T. reesei* cellulase composition in the presence of 2,4-pentanediol and *T. aurantiacus* GH61A polypeptide was slightly improved, as indicated by the dioxy compound effect$_{(+GH61)}$, which was greater than 1 (FIG. 9B, grey bars) as defined by Equation 4. The effect of the *T. aurantiacus* GH61A polypeptide (GH61 effect) was greater than 1 (Equation 5) at later hydrolysis stages, indicating that the *T. aurantiacus* GH61A polypeptide enhanced hydrolysis of microcrystalline cellulose when 2,4-pentanediol was present (FIG. 9B, day 7 black bar), whereas the *T. aurantiacus* GH61A polypeptide did not enhance hydrolysis of microcrystalline cellulose in the absence of 2,4-pentanediol (Example 23). 2,4-Pentanediol in combination with GH61A polypeptide was, therefore, sufficient to generate a GH61-dependent enhancement of cellulose hydrolysis.

Figure 9C:
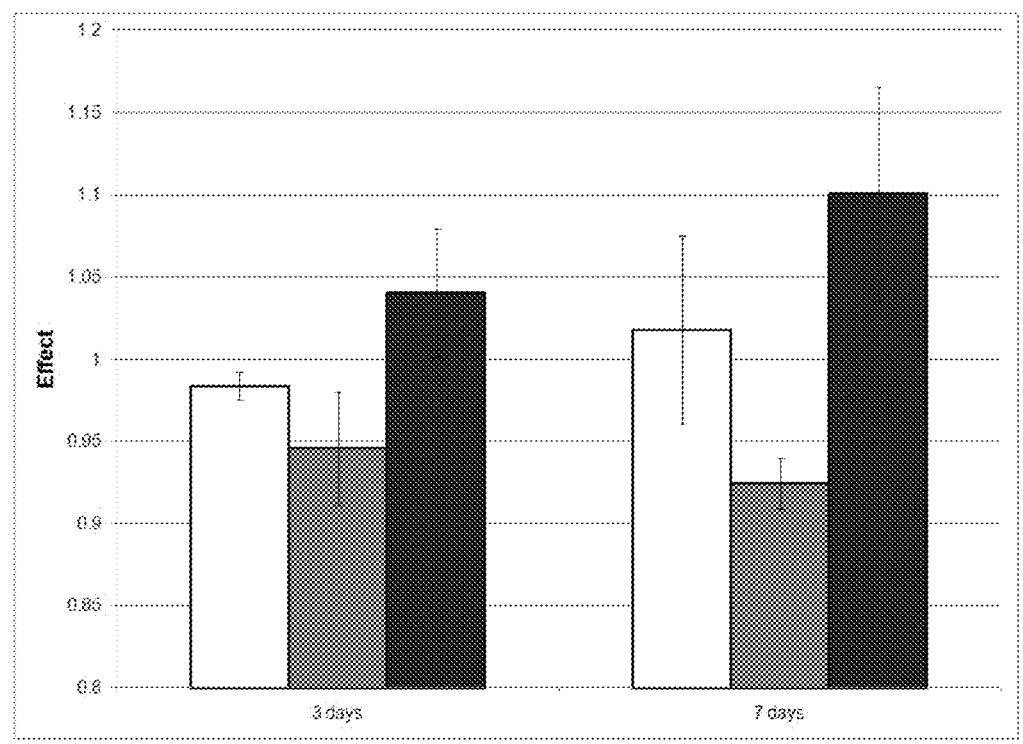

FIG. 9C shows that addition of tartrate did not substantially alter the hydrolysis of AVICEL® by the *T. reesei* cellulase composition in the absence of the *T. aurantiacus* GH61A polypeptide. This was indicated from the dioxy compound effect$_{(no\ GH61)}$, which was approximately 1 at all time points: 0.984±0.00843 at 3 days of hydrolysis and 1.02±0.0573 at 7 days of hydrolysis (FIG. 9C, white bars). More importantly, while GH61 polypeptide addition did not enhance the hydrolysis of AVICEL® (Example 23), the presence of both tartrate and GH61 polypeptide significantly enhanced hydrolysis. The GH61 effect was 1.04±0.0389 at 3 days and 1.11±0.0139 at 7 days of hydrolysis. The result of GH61 polypeptide addition to a saccharification of cellulose by the *T. reesei* cellulase composition containing tartrate was, therefore, to enhance cellulolysis.

Figure 9D:
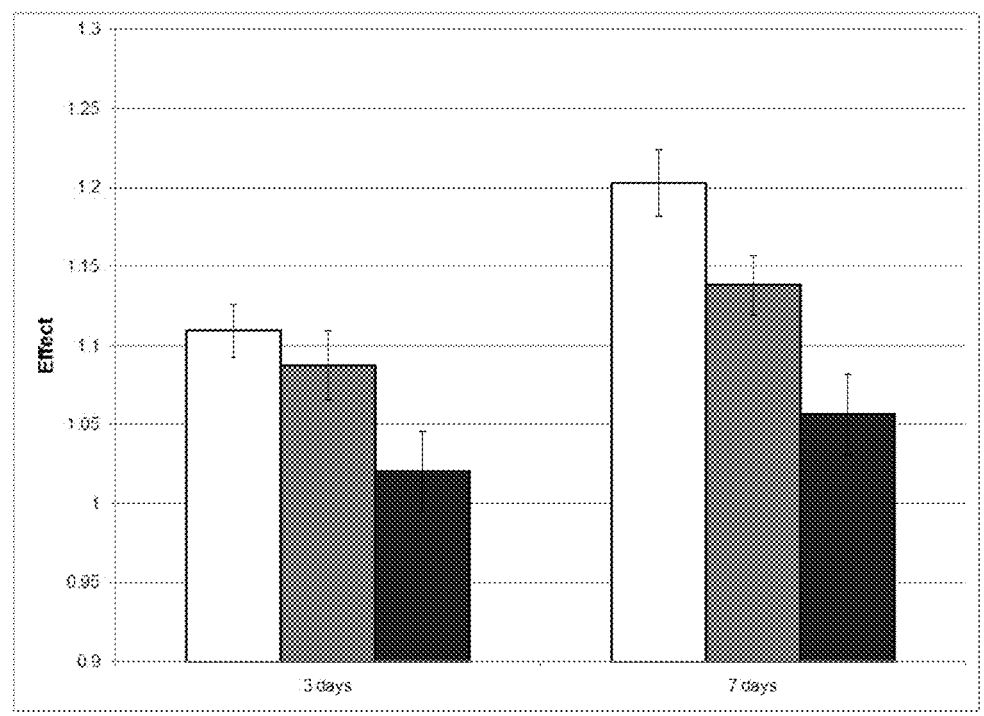
Figure 10:
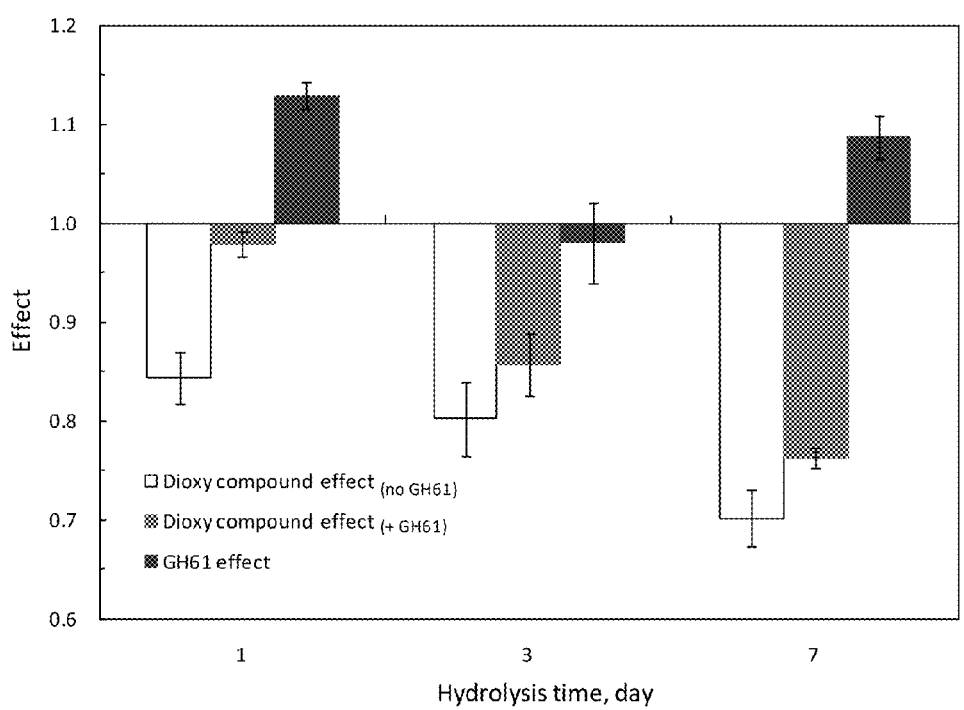
FIG. 10 shows (1) the effect of dihydroxyfumaric acid on hydrolysis of AVICEL® by a *T. reesei* cellulase composition in the absence of a GH61 polypeptide (dioxy compound effect$_{(no\ GH61)}$, white bar), (2) the effect of dihydroxyfumaric acid on hydrolysis of AVICEL® by a *T. reesei* cellulase composition in the presence of a GH61 polypeptide (dioxy compound effect$_{(+GH61)}$, grey bars), and (3) the effect of a GH61 polypeptide on hydrolysis of AVICEL® by a *T. reesei* cellulase composition in the presence of dihydroxyfumaric acid (GH61 effect, black bars) for 1, 3, and 7 days.
Figure 11:
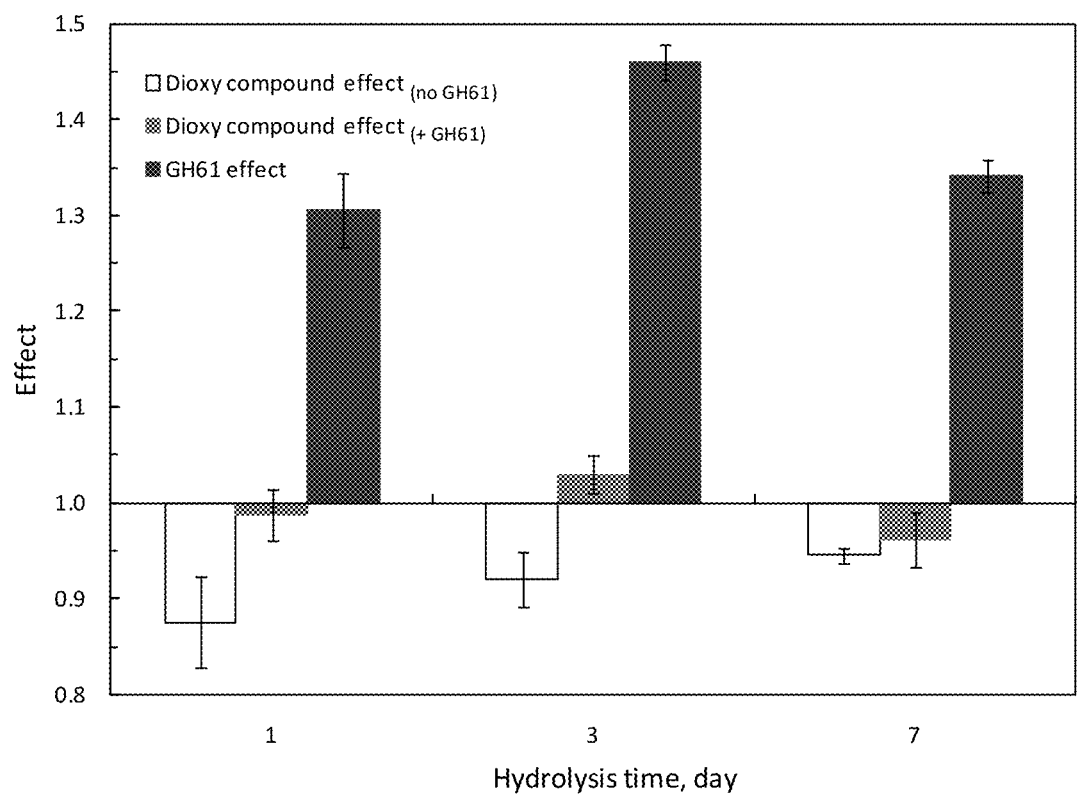
FIG. 11 shows (1) the effect of dihydroxyfumaric acid on hydrolysis of milled washed PCS by a *T. reesei* cellulase composition in the absence of a GH61 polypeptide (dioxy compound effect$_{(no\ GH61)}$, white bar), (2) the effect of dihydroxyfumaric acid on hydrolysis of milled washed PCS by a *T. reesei* cellulase composition in the presence of a GH61 polypeptide (dioxy compound effect$_{(+GH61)}$, grey bar), and (3) the effect of a GH61 polypeptide on hydrolysis of milled washed PCS by a *T. reesei* cellulase composition in the presence of dihydroxyfumaric acid (GH61 effect, black bar) for 1, 3, and 7 days of hydrolysis.
Figure 12A:
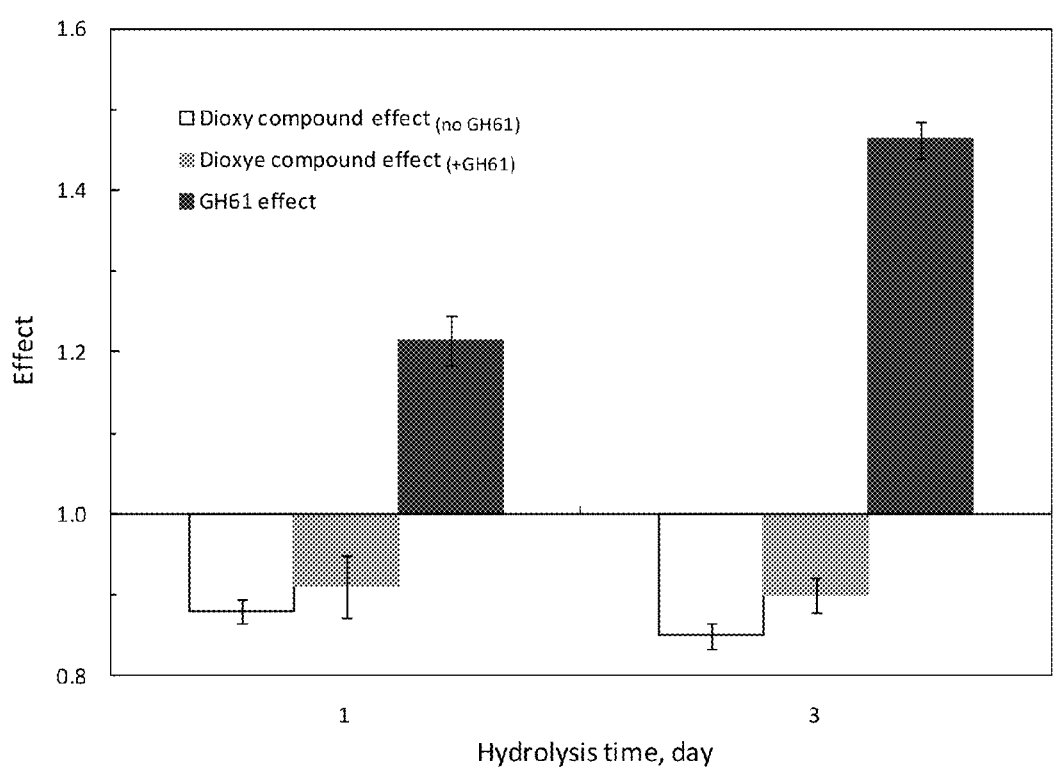
FIGS. 12A and 12B show (1) the effect of dihydroxyfumaric acid on hydrolysis of milled washed PCS by a *T. reesei* cellulase composition in the absence of a GH61 polypeptide (dioxy compound effect$_{(no\ GH61)}$, white bar), (2) the effect of dihydroxyfumaric acid on hydrolysis of milled washed PCS by a *T. reesei* cellulase composition in the presence of a GH61 polypeptide (dioxy compound effect$_{(+GH61)}$, grey bar), and (3) the effect of a GH61 polypeptide on hydrolysis of milled washed PCS by a *T. reesei* cellulase composition in the presence of dihydroxyfumaric acid (GH61 effect, black bars) for 1 and 3 days. The concentration of dihydroxyfumaric acid was 10 mM and the concentration of the *T. aurantiacus* GH61A polypeptide was 28 mg per liter (corresponding to 50% of the *T. reesei* cellulase composition).
Figure 12B:
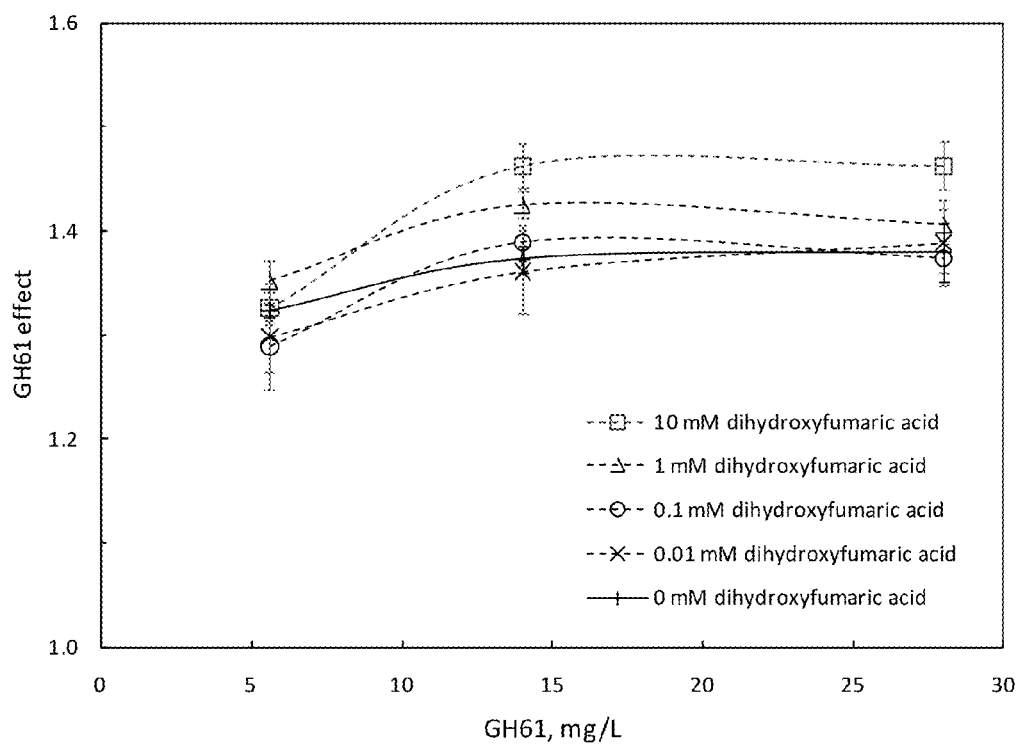
Figure 13A:
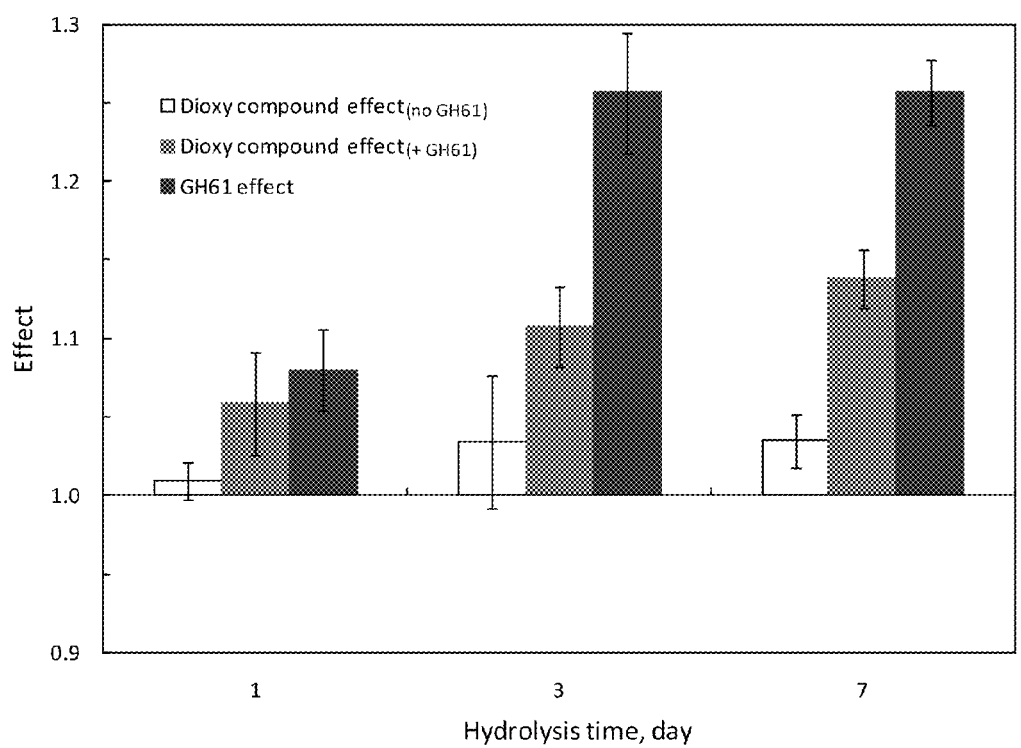
FIGS. 13A (dihydroxyfumaric acid), 13B (cis-2-butene-1,4-diol), and 13C (3,4-dihydroxy-3-cyclobutene-1,2-dione (squaric acid)) show (1) the effect of dioxy compounds on hydrolysis of milled unwashed PCS by a *Trichoderma reesei* cellulase composition in the absence of a GH61 polypeptide (dioxy compound effect$_{(no\ GH61)}$, white bars), (2) the effect of dioxy compounds on hydrolysis of milled unwashed PCS by a *Trichoderma reesei* cellulase composition in the presence of a GH61 polypeptide (dioxycompound effect$_{(+GH61)}$, grey bars), and (3) the effect of a GH61 polypeptide on hydrolysis of milled unwashed PCS by a *T. reesei* cellulase composition in the presence of dioxy compounds (GH61 effect, black bars) for 1, 3, and 7 days of hydrolysis.
Figure 13B:
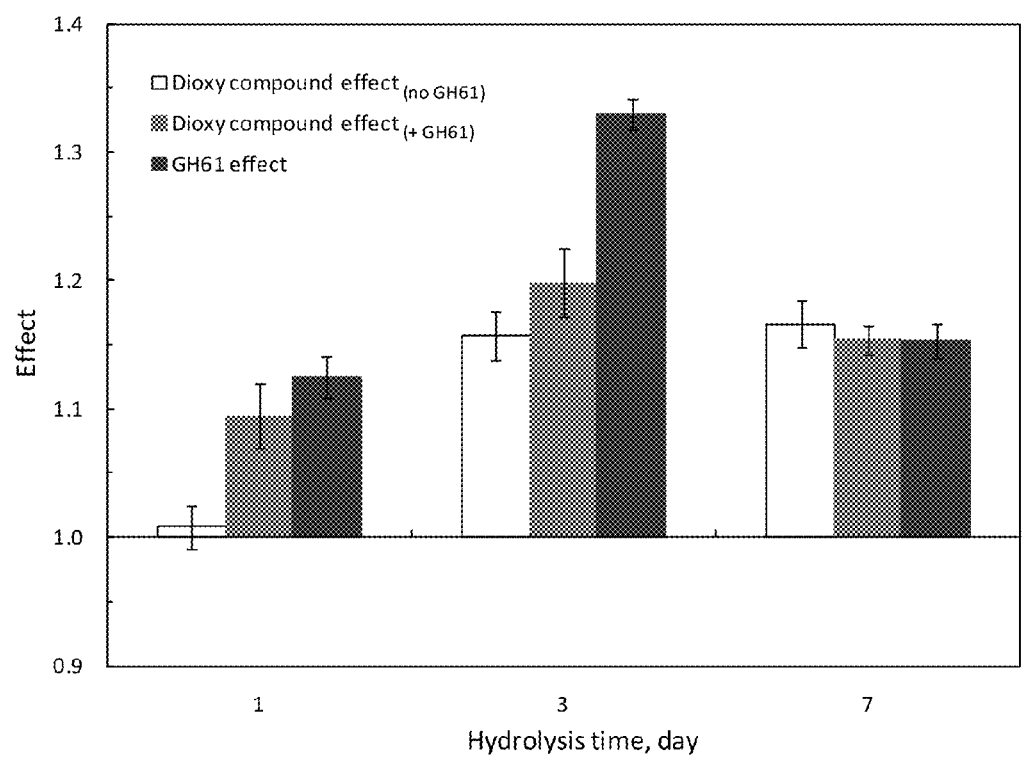
Figure 13C:
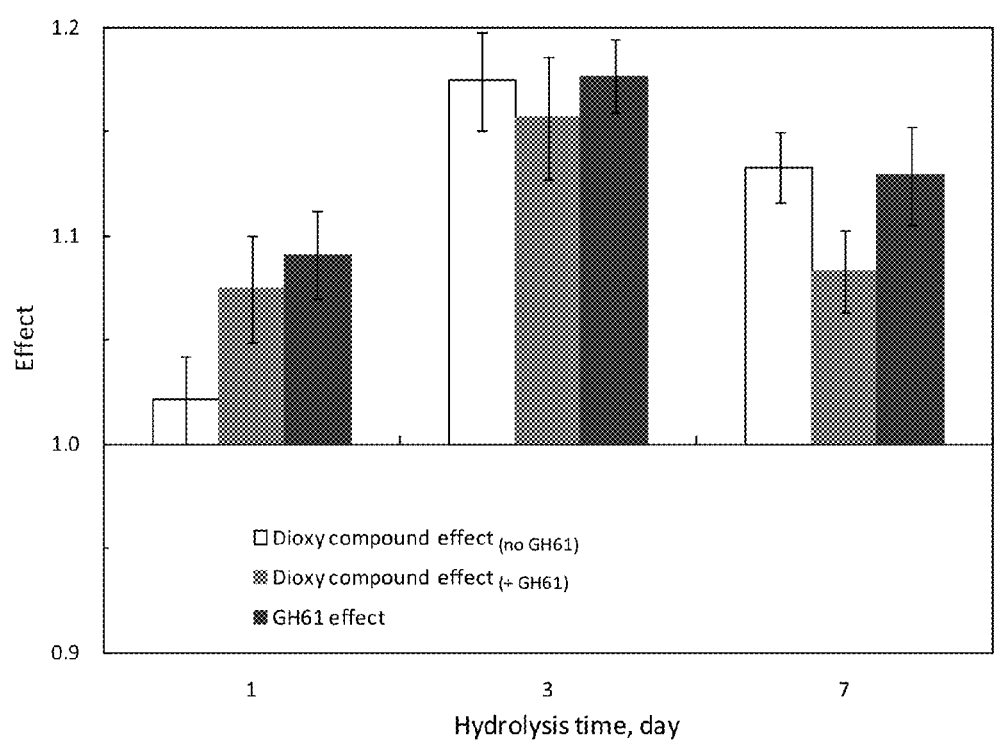

FIG. 9D shows that, like 1,2- or 3,4-pentadiol, addition of 3-ethoxy-1,2-propanediol resulted in higher hydrolysis of AVICEL® by the *T. reesei* cellulase composition in the absence of the *T. aurantiacus* GH61A polypeptide. This result was indicated from the dioxy compound effect$_{(no\ GH61)}$, which was greater than 1 at all time points: 1.11±0.0167 at 3 days of hydrolysis and 1.20±0.0210 at 7 days of hydrolysis (FIG. 9C, white bars). Likewise, 3-ethoxy-1,2-propanediol in the presence of the *T. aurantiacus* GH61A polypeptide enhanced hydrolysis, resulting in a dioxy compound effect$_{(+GH61)}$ of 1.08±0.0219 and 1.14±0.0187 at 3 and 7 days of hydrolysis, respectively. More importantly, while GH61 polypeptide addition alone did not enhance the hydrolysis of AVICEL® (Example 23), the presence of both 3-ethoxy-1,2-propanediol and the *T. aurantiacus* GH61A polypeptide significantly enhanced hydrolysis. The GH61 effect was 1.06±0.0254 at 7 days of hydrolysis. The result of GH61 polypeptide addition to a saccharification of AVICEL® by the *T. reesei* cellulase composition containing 3-ethoxy-1,2-propanediol was, therefore, to enhance cellulolysis.

The overall results demonstrated that cellulolytic enhancing activity of the GH61 polypeptide was apparent in the presence of a dioxy compound during hydrolysis of AVICEL® by the *T. reesei* cellulase composition. However, the *T. aurantiacus* GH61A polypeptide had no detectable effect on hydrolysis of AVICEL® by the *T. reesei* cellulase composition in the absence of a dioxy compound.

Example 27

Preparation of *Aspergillus fumigatus* GH61B Polypeptide Having Cellulolytic Enhancing Activity The *Aspergillus fumigatus* GH61B polypeptide having cellulolytic enhancing activity gene (SEQ ID NO: 29 [DNA sequence] and SEQ ID NO: 30 [deduced amino acid sequence]) was cloned and expressed in *Aspergillus oryzae* JaL250 as described in WO 2010/138754. A filtered shake flask broth containing the recombinantly produced *A. fumigatus* GH61B polypeptide having cellulolytic enhancing activity was first concentrated by a tangential flow concentrator (Pall Filtron, Northborough, Mass., USA) equipped with a 10 kDa polyethersulfone membrane (Pall Filtron, Northborough, Mass., USA), buffer exchanged into 20 mM Tris-HCl pH 8.0, and then purified using a Highload™ 26/60 Superdex 75 gel filtration column (GE Healthcare, Piscataway, N.J., USA) with a 750 ml isocratic gradient in 150 mM NaCl, 20 mM Tris-HCl pH 8.0. Fractions were collected and pooled based on SDS-PAGE. Protein concentration was determined using a Microplate BCA™ Protein Assay Kit in which bovine serum albumin was used as a protein standard.

Example 28

Preparation of *Trichoderma reesei* GH61B Polypeptide Having Cellulolytic Enhancing Activity The *Trichoderma reesei* GH61B polypeptide having cellulolytic enhancing activity gene (SEQ ID NO: 15 [DNA sequence] and SEQ ID NO: 16 [deduced amino acid sequence]) was cloned and expressed in *Aspergillus oryzae* JaL250 as described in WO 2007/089290. The recombinantly produced *T. reesei* GH61B polypeptide was first concentrated by ultrafiltration using a 10 kDa membrane, buffer exchanged into 20 mM Tris-HCl pH 8.0, and then purified using a 20 ml MONO Q® column (GE Healthcare, Piscataway, N.J., USA) with a 0-600 mM NaCl linear gradient in 20 mM Tris-HCl pH 8.0. Fractions were collected and pooled based on SDS-PAGE. The pooled fractions were concentrated by ultrafiltration using a 10 kDa membrane, and chromatographed using a 320 ml SUPERDEX® 75 SEC column (GE Healthcare, Piscataway, N.J., USA) with isocratic elution of approximately 1.3 liters of 150 mM NaCl-20 mM Tris-HCl pH 8.0. Fractions were collected and pooled based on SDS-PAGE. Pooled fractions were concentrated and desalted into 20 mM Tris-HCl pH 8.5 using a VIVASPIN® 20 10 kDa MWCO centrifugal concentration filter (GE Healthcare UK limited, Little Chalfont, Buckinghamshire, UK). Protein concentration was determined using a Microplate BCA™ Protein Assay Kit in which bovine serum albumin was used as a protein standard.

Example 29

Variable pH Phosphoric Acid Swollen Cellulose (PASC) Conversion Assay

A 1.0% PASC slurry was prepared as described in Example 17 and adjusted to 2 mM CaCl$_2$. This 1.0% PASC slurry was thoroughly resuspended by shaking, and quickly transferred to a 100 ml beaker and stirred rapidly with a magnetic stirrer. Five hundred μl aliquots of the 1.0% phosphoric acid swollen cellulose slurry were pipetted into wells of a 2.0 ml 96-deep-well plate (Axygen, Union City, Calif., USA) using a 1000 μl micropipette with a wide aperture tip (end of tip cut off about 2 mm from the base). One hundred μl of 1 M specified buffer were added to each well (specified buffer was sodium acetate pH 4, sodium acetate pH 5, Bis-Tris pH 6, or Tris-HCl pH 7.5). Two hundred μl of pyrogallol (SIGMA-ALDRICH, St. Louis, Mo., USA) dilution in water was added to each well. Enzyme mixtures were prepared and then added simultaneously to all wells in a volume of 200 μl, for a total of 1 ml in each reaction. The plate was then sealed using an ALPS-300™ plate heat sealer (Abgene, Epsom, United Kingdom), mixed thoroughly, and incubated at 50° C. for approximately 3 days. All experiments reported were performed in triplicate.

Primary analysis of the hydrolysis reactions was performed using an AGILENT® 1100 HPLC with CHEMSTATION® software equipped with an AMINEX™ HPX-87H column. After approximately 4 days, the deep-well plate was removed from the incubator and chilled overnight to 4° C. The plate was then mixed well by inversion and briefly centrifuged 52×g in a SORVALL® RT7 centrifuge (Thermo Fisher Scientific, Waltham, Mass., USA) for 10 seconds. Samples were then mixed by pipetting, and 200 μl from each well were transferred to a MULTISCREEN® HV centrifuge filter plate assembly. The centrifuge filter plate assembly was centrifuged at 2000 rpm in a SORVALL® RT7 centrifuge for 20 minutes. The filtrates were transferred to a 96 well autosampler plate (Nunc, Roskilde, Denmark) and diluted 1:1 with 5 mM $H_2SO_4$, sealed with a silicon sealing mat, and inserted into an HPLC injector module (set to 4° C.) for injection of 20 µl onto a CATION H™ guard column connected to a 4.6×250 mm AMINEX® HPX-87H column with elution by with 0.05% w/w benzoic acid in 5 mM $H_2SO_4$. Sugars were detected using a refractive index detector with quantification by integration compared to purified sugar standards.

All HPLC data processing was performed using MICROSOFT EXCEL™ software. Measured glucose concentrations were adjusted for the appropriate dilution factor. In this assay only glucose was measured since beta-glucosidase was at high levels in all samples but the controls. The degree of cellulose conversion was calculated using the following equation:

$$\% \ conversion = \frac{[glucose](mg/ml)}{[glucose \ in \ limit \ digest](mg/ml)} \times 100 \quad (Equation \ 1)$$

A limit digest was performed to determine the total concentration accessible glucose equivalents using 100 mg of *Trichoderma reesei* cellulase per gram cellulose (Celluclast Plus, Novozymes A/S, Bagsvaerd, Denmark), Triplicate data points were averaged and standard deviation was calculated.

Example 30

Effect of the Various pH Conditions on the Combination of *Thermoascus aurantiacus* GH61A Polypeptide Having Cellulolytic Enhancing Activity, Pyrogallol, and *Aspergillus oryzae* CEL3A Beta-Glucosidase on the Conversion of Phosphoric Acid Swollen Cellulose

*Thermoascus aurantiacus* GH61A having cellulolytic enhancing activity and pyrogallol were tested for their ability to enhance the conversion of phosphoric acid swollen cellulose by *Aspergillus oryzae* CEL3A beta-glucosidase at variable pH. The phosphoric acid swollen cellulose hydrolysis assay was performed as described in Example 29.

Figure 14:
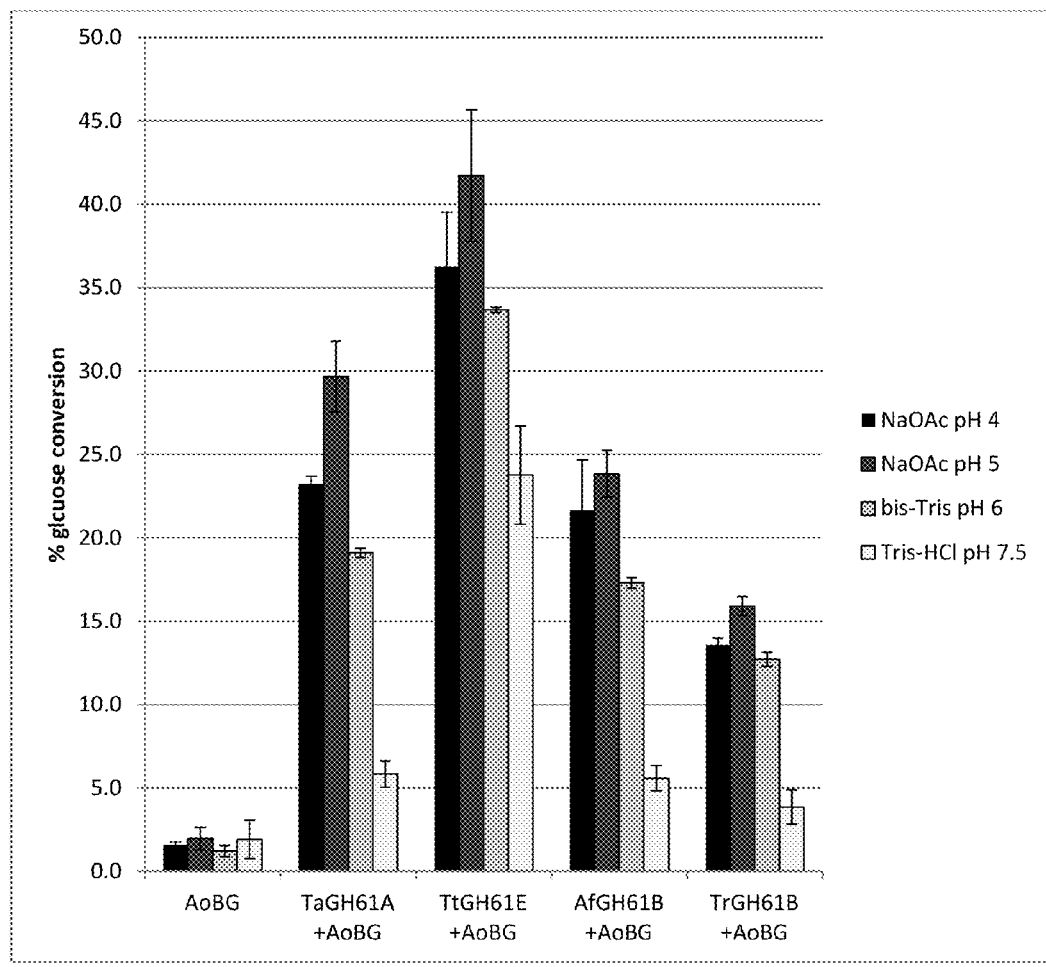
FIG. 14 shows the effect of the various pH conditions on the combination of *Thermoascus aurantiacus* GH61A polypeptide having cellulolytic enhancing activity, pyrogallol, and *Aspergillus oryzae* CEL3A beta-glucosidase on the conversion of phosphoric acid swollen cellulose.

The conversion of phosphoric acid swollen cellulose by *Aspergillus oryzae* CEL3A beta-glucosidase (10 mg protein per g cellulose); the combination of *Aspergillus oryzae* CEL3A beta-glucosidase (10 mg protein per g cellulose) with gallic acid (0.2% w/w); the combination of *Aspergillus oryzae* CEL3A beta-glucosidase (10 mg protein per g cellulose) with both *Thermoascus aurantiacus* GH61A polypeptide (10 mg protein per g cellulose) and gallic acid (0.2% w/w); the combination of *Aspergillus oryzae* CEL3A beta-glucosidase (10 mg protein per g cellulose) with both *Thielavia terrestris* GH61E polypeptide (10 mg protein per g cellulose) and gallic acid (0.2% w/w); the combination of *Aspergillus oryzae* CEL3A beta-glucosidase (10 mg protein per g cellulose) with both *Aspergillus fumigatus* GH61B polypeptide (10 mg protein per g cellulose) and gallic acid (0.2% w/w); and the combination of *Aspergillus oryzae* CEL3A beta-glucosidase (10 mg protein per g cellulose) with both *Trichoderma reesei* GH61B polypeptide (10 mg protein per g cellulose) and gallic acid (0.2% w/w) was determined as described in Example 29. Data were collected and analyzed, as described in Example 29, after 72 hours of incubation at 50° C. The results are shown in FIG. 14.

The combination of gallic acid (0.2% w/w) and *Aspergillus oryzae* CEL3A beta-glucosidase (10 mg protein per g cellulose) resulted in 1.6±0.2% conversion, 2.0±0.7% conversion, 1.2±0.5% conversion, and 1.9±1.2% conversion of phosphoric acid swollen cellulose at pH 4, pH 5, pH 6, and pH 7.5, respectively. The combination of gallic acid (0.2% w/w) with both *Thermoascus aurantiacus* GH61A polypeptide (10 mg protein per g cellulose) and *Aspergillus oryzae* CEL3A beta-glucosidase (10 mg protein per g cellulose) resulted in 23.2±0.5% conversion, 29.7±2.1% conversion, 19.1±0.3% conversion, and 5.8±0.8% conversion of phosphoric acid swollen cellulose at pH 4, pH 5, pH 6, and pH 7.5, respectively. The combination of gallic acid (0.2% w/w) with both *Thielavia terrestris* GH61E polypeptide (10 mg protein per g cellulose) and *Aspergillus oryzae* CEL3A beta-glucosidase (10 mg protein per g cellulose) resulted in 36.3±3.2% conversion, 41.7±3.9% conversion, 33.7±0.2% conversion, and 23.8±3.0% conversion of phosphoric acid swollen cellulose at pH 4, pH 5, pH 6, and pH 7.5, respectively. The combination of gallic acid (0.2% w/w) with both *Aspergillus fumigatus* GH61B polypeptide (10 mg protein per g cellulose) and *Aspergillus oryzae* CEL3A beta-glucosidase (10 mg protein per g cellulose) resulted in 21.7±3.0% conversion, 23.8±1.4% conversion, 17.3±0.3% conversion, and 5.6±0.7% conversion of phosphoric acid swollen cellulose at pH 4, pH 5, pH 6, and pH 7.5, respectively. The combination of gallic acid (0.2% w/w) with both *Trichoderma reesei* GH61B polypeptide (10 mg protein per g cellulose) and *Aspergillus oryzae* CEL3A beta-glucosidase (10 mg protein per g cellulose) resulted in 13.6±0.2% conversion, 15.9±0.6% conversion, 12.7±0.4% conversion, and 3.9±1.0% conversion of phosphoric acid swollen cellulose at pH 4, pH 5, pH 6, and pH 7.5, respectively.

Example 31

Enhancement of Microcrystalline Cellulose Cellulolysis by the *T. reesei* Cellulose Composition Using Combinations of Compounds and Various GH61 Polypeptides Combinations of compounds including: pyrogallol, 2-aminophenol, quercitin, 2-hydroxy-1,4-naphthoquinone, morin hydrate and naringenin (Sigma, St. Louis, Mo.) were tested in conjunction with various GH61 polypeptides for their combined ability to enhance cellulolysis by *T. reesei* cellulases. Saccharification reactions were performed as described (Example 8), using 29.5 mg per ml microcrystalline cellulose (AVICEL®) and 4 mg per g cellulose of *T. reesei* cellulase composition in 50 mM sodium acetate, 1 mM manganese sulfate at pH 5.0 at either a total compound concentration of 3 mM (1 mM of each compound) or a total concentration of 1 mM (0.33 mM of each compound) with GH61s including *Thermoascus aurantiacus* GH61A polypeptide and *Aspergillus fumigatus* GH61B polypeptide. Solutions of each compound were made in either 20% or 50% (v/v) methanol in 50 mM sodium acetate pH 5.0 with 1 mM manganese sulfate. These were added to saccharification reactions at a final concentration of 1 mM or 3 mM as described above. As a control, methanol was added to saccharification reactions at equivalent final concentrations.

Figure 15A:
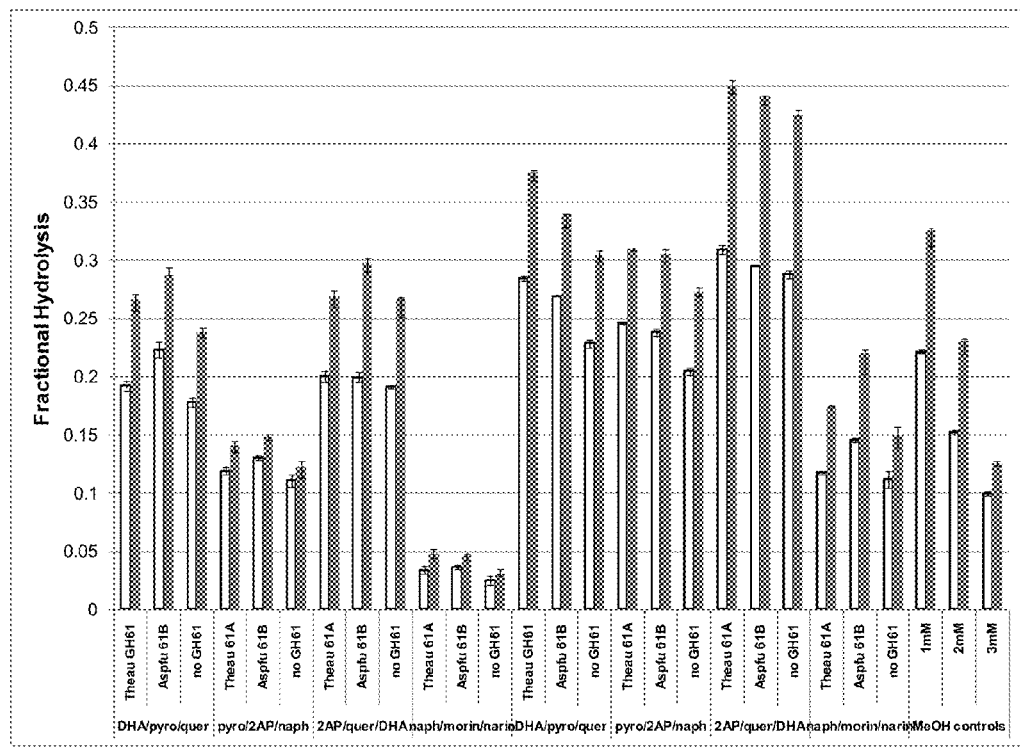
FIG. 15 shows (A) the fractional hydrolysis of AVICEL® by the *T. reesei* cellulase composition with various GH61 polypeptides as indicated, and combinations of compounds as indicated; and (B) the GH61 effect for mixtures of compounds at 1 mM and 3 mM concentration for various GH61 polypeptides as indicated. White bars: 3-days of hydrolysis; black bars: 7-days of hydrolysis. DHA: dehydroascorbate; pyro: pyrogallol; quer: quercitin hydrate; 2AP: 2-aminophenol; naph: 2-hydroxy-1,4-naphthoquinone; morin: morin hydrate; narin: naringenin; Theau: *Thermoascus aurantiacus* GH61A polypeptide; Aspfu: *Aspergillus fumigatus* GH61B polypeptide and 15B show the fractional hydrolysis of AVICEL® by the *T. reesei* cellulase composition with various GH61 polypeptides as indicated, and combinations of compounds.
Figure 15B:
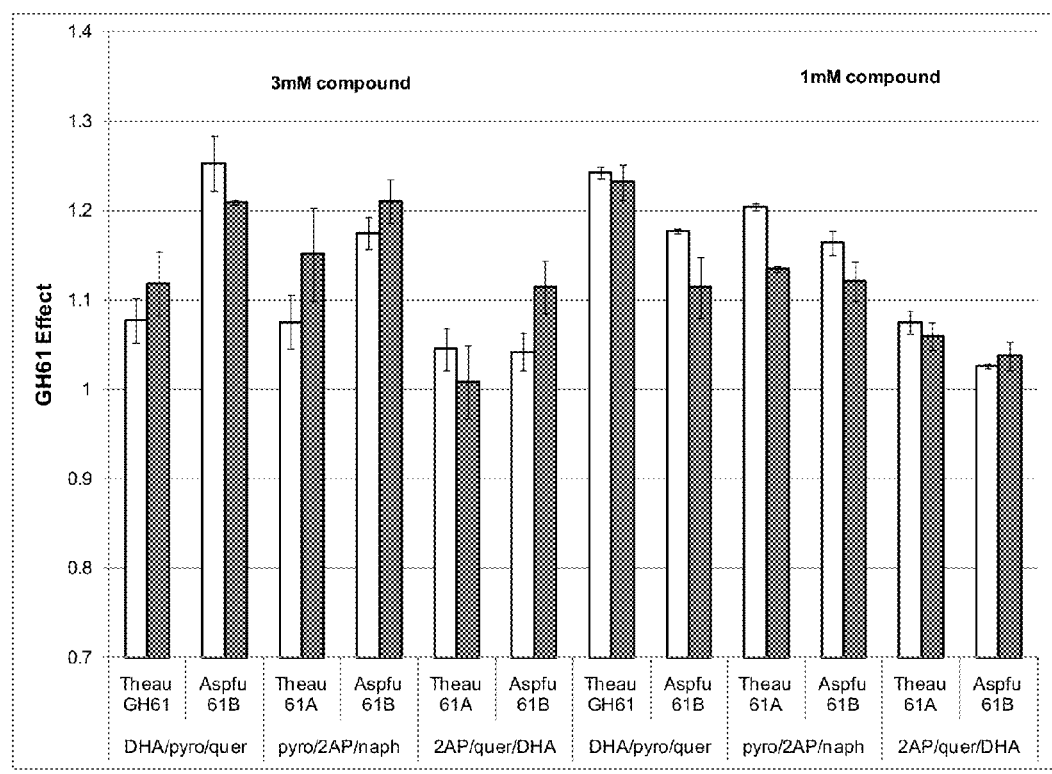

FIG. 15A shows the fractional hydrolysis of AVICEL® by the *T. reesei* cellulase composition with various GH61 polypeptides as indicated, and combinations of compounds as indicated. FIG. 15B shows the GH61 effect for each of these mixtures. The compound mixtures included: dehydroascorbate (DHA), pyrogallol (pyro) and quercitin (querc); pyrogallol, 2-aminophenol (2-AP), 2-hydroxy-1,4-naphthoquinone (naphtho); 2-aminophenol, quercitin, dehydroascorbate and 2-hydroxy-1,4-naphthoquinone, morin hydrate, naringenin. In each case the overall hydrolysis was enhanced by the combined presence of the compound mixtures and the GH61 polypeptides. In each case, the apparent fractional hydrolysis was higher at 1 mM concentration of compounds than either 3 mM compounds or control saccharifications. For most mixtures of compounds examined at 1 mM, *T. aurantiacus* GH61A polypeptide gave the greatest overall conversion, whereas at 3 mM, *A. fumigatus* GH61B generally gave the highest overall conversion.

The present invention is further described by the following numbered paragraphs:

[1] A composition comprising: (a) a polypeptide having cellulolytic enhancing activity and (b) a dioxy compound, wherein the combination of the polypeptide having cellulolytic enhancing activity and the dioxy compound enhances hydrolysis of a cellulosic material by a cellulolytic enzyme.

[2] The composition of paragraph 1, wherein the dioxy compound is a compound of formula (I):

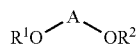

(I)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

A is a bond or an optionally substituted moiety selected from alkylene, alkenylene, alkynylene, cycloalkylene, heterocycloalkylene, arylene, and heteroarylene;

or a salt or solvate thereof.

[3] The composition of paragraph 2, wherein A is an optionally substituted moiety selected from alkylene, alkenylene, alkynylene, and cycloalkylene.

[4] The composition of paragraph 2, wherein A is an optionally substituted alkylene.

[5] The composition of paragraph 2, wherein A is an optionally substituted $C_1$-$C_6$ alkylene.

[6] The composition of paragraph 2, wherein A is an optionally substituted alkenylene.

[7] The composition of paragraph 2, wherein A is an optionally substituted $C_2$-$C_6$ alkenylene.

[8] The composition of paragraph 2, wherein A is an optionally substituted alkynylene.

[9] The composition of paragraph 2, wherein A is an optionally substituted $C_2$-$C_6$ alkynylene.

[10] The composition of paragraph 2, wherein A is an optionally substituted cycloalkylene.

[11] The composition of paragraph 2, wherein A is an optionally substituted $C_5$-$C_6$ cycloalkylene.

[12] The composition of paragraph 2, wherein A is an optionally substituted moiety selected from arylene and heteroarylene.

[13] The composition of paragraph 2, wherein A is an optionally substituted arylene (e.g., an optionally substituted 5 or 6-membered arylene).

[14] The composition of paragraph 2, wherein A is an optionally substituted heteroarylene (e.g., an optionally substituted 5 or 6-membered heteroarylene).

[15] The composition of paragraph 2, wherein A is an optionally substituted moiety selected from phenylene, pyrazolylene, furanylene, imidazolylene, isoxazolylene, oxadiazolylene, oxazolylene, pyrrolylene, pyridylene, pyrimidylene, pyridazinylene, thiazolylene, triazolylene, thienylene, dihydrothieno-pyrazolylene, thianaphthenylene, carbazolylene, benzimidazolylene, benzothienylene, benzofuranylene, indolylene, quinolinylene, benzotriazolylene, benzothiazolylene, benzooxazolylene, benzimidazolylene, isoquinolinylene, isoindolylene, acridinylene, benzoisazolylene, dimethylhydantoinene, pyrazinylene, tetrahydrofuranylene, pyrrolinylene, pyrrolidinylene, morpholinylene, indolylene, diazepinylene, azepinylene, thiepinylene, piperidinylene, and oxepinylene. In some aspects, A is an optionally substituted phenylene.

[16] The composition of paragraph 2, wherein the dioxy compound is of formula (II):

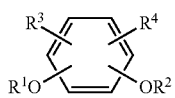

(II)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

$R^3$ and $R^4$ are independently hydrogen, halogen, —O$R^8$, —NO$_2$, —N($R^9$)($R^{10}$), —CN, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2R^{17}$, —SO$_2$N($R^{18}$)($R^{19}$), —S$R^{20}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^3$ and $R^4$ combine to form an optionally substituted fused ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, and $R^{20}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and $R^{17}$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or a salt or solvate thereof.

[17] The composition of any one of paragraphs 2-16, wherein when one of $R^1$ and $R^2$ is hydrogen, the other of $R^1$ and $R^2$ is not methyl.

[18] The composition of any one of paragraphs 2-16, wherein when one of $R^1$ and $R^2$ is hydrogen, the other of $R^1$ and $R^2$ is not alkyl.

[19] The composition of any one of paragraphs 2-18, wherein when one of $R^1$ and $R^2$ is hydrogen, the other of $R^1$ and $R^2$ is hydrogen, —C(O)$R^5$, —C(O)O$R^6$, —C(O)NH$R^7$, or an optionally substituted moiety selected from alkenyl, alkynyl, cycloalkyl, cycloalkyl-alkyl, heterocycloalkyl, heterocycloalkyl-alkyl, aryl, aralkyl, heteroaryl, and heteroaralkyl.

[20] The composition of any one of paragraphs 2-18, wherein $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether.

[21] The composition of any one of paragraphs 2-18, wherein $R^1$ and $R^2$ are independently hydrogen, or an optionally substituted moiety selected from alkyl, alkenyl, alkynyl, cycloalkyl, or cycloalkyl-alkyl.

[22] The composition of any one of paragraphs 2-18, wherein $R^1$ and $R^2$ are independently hydrogen, or an optionally substituted moiety selected from alkyl, alkenyl, and alkynyl.

[23] The composition of any one of paragraphs 2-18, wherein $R^1$ and $R^2$ are independently hydrogen, or an optionally substituted alkyl.

[24] The composition of any one of paragraphs 2-18, wherein $R^1$ and $R^2$ are independently hydrogen, or an optionally substituted $C_1$-$C_5$ alkyl.

[25] The composition of any one of paragraphs 2-18, wherein $R^1$ and $R^2$ are independently hydrogen, or a $C_1$-$C_5$ alkyl.

[26] The composition of any one of paragraphs 2-18, wherein $R^1$ and $R^2$ are independently hydrogen, or an optionally substituted methyl.

[27] The composition of any one of paragraphs 2-18, wherein $R^1$ and $R^2$ are independently hydrogen or methyl.

[28] The composition of any one of paragraphs 2-18, wherein at least one of $R^1$ and $R^2$ is hydrogen.

[29] The composition of any one of paragraphs 2-18, wherein both $R^1$ and $R^2$ are hydrogen.

[30] The composition of any one of paragraphs 2-18, wherein at least one of $R^1$ and $R^2$ is an optionally substituted $C_1$-$C_5$ alkyl.

[31] The composition of any one of paragraphs 2-18, wherein at least one of $R^1$ and $R^2$ is an optionally substituted methyl.

[32] The composition of any one of paragraphs 2-18, wherein at least one of $R^1$ and $R^2$ is methyl.

[33] The composition of any one of paragraphs 2-18, wherein both $R^1$ and $R^2$ are an optionally substituted $C_1$-$C_5$ alkyl.

[34] The composition of any one of paragraphs 2-18, wherein both $R^1$ and $R^2$ are $C_1$-$C_5$ alkyl.

[35] The composition of any one of paragraphs 2-18, wherein both $R^1$ and $R^2$ are methyl.

[36] The composition of any one of paragraphs 16-35, wherein $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[37] The composition of any one of paragraphs 16-35, wherein $R^3$ and $R^4$ are independently hydrogen, or an optionally substituted moiety selected from alkyl, alkenyl, alkynyl, cycloalkyl, or cycloalkyl-alkyl.

[38] The composition of any one of paragraphs 16-35, wherein $R^3$ and $R^4$ are independently hydrogen, or an optionally substituted moiety selected from alkyl, alkenyl, and alkynyl.

[39] The composition of any one of paragraphs 16-35, wherein $R^3$ and $R^4$ are independently hydrogen, halogen, —OH, —OR$^8$, —NO$_2$, —N(R$^9$)(R$^{10}$), —C(O)R$^5$, —C(O)OR$^6$, —C(O)NHR$^7$, —OC(O)R$^{11}$, —NHC(O)R$^{12}$, —OC(O)OR$^{13}$, —NHC(O)OR$^{14}$, —OC(O)NHR$^{15}$, —NHC(O)NHR$^{16}$, —SO$_2$R$^{17}$, or —SO$_2$N(R$^{18}$)(R$^{19}$).

[40] The composition of any one of paragraphs 16-35, wherein $R^3$ and $R^4$ are independently hydrogen, halogen, —OH, —OR$^8$, —C(O)R$^5$, —C(O)OR$^6$, —C(O)NHR$^7$, —OC(O)R$^{11}$, —NHC(O)R$^{12}$, —OC(O)OR$^{13}$, —NHC(O)OR$^{14}$, —OC(O)NHR$^{15}$, —NHC(O)NHR$^{16}$, or an optionally substituted moiety selected from alkyl, alkenyl, and alkynyl.

[41] The composition of any one of paragraphs 16-35, wherein $R^3$ and $R^4$ are independently hydrogen, halogen, —OH, —O—(C$_1$-C$_4$)alkyl, —C(O)—(C$_1$-C$_4$)alkyl, —C(O)OH, —C(O)O—(C$_1$-C$_4$)alkyl, —C(O)NH—(C$_1$-C$_4$)alkyl, —OC(O)—(C$_1$-C$_4$)alkyl, —NHC(O)—(C$_1$-C$_4$)alkyl, —OC(O)O—(C$_1$-C$_4$)alkyl, —NHC(O)O—(C$_1$-C$_4$)alkyl, —OC(O)NH—(C$_1$-C$_4$)alkyl, —NHC(O)NH—(C$_1$-C$_4$)alkyl, or an optionally substituted moiety selected from alkyl, alkenyl, and alkynyl.

[42] The composition of any one of paragraphs 16-35, wherein $R^3$ and $R^4$ are independently hydrogen, halogen, —OH, —O—(C$_1$-C$_4$)alkyl, —C(O)—(C$_1$-C$_4$)alkyl, —C(O)OH, —C(O)O—(C$_1$-C$_4$)alkyl, —C(O)NH—(C$_1$-C$_4$)alkyl, —OC(O)—(C$_1$-C$_4$)alkyl, —NHC(O)—(C$_1$-C$_4$)alkyl, —OC(O)O—(C$_1$-C$_4$)alkyl, —NHC(O)O—(C$_1$-C$_4$)alkyl, —OC(O)NH—(C$_1$-C$_4$)alkyl, —NHC(O)NH—(C$_1$-C$_4$)alkyl, or a moiety selected from alkyl, alkenyl, and alkynyl.

[43] The composition of any one of paragraphs 16-35, wherein $R^3$ and $R^4$ are independently hydrogen, halogen, —OH, —O—(C$_1$-C$_4$)alkyl, —C(O)—(C$_1$-C$_4$)alkyl, —C(O)OH, —C(O)O—(C$_1$-C$_4$)alkyl, or a moiety selected from alkyl, alkenyl, and alkynyl.

[44] The composition of any one of paragraphs 16-35, wherein one of $R^3$ and $R^4$ is —OH.

[45] The composition of any one of paragraphs 16-35, wherein at least one of $R^3$ and $R^4$ is hydrogen.

[46] The composition of any one of paragraphs 16-35, wherein both $R^3$ and $R^4$ are hydrogen.

[47] The composition of any one of paragraphs 16-35, wherein at least one of $R^3$ and $R^4$ is other than hydrogen.

[48] The composition of any one of paragraphs 16-35, wherein both $R^3$ and $R^4$ are other than hydrogen.

[49] The composition of any one of paragraphs 16-35, wherein both $R^1$ and $R^2$ are hydrogen; and wherein one of $R^3$ and $R^4$ is —OH.

[50] The composition of any one of paragraphs 16-35, wherein both $R^1$ and $R^2$ are optionally substituted alkyl; and wherein one of $R^3$ and $R^4$ is —OH.

[51] The composition of any one of paragraphs 16-35, wherein both $R^1$ and $R^2$ are optionally substituted —(C$_1$-C$_5$)alkyl; and wherein one of $R^3$ and $R^4$ is —OH.

[52] The composition of any one of paragraphs 16-35, wherein both $R^1$ and $R^2$ are optionally substituted methyl; and wherein one of $R^3$ and $R^4$ is —OH.

[53] The composition of paragraph 16, wherein the dioxy compound is of the formula (II-A):

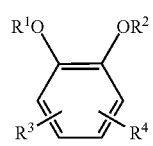

(II-A)

wherein $R^1$, $R^2$, $R^3$, and $R^4$ are as defined in any one of the preceding paragraphs;

or a salt or solvate thereof.

[54] The composition of paragraph 53, wherein when one of $R^1$ and $R^2$ is hydrogen, the other of $R^1$ and $R^2$ is not methyl.

[55] The composition of paragraph 53, wherein when one of $R^1$ and $R^2$ is hydrogen, the other of $R^1$ and $R^2$ is not alkyl.

[56] The composition of paragraph 53, wherein when one of $R^1$ and $R^2$ is hydrogen, the other of $R^1$ and $R^2$ is hydrogen, —C(O)R$^5$, —C(O)OR$^6$, —C(O)NHR$^7$, or an optionally substituted moiety selected from alkenyl, alkynyl, cycloalkyl, cycloalkyl-alkyl, heterocycloalkyl, heterocycloalkyl-alkyl, aryl, aralkyl, heteroaryl, and heteroaralkyl.

[57] The composition of any one of paragraphs 53-56, wherein $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether.

[58] The composition of any one of paragraphs 53-56, wherein $R^1$ and $R^2$ are independently hydrogen, or an optionally substituted moiety selected from alkyl, alkenyl, alkynyl, cycloalkyl, or cycloalkyl-alkyl.

[59] The composition of any one of paragraphs 53-56, wherein $R^1$ and $R^2$ are independently hydrogen, or an optionally substituted moiety selected from alkyl, alkenyl, and alkynyl.

[60] The composition of any one of paragraphs 53-56, wherein $R^1$ and $R^2$ are independently hydrogen, or an optionally substituted alkyl.

[61] The composition of any one of paragraphs 53-56, wherein $R^1$ and $R^2$ are independently hydrogen, or an optionally substituted $C_1$-$C_5$ alkyl.

[62] The composition of any one of paragraphs 53-56, wherein $R^1$ and $R^2$ are independently hydrogen, or a $C_1$-$C_5$ alkyl.

[63] The composition of any one of paragraphs 53-56, wherein $R^1$ and $R^2$ are independently hydrogen, or an optionally substituted methyl.

[64] The composition of any one of paragraphs 53-56, wherein $R^1$ and $R^2$ are independently hydrogen or methyl.

[65] The composition of any one of paragraphs 53-56, wherein at least one of $R^1$ and $R^2$ is hydrogen.

[66] The composition of any one of paragraphs 53-56, wherein both $R^1$ and $R^2$ are hydrogen.

[67] The composition of any one of paragraphs 53-56, wherein at least one of $R^1$ and $R^2$ is an optionally substituted $C_1$-$C_5$ alkyl.

[68] The composition of any one of paragraphs 53-56, wherein at least one of $R^1$ and $R^2$ is an optionally substituted methyl.

[69] The composition of any one of paragraphs 53-56, wherein at least one of $R^1$ and $R^2$ is methyl.

[70] The composition of any one of paragraphs 53-56, wherein both $R^1$ and $R^2$ are an optionally substituted $C_1$-$C_5$ alkyl.

[71] The composition of any one of paragraphs 53-56, wherein both $R^1$ and $R^2$ are $C_1$-$C_5$ alkyl.

[72] The composition of any one of paragraphs 53-56, wherein both $R^1$ and $R^2$ are methyl.

[73] The composition of paragraph 53, wherein the dioxy compound is of the formula (II-B):

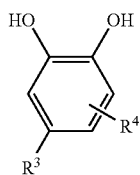

(II-B)

wherein $R^3$, and $R^4$ are as defined in any one of the preceding paragraphs;
or a salt or solvate thereof.

[74] The composition of any one of paragraphs 53-73, wherein $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[75] The composition of any one of paragraphs 53-73, wherein $R^3$ and $R^4$ are independently hydrogen, or an optionally substituted moiety selected from alkyl, alkenyl, alkynyl, cycloalkyl, or cycloalkyl-alkyl.

[76] The composition of any one of paragraphs 53-73, wherein $R^3$ and $R^4$ are independently hydrogen, or an optionally substituted moiety selected from alkyl, alkenyl, and alkynyl.

[77] The composition of any one of paragraphs 53-73, wherein $R^3$ and $R^4$ are independently hydrogen, halogen, —OH, —$OR^8$, —$NO_2$, —$N(R^9)(R^{10})$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, —$SO_2R^{17}$, or —$SO_2N(R^{18})(R^{19})$.

[78] The composition of any one of paragraphs 53-73, wherein $R^3$ and $R^4$ are independently hydrogen, halogen, —OH, —$OR^8$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, or an optionally substituted moiety selected from alkyl, alkenyl, and alkynyl.

[79] The composition of any one of paragraphs 53-73, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl.

[80] The composition of any one of paragraphs 53-73, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl.

[81] The composition of any one of paragraphs 53-73, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl.

[82] The composition of any one of paragraphs 53-73, wherein one of $R^3$ and $R^4$ is —OH.

[83] The composition of any one of paragraphs 53-73, wherein at least one of $R^3$ and $R^4$ is hydrogen.

[84] The composition of any one of paragraphs 53-73, wherein both $R^3$ and $R^4$ are hydrogen.

[85] The composition of any one of paragraphs 53-73, wherein at least one of $R^3$ and $R^4$ is other than hydrogen.

[86] The composition of any one of paragraphs 53-73, wherein both $R^3$ and $R^4$ are other than hydrogen.

[87] The composition of any one of paragraphs 53-73, wherein both $R^1$ and $R^2$ are hydrogen; and wherein one of $R^3$ and $R^4$ is —OH.

[88] The composition of any one of paragraphs 53-87, wherein both $R^1$ and $R^2$ are optionally substituted alkyl; and wherein one of $R^3$ and $R^4$ is —OH.

[89] The composition of any one of paragraphs 53-87, wherein both $R^1$ and $R^2$ are optionally substituted —($C_1$-$C_5$) alkyl; and wherein one of $R^3$ and $R^4$ is —OH.

[90] The composition of any one of paragraphs 53-87, wherein both $R^1$ and $R^2$ are optionally substituted methyl; and wherein one of $R^3$ and $R^4$ is —OH.

[91] The composition of paragraph 16, wherein the dioxy compound is of the formula (II-C):

(II-C)

wherein $R^1$, $R^2$, $R^3$, and $R^4$ are as defined in any one of the preceding paragraphs;
or a salt or solvate thereof.

[92] The composition of paragraph 91, wherein $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[93] The composition of paragraph 91, wherein $R^1$ and $R^2$ are independently hydrogen, or an optionally substituted moiety selected from alkyl, alkenyl, alkynyl, cycloalkyl, or cycloalkyl-alkyl.

[94] The composition of paragraph 91, wherein $R^1$ and $R^2$ are independently hydrogen, or an optionally substituted moiety selected from alkyl, alkenyl, and alkynyl.

[95] The composition of paragraph 91, wherein $R^1$ and $R^2$ are independently hydrogen, or an optionally substituted alkyl.

[96] The composition of paragraph 91, wherein $R^1$ and $R^2$ are independently hydrogen, or an optionally substituted $C_1$-$C_5$ alkyl.

[97] The composition of paragraph 91, wherein $R^1$ and $R^2$ are independently hydrogen, or a $C_1$-$C_5$ alkyl.

[98] The composition of paragraph 91, wherein $R^1$ and $R^2$ are independently hydrogen, or an optionally substituted methyl.

[99] The composition of paragraph 91, wherein $R^1$ and $R^2$ are independently hydrogen or methyl.

[100] The composition of paragraph 91, wherein at least one of $R^1$ and $R^2$ is hydrogen.

[101] The composition of paragraph 91, wherein both $R^1$ and $R^2$ are hydrogen.

[102] The composition of paragraph 91, wherein at least one of $R^1$ and $R^2$ is an optionally substituted $C_1$-$C_5$ alkyl.

[103] The composition of paragraph 91, wherein at least one of $R^1$ and $R^2$ is an optionally substituted methyl.

[104] The composition of paragraph 91, wherein at least one of $R^1$ and $R^2$ is methyl.

[105] The composition of paragraph 91, wherein both $R^1$ and $R^2$ are an optionally substituted $C_1$-$C_5$ alkyl.

[106] The composition of paragraph 91, wherein both $R^1$ and $R^2$ are $C_1$-$C_5$ alkyl.

[107] The composition of paragraph 91, wherein both $R^1$ and $R^2$ are methyl.

[108] The composition of any one of paragraphs 91-107, wherein $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[109] The composition of any one of paragraphs 91-107, wherein $R^3$ and $R^4$ are independently hydrogen, or an optionally substituted moiety selected from alkyl, alkenyl, alkynyl, cycloalkyl, or cycloalkyl-alkyl.

[110] The composition of any one of paragraphs 91-107, wherein $R^3$ and $R^4$ are independently hydrogen, or an optionally substituted moiety selected from alkyl, alkenyl, and alkynyl.

[111] The composition of any one of paragraphs 91-107, wherein $R^3$ and $R^4$ are independently hydrogen, halogen, —OH, —$OR^8$, —$NO_2$, —$N(R^9)(R^{10})$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, —$SO_2R^{17}$, or —$SO_2N(R^{18})(R^{19})$.

[112] The composition of any one of paragraphs 91-107, wherein $R^3$ and $R^4$ are independently hydrogen, halogen, —OH, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, or an optionally substituted moiety selected from alkyl, alkenyl, and alkynyl.

[113] The composition of any one of paragraphs 91-107, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl.

[114] The composition of any one of paragraphs 91-107, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl.

[115] The composition of any one of paragraphs 91-107, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl.

[116] The composition of any one of paragraphs 91-107, wherein one of $R^3$ and $R^4$ is —OH.

[117] The composition of any one of paragraphs 91-107, wherein at least one of $R^3$ and $R^4$ is hydrogen.

[118] The composition of any one of paragraphs 91-107, wherein both $R^3$ and $R^4$ are hydrogen.

[119] The composition of any one of paragraphs 91-107, wherein at least one of $R^3$ and $R^4$ is other than hydrogen.

[120] The composition of any one of paragraphs 91-107, wherein both $R^3$ and $R^4$ are other than hydrogen.

[121] The composition of any one of paragraphs 91-120, wherein both $R^1$ and $R^2$ are hydrogen; and wherein one of $R^3$ and $R^4$ is —OH.

[122] The composition of any one of paragraphs 91-120, wherein both $R^1$ and $R^2$ are optionally substituted alkyl; and wherein one of $R^3$ and $R^4$ is —OH.

[123] The composition of any one of paragraphs 91-120, wherein both $R^1$ and $R^2$ are optionally substituted —($C_1$-$C_5$) alkyl; and wherein one of $R^3$ and $R^4$ is —OH.

[124] The composition of any one of paragraphs 91-120, wherein both $R^1$ and $R^2$ are optionally substituted methyl; and wherein one of $R^3$ and $R^4$ is —OH.

[125] The composition of any one of paragraphs 91-124, wherein the dioxy compound is of the formula (II-D):

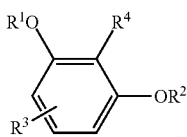

(II-D)

or a salt or solvate thereof.

[126] The composition of paragraph 125, wherein the dioxy compound is of the formula (II-E):

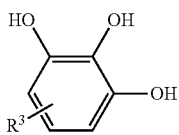

(II-E)

or a salt or solvate thereof.

[127] The composition of paragraph 2, wherein the dioxy compound is selected from the group consisting of: (I-1): pyrocatechol or catechol; (I-2): caffeic acid; (I-3): 3,4-dihydroxybenzoic acid; (I-4): 4-tert-butyl-5-methoxy-1,2-benzenediol; (I-5): pyrogallol; (I-6): gallic acid; (I-7): methyl-3,4,5-trihydroxybenzoate; (I-8): 2,3,4-trihydroxybenzophenone; (I-9): 2,6-dimethoxyphenol; (I-10): sinapinic acid; (I-12): 3,5-dihydroxybenzoic acid; (I-12): 4-chloro-1,2-benzenediol; (I-13): 4-nitro-1,2-benzenediol; (I-14): tannic acid; (I-15): ethyl gallate; (I-16): methyl glycolate; (I-17): dihydroxyfumaric acid; (I-18): 2-butyne-1,4-diol; (I-19): croconic acid; (I-20): 1,3-propanediol; (I-21): tartaric acid; (I-22): 2,4-pentanediol; (I-23): 3-ethyoxy-1,2-propanediol; (I-24): 2,4,4'-trihydroxybenzophenone; (I-25): cis-2-butene-1,4-diol; (I-26): 3,4-dihydroxy-3-cyclobutene-1,2-dione; (I-27): dihydroxyacetone; (I-28): acrolein acetal; (I-29): methyl-4-hydroxybenzoate; (I-30): 4-hydroxybenzoic acid; and (I-31): methyl-3,5-dimethoxy-4-hydroxybenzoate; and (I-32): pyrocatechol violet or a salt or solvate thereof.

[128] The composition of any one of paragraphs 1-127, which further comprises (c) one or more (e.g., several) enzymes selected from the group consisting of a cellulase, a hemicellulase, an expansin, an esterase, a laccase, a ligninolytic enzyme, a pectinase, a peroxidase, a protease, and a swollenin.

[129] The composition of paragraph 128, wherein the cellulase is one or more (e.g., several) enzymes selected from the group consisting of an endoglucanase, a cellobiohydrolase, and a beta-glucosidase.

[130] The composition of paragraph 128, wherein the hemicellulase is one or more (e.g., several) enzymes selected from the group consisting of a xylanase, an acetylxylan esterase, a feruloyl esterase, an arabinofuranosidase, a xylosidase, and a glucuronidase.

[131] A method for degrading or converting a cellulosic material, comprising: treating the cellulosic material with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition.

[132] The method of paragraph 131, wherein the cellulosic material is pretreated.

[133] The method of paragraph 131 or 132, further comprising recovering the degraded cellulosic material.

[134] The method of any one of paragraphs 131-133, wherein the enzyme composition comprises one or more (e.g., several) enzymes selected from the group consisting of a cellulase, a hemicellulase, an expansin, an esterase, a laccase, a ligninolytic enzyme, a pectinase, a peroxidase, a protease, and a swollenin.

[135] The method of paragraph 134, wherein the cellulase is one or more (e.g., several) enzymes selected from the group consisting of an endoglucanase, a cellobiohydrolase, and a beta-glucosidase.

[136] The method of paragraph 134, wherein the hemicellulase is one or more (e.g., several) enzymes selected from the group consisting of a xylanase, an acetylxylan esterase, a feruloyl esterase, an arabinofuranosidase, a xylosidase, and a glucuronidase.

[137] The method of any of paragraphs 131-136, wherein the degraded cellulosic material is a sugar.

[138] The method of paragraph 137, wherein the sugar is selected from the group consisting of glucose, xylose, mannose, galactose, and arabinose.

[139] A method for producing a fermentation product, comprising:
(a) saccharifying a cellulosic material with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition;
(b) fermenting the saccharified cellulosic material with one or more fermenting microorganisms to produce the fermentation product; and
(c) recovering the fermentation product from the fermentation.

[140] The method of paragraph 139, wherein the cellulosic material is pretreated.

[141] The method of paragraph 139 or 140, wherein the enzyme composition comprises one or more (e.g., several) enzymes selected from the group consisting of a cellulase, a hemicellulase, an expansin, an esterase, a laccase, a ligninolytic enzyme, a pectinase, a peroxidase, a protease, and a swollenin.

[142] The method of paragraph 141, wherein the cellulase is one or more (e.g., several) enzymes selected from the group consisting of an endoglucanase, a cellobiohydrolase, and a beta-glucosidase.

[143] The method of paragraph 141, wherein the hemicellulase is one or more (e.g., several) enzymes selected from the group consisting of a xylanase, an acetylxylan esterase, a feruloyl esterase, an arabinofuranosidase, a xylosidase, and a glucuronidase.

[144] The method of any one of paragraphs 139-143, wherein steps (a) and (b) are performed simultaneously in a simultaneous saccharification and fermentation.

[145] The method of any one of paragraphs 139-144, wherein the fermentation product is an alcohol, an alkane, a cycloalkane, an alkene, an amino acid, a gas, isoprene, a ketone, an organic acid, or polyketide.

[146] A method of fermenting a cellulosic material, comprising: fermenting the cellulosic material with one or more fermenting microorganisms, wherein the cellulosic material is saccharified with an enzyme composition in the presence of a polypeptide having cellulolytic enhancing activity and a dioxy compound, wherein the combination of the polypeptide having cellulolytic enhancing activity and the dioxy compound enhances hydrolysis of the cellulosic material by the enzyme composition.

[147] The method of paragraph 146, wherein the cellulosic material is pretreated before saccharification.

[148] The method of paragraph 146 or 147, wherein the enzyme composition comprises one or more (e.g., several) enzymes selected from the group consisting of a cellulase, a hemicellulase, an expansin, an esterase, a laccase, a ligninolytic enzyme, a pectinase, a peroxidase, a protease, and a swollenin.

[149] The method of paragraph 148, wherein the cellulase is one or more (e.g., several) enzymes selected from the group consisting of an endoglucanase, a cellobiohydrolase, and a beta-glucosidase.

[150] The method of paragraph 148, wherein the hemicellulase is one or more (e.g., several) enzymes selected from the group consisting of a xylanase, an acetylxylan esterase, a feruloyl esterase, an arabinofuranosidase, a xylosidase, and a glucuronidase.

[151] The method of any one of paragraphs 146-150, wherein the fermenting of the cellulosic material produces a fermentation product.

[152] The method of paragraph 151, further comprising recovering the fermentation product from the fermentation.

[153] The method of paragraph 151 or 152, wherein the fermentation product is an alcohol, an alkane, a cycloalkane, an alkene, an amino acid, a gas, isoprene, a ketone, an organic acid, or polyketide.

[154] The method of any one of paragraphs 131-153, wherein the dioxy compound is a compound of formula (I):

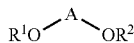

(I)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

A is a bond or an optionally substituted moiety selected from alkylene, alkenylene, alkynylene, cycloalkylene, heterocycloalkylene, arylene, and heteroarylene;

or a salt or solvate thereof.

[155] The method of paragraph 154, wherein A is an optionally substituted moiety selected from alkylene, alkenylene, alkynylene, and cycloalkylene.

[156] The method of paragraph 154, wherein A is an optionally substituted alkylene.

[157] The method of paragraph 154, wherein A is an optionally substituted $C_1$-$C_6$ alkylene.

[158] The method of paragraph 154, wherein A is an optionally substituted alkenylene.

[159] The method of paragraph 154, wherein A is an optionally substituted $C_2$-$C_6$ alkenylene.

[160] The method of paragraph 154, wherein A is an optionally substituted alkynylene.

[161] The method of paragraph 154, wherein A is an optionally substituted $C_2$-$C_6$ alkynylene.

[162] The method of paragraph 154, wherein A is an optionally substituted cycloalkylene.

[163] The method of paragraph 154, wherein A is an optionally substituted $C_5$-$C_6$ cycloalkylene.

[164] The method of paragraph 154, wherein A is an optionally substituted moiety selected from arylene and heteroarylene.

[165] The method of paragraph 154, wherein A is an optionally substituted arylene (e.g., an optionally substituted 5 or 6-membered arylene).

[166] The method of paragraph 154, wherein A is an optionally substituted heteroarylene (e.g., an optionally substituted 5 or 6-membered heteroarylene).

[167] The method of paragraph 154, wherein A is an optionally substituted moiety selected from phenylene, pyrazolylene, furanylene, imidazolylene, isoxazolylene, oxadiazolylene, oxazolylene, pyrrolylene, pyridylene, pyrimidylene, pyridazinylene, thiazolylene, triazolylene, thienylene, dihydrothieno-pyrazolylene, thianaphthenylene, carbazolylene, benzimidazolylene, benzothienylene, benzofuranylene, indolylene, quinolinylene, benzotriazolylene, benzothiazolylene, benzooxazolylene, benzimidazolylene, isoquinolinylene, isoindolylene, acridinylene, benzoisazolylene, dimethylhydantoinene, pyrazinylene, tetrahydrofuranylene, pyrrolinylene, pyrrolidinylene, morpholinylene, indolylene, diazepinylene, azepinylene, thiepinylene, piperidinylene, and oxepinylene. In some aspects, A is an optionally substituted phenylene.

[168] The method of paragraph 154, wherein the dioxy compound is of formula (II):

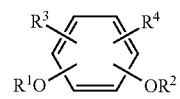

(II)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

$R^3$ and $R^4$ are independently hydrogen, halogen, —O$R^8$, —NO$_2$, —N($R^9$)($R^{10}$), —CN, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2$$R^{17}$, —SO$_2$N($R^{18}$)($R^{19}$), —S$R^{20}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^3$ and $R^4$ combine to form an optionally substituted fused ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, and $R^{20}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and $R^{17}$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or a salt or solvate thereof.

[169] The method of any one of paragraphs 154-168, wherein when one of $R^1$ and $R^2$ is hydrogen, the other of $R^1$ and $R^2$ is not methyl.

[170] The method of any one of paragraphs 154-168, wherein when one of $R^1$ and $R^2$ is hydrogen, the other of $R^1$ and $R^2$ is not alkyl.

[171] The method of any one of paragraphs 154-170, wherein when one of $R^1$ and $R^2$ is hydrogen, the other of $R^1$ and $R^2$ is hydrogen, —C(O)$R^5$, —C(O)O$R^6$, —C(O)NH$R^7$, or an optionally substituted moiety selected from alkenyl, alkynyl, cycloalkyl, cycloalkyl-alkyl, heterocycloalkyl, heterocycloalkyl-alkyl, aryl, aralkyl, heteroaryl, and heteroaralkyl.

[172] The method of any one of paragraphs 154-170, wherein $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether.

[173] The method of any one of paragraphs 154-170, wherein $R^1$ and $R^2$ are independently hydrogen, or an optionally substituted moiety selected from alkyl, alkenyl, alkynyl, cycloalkyl, or cycloalkyl-alkyl.

[174] The method of any one of paragraphs 154-170, wherein $R^1$ and $R^2$ are independently hydrogen, or an optionally substituted moiety selected from alkyl, alkenyl, and alkynyl.

[175] The method of any one of paragraphs 154-170, wherein $R^1$ and $R^2$ are independently hydrogen, or an optionally substituted alkyl.

[176] The method of any one of paragraphs 154-170, wherein $R^1$ and $R^2$ are independently hydrogen, or an optionally substituted $C_1$-$C_5$ alkyl.

[177] The method of any one of paragraphs 154-170, wherein $R^1$ and $R^2$ are independently hydrogen, or a $C_1$-$C_5$ alkyl.

[178] The method of any one of paragraphs 154-170, wherein $R^1$ and $R^2$ are independently hydrogen, or an optionally substituted methyl.

[179] The method of any one of paragraphs 154-170, wherein $R^1$ and $R^2$ are independently hydrogen or methyl.

[180] The method of any one of paragraphs 154-170, wherein at least one of $R^1$ and $R^2$ is hydrogen.

[181] The method of any one of paragraphs 154-170, wherein both $R^1$ and $R^2$ are hydrogen.

[182] The method of any one of paragraphs 154-170, wherein at least one of $R^1$ and $R^2$ is an optionally substituted $C_1$-$C_5$ alkyl.

[183] The method of any one of paragraphs 154-170, wherein at least one of $R^1$ and $R^2$ is an optionally substituted methyl.

[184] The method of any one of paragraphs 154-170, wherein at least one of $R^1$ and $R^2$ is methyl.

[185] The method of any one of paragraphs 154-170, wherein both $R^1$ and $R^2$ are an optionally substituted $C_1$-$C_5$ alkyl.

[186] The method of any one of paragraphs 154-170, wherein both $R^1$ and $R^2$ are $C_1$-$C_5$ alkyl.

[187] The method of any one of paragraphs 154-170, wherein both $R^1$ and $R^2$ are methyl.

[188] The method of any one of paragraphs 168-187, wherein $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[189] The method of any one of paragraphs 168-187, wherein $R^3$ and $R^4$ are independently hydrogen, or an optionally substituted moiety selected from alkyl, alkenyl, alkynyl, cycloalkyl, or cycloalkyl-alkyl.

[190] The method of any one of paragraphs 168-187, wherein $R^3$ and $R^4$ are independently hydrogen, or an optionally substituted moiety selected from alkyl, alkenyl, and alkynyl.

[191] The method of any one of paragraphs 168-187, wherein $R^3$ and $R^4$ are independently hydrogen, halogen, —OH, —O$R^8$, —NO$_2$, —N($R^9$)($R^{10}$), —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2$$R^{17}$, or —SO$_2$N($R^{18}$)($R^{19}$).

[192] The method of any one of paragraphs 168-187, wherein $R^3$ and $R^4$ are independently hydrogen, halogen, —OH, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, or an optionally substituted moiety selected from alkyl, alkenyl, and alkynyl.

[193] The method of any one of paragraphs 168-187, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl.

[194] The method of any one of paragraphs 168-187, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl.

[195] The method of any one of paragraphs 168-187, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl.

[196] The method of any one of paragraphs 168-187, wherein one of $R^3$ and $R^4$ is —OH.

[197] The method of any one of paragraphs 168-187, wherein at least one of $R^3$ and $R^4$ is hydrogen.

[198] The method of any one of paragraphs 168-187, wherein both $R^3$ and $R^4$ are hydrogen.

[199] The method of any one of paragraphs 168-187, wherein at least one of $R^3$ and $R^4$ is other than hydrogen.

[200] The method of any one of paragraphs 168-187, wherein both $R^3$ and $R^4$ are other than hydrogen.

[201] The method of any one of paragraphs 168-200, wherein both $R^1$ and $R^2$ are hydrogen; and wherein one of $R^3$ and $R^4$ is —OH.

[202] The method of any one of paragraphs 168-200, wherein both $R^1$ and $R^2$ are optionally substituted alkyl; and wherein one of $R^3$ and $R^4$ is —OH.

[203] The method of any one of paragraphs 168-200, wherein both $R^1$ and $R^2$ are optionally substituted —($C_1$-$C_5$) alkyl; and wherein one of $R^3$ and $R^4$ is —OH.

[204] The method of any one of paragraphs 168-200, wherein both $R^1$ and $R^2$ are optionally substituted methyl; and wherein one of $R^3$ and $R^4$ is —OH.

[205] The method of paragraph 168, wherein the dioxy compound is of the formula (II-A):

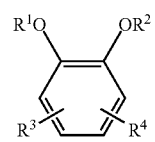

(II-A)

wherein $R^1$, $R^2$, $R^3$, and $R^4$ are as defined in any one of the preceding paragraphs;

or a salt or solvate thereof.

[206] The method of paragraph 205, wherein when one of $R^1$ and $R^2$ is hydrogen, the other of $R^1$ and $R^2$ is not methyl.

[207] The method of paragraph 205, wherein when one of $R^1$ and $R^2$ is hydrogen, the other of $R^1$ and $R^2$ is not alkyl.

[208] The method of paragraph 205, wherein when one of $R^1$ and $R^2$ is hydrogen, the other of $R^1$ and $R^2$ is hydrogen, —C(O)$R^5$, —C(O)O$R^6$, —C(O)NH$R^7$, or an optionally substituted moiety selected from alkenyl, alkynyl, cycloalkyl, cycloalkyl-alkyl, heterocycloalkyl, heterocycloalkyl-alkyl, aryl, aralkyl, heteroaryl, and heteroaralkyl.

[209] The method of any one of paragraphs 205-208, wherein $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether.

[210] The method of any one of paragraphs 205-208, wherein $R^1$ and $R^2$ are independently hydrogen, or an optionally substituted moiety selected from alkyl, alkenyl, alkynyl, cycloalkyl, or cycloalkyl-alkyl.

[211] The method of any one of paragraphs 205-208, wherein $R^1$ and $R^2$ are independently hydrogen, or an optionally substituted moiety selected from alkyl, alkenyl, and alkynyl.

[212] The method of any one of paragraphs 205-208, wherein $R^1$ and $R^2$ are independently hydrogen, or an optionally substituted alkyl.

[213] The method of any one of paragraphs 205-208, wherein $R^1$ and $R^2$ are independently hydrogen, or an optionally substituted $C_1$-$C_5$ alkyl.

[214] The method of any one of paragraphs 205-208, wherein $R^1$ and $R^2$ are independently hydrogen, or a $C_1$-$C_5$ alkyl.

[215] The method of any one of paragraphs 205-208, wherein $R^1$ and $R^2$ are independently hydrogen, or an optionally substituted methyl.

[216] The method of any one of paragraphs 205-208, wherein $R^1$ and $R^2$ are independently hydrogen or methyl.

[217] The method of any one of paragraphs 205-208, wherein at least one of $R^1$ and $R^2$ is hydrogen.

[218] The method of any one of paragraphs 205-208, wherein both $R^1$ and $R^2$ are hydrogen.

[219] The method of any one of paragraphs 205-208, wherein at least one of $R^1$ and $R^2$ is an optionally substituted $C_1$-$C_5$ alkyl.

[220] The method of any one of paragraphs 205-208, wherein at least one of $R^1$ and $R^2$ is an optionally substituted methyl.

[221] The method of any one of paragraphs 205-208, wherein at least one of $R^1$ and $R^2$ is methyl.

[222] The method of any one of paragraphs 205-208, wherein both $R^1$ and $R^2$ are an optionally substituted $C_1$-$C_5$ alkyl.

[223] The method of any one of paragraphs 205-208, wherein both $R^1$ and $R^2$ are $C_1$-$C_5$ alkyl.

[224] The method of any one of paragraphs 205-208, wherein both $R^1$ and $R^2$ are methyl.

[225] The method of paragraph 205, wherein the dioxy compound is of the formula (II-B):

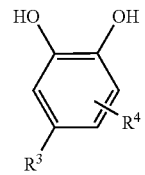

(II-B)

wherein $R^3$, and $R^4$ are as defined in any one of the preceding paragraphs;
or a salt or solvate thereof.

[226] The method of any one of paragraphs 205-225, wherein $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[227] The method of any one of paragraphs 205-225, wherein $R^3$ and $R^4$ are independently hydrogen, or an optionally substituted moiety selected from alkyl, alkenyl, alkynyl, cycloalkyl, or cycloalkyl-alkyl.

[228] The method of any one of paragraphs 205-225, wherein $R^3$ and $R^4$ are independently hydrogen, or an optionally substituted moiety selected from alkyl, alkenyl, and alkynyl.

[229] The method of any one of paragraphs 205-225, wherein $R^3$ and $R^4$ are independently hydrogen, halogen, —OH, —O$R^8$, —NO$_2$, —N($R^9$)($R^{10}$), —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2$$R^{17}$, or —SO$_2$N($R^{18}$)($R^{19}$).

[230] The method of any one of paragraphs 205-225, wherein $R^3$ and $R^4$ are independently hydrogen, halogen, —OH, —O$R^8$, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, or an optionally substituted moiety selected from alkyl, alkenyl, and alkynyl.

[231] The method of any one of paragraphs 205-225, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl.

[232] The method of any one of paragraphs 205-225, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl.

[233] The method of any one of paragraphs 205-225, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl.

[234] The method of any one of paragraphs 205-225, wherein one of $R^3$ and $R^4$ is —OH.

[235] The method of any one of paragraphs 205-225, wherein at least one of $R^3$ and $R^4$ is hydrogen.

[236] The method of any one of paragraphs 205-225, wherein both $R^3$ and $R^4$ are hydrogen.

[237] The method of any one of paragraphs 205-225, wherein at least one of $R^3$ and $R^4$ is other than hydrogen.

[238] The method of any one of paragraphs 205-225, wherein both $R^3$ and $R^4$ are other than hydrogen.

[239] The method of any one of paragraphs 205-238, wherein both $R^1$ and $R^2$ are hydrogen; and wherein one of $R^3$ and $R^4$ is —OH.

[240] The method of any one of paragraphs 205-238, wherein both $R^1$ and $R^2$ are optionally substituted alkyl; and wherein one of $R^3$ and $R^4$ is —OH.

[241] The method of any one of paragraphs 205-238, wherein both $R^1$ and $R^2$ are optionally substituted —($C_1$-$C_5$) alkyl; and wherein one of $R^3$ and $R^4$ is —OH.

[242] The method of any one of paragraphs 205-238, wherein both $R^1$ and $R^2$ are optionally substituted methyl; and wherein one of $R^3$ and $R^4$ is —OH.

[243] The method of paragraph 168, wherein the dioxy compound is of the formula (II-C):

(II-C)

wherein $R^1$, $R^2$, $R^3$, and $R^4$ are as defined in any one of the preceding paragraphs; or a salt or solvate thereof.

[244] The method of paragraph 243, wherein $R^1$ and $R^2$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[245] The method of paragraph 243, wherein $R^1$ and $R^2$ are independently hydrogen, or an optionally substituted moiety selected from alkyl, alkenyl, alkynyl, cycloalkyl, or cycloalkyl-alkyl.

[246] The method of paragraph 243, wherein $R^1$ and $R^2$ are independently hydrogen, or an optionally substituted moiety selected from alkyl, alkenyl, and alkynyl.

[247] The method of paragraph 243, wherein $R^1$ and $R^2$ are independently hydrogen, or an optionally substituted alkyl.

[248] The method of paragraph 243, wherein $R^1$ and $R^2$ are independently hydrogen, or an optionally substituted $C_1$-$C_5$ alkyl.

[249] The method of paragraph 243, wherein $R^1$ and $R^2$ are independently hydrogen, or a $C_1$-$C_5$ alkyl.

[250] The method of paragraph 243, wherein $R^1$ and $R^2$ are independently hydrogen, or an optionally substituted methyl.

[251] The method of paragraph 243, wherein $R^1$ and $R^2$ are independently hydrogen or methyl.

[252] The method of paragraph 243, wherein at least one of $R^1$ and $R^2$ is hydrogen.

[253] The method of paragraph 243, wherein both $R^1$ and $R^2$ are hydrogen.

[254] The method of paragraph 243, wherein at least one of $R^1$ and $R^2$ is an optionally substituted $C_1$-$C_5$ alkyl.

[255] The method of paragraph 243, wherein at least one of $R^1$ and $R^2$ is an optionally substituted methyl.

[256] The method of paragraph 243, wherein at least one of $R^1$ and $R^2$ is methyl.

[257] The method of paragraph 243, wherein both $R^1$ and $R^2$ are an optionally substituted $C_1$-$C_5$ alkyl.

[258] The method of paragraph 243, wherein both $R^1$ and $R^2$ are $C_1$-$C_5$ alkyl.

[259] The method of paragraph 243, wherein both $R^1$ and $R^2$ are methyl.

[260] The method of any one of paragraphs 243-259, wherein $R^3$ and $R^4$ are independently hydrogen, halogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl.

[261] The method of any one of paragraphs 243-259, wherein $R^3$ and $R^4$ are independently hydrogen, or an optionally substituted moiety selected from alkyl, alkenyl, alkynyl, cycloalkyl, or cycloalkyl-alkyl.

[262] The method of any one of paragraphs 243-259, wherein $R^3$ and $R^4$ are independently hydrogen, or an optionally substituted moiety selected from alkyl, alkenyl, and alkynyl.

[263] The method of any one of paragraphs 243-259, wherein $R^3$ and $R^4$ are independently hydrogen, halogen, —OH, —$OR^8$, —$NO_2$, —$N(R^9)(R^{10})$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, —$SO_2R^{17}$, or —$SO_2N(R^{18})(R^{19})$.

[264] The method of any one of paragraphs 243-259, wherein $R^3$ and $R^4$ are independently hydrogen, halogen, —OH, —$OR^8$, —$C(O)R^5$, —$C(O)OR^6$, —$C(O)NHR^7$, —$OC(O)R^{11}$, —$NHC(O)R^{12}$, —$OC(O)OR^{13}$, —$NHC(O)OR^{14}$, —$OC(O)NHR^{15}$, —$NHC(O)NHR^{16}$, or an optionally substituted moiety selected from alkyl, alkenyl, and alkynyl.

[265] The method of any one of paragraphs 243-259, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or an optionally substituted moiety selected from alkyl, alkenyl, and alkynyl.

[266] The method of any one of paragraphs 243-259, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, —C(O)NH—($C_1$-$C_4$)alkyl, —OC(O)—($C_1$-$C_4$)alkyl, —NHC(O)—($C_1$-$C_4$)alkyl, —OC(O)O—($C_1$-$C_4$)alkyl, —NHC(O)O—($C_1$-$C_4$)alkyl, —OC(O)NH—($C_1$-$C_4$)alkyl, —NHC(O)NH—($C_1$-$C_4$)alkyl, or a moiety selected from alkyl, alkenyl, and alkynyl.

[267] The method of any one of paragraphs 243-259, wherein $R^3$ and $R^4$ are independently hydrogen, halogen, —OH, —O—($C_1$-$C_4$)alkyl, —C(O)—($C_1$-$C_4$)alkyl, —C(O)OH, —C(O)O—($C_1$-$C_4$)alkyl, or a moiety selected from alkyl, alkenyl, and alkynyl.

[268] The method of any one of paragraphs 243-259, wherein one of $R^3$ and $R^4$ is —OH.

[269] The method of any one of paragraphs 243-259, wherein at least one of $R^3$ and $R^4$ is hydrogen.

[270] The method of any one of paragraphs 243-259, wherein both $R^3$ and $R^4$ are hydrogen.

[271] The method of any one of paragraphs 243-259, wherein at least one of $R^3$ and $R^4$ is other than hydrogen.

[272] The method of any one of paragraphs 243-259, wherein both $R^3$ and $R^4$ are other than hydrogen.

[273] The method of any one of paragraphs 243-273, wherein both $R^1$ and $R^2$ are hydrogen; and wherein one of $R^3$ and $R^4$ is —OH.

[274] The method of any one of paragraphs 243-273, wherein both $R^1$ and $R^2$ are optionally substituted alkyl; and wherein one of $R^3$ and $R^4$ is —OH.

[275] The method of any one of paragraphs 243-273, wherein both $R^1$ and $R^2$ are optionally substituted —$(C_1$-$C_5)$ alkyl; and wherein one of $R^3$ and $R^4$ is —OH.

[276] The method of any one of paragraphs 243-273, wherein both $R^1$ and $R^2$ are optionally substituted methyl; and wherein one of $R^3$ and $R^4$ is —OH.

[277] The method of any one of paragraphs 243-276, wherein the dioxy compound is of the formula, of the formula (II-D):

(II-D)

or a salt or solvate thereof.

[278] The method of paragraph 277, wherein the dioxy compound is of the formula (II-E):

(II-E)

or a salt or solvate thereof.

[279] The method of paragraph 154, wherein the dioxy compound is selected from the group consisting of: (I-1): pyrocatechol or catechol; (I-2): caffeic acid; (I-3): 3,4-dihydroxybenzoic acid; (I-4): 4-tert-butyl-5-methoxy-1,2-benzenediol; (I-5): pyrogallol; (I-6): gallic acid; (I-7): methyl-3,4,5-trihydroxybenzoate; (I-8): 2,3,4-trihydroxybenzophenone; (I-9): 2,6-dimethoxyphenol; (I-10): sinapinic acid; (I-12): 3,5-dihydroxybenzoic acid; (I-12): 4-chloro-1,2-benzenediol; (I-13): 4-nitro-1,2-benzenediol; (I-14): tannic acid; (I-15): ethyl gallate; (I-16): methyl glycolate; (I-17): dihydroxyfumaric acid; (I-18): 2-butyne-1,4-diol; (I-19): croconic acid; (I-20): 1,3-propanediol; (I-21): tartaric acid; (I-22): 2,4-pentanediol; (I-23): 3-ethyoxy-1,2-propanediol; (I-24): 2,4,4'-trihydroxybenzophenone; (I-25): cis-2-butene-1,4-diol; (I-26): 3,4-dihydroxy-3-cyclobutene-1,2-dione; (I-27): dihydroxyacetone; (I-28): acrolein acetal; (I-29): methyl-4-hydroxybenzoate; (I-30): 4-hydroxybenzoic acid; (I-31): methyl-3,5-dimethoxy-4-hydroxybenzoate; and (I-32): and pyrocatechol violet or a salt or solvate thereof.

[280] The method of any of paragraphs 131-279, wherein an effective amount of the dioxy compound to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, and about $10^{-3}$ to about $10^{-2}$.

[281] The method of any of paragraphs 131-279, wherein an effective amount of the dioxy compound to cellulose is about $10^{-6}$ to about 10 per g of cellulose, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, and about $10^{-3}$ to about $10^{-2}$ per g of cellulose.

[282] The method of any of paragraphs 131-279, wherein an effective amount of the dioxy compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An enzyme composition comprising: (a) a glycoside hydrolase family 61 (GH61) polypeptide having cellulolytic enhancing activity and (b) a dioxy compound, wherein the combination of the GH61 polypeptide having cellulolytic enhancing activity and the dioxy compound enhances hydrolysis of a cellulosic material by the enzyme composition compared to the GH61 polypeptide alone or the dioxy compound alone according to the following formula with a ratio greater than 1:

GH61 effect=% conversion$_{(+GH61+dioxy\ compound)}$
% conversion$_{(no\ GH61+dioxy\ compound)}$;

wherein the dioxy compound is a compound of formula (I):

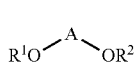
(I)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;
A is a substituted moiety selected from alkylene, alkenylene, alkynylene, cycloalkylene, heterocycloalkylene, arylene, and heteroarylene;
or a salt or solvate thereof.

2. The composition of claim 1, wherein the dioxy compound is of formula (II):

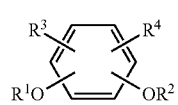
(II)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;
$R^3$ and $R^4$ are independently hydrogen, halogen, —O$R^8$, —NO$_2$, —N($R^9$)($R^{10}$), —CN, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2R^{17}$, —SO$_2$N($R^{18}$)($R^{19}$), —S$R^{20}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^3$ and $R^4$ combine to form an optionally substituted fused ring;
$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, and $R^{20}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and $R^{17}$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or a salt or solvate thereof.

3. The composition of claim 2, wherein the dioxy compound is of the formula (II-A):

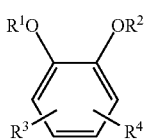

wherein $R^1$, $R^2$, $R^3$, and $R^4$ are as defined in any one of the preceding claims;

or a salt or solvate thereof.

4. The composition of claim 3, wherein the dioxy compound is of the formula (II-B):

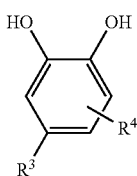

wherein $R^3$, and $R^4$ are as defined in any one of the preceding claims;

or a salt or solvate thereof.

5. The composition of claim 2, wherein the dioxy compound is of the formula (II-C):

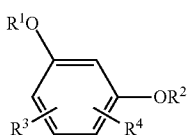

wherein $R^1$, $R^2$, $R^3$, and $R^4$ are as defined in any one of the preceding claims;

or a salt or solvate thereof.

6. The composition of claim 5, wherein the dioxy compound is of the formula (II-D):

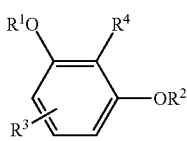

or a salt or solvate thereof.

7. The composition of claim 6, wherein the dioxy compound is of the formula (II-E):

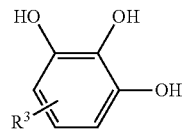

or a salt or solvate thereof.

8. The composition of claim 1, wherein the dioxy compound is selected from the group consisting of: (I-1): pyrocatechol or catechol; (I-2): caffeic acid; (I-3): 3,4-dihydroxybenzoic acid; (I-4): 4-tert-butyl-5-methoxy-1,2-benzenediol; (I-5): pyrogallol; (I-6): gallic acid; (I-7): Methyl-3,4,5-trihydroxybenzoate; (I-8): 2,3,4-trihydroxybenzophenone; (I-9): 2,6-dimethoxyphenol; (I-10): sinapinic acid; (I-12): 3,5-dihydroxybenzoic acid; (I-12): 4-chloro-1,2-benzenediol; (I-13): 4-nitro-1,2-benzenediol; (I-14): tannic acid; (I-15): ethyl gallate; (I-16): methyl glycolate; (I-17): dihydroxyfumaric acid; (I-18): 2-butyne-1,4-diol; (I-19): croconic acid; (I-20): 1,3-propanediol; (I-21): tartaric acid; (I-22): 2,4-pentanediol; (I-23): 3-ethyoxy-1,2-propanediol; (I-24): 2,4,4'-trihydroxybenzophenone; (I-25): cis-2-butene-1,4-diol; (I-26): 3,4-dihydroxy-3-cyclobutene-1,2-dione; (I-27): dihydroxyacetone; (I-28): acrolein acetal; (I-29): methyl-4-hydroxybenzoate; (I-30): 4-hydroxybenzoic acid; (I-31): methyl-3,5-dimethoxy-4-hydroxybenzoate; and (I-32): and pyrocatechol violet; or a salt or solvate thereof.

9. The composition of claim 1, which further comprises (c) one or more enzymes selected from the group consisting of a cellulase, a hemicellulase, an esterase, an expansin, a laccase, a ligninolytic enzyme, a pectinase, a peroxidase, a protease, and a swollenin.

10. A method for degrading or converting a cellulosic material, comprising: treating the cellulosic material with an enzyme composition comprising a GH61 polypeptide having cellulolytic enhancing activity and a dioxy compound, wherein the combination of the GH61 polypeptide having cellulolytic enhancing activity and the dioxy compound enhances hydrolysis of the cellulosic material by the enzyme composition compared to the GH61 polypeptide alone or the dioxy compound alone according to the following formula with a ratio greater than 1:

$$\text{GH61 effect} = \frac{\% \text{ conversion}_{(+GH61+dioxy\ compound)}}{\% \text{ conversion}_{(no\ GH61+dioxy\ compound)}};$$

wherein the dioxy compound is a compound of formula (I):

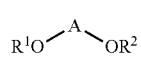

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

A is a substituted moiety selected from alkylene, alkenylene, alkynylene, cycloalkylene, heterocycloalkylene, arylene, and heteroarylene;

or a salt or solvate thereof.

11. A method for producing a fermentation product, comprising:

(a) saccharifying a cellulosic material with an enzyme composition comprising a GH61 polypeptide having cellulolytic enhancing activity and a dioxy compound, wherein the combination of the GH61 polypeptide having cellulolytic enhancing activity and the dioxy compound enhances hydrolysis of the cellulosic material by the enzyme composition compared to the GH61 polypeptide alone or the dioxy compound alone according to the following formula with a ratio greater than 1:

GH61 effect=% conversion$_{(+GH61+dioxy\ compound)}$ / % conversion$_{(no\ GH61+dioxy\ compound)}$;

wherein the dioxy compound is a compound of formula (I):

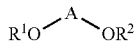

(I)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

A is a substituted moiety selected from alkylene, alkenylene, alkynylene, cycloalkylene, heterocycloalkylene, arylene, and heteroarylene;

or a salt or solvate thereof;

(b) fermenting the saccharified cellulosic material with one or more fermenting microorganisms to produce the fermentation product; and (c) recovering the fermentation product from the fermentation.

12. A method of fermenting a cellulosic material, comprising: fermenting the cellulosic material with one or more fermenting microorganisms, wherein the cellulosic material is saccharified with an enzyme composition comprising a GH61 polypeptide having cellulolytic enhancing activity and a dioxy compound, wherein the combination of the GH61 polypeptide having cellulolytic enhancing activity and the dioxy compound enhances hydrolysis of the cellulosic material by the enzyme composition compared to the GH61 polypeptide alone or the dioxy compound alone according to the following formula with a ratio greater than 1:

GH61 effect=% conversion$_{(+GH61+dioxy\ compound)}$ / % conversion$_{(no\ GH61+dioxy\ compound)}$;

wherein the dioxy compound is a compound of formula (I):

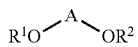

(I)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

A is a substituted moiety selected from alkylene, alkenylene, alkynylene, cycloalkylene, heterocycloalkylene, arylene, and heteroarylene;

or a salt or solvate thereof.

13. The method of claim 12, wherein the fermenting of the cellulosic material produces a fermentation product.

14. The method of claim 10, wherein the dioxy compound is selected from the group consisting of: (I-1): pyrocatechol or catechol; (I-2): caffeic acid; (I-3): 3,4-dihydroxybenzoic acid; (I-4): 4-tert-butyl-5-methoxy-1,2-benzenediol; (I-5): pyrogallol; (I-6): gallic acid; (I-7): Methyl-3,4,5-trihydroxybenzoate; (I-8): 2,3,4-trihydroxybenzophenone; (I-9): 2,6-dimethoxyphenol; (I-10): sinapinic acid; (I-12): 3,5-dihydroxybenzoic acid; (I-12): 4-chloro-1,2-benzenediol; (I-13): 4-nitro-1,2-benzenediol; (I-14): tannic acid; (I-15): ethyl gallate; (I-16): methyl glycolate; (I-17): dihydroxyfumaric acid; (I-18): 2-butyne-1,4-diol; (I-19): croconic acid; (I-20): 1,3-propanediol; (I-21): tartaric acid; (I-22): 2,4-pentanediol; (I-23): 3-ethyoxy-1,2-propanediol; (I-24): 2,4,4'-trihydroxybenzophenone; (I-25): cis-2-butene-1,4-diol; (I-26): 3,4-dihydroxy-3-cyclobutene-1,2-dione; (I-27): dihydroxyacetone; (I-28): acrolein acetal; (I-29): methyl-4-hydroxybenzoate; (I-30): 4-hydroxybenzoic acid; (I-31): methyl-3,5-dimethoxy-4-hydroxybenzoate; and (I-32): and pyrocatechol violet; or a salt or solvate thereof.

15. The method of claim 11, wherein the dioxy compound is selected from the group consisting of: (I-1): pyrocatechol or catechol; (I-2): caffeic acid; (I-3): 3,4-dihydroxybenzoic acid; (I-4): 4-tert-butyl-5-methoxy-1,2-benzenediol; (I-5): pyrogallol; (I-6): gallic acid; (I-7): Methyl-3,4,5-trihydroxybenzoate; (I-8): 2,3,4-trihydroxybenzophenone; (I-9): 2,6-dimethoxyphenol; (I-10): sinapinic acid; (I-12): 3,5-dihydroxybenzoic acid; (I-12): 4-chloro-1,2-benzenediol; (I-13): 4-nitro-1,2-benzenediol; (I-14): tannic acid; (I-15): ethyl gallate; (I-16): methyl glycolate; (I-17): dihydroxyfumaric acid; (I-18): 2-butyne-1,4-diol; (I-19): croconic acid; (I-20): 1,3-propanediol; (I-21): tartaric acid; (I-22): 2,4-pentanediol; (I-23): 3-ethyoxy-1,2-propanediol; (I-24): 2,4,4'-trihydroxybenzophenone; (I-25): cis-2-butene-1,4-diol; (I-26): 3,4-dihydroxy-3-cyclobutene-1,2-dione; (I-27): dihydroxyacetone; (I-28): acrolein acetal; (I-29): methyl-4-hydroxybenzoate; (I-30): 4-hydroxybenzoic acid; (I-31): methyl-3,5-dimethoxy-4-hydroxybenzoate; and (I-32): and pyrocatechol violet; or a salt or solvate thereof.

16. The method of claim 12, wherein the dioxy compound is selected from the group consisting of: (I-1): pyrocatechol or catechol; (I-2): caffeic acid; (I-3): 3,4-dihydroxybenzoic acid; (I-4): 4-tert-butyl-5-methoxy-1,2-benzenediol; (I-5): pyrogallol; (I-6): gallic acid; (I-7): Methyl-3,4,5-trihydroxybenzoate; (I-8): 2,3,4-trihydroxybenzophenone; (I-9): 2,6-dimethoxyphenol; (I-10): sinapinic acid; (I-12): 3,5-dihydroxybenzoic acid; (I-12): 4-chloro-1,2-benzenediol; (I-13): 4-nitro-1,2-benzenediol; (I-14): tannic acid; (I-15): ethyl gallate; (I-16): methyl glycolate; (I-17): dihydroxyfumaric acid; (I-18): 2-butyne-1,4-diol; (I-19): croconic acid; (I-20): 1,3-propanediol; (I-21): tartaric acid; (I-22): 2,4-pentanediol; (I-23): 3-ethyoxy-1,2-propanediol; (I-24): 2,4,4'-trihydroxybenzophenone; (I-25): cis-2-butene-1,4-diol; (I-26): 3,4-dihydroxy-3-cyclobutene-1,2-dione; (I-27): dihydroxyacetone; (I-28): acrolein acetal; (I-29): methyl-4-hydroxybenzoate; (I-30): 4-hydroxybenzoic acid; (I-31): methyl-3,5-dimethoxy-4-hydroxybenzoate; and (I-32): and pyrocatechol violet; or a salt or solvate thereof.

17. The composition of claim 9, wherein the cellulase is one or more enzymes selected from the group consisting of an endoglucanase, a cellobiohydrolase, and a beta-glucosidase.

18. The composition of claim 9, wherein the hemicellulase is one or more enzymes selected from the group consisting of a xylanase, an acetylxylan esterase, a feruloyl esterase, an arabinofuranosidase, a xylosidase, and a glucuronidase.

19. The method of claim 10, wherein the dioxy compound is of formula (II):

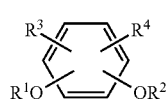

(II)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

$R^3$ and $R^4$ are independently hydrogen, halogen, —O$R^8$, —NO$_2$, —N($R^9$)($R^{10}$), —CN, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2R^{17}$, —SO$_2$N($R^{18}$)($R^{19}$), —S$R^{20}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^3$ and $R^4$ combine to form an optionally substituted fused ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, and $R^{20}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and $R^{17}$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or a salt or solvate thereof.

20. The method of claim 19, wherein the dioxy compound is of the formula (II-A):

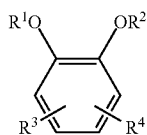

(II-A)

wherein $R^1$, $R^2$, $R^3$, and $R^4$ are as defined in any one of the preceding claims;

or a salt or solvate thereof.

21. The method of claim 20, wherein the dioxy compound is of the formula (II-B):

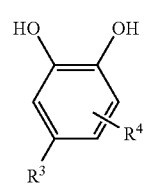

(II-B)

wherein $R^3$, and $R^4$ are as defined in any one of the preceding claims;

or a salt or solvate thereof.

22. The method of claim 19, wherein the dioxy compound is of the formula (II-C):

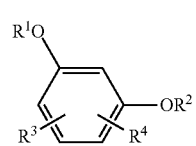

(II-C)

wherein $R^1$, $R^2$, $R^3$, and $R^4$ are as defined in any one of the preceding claims;

or a salt or solvate thereof.

23. The method of claim 22, wherein the dioxy compound is of the formula (II-D):

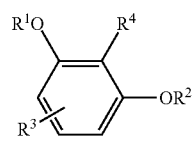

(II-D)

or a salt or solvate thereof.

24. The method of claim 23, wherein the dioxy compound is of the formula (II-E):

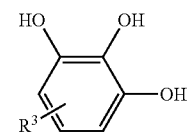

(II-E)

or a salt or solvate thereof.

25. The method of claim 11, wherein the dioxy compound is of formula (II):

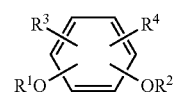

(II)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

$R^3$ and $R^4$ are independently hydrogen, halogen, —O$R^8$, —NO$_2$, —N($R^9$)($R^{10}$), —CN, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2R^{17}$, —SO$_2$N($R^{18}$)($R^{19}$), —S$R^{20}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^3$ and $R^4$ combine to form an optionally substituted fused ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, and $R^{20}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and $R^{17}$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or a salt or solvate thereof.

26. The method of claim 25, wherein the dioxy compound is of the formula (II-A):

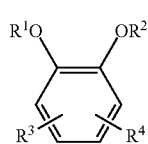
(II-A)

wherein $R^1$, $R^2$, $R^3$, and $R^4$ are as defined in any one of the preceding claims;

or a salt or solvate thereof.

27. The method of claim 26, wherein the dioxy compound is of the formula (II-B):

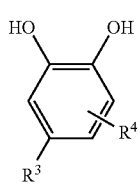
(II-B)

wherein $R^3$, and $R^4$ are as defined in any one of the preceding claims;

or a salt or solvate thereof.

28. The method of claim 25, wherein the dioxy compound is of the formula (II-C):

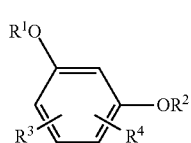
(II-C)

wherein $R^1$, $R^2$, $R^3$, and $R^4$ are as defined in any one of the preceding claims;

or a salt or solvate thereof.

29. The method of claim 28, wherein the dioxy compound is of the formula (II-D):

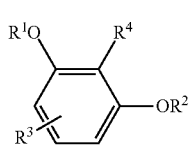
(II-D)

or a salt or solvate thereof.

30. The method of claim 29, wherein the dioxy compound is of the formula (II-E):

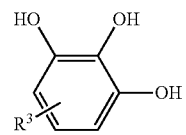
(II-E)

or a salt or solvate thereof.

31. The method of claim 12, wherein the dioxy compound is of formula (II):

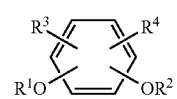
(II)

wherein $R^1$ and $R^2$ are independently hydrogen, —C(O)$R^5$, —C(O)O$R^6$, —C(O)NH$R^7$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ together form an optionally substituted cyclic diether;

$R^3$ and $R^4$ are independently hydrogen, halogen, —O$R^8$, —NO$_2$, —N($R^9$)($R^{10}$), —CN, —C(O)$R^5$, —C(O)O$R^6$, —C(O)NH$R^7$, —OC(O)$R^{11}$, —NHC(O)$R^{12}$, —OC(O)O$R^{13}$, —NHC(O)O$R^{14}$, —OC(O)NH$R^{15}$, —NHC(O)NH$R^{16}$, —SO$_2$$R^{17}$, —SO$_2$N($R^{18}$)($R^{19}$), —S$R^{20}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^3$ and $R^4$ combine to form an optionally substituted fused ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, and $R^{20}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and $R^{17}$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or a salt or solvate thereof.

32. The method of claim 31, wherein the dioxy compound is of the formula (II-A):

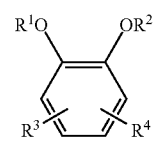
(II-A)

wherein $R^1$, $R^2$, $R^3$, and $R^4$ are as defined in any one of the preceding claims;

or a salt or solvate thereof.

33. The method of claim 32, wherein the dioxy compound is of the formula (II-B):

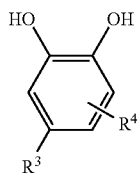

(II-B)

wherein $R^3$, and $R^4$ are as defined in any one of the preceding claims;
or a salt or solvate thereof.

34. The method of claim 31, wherein the dioxy compound is of the formula (II-C):

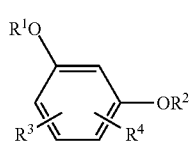

(II-C)

wherein $R^1$, $R^2$, $R^3$, and $R^4$ are as defined in any one of the preceding claims;
or a salt or solvate thereof.

35. The method of claim 34, wherein the dioxy compound is of the formula (II-D):

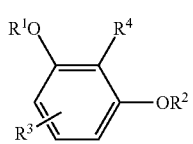

(II-D)

or a salt or solvate thereof.

36. The method of claim 35, wherein the dioxy compound is of the formula (II-E):

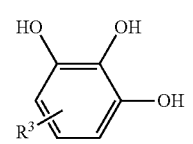

(II-E)

or a salt or solvate thereof.

37. The method of claim 10, wherein an effective amount of the dioxy compound to cellulose is about $10^{-6}$ to about 10 g per g of cellulose.

38. The method of claim 10, wherein an effective amount of the dioxy compound to cellulose is about $10^{-6}$ to about 1 g per g of cellulose.

39. The method of claim 10, wherein an effective amount of the dioxy compound to cellulose is about $10^{-5}$ to about 1 g per g of cellulose.

40. The method of claim 10, wherein an effective amount of the dioxy compound to cellulose is about $10^{-5}$ to about $10^{-1}$ g per g of cellulose.

41. The method of claim 10, wherein an effective amount of the dioxy compound to cellulose is about $10^{-4}$ to about $10^{-1}$ g per g of cellulose.

42. The method of claim 10, wherein an effective amount of the dioxy compound to cellulose is about $10^{-3}$ to about $10^{-2}$ g per g of cellulose.

43. The method of claim 11, wherein an effective amount of the dioxy compound to cellulose is about $10^{-6}$ to about 10 g per g of cellulose.

44. The method of claim 11, wherein an effective amount of the dioxy compound to cellulose is about $10^{-6}$ to about 1 g per g of cellulose.

45. The method of claim 11, wherein an effective amount of the dioxy compound to cellulose is about $10^{-5}$ to about 1 g per g of cellulose.

46. The method of claim 11, wherein an effective amount of the dioxy compound to cellulose is about $10^{-5}$ to about $10^{-1}$ g per g of cellulose.

47. The method of claim 11, wherein an effective amount of the dioxy compound to cellulose is about $10^{-4}$ to about $10^{-1}$ g per g of cellulose.

48. The method of claim 11, wherein an effective amount of the dioxy compound to cellulose is about $10^{-3}$ to about $10^{-2}$ g per g of cellulose.

49. The method of claim 12, wherein an effective amount of the dioxy compound to cellulose is about $10^{-6}$ to about 10 g per g of cellulose.

50. The method of claim 12, wherein an effective amount of the dioxy compound to cellulose is about $10^{-6}$ to about 1 g per g of cellulose.

51. The method of claim 12, wherein an effective amount of the dioxy compound to cellulose is about $10^{-5}$ to about 1 g per g of cellulose.

52. The method of claim 12, wherein an effective amount of the dioxy compound to cellulose is about $10^{-5}$ to about $10^{-1}$ g per g of cellulose.

53. The method of claim 12, wherein an effective amount of the dioxy compound to cellulose is about $10^{-4}$ to about $10^{-1}$ g per g of cellulose.

54. The method of claim 12, wherein an effective amount of the dioxy compound to cellulose is about $10^{-3}$ to about $10^{-2}$ g per g of cellulose.

* * * * *

SEQUENCE LISTING

<160> NUMBER OF SEQ ID NOS: 172

<210> SEQ ID NO 1
<211> LENGTH: 1846
<212> TYPE: DNA
<213> ORGANISM: Thielavia terrestris

<400> SEQUENCE: 1

```
aattgaagga gggagtggcg gagtggccac caagtcaggc ggctgtcaac taaccaagga      60
tgggaacagt tcggctcgcc ttgcccgagg gcagcgttcc ctgatgggga cgaaccatgg     120
gactggggtc agctgctgta taaaagttca aatcgatgat ctctcagatg gcgctgctgg     180
ggtgttctgc gcttttccat cctcgcaacc tggtatccca ctagtccagc gttcggcacc     240
atgaagtcgt tcaccattgc cgccttggca gccctatggg cccaggaggc cgccgcccac     300
gcgaccttcc aggacctctg gattgatgga gtcgactacg gctcgcaatg tgtccgcctc     360
ccggcgtcca actcccccgt caccaatgtt gcgtccgacg atatccgatg caatgtcggc     420
acctcgaggc ccaccgtcaa gtgcccggtc aaggccggct ccacggtcac gatcgagatg     480
```

```
caccaggttc gcacgcctct ctgcgtaggc cccccagcta ctatatggca ctaacacgac    540
ctccagcaac ctggcgaccg gtcttgcgcc aacgaggcta tcggcggcga ccactacggc    600
cccgtaatgg tgtacatgtc caaggtcgat gacgcggtga cagccgacgg ttcatcgggc    660
tggttcaagg tgttccagga cagctgggcc aagaacccgt cgggttcgac gggcgacgac    720
gactactggg gcaccaagga cctcaactcg tgctgcggca agatgaacgt caagatcccc    780
gaagacatcg agccgggcga ctacctgctc cgcgccgagg ttatcgcgct gcacgtggcc    840
gccagctcgg gcggcgcgca gttctacatg tcctgctacc agctgaccgt gacgggctcc    900
ggcagcgcca cccctcgac cgtgaatttc ccggggcgcct actcggccag cgacccgggc    960
atcctgatca acatccacgc gcccatgtcg acctacgtcg tcccgggccc gaccgtgtac   1020
gcgggcggct cgaccaagtc ggctggcagc tcctgctccg gctgcgaggc gacctgcacg   1080
gttggttccg gccccagcgc gacactgacg cagcccacct ccaccgcgac cgcgacctcc   1140
gcccctggcg gcggcggctc cggctgcacg gcggccaagt accagcagtg cggcggcacc   1200
ggctacactg ggtgcaccac ctgcgctgta agttccctcg tgatatgcag cggaacaccg   1260
tctggactgt tttgctaact cgcgtcgtag tccgggtcta cctgcagcgc cgtctcgcct   1320
ccgtactact cgcagtgcct ctaagccggg agcgcttgct cagcgggctg ctgtgaagga   1380
gctccatgtc cccatgccgc catggccgga gtaccgggct gagcgcccaa ttcttgtata   1440
tagttgagtt ttcccaatca tgaatacata tgcatctgca tggactgttg cgtcgtcagt   1500
ctacatcctt tgctccactg aactgtgaga ccccatgtca tccggaccat cgatcggtg   1560
ctcgctctac catctcggtt gatgggtctg ggcttgagag tcactggcac gtcctcggcg   1620
gtaatgaaat gtggaggaaa gtgtgagctg tctgacgcac tcggcgctga tgagacgttg   1680
agcgcggccc acactggtgt tctgtaagcc agcacacaaa agaatactcc aggatggccc   1740
atagcggcaa atatacagta tcagggatgc aaaaagtgca aagtaaggg gctcaatcgg   1800
ggatcgaacc cgagacctcg cacatgactt atttcaagtc agggt         1846
```

```
<210> SEQ ID NO 2
<211> LENGTH: 326
<212> TYPE: PRT
<213> ORGANISM: Thielavia terrestris

<400> SEQUENCE: 2

Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
    50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
```

```
                130                 135                 140
Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
                180                 185                 190

Tyr Gln Leu Thr Val Thr Gly Ser Gly Ser Ala Thr Pro Ser Thr Val
            195                 200                 205

Asn Phe Pro Gly Ala Tyr Ser Ala Ser Asp Pro Gly Ile Leu Ile Asn
210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
                260                 265                 270

Thr Ser Thr Ala Thr Ala Thr Ser Ala Pro Gly Gly Gly Ser Gly
            275                 280                 285

Cys Thr Ala Ala Lys Tyr Gln Gln Cys Gly Gly Thr Gly Tyr Thr Gly
            290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 3
<211> LENGTH: 880
<212> TYPE: DNA
<213> ORGANISM: Thielavia terrestris

<400> SEQUENCE: 3
accccgggat cactgcccct aggaaccagc acacctcggt ccaatcatgc ggttcgacgc      60
cctctccgcc ctcgctcttg cgccgcttgt ggctggccac ggcgccgtga ccagctacat     120
catcggcggc aaaacctatc ccggctacga gggcttctcg cctgcctcga gcccgccgac     180
gatccagtac cagtggcccg actacaaccc gaccctgagc gtgaccgacc cgaagatgcg     240
ctgcaacggc ggcacctcgg cagagctcag cgcgcccgtc caggccggcg agaacgtgac     300
ggccgtctgg aagcagtgga cccaccagca aggccccgtc atggtctgga tgttcaagtg     360
ccccggcgac ttctcgtcgt gccacggcga cggcaagggc tggttcaaga tcgaccagct     420
gggcctgtgg ggcaacaacc tcaactcgaa caactgggc accgcgatcg tctacaagac     480
cctccagtgg agcaacccga tccccaagaa cctcgcgccg gcaactacc tcatccgcca     540 cgagctgctc gccctgcacc aggccaacac gccgcagttc tacgccgagt gcgcccagct     600
ggtcgtctcc ggcagcggct ccgccctgcc cccgtccgac tacctctaca gcatccccgt     660
ctacgcgccc cagaacgacc ccggcatcac cgtgagtggg cttccgttcc gcggcgagct     720
ctgtggaaat cttgctgacg atgggctagg ttgacatcta caacggcggg cttacctcct     780
acaccccgcc cggcggcccc gtctggtctg gcttcgagtt ttaggcgcat tgagtcgggg     840
gctacgaggg gaaggcatct gttcgcatga gcgtgggtac                          880

<210> SEQ ID NO 4
<211> LENGTH: 239
```

<212> TYPE: PRT
<213> ORGANISM: Thielavia terrestris

<400> SEQUENCE: 4

```
Met Arg Phe Asp Ala Leu Ser Ala Leu Ala Leu Ala Pro Leu Val Ala
1               5                   10                  15

Gly His Gly Ala Val Thr Ser Tyr Ile Ile Gly Lys Thr Tyr Pro
                20                  25                  30

Gly Tyr Glu Gly Phe Ser Pro Ala Ser Ser Pro Thr Ile Gln Tyr
        35                  40                  45

Gln Trp Pro Asp Tyr Asn Pro Thr Leu Ser Val Thr Asp Pro Lys Met
    50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Asn Trp Gly Thr Ala Ile Val Tyr Lys
    130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
    210                 215                 220

Ser Tyr Thr Pro Pro Gly Gly Pro Val Trp Ser Gly Phe Glu Phe
225                 230                 235
```

<210> SEQ ID NO 5
<211> LENGTH: 1000
<212> TYPE: DNA
<213> ORGANISM: Thielavia terrestris

<400> SEQUENCE: 5

```
ctcctgttcc tgggccaccg cttgttgcct gcactattgg tagagttggt ctattgctag      60
agttggccat gcttctcaca tcagtcctcg gctcggctgc cctgcttgct agcggcgctg     120
cggcacacgg cgccgtgacc agctacatca tcgccggcaa gaattacccg gggtgggtag     180
ctgattattg agggcgcatt caaggttcat accggtgtgc atggctgaca accggctggc     240
agataccaag gcttttctcc tgcgaactcg ccgaacgtca tccaatggca atggcatgac     300
tacaaccccg tcttgtcgtg cagcgactcg aagcttcgct gcaacggcgg cacgtcggcc     360
accctgaacg ccacggccgc accgggcgac accatcaccg ccatctgggc gcagtggacg     420
cacagccagg gccccatcct ggtgtggatg tacaagtgcc cgggctcctt cagctcctgt     480
gacggctccg cgctggctg gttcaagatc gacgaggccg gcttccacgg cgacggcgtc     540
aaggtcttcc tcgacaccga gaacccgtcc ggctgggaca tcgccaagct cgtcggcggc     600
aacaagcagt ggagcagcaa ggtccccgag ggcctcgccc ccggcaacta cctcgtccgc     660
```

```
cacgagttga tcgccctgca ccaggccaac aacccgcagt tctacccgga gtgcgcccag    720
gtcgtcatca ccggctccgg caccgcgcag ccggatgcct catacaaggc ggctatcccc    780
ggctactgca accagaatga cccgaacatc aaggtgagat ccaggcgtaa tgcagtctac    840
tgctggaaag aaagtggtcc aagctaaacc gcgctccagg tgcccatcaa cgaccactcc    900
atccctcaga cctacaagat tcccggccct cccgtcttca agggcaccgc cagcaagaag    960
gcccgggact tcaccgcctg aagttgttga atcgatggag                         1000
```

<210> SEQ ID NO 6
<211> LENGTH: 258
<212> TYPE: PRT
<213> ORGANISM: Thielavia terrestris

<400> SEQUENCE: 6

```
Met Leu Leu Thr Ser Val Leu Gly Ser Ala Ala Leu Ala Ser Gly
1               5                   10                  15

Ala Ala Ala His Gly Ala Val Thr Ser Tyr Ile Ile Ala Gly Lys Asn
                20                  25                  30

Tyr Pro Gly Tyr Gln Gly Phe Ser Pro Ala Asn Ser Pro Asn Val Ile
            35                  40                  45

Gln Trp Gln Trp His Asp Tyr Asn Pro Val Leu Ser Cys Ser Asp Ser
        50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190

Ala Gln Val Val Ile Thr Gly Ser Gly Thr Ala Gln Pro Asp Ala Ser
        195                 200                 205

Tyr Lys Ala Ala Ile Pro Gly Tyr Cys Asn Gln Asn Asp Pro Asn Ile
    210                 215                 220

Lys Val Pro Ile Asn Asp His Ser Ile Pro Gln Thr Tyr Lys Ile Pro
225                 230                 235                 240

Gly Pro Pro Val Phe Lys Gly Thr Ala Ser Lys Lys Ala Arg Asp Phe
                245                 250                 255

Thr Ala
```

<210> SEQ ID NO 7
<211> LENGTH: 681
<212> TYPE: DNA
<213> ORGANISM: Thielavia terrestris

<400> SEQUENCE: 7

```
atgctcgcaa acggtgccat cgtcttcctg gccgccgccc tcggcgtcag tggccactac    60
acctggccac gggttaacga cggcgccgac tggcaacagg tccgtaaggc ggacaactgg   120
caggacaacg gctacgtcgg ggatgtcacg tcgccacaga tccgctgttt ccaggcgacc   180
ccgtccccgg ccccatccgt cctcaacacc acggccggct cgaccgtgac ctactgggcc   240
aaccccgacg tctaccaccc cgggcctgtg cagttttaca tggcccgcgt gcccgatggc   300
gaggacatca actcgtggaa cggcgacggc gccgtgtggt tcaaggtgta cgaggaccat   360
cctacctttg gcgctcagct cacatggccc agcacgggca gagctcgtt cgcggttccc    420
atcccccgt gcatcaagtc cggctactac ctcctccggg cggagcaaat cggcctgcac    480
gtcgcccaga gcgtaggcgg agcgcagttc tacatctcat gcgcccagct cagcgtcacc   540
ggcggcggca gcaccgagcc gccgaacaag gtggccttcc ccggcgctta cagtgcgacg   600
gacccgggca ttctgatcaa catctactac cctgttccca cgtcctacca gaaccccggc   660
ccggccgtct tcagctgctg a                                             681

<210> SEQ ID NO 8
<211> LENGTH: 226
<212> TYPE: PRT
<213> ORGANISM: Thielavia terrestris

<400> SEQUENCE: 8

Met Leu Ala Asn Gly Ala Ile Val Phe Leu Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225

<210> SEQ ID NO 9
```

<211> LENGTH: 960
<212> TYPE: DNA
<213> ORGANISM: Thielavia terrestris

<400> SEQUENCE: 9

```
atgaagggac ttttcagtgc cgccgccctc tccctggccg tcggccaggc ttcggcccat      60
tacatcttcc agcaactctc catcaacggg aaccagtttc cggtgtacca atatattcgc     120
aagaacacca attataacag tcccgttacc gatctcacgt ccgacgatct tcggtgcaat     180
gtcggcgccc agggtgctgg gacagacacc gtcacggtga aggccggcga ccagttcacc     240
ttcaccctttg acaccctgt ttaccaccag gggcccatct ccatctacat gtccaaggcc     300
ccgggcgcgg cgtcagacta cgatggcagc ggcggctggt tcaagatcaa ggactggggc     360
ccgactttca cgccgacgg cacgccacc tgggacatgg ccggctcata cctacaac       420
atcccgacct gcattcccga cggcgactat ctgctccgca tccagtcgct ggccatccac     480
aaccctggc cggcgggcat cccgcagttc tacatctcct gcgcccagat caccgtgacc     540
ggcggcggca acggcaaccc tggcccgacg gccctcatcc ccggcgcctt caaggacacc     600
gacccgggct acacggtgaa catctacacg aacttccaca actacacggt tccggcccg     660
gaggtcttca gctgcaacgg cggcggctcg aacccgcccc cgccggtgag tagcagcacg     720
cccgcgacca cgacgctggt cacgtcgacg cgcaccacgt cctccacgtc ctccgcctcg     780
acgccggcct cgaccggcgg ctgcaccgtc gccaagtggg gccagtgcgg cggcaacggg     840
tacaccggct gcacgacctg cgcggccggg tccacctgca gcaagcagaa cgactactac     900
tcgcagtgct gtaagggag gccgcaaagc atgaggtgtt tgaagaggag gagagggtc      960
```

<210> SEQ ID NO 10
<211> LENGTH: 304
<212> TYPE: PRT
<213> ORGANISM: Thielavia terrestris

<400> SEQUENCE: 10

```
Met Lys Gly Leu Phe Ser Ala Ala Leu Ser Leu Ala Val Gly Gln
1               5                   10                  15

Ala Ser Ala His Tyr Ile Phe Gln Gln Leu Ser Ile Asn Gly Asn Gln
                20                  25                  30

Phe Pro Val Tyr Gln Tyr Ile Arg Lys Asn Thr Asn Tyr Asn Ser Pro
            35                  40                  45

Val Thr Asp Leu Thr Ser Asp Asp Leu Arg Cys Asn Val Gly Ala Gln
        50                  55                  60

Gly Ala Gly Thr Asp Thr Val Thr Val Lys Ala Gly Asp Gln Phe Thr
65                  70                  75                  80

Phe Thr Leu Asp Thr Pro Val Tyr His Gln Gly Pro Ile Ser Ile Tyr
                85                  90                  95

Met Ser Lys Ala Pro Gly Ala Ala Ser Asp Tyr Asp Gly Ser Gly Gly
                100                 105                 110

Trp Phe Lys Ile Lys Asp Trp Gly Pro Thr Phe Asn Ala Asp Gly Thr
            115                 120                 125

Ala Thr Trp Asp Met Ala Gly Ser Tyr Thr Tyr Asn Ile Pro Thr Cys
        130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175
```

```
Ile Thr Val Thr Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
    210                 215                 220

Cys Asn Gly Gly Ser Asn Pro Pro Pro Val Ser Ser Thr
225             230             235                 240

Pro Ala Thr Thr Thr Leu Val Thr Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
            275                 280                 285

Ala Gly Ser Thr Cys Ser Lys Gln Asn Asp Tyr Tyr Ser Gln Cys Leu
            290                 295                 300
```

<210> SEQ ID NO 11
<211> LENGTH: 954
<212> TYPE: DNA
<213> ORGANISM: Thielavia terrestris

<400> SEQUENCE: 11

```
atgaagggcc tcagcctcct cgccgctgcg tcggcagcga ctgctcatac catcttcgtg     60
cagctcgagt caggggggaac gacctatccg gtatcctacg gcatccggga ccctagctac   120
gacggtccca tcaccgacgt cacctccgac tcactggctt gcaatggtcc cccgaacccc   180
acgacgccgt ccccgtacat catcaacgtc accgccggca ccacggtcgc ggcgatctgg   240
aggcacaccc tcacatccgg ccccgacgat gtcatggacg ccagccacaa ggggccgacc   300
ctggcctacc tcaagaaggt cgatgatgcc ttgaccgaca cgggtatcgg cggcggctgg   360
ttcaagatcc aggaggccgg ttacgacaat ggcaattggg ctaccagcac ggtgatcacc   420
aacggtggct ccaatatat tgacatcccc gcctgcattc ccaacggcca gtatctgctc   480
cgcgccgaga tgatcgcgct ccacgccgcc agcacgcagg tggtgcccca gctctacatg   540
gagtgcgcgc agatcaacgt ggtgggcggc tccggcagcg ccagcccgca gacgtacagc   600
atcccgggca tctaccaggc aaccgacccg ggctgctga tcaacatcta ctccatgacg   660
ccgtccagcc agtacaccat tccgggtccg ccctgttca cctgcagcgg cagcggcaac   720
aacggcggcg gcagcaaccc gtcgggcggg cagaccacga cggcgaagcc cacgacgacg   780
acggcggcga cgaccacctc ctccgccgct cctaccagca gccagggggg cagcagcggt   840
tgcaccgttc cccagtggca gcagtgcggt ggcatctcgt tcaccggctg caccaccctg   900
gcggcgggct acacctgcaa gtatctgaac gactattact cgcaatgcca gtaa          954
```

<210> SEQ ID NO 12
<211> LENGTH: 317
<212> TYPE: PRT
<213> ORGANISM: Thielavia terrestris

<400> SEQUENCE: 12

```
Met Lys Gly Leu Ser Leu Leu Ala Ala Ala Ser Ala Ala Thr Ala His
1               5                   10                  15

Thr Ile Phe Val Gln Leu Glu Ser Gly Gly Thr Thr Tyr Pro Val Ser
            20                  25                  30

Tyr Gly Ile Arg Asp Pro Ser Tyr Asp Gly Pro Ile Thr Asp Val Thr
```

```
                35                  40                  45
Ser Asp Ser Leu Ala Cys Asn Gly Pro Pro Asn Pro Thr Thr Pro Ser
 50                  55                  60

Pro Tyr Ile Ile Asn Val Thr Ala Gly Thr Thr Val Ala Ala Ile Trp
 65                  70                  75                  80

Arg His Thr Leu Thr Ser Gly Pro Asp Asp Val Met Asp Ala Ser His
                 85                  90                  95

Lys Gly Pro Thr Leu Ala Tyr Leu Lys Lys Val Asp Asp Ala Leu Thr
            100                 105                 110

Asp Thr Gly Ile Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Ala Lys
                245                 250                 255

Pro Thr Thr Thr Thr Ala Ala Thr Thr Thr Ser Ser Ala Ala Pro Thr
            260                 265                 270

Ser Ser Gln Gly Gly Ser Ser Gly Cys Thr Val Pro Gln Trp Gln Gln
        275                 280                 285

Cys Gly Gly Ile Ser Phe Thr Gly Cys Thr Cys Ala Ala Gly Tyr
            290                 295                 300

Thr Cys Lys Tyr Leu Asn Asp Tyr Tyr Ser Gln Cys Gln
305                 310                 315
```

<210> SEQ ID NO 13
<211> LENGTH: 799
<212> TYPE: DNA
<213> ORGANISM: Thermoascus aurantiacus

<400> SEQUENCE: 13

```
atgtcctttt ccaagataat tgctactgcc ggcgttcttg cctctgcttc tctagtggct    60
ggccatggct tcgttcagaa catcgtgatt gatggtaaaa agtatgtcat tgcaagacgc   120
acataagcgg caacagctga caatcgacag ttatggcggg tatctagtga accagtatcc   180
atacatgtcc aatcctccag aggtcatcgc ctggtctact acggcaactg atcttggatt   240
tgtggacggt actggatacc aaaccccaga tatcatctgc catagggcg ccaagcctgg   300
agccctgact gctccagtct ctccaggagg aactgttgag cttcaatgga ctccatggcc   360
tgattctcac catggcccag ttatcaacta ccttgctccg tgcaatggtg attgttccac   420
tgtggataag acccaattag aattcttcaa aattgccgag agcggtctca tcaatgatga   480
caatcctcct gggatctggg cttcagacaa tctgatagca gccaacaaca gctggactgt   540
```

```
caccattcca accacaattg cacctggaaa ctatgttctg aggcatgaga ttattgctct    600
tcactcagct cagaaccagg atggtgccca gaactatccc cagtgcatca atctgcaggt    660
cactggaggt ggttctgata ccctgctgg aactcttgga acggcactct accacgatac    720
cgatcctgga attctgatca acatctatca gaaactttcc agctatatca tccctggtcc    780
tcctctgtat actggttaa                                                  799
```

<210> SEQ ID NO 14
<211> LENGTH: 249
<212> TYPE: PRT
<213> ORGANISM: Thermoascus aurantiacus

<400> SEQUENCE: 14

```
Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
                20                  25                  30

Lys Tyr Tyr Gly Gly Tyr Leu Val Asn Gln Tyr Pro Tyr Met Ser Asn
            35                  40                  45

Pro Pro Glu Val Ile Ala Trp Ser Thr Thr Ala Thr Asp Leu Gly Phe
    50                  55                  60

Val Asp Gly Thr Gly Tyr Gln Thr Pro Asp Ile Ile Cys His Arg Gly
65                  70                  75                  80

Ala Lys Pro Gly Ala Leu Thr Ala Pro Val Ser Pro Gly Gly Thr Val
                85                  90                  95

Glu Leu Gln Trp Thr Pro Trp Pro Asp Ser His His Gly Pro Val Ile
            100                 105                 110

Asn Tyr Leu Ala Pro Cys Asn Gly Asp Cys Ser Thr Val Asp Lys Thr
        115                 120                 125

Gln Leu Glu Phe Phe Lys Ile Ala Glu Ser Gly Leu Ile Asn Asp Asp
    130                 135                 140

Asn Pro Pro Gly Ile Trp Ala Ser Asp Asn Leu Ile Ala Ala Asn Asn
145                 150                 155                 160

Ser Trp Thr Val Thr Ile Pro Thr Thr Ile Ala Pro Gly Asn Tyr Val
                165                 170                 175

Leu Arg His Glu Ile Ile Ala Leu His Ser Ala Gln Asn Gln Asp Gly
            180                 185                 190

Ala Gln Asn Tyr Pro Gln Cys Ile Asn Leu Gln Val Thr Gly Gly Gly
        195                 200                 205

Ser Asp Asn Pro Ala Gly Thr Leu Gly Thr Ala Leu Tyr His Asp Thr
    210                 215                 220

Asp Pro Gly Ile Leu Ile Asn Ile Tyr Gln Lys Leu Ser Ser Tyr Ile
225                 230                 235                 240

Ile Pro Gly Pro Pro Leu Tyr Thr Gly
                245
```

<210> SEQ ID NO 15
<211> LENGTH: 1172
<212> TYPE: DNA
<213> ORGANISM: Trichoderma reesei

<400> SEQUENCE: 15

```
ggatctaagc cccatcgata tgaagtcctg cgccattctt gcagcccttg gctgtcttgc    60
cgggagcgtt ctcggccatg acaagtcca aaacttcacg atcaatggac aatacaatca    120
gggtttcatt ctcgattact actatcagaa gcagaatact ggtcacttcc ccaacgttgc    180
```

```
tggctggtac gccgaggacc tagacctggg cttcatctcc cctgaccaat acaccacgcc    240
cgacattgtc tgtcacaaga acgcggcccc aggtgccatt tctgccactg cagcggccgg    300
cagcaacatc gtcttccaat ggggccctgg cgtctggcct caccctacg gtcccatcgt    360 tacctacgtg gctgagtgca gcggatcgtg cacgaccgtg aacaagaaca acctgcgctg    420
ggtcaagatt caggaggccg gcatcaacta taacacccaa gtctgggcgc agcaggatct    480
gatcaaccag ggcaacaagt ggactgtgaa gatcccgtcg agcctcaggc ccggaaacta    540
tgtcttccgc catgaacttc ttgctgccca tggtgcctct agtgcgaacg gcatgcagaa    600
ctatcctcag tgcgtgaaca tcgccgtcac aggctcgggc acgaaagcgc tccctgccgg    660
aactcctgca actcagctct acaagcccac tgaccctggc atcttgttca accctttacac   720 aacaatcacg agctacacca tccctggccc agccctgtgg caaggctaga tccaggggta    780
cggtgttggc gttcgtgaag tcggagctgt tgacaaggat atctgatgat gaacggagag    840
gactgatggc cgtgactgag tgtatatatt tttgatgacc aaattgtata cgaaatccga    900
acgcatggtg atcattgttt atccctgtag tatattgtct ccaggctgct aagagcccac    960
cgggtgtatt acggcaacaa agtcaggaat ttgggtggca atgaacgcag gtctccatga   1020
atgtatatgt gaagaggcat cggctggcat gggcattacc agatataggc cctgtgaaac   1080
atatagtact tgaacgtgct actggaacgg atcataagca agtcatcaac atgtgaaaaa   1140
acactacatg taaaaaaaaa aaaaaaaaaa aa                                 1172
```

<210> SEQ ID NO 16
<211> LENGTH: 249
<212> TYPE: PRT
<213> ORGANISM: Trichoderma reesei

<400> SEQUENCE: 16

```
Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Gln Lys Gln Asn Thr Gly
        35                  40                  45

His Phe Pro Asn Val Ala Gly Trp Tyr Ala Glu Asp Leu Asp Leu Gly
    50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Gly Ser Asn
                85                  90                  95

Ile Val Phe Gln Trp Gly Pro Gly Val Trp Pro His Pro Tyr Gly Pro
            100                 105                 110

Ile Val Thr Tyr Val Val Glu Cys Ser Gly Ser Cys Thr Thr Val Asn
        115                 120                 125

Lys Asn Asn Leu Arg Trp Val Lys Ile Gln Glu Ala Gly Ile Asn Tyr
    130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
            180                 185                 190
```

```
Gln Asn Tyr Pro Gln Cys Val Asn Ile Ala Val Thr Gly Ser Gly Thr
            195                 200                 205

Lys Ala Leu Pro Ala Gly Thr Pro Ala Thr Gln Leu Tyr Lys Pro Thr
    210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245

<210> SEQ ID NO 17
<211> LENGTH: 924
<212> TYPE: DNA
<213> ORGANISM: Myceliophthora thermophila

<400> SEQUENCE: 17
atgaagttca cctcgtccct cgctgtcctg gccgctgccg gcgcccaggc tcactgttag      60
tcgaccctcg aacccaacac ccccctcccc cctttctcc tccatctcct cggcctcact    120
tagtagccgc tgacaacgac tagataccct ccctagggcc ggcactggtg gctcgctctc    180
tggcgagtgg gaggtggtcc gcatgaccga gaaccattac tcgcacggcc cggtcaccga    240
tgtcaccagc cccgagatga cctgctatca gtccggcgtg cagggtgcgc ccagaccgt     300 ccaggtcaag gcgggctccc aattcacctt cagcgtggat ccctcgatcg gccaccccgg    360
ccctctccag ttctacatgg ctaaggtgcc gtcgggccag acggccgcca cctttgacgg    420
cacgggagcc gtgtggttca agatctacca agacggcccg aacggcctcg caccgacag     480 cattacctgg cccagcgccg gttcgtgact tcctccccac tcgcttttt ttttttattt     540 tttatttttt tttcttcgg aactcaagaa tctttctctc tctctcccgt ctttggcctt     600
gaacaacact aaaactcttc cttactgtat taattaggca aaaccgaggt ctcggtcacc    660
atccccagct gcatcgatga tggcgagtac ctgctccggg tcgagcacat cgcgctccac    720
agcgccagca gcgtgggcgg cgctcagttc tacattgcct cgcccagct ctccgtcacc     780 ggcggctccg gcaccctcaa cacgggctcg ctcgtctccc tgcccggcgc ctacaaggcc    840
accgacccgg gcatcctctt ccagctctac tggcccatcc cgaccgagta catcaacccc    900
ggcccggccc ccgtctcttg ctaa                                           924

<210> SEQ ID NO 18
<211> LENGTH: 232
<212> TYPE: PRT
<213> ORGANISM: Myceliophthora thermophila

<400> SEQUENCE: 18

Met Lys Phe Thr Ser Ser Leu Ala Val Leu Ala Ala Gly Ala Gln
1               5                   10                  15

Ala His Tyr Thr Phe Pro Arg Ala Gly Thr Gly Gly Ser Leu Ser Gly
                20                  25                  30

Glu Trp Glu Val Val Arg Met Thr Glu Asn His Tyr Ser His Gly Pro
            35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
```

100                 105                 110
Gly Ala Val Trp Phe Lys Ile Tyr Gln Asp Gly Pro Asn Gly Leu Gly
            115                 120                 125

Thr Asp Ser Ile Thr Trp Pro Ser Ala Gly Lys Thr Glu Val Ser Val
        130                 135                 140

Thr Ile Pro Ser Cys Ile Asp Asp Gly Glu Tyr Leu Leu Arg Val Glu
145                 150                 155                 160

His Ile Ala Leu His Ser Ala Ser Ser Val Gly Gly Ala Gln Phe Tyr
                165                 170                 175

Ile Ala Cys Ala Gln Leu Ser Val Thr Gly Gly Ser Gly Thr Leu Asn
            180                 185                 190

Thr Gly Ser Leu Val Ser Leu Pro Gly Ala Tyr Lys Ala Thr Asp Pro
        195                 200                 205

Gly Ile Leu Phe Gln Leu Tyr Trp Pro Ile Pro Thr Glu Tyr Ile Asn
            210                 215                 220

Pro Gly Pro Ala Pro Val Ser Cys
225                 230

<210> SEQ ID NO 19
<211> LENGTH: 854
<212> TYPE: DNA
<213> ORGANISM: Myceliophthora thermophila

<400> SEQUENCE: 19
atgaaggccc tctctctcct tgcggctgcc tcggcagtct ctgcgcatac catcttcgtc    60
cagctcgaag cagacggcac gaggtacccg gtctcgtacg ggatccggga cccaagctac   120
gacggcccca tcaccgacgt cacatccaac gacgttgctt gcaacggcgg ccgaacccg   180
acgaccccct ccagcgacgt catcaccgtc accgcgggca ccggtcaa ggccatctgg   240
aggcacaccc tccaatccgg cccggacgat gtcatggacg ccagccacaa gggcccgacc   300
ctggcctacc tcaagaaggt cggcgatgcc accaaggact cggcgtcgg cggtggctgg   360
ttcaagattc aggaggacgg ctacaacaac ggccagtggg gcaccagcac cgttatctcc   420
aacggcggcg agcactacat gtgagccatt cctccgagag aagaccaaga ctcttgacga   480
tctcgctgac ccgtgcaaca gtgacatcc cggcctgcat ccccgagggt cagtacctcc   540
tccgcgccga tgatcgcc ctccacgcgg ccgggtcccc cggcggtgcc cagctctacg   600
taagcctctg cccttccccc cttcctcttg atcgaatcgg actgcccacc ccccttttcg   660
actccgacta caccgttgc cagatggaat gtgcccagat caacatcgtc ggcggctccg   720
gctcggtgcc cagctcgacc gtcagcttcc ccggcgcgta cagccccaac gacccgggtc   780
tcctcatcaa catctattcc atgtcgccct cgagctcgta caccatcccg ggcccgcccg   840
tcttcaagtg ctag                                                    854

<210> SEQ ID NO 20
<211> LENGTH: 235
<212> TYPE: PRT
<213> ORGANISM: Myceliophthora thermophila

<400> SEQUENCE: 20

Met Lys Ala Leu Ser Leu Leu Ala Ala Ala Ser Ala Val Ser Ala His
1               5                   10                  15

Thr Ile Phe Val Gln Leu Glu Ala Asp Gly Thr Arg Tyr Pro Val Ser
            20                  25                  30

Tyr Gly Ile Arg Asp Pro Ser Tyr Asp Gly Pro Ile Thr Asp Val Thr

```
                    35                  40                  45
Ser Asn Asp Val Ala Cys Asn Gly Gly Pro Asn Pro Thr Thr Pro Ser
 50                  55                  60

Ser Asp Val Ile Thr Val Thr Ala Gly Thr Thr Val Lys Ala Ile Trp
 65                  70                  75                  80

Arg His Thr Leu Gln Ser Gly Pro Asp Asp Val Met Asp Ala Ser His
                 85                  90                  95

Lys Gly Pro Thr Leu Ala Tyr Leu Lys Lys Val Gly Asp Ala Thr Lys
            100                 105                 110

Asp Ser Gly Val Gly Gly Trp Phe Lys Ile Gln Glu Asp Gly Tyr
        115                 120                 125

Asn Asn Gly Gln Trp Gly Thr Ser Thr Val Ile Ser Asn Gly Gly Glu
130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
        195                 200                 205

Asp Pro Gly Leu Leu Ile Asn Ile Tyr Ser Met Ser Pro Ser Ser Ser
210                 215                 220

Tyr Thr Ile Pro Gly Pro Pro Val Phe Lys Cys
225                 230                 235

<210> SEQ ID NO 21
<211> LENGTH: 1242
<212> TYPE: DNA
<213> ORGANISM: Myceliophthora thermophila

<400> SEQUENCE: 21
atgaagtcct tcgccctcac cactctggcc gccctggccg gcaacgccgc cgctcacgcg      60
accttccagg ccctctgggt cgacggcgtc gactacggcg cgcagtgtgc ccgtctgccc     120
gcgtccaact ccccggtcac cgacgtgacc tccaacgcga tccgctgcaa cgccaacccg     180
tcgcccgctc ggggcaagtg cccggtcaag gccggctcga ccgttacggt cgagatgcat     240
caggtacgtt ggatgaatga aggggaaag gaagcagagg cagaagggga aggcgaaggg     300
aaagaaaaag aaaagaaat ggaaagaaa aagaaatgga aagaaaag aaaaatgaaa     360 aagaaagtgg aaaccgtcag actaactggg gctcctcccc cccaccctc ctttgatatc     420 agcaacccgg tgaccggtcg tgcagcagcg aggcgatcgg cggggcgcac tacgccccg     480 tcatggtgta catgtccaag gtgtcggacg cggcgtcggc ggacgggtcg tcgggctggt     540
tcaaggtgtt cgaggacggc tgggccaaga accgtccgg cgggtcgggc gacgacgact     600
actggggcac caaggacctg aactcgtgct gcgggaagat gaacgtcaag atccccgccg     660
acctgccctc gggcgactac ctgctccggg ccgaggccct cgcgctgcac acggcgggca     720
gcgccggcgg cgcccagttc tacatgacgt gctaccagct caccgtgacg gctccggca     780 gcgccagccc gcccaccgtc tccttcccgg gcgcctacaa ggccaccgac ccgggcatcc     840
tcgtcaacat ccacgccccg ctgtccggct acaccgtgcc cggcccggcc gtctactccg     900
gcggctccac caagaggcc ggcagcgcct tcaccggctg cgagtccacc tgcgccgtcg     960
gctccggccc caccgccacc gtctcccagt cgcccggttc caccgccacc tccgcccccg    1020
```

```
gcggcggcgg cggctgcacc gtccagaagt accagcagtg cggcggcgag ggctacaccg    1080
gctgcaccaa ctgcgcggta cgttttcaa cccgttttt ttttttcctt ccctaccta      1140 tttggttacc taattaatta ctttccggct gctgactttt tgctttagtc cggctctacc    1200
tgcagcgccg tctcgccgcc ctactactcg cagtgcgtct aa                       1242
```

<210> SEQ ID NO 22
<211> LENGTH: 323
<212> TYPE: PRT
<213> ORGANISM: Myceliophthora thermophila

<400> SEQUENCE: 22

```
Met Lys Ser Phe Ala Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Tyr Trp Gly Thr
    130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Cys Thr Val
        275                 280                 285

Gln Lys Tyr Gln Gln Cys Gly Gly Glu Gly Tyr Thr Gly Cys Thr Asn
    290                 295                 300

Cys Ala Ser Gly Ser Thr Cys Ser Ala Val Ser Pro Pro Tyr Tyr Ser
305                 310                 315                 320

Gln Cys Val
```

<210> SEQ ID NO 23
<211> LENGTH: 1253
<212> TYPE: DNA
<213> ORGANISM: Myceliophthora thermophila

<400> SEQUENCE: 23

| | | |
|---|---|---|
| atgaagcctt ttagcctcgt cgccctggcg accgccgtga gcggccatgc catcttccag | 60 |
| cgggtgtcgg tcaacgggca ggaccagggc cagctcaagg gggtgcgggc gccgtcgagc | 120 |
| aactccccga tccagaacgt caacgatgcc aacatggcct gcaacgccaa cattgtgtac | 180 |
| cacgacagca ccatcatcaa ggtgcccgcg ggagcccgcg tcggcgcgtg gtggcagcac | 240 |
| gtcatcggcg ggccgcaggg cgccaacgac ccggacaacc cgatcgcggc ctcccacaag | 300 |
| ggtatgatga tcgatgatgc ctctctcttc ccccgttctt gatggacagg cgatggctcc | 360 |
| caggaacacg cgtgactgac caccgaatcc aggccccatc caggtctacc tggccaaggt | 420 |
| ggacaacgcg gcgacggcgt cgccgtcggg cctcaggtgg ttcaaggtgg ccgagcgcgg | 480 |
| cctgaacaac ggcgtgtggg ccgtcgatga gctcatcgcc aacaacggct ggcactactt | 540 |
| cgacctgccg tcgtgcgtgg cccccggcca gtacctgatg cgcgtcgagc tgctcgccct | 600 |
| gcacagcgcc tcaagccccg gcggcgccca gttctacatg ggctgcgcac agatcgaagg | 660 |
| tgcgtcgatc tttgttctcc ttccgtgtcc tctctgatcc tttctctctt cttttctttt | 720 |
| cttttactcc ctttccttcc atcttcggag aagcaacgaa gggggaaagg gatagaagag | 780 |
| aggaatgaga gacgacgaaa gagaggattg gggaaagaca agacagggaa aaaaagacaa | 840 |
| gaaaaaaaaa aaaaaaaaaa aacagagtga gctaacaaga acaatcagtc actggctccg | 900 |
| gcaccaactc gggctccgac tttgtctcgt tccccggcgc ctactcggcc aacgatccgg | 960 |
| gcatcttgct aagcatctac gacagctcgg caagcccac caacggcggg cgctcgtacc | 1020 |
| cgatccccgg cccgcgcccc atctcctgct ccggcagcgg cgacggcggc aacaacggcg | 1080 |
| gcggcggcga cgacaacaac aataacaacg gtggtggcaa caacggcggc ggcggcggcg | 1140 |
| gcagcgtccc cctgtacggg cagtgcggcg gcatcggcta cacgggcccg accacctgtg | 1200 |
| cccagggaac ttgcaaggtg tcgaacgaat actacagcca gtgcctcccc tag | 1253 |

<210> SEQ ID NO 24
<211> LENGTH: 310
<212> TYPE: PRT
<213> ORGANISM: Myceliophthora thermophila

<400> SEQUENCE: 24

Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
            20                  25                  30

Lys Gly Val Arg Ala Pro Ser Ser Asn Ser Pro Ile Gln Asn Val Asn
        35                  40                  45

Asp Ala Asn Met Ala Cys Asn Ala Asn Ile Val Tyr His Asp Ser Thr
    50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95

Ala Ser His Lys Gly Pro Ile Gln Val Tyr Leu Ala Lys Val Asp Asn
            100                 105                 110

| | | | | | | | | | | | | |
|---|---|---|---|---|---|---|---|---|---|---|---|---|
|Ala|Ala|Thr|Ala|Ser|Pro|Ser|Gly|Leu|Arg|Trp|Phe|Lys|Val|Ala|Glu|
| | |115| | | |120| | | |125| | |

Ala Ala Thr Ala Ser Pro Ser Gly Leu Arg Trp Phe Lys Val Ala Glu
           115          120           125

Arg Gly Leu Asn Asn Gly Val Trp Ala Val Asp Glu Leu Ile Ala Asn
    130           135          140

Asn Gly Trp His Tyr Phe Asp Leu Pro Ser Cys Val Ala Pro Gly Gln
145          150           155          160

Tyr Leu Met Arg Val Glu Leu Leu Ala Leu His Ser Ala Ser Ser Pro
        165           170          175

Gly Gly Ala Gln Phe Tyr Met Gly Cys Ala Gln Ile Glu Val Thr Gly
        180           185          190

Ser Gly Thr Asn Ser Gly Ser Asp Phe Val Ser Phe Pro Gly Ala Tyr
    195           200          205

Ser Ala Asn Asp Pro Gly Ile Leu Leu Ser Ile Tyr Asp Ser Ser Gly
        210           215          220

Lys Pro Thr Asn Gly Gly Arg Ser Tyr Pro Ile Pro Gly Pro Arg Pro
225          230           235          240

Ile Ser Cys Ser Gly Ser Gly Asp Gly Asn Asn Gly Gly Gly
        245           250          255

Asp Asp Asn Asn Asn Asn Gly Gly Asn Gly Gly Gly
    260           265          270

Gly Gly Ser Val Pro Leu Tyr Gly Gln Cys Gly Gly Ile Gly Tyr Thr
    275           280          285

Gly Pro Thr Thr Cys Ala Gln Gly Thr Cys Lys Val Ser Asn Glu Tyr
    290           295          300

Tyr Ser Gln Cys Leu Pro
305          310

<210> SEQ ID NO 25
<211> LENGTH: 814
<212> TYPE: DNA
<213> ORGANISM: Myceliophthora thermophila

<400> SEQUENCE: 25

```
atgaagctct ccctcttctc cgtcctggcc actgccctca ccgtcgaggg gcatgccatc    60
ttccagaagg tctccgtcaa cggagcggac cagggctccc tcaccggcct ccgcgctccc   120
aacaacaaca accccgtgca ggatgtcaac agccaggaca tgatctgcgg ccagtcggga   180
tcgacgtcga acactatcat cgaggtcaag gccggcgata ggatcggtgc ctggtatcag   240
catgtcatcg gcggtgccca gttccccaac gacccagaca cccgattgc caagtcgcac   300
aagggccccg tcatggccta cctcgccaag gttgacaatg ccgcaaccgc cagcaagacg   360
ggcctgaagt ggtatgtatt cccgcggccc gagggacatc gggttgggca agtcgagact   420
gacggagctc gcttctccgt ataggttcaa gatttgggag ataccttta atcccagcac   480
caagacctgg ggtgtcgaca acctcatcaa taacaacggc tgggtgtact caacctccc   540
gcagtgcatc gccgacggca actacctcct ccgcgtcgag gtcctcgctc tgcactcggc   600
ctactctcag ggccaggctc agttctacca gtcctgcgcc cagatcaacg tatccggcgg   660
cggctccttc acaccgccgt cgactgtcag cttcccgggt gcctacagcg ccagcgaccc   720
cggtatcctg atcaacatct acggcgccac cggccagccc gacaacaacg ccagccgta   780
cactgcccct gggcccgcgc ccatctcctg ctga                               814
```

<210> SEQ ID NO 26
<211> LENGTH: 246
<212> TYPE: PRT

<213> ORGANISM: Myceliophthora thermophila

<400> SEQUENCE: 26

```
Met Lys Leu Ser Leu Phe Ser Val Leu Ala Thr Ala Leu Thr Val Glu
1               5                   10                  15
Gly His Ala Ile Phe Gln Lys Val Ser Val Asn Gly Ala Asp Gln Gly
            20                  25                  30
Ser Leu Thr Gly Leu Arg Ala Pro Asn Asn Asn Pro Val Gln Asp
        35                  40                  45
Val Asn Ser Gln Asp Met Ile Cys Gly Gln Ser Gly Ser Thr Ser Asn
    50                  55                  60
Thr Ile Ile Glu Val Lys Ala Gly Asp Arg Ile Gly Ala Trp Tyr Gln
65                  70                  75                  80
His Val Ile Gly Gly Ala Gln Phe Pro Asn Asp Pro Asp Asn Pro Ile
                85                  90                  95
Ala Lys Ser His Lys Gly Pro Val Met Ala Tyr Leu Ala Lys Val Asp
            100                 105                 110
Asn Ala Ala Thr Ala Ser Lys Thr Gly Leu Lys Trp Phe Lys Ile Trp
        115                 120                 125
Glu Asp Thr Phe Asn Pro Ser Thr Lys Thr Trp Gly Val Asp Asn Leu
    130                 135                 140
Ile Asn Asn Gly Trp Val Tyr Phe Asn Leu Pro Gln Cys Ile Ala
145                 150                 155                 160
Asp Gly Asn Tyr Leu Leu Arg Val Glu Val Leu Ala Leu His Ser Ala
                165                 170                 175
Tyr Ser Gln Gly Gln Ala Gln Phe Tyr Gln Ser Cys Ala Gln Ile Asn
            180                 185                 190
Val Ser Gly Gly Ser Phe Thr Pro Pro Ser Thr Val Ser Phe Pro
        195                 200                 205
Gly Ala Tyr Ser Ala Ser Asp Pro Gly Ile Leu Ile Asn Ile Tyr Gly
    210                 215                 220
Ala Thr Gly Gln Pro Asp Asn Asn Gly Gln Pro Tyr Thr Ala Pro Gly
225                 230                 235                 240
Pro Ala Pro Ile Ser Cys
                245
```

<210> SEQ ID NO 27
<211> LENGTH: 1115
<212> TYPE: DNA
<213> ORGANISM: Thermoascus aurantiacus

<400> SEQUENCE: 27

```
atgtcgttct cgaagattgc tgcgatcacc ggggccatta cctatgcgtc tctggccgcc    60
gctcacggtt atgttacagg aatcgtagcc gatggcacct agtatgtaac gctcatgcca   120
agatccgcat tgctgtacta acaattagca gctacggggg ctatatcgtg acccaatacc   180
cctacatgtc gacaccgccg gatgtcatcg cctggtctac caaagcaact gatcttggtt   240
tcgtggatcc cagtagctat gcttcgtctg atattatctg ccacaagggt gctgagcctg   300
gtgccctgag cgccaaggtg gctgctggag gaccgtcga gctgcagtgg acggattggc   360
ctgagagtca aagggccccg gtcattgact acctcgccgc ctgtaacggg gactgctcga   420
ctgtcgacaa gaccaaacta gagttcttca agattgatga gagtggccta attgacggca   480
gcagcgcccc aggcacatgg gcctctgaca acttgattgc caataacaac agctggaccg   540
tcaccatccc gagcacgatt gctcccggca actatgtcct gagacatgaa atcattgccc   600
```

-continued

```
tccactccgc cggaaataca aatggtgctc agaactaccc ccagtgtatc aaccttgagg      660
tcacaggcag tggcaccgac accctgccg gcaccctcgg aacggagctt tataaggcaa       720
cggaccctgg cattctggtc aacatctacc agaccctgac cagctacgat attcccggcc     780
ctgctctgta caccggtggt agctctggta gctctggttc ctccaacacc gccaaggca      840 ccacttcgac ggcttctagc tctatcgtga ccccgacgcc tgttaacaac ccaaccgtta     900
ctcagactgc cgttgttgat gtcacccaga ctgtttccca gaatgctgcc gtcgccacca     960
cgactccggc ctccactgca gttgctacag ctgtcccaac gggaaccacc tttagctttg    1020
attcgatgac ctcggatgaa ttcgtcagcc tgatgcgtgc gaccgtgaat tggctgcttt    1080
ctaacaagaa gcatgcccgg gatctttctt actaa                               1115
```

<210> SEQ ID NO 28
<211> LENGTH: 354
<212> TYPE: PRT
<213> ORGANISM: Thermoascus aurantiacus

<400> SEQUENCE: 28

```
Met Ser Phe Ser Lys Ile Ala Ala Ile Thr Gly Ala Ile Thr Tyr Ala
1               5                   10                  15

Ser Leu Ala Ala Ala His Gly Tyr Val Thr Gly Ile Val Ala Asp Gly
            20                  25                  30

Thr Tyr Gly Gly Tyr Ile Val Thr Gln Tyr Pro Tyr Met Ser Thr
        35                  40                  45

Pro Pro Asp Val Ile Ala Trp Ser Thr Lys Ala Thr Asp Leu Gly Phe
    50                  55                  60

Val Asp Pro Ser Ser Tyr Ala Ser Ser Asp Ile Ile Cys His Lys Gly
65                  70                  75                  80

Ala Glu Pro Gly Ala Leu Ser Ala Lys Val Ala Ala Gly Gly Thr Val
                85                  90                  95

Glu Leu Gln Trp Thr Asp Trp Pro Glu Ser His Lys Gly Pro Val Ile
            100                 105                 110

Asp Tyr Leu Ala Ala Cys Asn Gly Asp Cys Ser Thr Val Asp Lys Thr
        115                 120                 125

Lys Leu Glu Phe Phe Lys Ile Asp Glu Ser Gly Leu Ile Asp Gly Ser
    130                 135                 140

Ser Ala Pro Gly Thr Trp Ala Ser Asp Asn Leu Ile Ala Asn Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Thr Asn Gly
            180                 185                 190

Ala Gln Asn Tyr Pro Gln Cys Ile Asn Leu Glu Val Thr Gly Ser Gly
        195                 200                 205

Thr Asp Thr Pro Ala Gly Thr Leu Gly Thr Glu Leu Tyr Lys Ala Thr
    210                 215                 220

Asp Pro Gly Ile Leu Val Asn Ile Tyr Gln Thr Leu Thr Ser Tyr Asp
225                 230                 235                 240

Ile Pro Gly Pro Ala Leu Tyr Thr Gly Gly Ser Ser Gly Ser Ser Gly
                245                 250                 255

Ser Ser Asn Thr Ala Lys Ala Thr Thr Ser Thr Ala Ser Ser Ser Ile
            260                 265                 270

Val Thr Pro Thr Pro Val Asn Asn Pro Thr Val Thr Gln Thr Ala Val
```

```
                275                 280                 285
Val Asp Val Thr Gln Thr Val Ser Gln Asn Ala Ala Val Ala Thr Thr
            290                 295                 300

Thr Pro Ala Ser Thr Ala Val Ala Thr Ala Val Pro Thr Gly Thr Thr
305                 310                 315                 320

Phe Ser Phe Asp Ser Met Thr Ser Asp Glu Phe Val Ser Leu Met Arg
                325                 330                 335

Ala Thr Val Asn Trp Leu Leu Ser Asn Lys Lys His Ala Arg Asp Leu
            340                 345                 350

Ser Tyr

<210> SEQ ID NO 29
<211> LENGTH: 862
<212> TYPE: DNA
<213> ORGANISM: Aspergillus fumigatus

<400> SEQUENCE: 29
atgactttgt ccaagatcac ttccattgct ggccttctgg cctcagcgtc tctcgtggct    60
ggccacggct ttgtttctgg cattgttgct gatgggaaat agtatgtgct gaaccacac    120 aaatgacagc tgcaacagct aacttctatt ccagttacgg agggtacctt gttaaccaat   180 accctacat gagcaaccct cccgacacca ttgcctggtc caccaccgcc accgacctcg    240
gctttgtgga cggcaccggc taccagtctc cggatattat ctgccacaga gacgcaaaga   300
atggcaagtt gaccgcaacc gttgcagccg gttcacagat cgaattccag tggacgacgt   360
ggccagagtc tcaccatgga ccggtacgac gccgaagaga gagaacata ttgtgaccag    420 ataggctaac atagcatagt tgattactta cctcgctcca tgcaacggcg actgtgccac   480
cgtggacaag accaccctga gtttgtcaa gatcgccgct caaggcttga tcgacggctc   540
caacccacct ggtgtttggg ctgatgatga atgatcgcc aacaacaaca cggccacagt    600
gaccattcct gcctcctatg cccccggaaa ctacgtcctt cgccacgaga tcatcgccct   660
tcactctgcg ggtaacctga acggcgcgca gaactacccc cagtgtttca acatccaaat   720
caccggtggc ggcagtgctc agggatctgg caccgctggc acgtccctgt acaagaatac   780
tgatcctggc atcaagtttg acatctactc ggatctgagc ggtggatacc ctattcctgg   840
tcctgcactg ttcaacgctt aa                                            862

<210> SEQ ID NO 30
<211> LENGTH: 250
<212> TYPE: PRT
<213> ORGANISM: Aspergillus fumigatus

<400> SEQUENCE: 30

Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
            20                  25                  30

Lys Tyr Tyr Gly Gly Tyr Leu Val Asn Gln Tyr Pro Tyr Met Ser Asn
        35                  40                  45

Pro Pro Asp Thr Ile Ala Trp Ser Thr Thr Ala Thr Asp Leu Gly Phe
    50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95
```

```
Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
    130                 135                 140

Asn Pro Pro Gly Val Trp Ala Asp Asp Glu Met Ile Ala Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
            245                 250

<210> SEQ ID NO 31
<211> LENGTH: 1021
<212> TYPE: DNA
<213> ORGANISM: Penicillium pinophilum

<400> SEQUENCE: 31
atgccttcta ctaaagtcgc tgcccttttct gctgttctag ctttggcctc cacggttgct    60
ggccatggtt ttgtgcaaaa catcgttatc gacggtaaat cgtaagcagt gatgcatcca   120
ttattaaact agacatgctt acaaaaaaat cagttactct ggatacctcg tgaatcagtt   180
ccctacgag tccaacccac cagctgttat tgggtgggca caactgcaa ccgacctggg    240
attcgtcgct cccagtgagt acaccaatgc agacattatc tgccacaaga acgccacacc   300
tggcgcgctt tctgctccag ttgctgcagg gggcactgtc gagctccagt ggactacatg   360
gcccgatagt catcacggtc ctgtcatcag ctacctcgcc aactgcaatg caattgttc    420
taccgtggat aagactaagc tagactttgt caagattgac caaggtggtt tgatcgacga   480
tactaccccc ccgggtacat gggcttccga caaacttatc gctgccaaca acagctggac   540
tgtaactatc ccctccacca tcgcgcctgg aaactacgtt ttgcgccacg aaatcattgc   600
tcttcactcc gctggaaacg cagacggtgc ccaaaactac cctcaatgca tcaacttgga   660
gatcaccgga agcggaaccg ccgctccctc tggtaccgct ggcgaaaagc tctacacctc   720
tactgacccc ggtatcttgg tcaatatcta ccaatccttg tcgacctacg ttattcccgg   780
accaactctg tggagcggtg ctgccaatgg cgctgttgcc actggttctg ctactgcggt   840
tgctacgact gccactgctt ctgcgaccgc tactcctacc acacttgtta cctctgtcgc   900
tccagcttca tctaccttg ccactgctgt tgtgaccact gtcgctcctg cagtaactga   960
tgtcgtgact gtcaccgatg tagttaccgt gaccaccgtc atcaccacta ctgtccttg   1020
a                                                                    1021

<210> SEQ ID NO 32
<211> LENGTH: 322
<212> TYPE: PRT
```

<213> ORGANISM: Penicillium pinophilum

<400> SEQUENCE: 32

```
Met Pro Ser Thr Lys Val Ala Ala Leu Ser Ala Val Leu Ala Leu Ala
1               5                   10                  15
Ser Thr Val Ala Gly His Gly Phe Val Gln Asn Ile Val Ile Asp Gly
            20                  25                  30
Lys Ser Tyr Ser Gly Tyr Leu Val Asn Gln Phe Pro Tyr Glu Ser Asn
        35                  40                  45
Pro Pro Ala Val Ile Gly Trp Ala Thr Thr Ala Thr Asp Leu Gly Phe
    50                  55                  60
Val Ala Pro Ser Glu Tyr Thr Asn Ala Asp Ile Ile Cys His Lys Asn
65                  70                  75                  80
Ala Thr Pro Gly Ala Leu Ser Ala Pro Val Ala Gly Gly Thr Val
                85                  90                  95
Glu Leu Gln Trp Thr Thr Trp Pro Asp Ser His His Gly Pro Val Ile
            100                 105                 110
Ser Tyr Leu Ala Asn Cys Asn Gly Asn Cys Ser Thr Val Asp Lys Thr
        115                 120                 125
Lys Leu Asp Phe Val Lys Ile Asp Gln Gly Gly Leu Ile Asp Asp Thr
    130                 135                 140
Thr Pro Pro Gly Thr Trp Ala Ser Asp Lys Leu Ile Ala Ala Asn Asn
145                 150                 155                 160
Ser Trp Thr Val Thr Ile Pro Ser Thr Ile Ala Pro Gly Asn Tyr Val
                165                 170                 175
Leu Arg His Glu Ile Ile Ala Leu His Ser Ala Gly Asn Ala Asp Gly
            180                 185                 190
Ala Gln Asn Tyr Pro Gln Cys Ile Asn Leu Glu Ile Thr Gly Ser Gly
        195                 200                 205
Thr Ala Ala Pro Ser Gly Thr Ala Gly Glu Lys Leu Tyr Thr Ser Thr
    210                 215                 220
Asp Pro Gly Ile Leu Val Asn Ile Tyr Gln Ser Leu Ser Thr Tyr Val
225                 230                 235                 240
Ile Pro Gly Pro Thr Leu Trp Ser Gly Ala Ala Asn Gly Ala Val Ala
                245                 250                 255
Thr Gly Ser Ala Thr Ala Val Ala Thr Thr Ala Thr Ala Ser Ala Thr
            260                 265                 270
Ala Thr Pro Thr Thr Leu Val Thr Ser Val Pro Ala Ser Ser Thr
        275                 280                 285
Phe Ala Thr Ala Val Val Thr Thr Val Ala Pro Ala Val Thr Asp Val
    290                 295                 300
Val Thr Val Thr Asp Val Val Thr Val Thr Val Ile Thr Thr Thr
305                 310                 315                 320
Val Leu
```

<210> SEQ ID NO 33
<211> LENGTH: 1486
<212> TYPE: DNA
<213> ORGANISM: Thermoascus sp.

<400> SEQUENCE: 33

```
atgttgtcgt tcgcttctgc caagtcagct gtgctgacga cccttctact tcttggatcc    60
gctcaggctc acactttgat gaccaccctg tttgtggatg gcgtcaatca gggagatggt   120
gtctgtattc gcatgaacaa caacggtagt actgccaaca cctatatcca gcctgtcacg   180
```

```
agcaaggata ttgcctgcgg taagtacagt accggtccag atatcatact ctatttcaat    240
ccgacaacag tcagagctgg agagcaatgc taaacatccc caggcattca aggcgaaatt    300
ggcgccgctc gagtctgtcc agccaaggct tcatccaccc tcacgttcca attccgagag    360
cagccatcca acccgaattc cgctcctctc gatccctcgc acaaaggccc cgctgcggtg    420
tacctgaaaa aggtagactc cgccatcgcg agcaacaacg ccgctggaga cggctggttc    480
aagatctggg agtccgtcta cgacgagtcc acgggcaaat ggggtacgac caagatgatc    540
gagaacaacg ggcacatctc tgtcaaggtc cccgacgata tcgagggtgg gtattatctc    600
gcgcgtacgg agcttctggc gctgcacgcg gcgaacgaag gggatccgca gttctacgtt    660
ggctgcgcgc agctgttcat cgattcagcg gggacagcga aaccgcctac tgtctctatt    720
ggagagggga cctacgatct gagcatgcct gccatgacgt acaatatcta ccagactccg    780
ttggctctac ataccccgat gtatgggcct cctgtctaca cacctggctc tggctcgggt    840
tctggctctg gttccgggtc agcttctgca acgagatctt ctgctattcc tactgccacc    900
gctgttacgg actgttcttc gaagaggac agggaagact cagtcatggc aaccggtgtt    960
cccgttgcaa gaagcacact cagaacctgg gttgacagac tgtcatggca tggtaaggcc    1020
cgtgagaacg tgaaaccagc cgccaggaga agcgcccttg tccagaccga gggtctgaag    1080
ccggaaggct gcatcttcgt caacggcaac tggtgcggtt tcgaggtccc cgattacaac    1140
gatgcggaaa gctgctgggc tgtacgttcc cgtctaatta cttaaaacga aataaaagct    1200
aacagtactt ttcttttcct aatcccaggc ctccgacaac tgctggaaac agtccgactc    1260
gtgctggaac cagaccccagc ccaccggcta caacaactgc cagatctggc aagaccagaa    1320
atgcaagccc atccaggact cgtgtagcca atccaacccg actggaccgc cgaacaaggg    1380
caaggatata actccaacgt ggccgcccct ggagggctcg atgaagacct tcaccaagcg    1440
cactgtcagt taccgtgatt ggattatgaa aaggaaagga gcataa              1486
```

<210> SEQ ID NO 34
<211> LENGTH: 444
<212> TYPE: PRT
<213> ORGANISM: Thermoascus sp.

<400> SEQUENCE: 34

```
Met Leu Ser Phe Ala Ser Ala Lys Ser Ala Val Leu Thr Thr Leu Leu
1               5                  10                  15

Leu Leu Gly Ser Ala Gln Ala His Thr Leu Met Thr Thr Leu Phe Val
            20                  25                  30

Asp Gly Val Asn Gln Gly Asp Gly Val Cys Ile Arg Met Asn Asn Asn
        35                  40                  45

Gly Ser Thr Ala Asn Thr Tyr Ile Gln Pro Val Thr Ser Lys Asp Ile
    50                  55                  60

Ala Cys Gly Ile Gln Gly Glu Ile Gly Ala Ala Arg Val Cys Pro Ala
65                  70                  75                  80

Lys Ala Ser Ser Thr Leu Thr Phe Gln Phe Arg Glu Gln Pro Ser Asn
                85                  90                  95

Pro Asn Ser Ala Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Gly Trp Phe Lys Ile Trp Glu Ser Val Tyr Asp Glu Ser Thr Gly
    130                 135                 140
```

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ala Ala Asn Glu Gly Asp Pro Gln Phe Tyr Val
            180                 185                 190

Gly Cys Ala Gln Leu Phe Ile Asp Ser Ala Gly Thr Ala Lys Pro Pro
        195                 200                 205

Thr Val Ser Ile Gly Glu Gly Thr Tyr Asp Leu Ser Met Pro Ala Met
210                 215                 220

Thr Tyr Asn Ile Tyr Gln Thr Pro Leu Ala Leu Pro Tyr Pro Met Tyr
225                 230                 235                 240

Gly Pro Pro Val Tyr Thr Pro Gly Ser Gly Ser Gly Ser Gly Ser Gly
                245                 250                 255

Ser Gly Ser Ala Ser Ala Thr Arg Ser Ser Ala Ile Pro Thr Ala Thr
            260                 265                 270

Ala Val Thr Asp Cys Ser Ser Glu Glu Asp Arg Glu Asp Ser Val Met
        275                 280                 285

Ala Thr Gly Val Pro Val Ala Arg Ser Thr Leu Arg Thr Trp Val Asp
290                 295                 300

Arg Leu Ser Trp His Gly Lys Ala Arg Glu Asn Val Lys Pro Ala Ala
305                 310                 315                 320

Arg Arg Ser Ala Leu Val Gln Thr Glu Gly Leu Lys Pro Glu Gly Cys
                325                 330                 335

Ile Phe Val Asn Gly Asn Trp Cys Gly Phe Glu Val Pro Asp Tyr Asn
            340                 345                 350

Asp Ala Glu Ser Cys Trp Ala Ala Ser Asp Asn Cys Trp Lys Gln Ser
        355                 360                 365

Asp Ser Cys Trp Asn Gln Thr Gln Pro Thr Gly Tyr Asn Asn Cys Gln
370                 375                 380

Ile Trp Gln Asp Gln Lys Cys Lys Pro Ile Gln Asp Ser Cys Ser Gln
385                 390                 395                 400

Ser Asn Pro Thr Gly Pro Pro Asn Lys Gly Lys Asp Ile Thr Pro Thr
                405                 410                 415

Trp Pro Pro Leu Glu Gly Ser Met Lys Thr Phe Thr Lys Arg Thr Val
            420                 425                 430

Ser Tyr Arg Asp Trp Ile Met Lys Arg Lys Gly Ala
        435                 440

<210> SEQ ID NO 35
<211> LENGTH: 835
<212> TYPE: DNA
<213> ORGANISM: Penicillium sp.

<400> SEQUENCE: 35
atgctgtctt cgacgactcg caccctcgcc tttacaggcc ttgcgggcct tctgtccgct     60
cccctggtca aggcccatgg ctttgtccag ggcattgtca tcggtgacca attgtaagtc    120
cctctcttgc agttctgtcg attaactgct ggactgcttg cttgactccc tgctgactcc    180
caacagctac agcgggtaca tcgtcaactc gttccctac gaatccaacc caccccccgt    240
catcggctgg ccacgaccg ccaccgacct gggcttcgtc gacggcacag ataccaagg    300 cccggacatc atctgccacc ggaatgcgac gcccgcgccg ctgacagccc cgtggccgc    360 cggcggcacc gtcgagctgc agtggacgcc gtggccggac agccaccacg gacccgtcat    420

```
cacctacctg gcgccgtgca acggcaactg ctcgaccgtc gacaagacga cgctggagtt   480
cttcaagatc gaccagcagg gcctgatcga cgacacgagc ccgccgggca cctgggcgtc   540
ggacaacctc atcgccaaca acaatagctg gaccgtcacc attcccaaca gcgtcgcccc   600
cggcaactac gtcctgcgcc acgagatcat cgccctgcac tcggccaaca acaaggacgg   660
cgcccagaac taccccagt gcatcaacat cgaggtcacg gcggcggct ccgacgcgcc   720 tgagggtact ctgggcgagg atctctacca tgacaccgac ccgggcattc tggtcgacat   780
ttacgagccc attgcgacgt ataccattcc ggggccgcct gagccgacgt tctag       835
```

<210> SEQ ID NO 36
<211> LENGTH: 253
<212> TYPE: PRT
<213> ORGANISM: Penicillium sp.

<400> SEQUENCE: 36

```
Met Leu Ser Ser Thr Thr Arg Thr Leu Ala Phe Thr Gly Leu Ala Gly
 1               5                  10                  15

Leu Leu Ser Ala Pro Leu Val Lys Ala His Gly Phe Val Gln Gly Ile
             20                  25                  30

Val Ile Gly Asp Gln Phe Tyr Ser Gly Tyr Ile Val Asn Ser Phe Pro
         35                  40                  45

Tyr Glu Ser Asn Pro Pro Val Ile Gly Trp Ala Thr Thr Ala Thr
     50                  55                  60

Asp Leu Gly Phe Val Asp Gly Thr Gly Tyr Gln Gly Pro Asp Ile Ile
 65                  70                  75                  80

Cys His Arg Asn Ala Thr Pro Ala Pro Leu Thr Ala Pro Val Ala Ala
                 85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 37
<211> LENGTH: 977
<212> TYPE: DNA
<213> ORGANISM: Thielavia terrestris

<400> SEQUENCE: 37

```
atgaagctgt catcccagct cgccgccctc acgctggccg cggcctccgt gtcaggccac      60
tacatcttcg agcagattgc ccatggcggc accaagttcc caccttacga gtacatccga     120
agaaacacga actataacag ccctgtcacc agtctctcgt cgaacgacct gcgatgcaac     180
gtaggcggcg agacggctgg caacacgacc gtcctcgacg tgaaggcggg cgactccttc     240
accttctact cggacgtggc cgtgtaccac caggggccca tctcactgtg cgtgccccgg     300
gccaactttg atcagtccca agcggactgt ccgctcgcct ggataaccac aattgactga     360
cagcccgcac agctacatgt ccaaggctcc cggctccgtc gtggactacg acggctccgg     420
cgactggttc aagatccacg actgggggcc gaccttcagc aacggccagg cctcgtggcc     480
gctgcgggt gcgtcccttc cctttccctc cccttcctc cccttcctc cccccttc          540
ccccttttc tgtctggtcg cacgcccgc tgacgtcccc gtagacaact accagtacaa       600
catcccgacg tgcatcccga acggcgagta cctgctgcgc atccagtcgc tggcgatcca     660
caacccgggc gccacgccgc agttctacat cagctgcgcg caggtccggg tctcgggcgg     720
cggcagcgcc tcccctccc caacggccaa gatcccggc gcgttcaagg cgaccgatcc       780
cgggtatacc gcgaatgtga gtgccctatg ttccttgcgc tccttgttcc ttgctccttg     840
ctcggcgtgc ttgaacgcta cgggctgtgg agggagggat ggatggatga ataggatgct     900
gactgatggt gggacaccag atttacaata acttccactc gtatacggtg ccgggtccgg     960
cggtctttca gtgctag                                                    977
```

<210> SEQ ID NO 38  
<211> LENGTH: 223  
<212> TYPE: PRT  
<213> ORGANISM: Thielavia terrestris

<400> SEQUENCE: 38

```
Met Lys Leu Ser Ser Gln Leu Ala Ala Leu Thr Leu Ala Ala Ala Ser
1               5                   10                  15

Val Ser Gly His Tyr Ile Phe Glu Gln Ile Ala His Gly Gly Thr Lys
            20                  25                  30

Phe Pro Pro Tyr Glu Tyr Ile Arg Arg Asn Thr Asn Tyr Asn Ser Pro
        35                  40                  45

Val Thr Ser Leu Ser Ser Asn Asp Leu Arg Cys Asn Val Gly Gly Glu
    50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
                85                  90                  95

Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
        115                 120                 125

Ala Ser Trp Pro Leu Arg Asp Asn Tyr Gln Tyr Asn Ile Pro Thr Cys
    130                 135                 140

Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
                165                 170                 175

Val Ser Gly Gly Gly Ser Ala Ser Pro Ser Pro Thr Ala Lys Ile Pro
            180                 185                 190

Gly Ala Phe Lys Ala Thr Asp Pro Gly Tyr Thr Ala Asn Ile Tyr Asn
```

195                 200                 205
Asn Phe His Ser Tyr Thr Val Pro Gly Pro Ala Val Phe Gln Cys
    210                 215                 220

<210> SEQ ID NO 39
<211> LENGTH: 878
<212> TYPE: DNA
<213> ORGANISM: Thielavia terrestris

<400> SEQUENCE: 39
atgaagttct cactggtgtc tctgctggct tacggcctct cggtcgaggc gcactccatc    60
ttccaggttc gtctcgcaca tcacgctcaa ctcggctcgt ggcgtaaggg caaggattaa   120
cacggccggc agagagtctc ggtcaacggc aagaccaag gcctgctcac cggcctccgc   180
gctccaagca acaacaaccc agtgcaagat gtcaacagcc agaacatgat ttgcggccag   240
tcgggctcca agtcgcagac cgttatcaac gtcaaggccg gcgacaggat cggctcgctc   300
tggcagcatg tcatcggcgg cgcccagttt tcgggtgacc cggacaaccc gatcgcccac   360
tcgcacaagg gccccgtgat ggcgtacctt gctaaggtcg acaatgccgc gtccgcgagc   420
caaacgggtc tgaagtggta agtagcgggc gacgctcagg ggacggggat cggggggcctg   480
ctccatccga gactaacacc gtggacaggt tcaagatctg gcaggacggg ttcgatacca   540
gcagcaagac atggggcgtc gacaacctga tcaagaacaa cggctgggtg tacttccacc   600
tgccgcagtg cctcgctccg ggccagtatc tcctgcgcgt cgaggttctg gcgctgcact   660
cggcgtacca gcagggccag gcccagttct accagtcctg cgcccagatc aacgtctccg   720
gctccgggtc cttcagcccg tcccagacgg tcagcatccc gggcgtctac agcgccaccg   780
acccgagcat cctcatcaac atctacggca gcacggggca gcccgacaac ggcggcaagg   840
cttacaaccc ccctggaccc gccccgatct cctgctga                          878

<210> SEQ ID NO 40
<211> LENGTH: 246
<212> TYPE: PRT
<213> ORGANISM: Thielavia terrestris

<400> SEQUENCE: 40

Met Lys Phe Ser Leu Val Ser Leu Leu Ala Tyr Gly Leu Ser Val Glu
1               5                   10                  15

Ala His Ser Ile Phe Gln Arg Val Ser Val Asn Gly Gln Asp Gln Gly
                20                  25                  30

Leu Leu Thr Gly Leu Arg Ala Pro Ser Asn Asn Pro Val Gln Asp
            35                  40                  45

Val Asn Ser Gln Asn Met Ile Cys Gly Gln Ser Gly Ser Lys Ser Gln
    50                  55                  60

Thr Val Ile Asn Val Lys Ala Gly Asp Arg Ile Gly Ser Leu Trp Gln
65                  70                  75                  80

His Val Ile Gly Gly Ala Gln Phe Ser Gly Asp Pro Asp Asn Pro Ile
                85                  90                  95

Ala His Ser His Lys Gly Pro Val Met Ala Tyr Leu Ala Lys Val Asp
                100                 105                 110

Asn Ala Ala Ser Ala Ser Gln Thr Gly Leu Lys Trp Phe Lys Ile Trp
            115                 120                 125

Gln Asp Gly Phe Asp Thr Ser Ser Lys Thr Trp Gly Val Asp Asn Leu
    130                 135                 140

Ile Lys Asn Asn Gly Trp Val Tyr Phe His Leu Pro Gln Cys Leu Ala

```
                        145                 150                 155                 160
            Pro Gly Gln Tyr Leu Leu Arg Val Glu Val Leu Ala Leu His Ser Ala
                            165                 170                 175

Tyr Gln Gln Gly Gln Ala Gln Phe Tyr Gln Ser Cys Ala Gln Ile Asn
                        180                 185                 190

Val Ser Gly Ser Gly Ser Phe Ser Pro Ser Gln Thr Val Ser Ile Pro
                    195                 200                 205

Gly Val Tyr Ser Ala Thr Asp Pro Ser Ile Leu Ile Asn Ile Tyr Gly
                210                 215                 220

Ser Thr Gly Gln Pro Asp Asn Gly Gly Lys Ala Tyr Asn Pro Pro Gly
            225                 230                 235                 240

Pro Ala Pro Ile Ser Cys
                            245

<210> SEQ ID NO 41
<211> LENGTH: 1253
<212> TYPE: DNA
<213> ORGANISM: Thielavia terrestris

<400> SEQUENCE: 41
atgaggacga cattcgccgc cgcgttggca gccttcgctg cgcaggaagt ggcaggccat        60
gccatcttcc aacagctctg ggtggacggc accgactata tacgtgctcc ccttttcctt       120
ttgtgtttgc ccatcctcga ttgataaccc gaggccatcc aatgctgact cttacagcac       180
ggctcctcct gcgtccgcat gccgctgtcg aactcgcccg tcacgaacgt cggcagcagg       240
gacatgatct gcaacgccgg cacgcgcccc gtcagcggga gtgccccgt caaggccggc        300 ggcaccgtga cggttgagat gcaccaggtg ggctgatttc ctgagcgtcc tattcctccc       360
ggaagcccct ttcccatcct ttgccctggc taaccccctcc gccctcccca gcaacccggg      420
gatcggtcgt gtaacaacga agccatcggc ggcgcccact ggggaccggt gcaggtgtac      480
ctcagcaagg tggaggacgc gagcacggcg acgggtcga cgggctggtt caagatcttc       540
gcggacacgt ggtccaagaa ggcgggcagc tcggtggggg acgacgacaa ctggggcacg       600
cgcgacctca cgcgtgctg cggcaagatg caggtcaaga tcccggcgga catcccgtcg       660
ggcgactacc tgctgcgggc ggaggcgctg gcgctgcaca cggcgggcca ggtgggcggc       720
gcgcagttct acatgagctg ctaccagatc accgtgtcgg gcggcggcag cgccagcccg      780
gccaccgtca agttccccgg cgcctacagc gccaacgacc cgggcatcca catcaacatc      840
cacgcggccg tgtccaacta cgtcgcgccc ggcccggccg tctattccgg cggcacgacc      900
aaggtggccg gtccgggtg ccaaggctgc gagaacacgt gcaaggtcgg ctcgtcgccc       960
acggcgacgg cgccgtcggg caagagcggg cgggttccg acggcggcgc tgggaccgac      1020
ggcgggtctt cgtcttcgag ccccgacacg ggcagcgcgt gcagcgtgca ggcctacggg      1080
cagtgcggcg ggaacgggta tcggggttgc acccagtgcg cggtaagttc ggggtcgtct      1140 gtctttgta ggaacatccg agaggcttgg ctgacgaggc gttgttgtag cccggctata       1200
cttgcaaggc ggtctctccg ccgtactatt cgcagtgcgc cccttcttct tag             1253

<210> SEQ ID NO 42
<211> LENGTH: 334
<212> TYPE: PRT
<213> ORGANISM: Thielavia terrestris

<400> SEQUENCE: 42

Met Arg Thr Thr Phe Ala Ala Ala Leu Ala Ala Phe Ala Ala Gln Glu
```

```
1               5                   10                  15
Val Ala Gly His Ala Ile Phe Gln Gln Leu Trp His Gly Ser Ser Cys
                20                  25                  30
Val Arg Met Pro Leu Ser Asn Ser Pro Val Thr Asn Val Gly Ser Arg
                35                  40                  45
Asp Met Ile Cys Asn Ala Gly Thr Arg Pro Val Ser Gly Lys Cys Pro
    50                  55                  60
Val Lys Ala Gly Gly Thr Val Thr Val Glu Met His Gln Gln Pro Gly
65                  70                  75                  80
Asp Arg Ser Cys Asn Asn Glu Ala Ile Gly Gly Ala His Trp Gly Pro
                85                  90                  95
Val Gln Val Tyr Leu Ser Lys Val Glu Asp Ala Ser Thr Ala Asp Gly
                100                 105                 110
Ser Thr Gly Trp Phe Lys Ile Phe Ala Asp Thr Trp Ser Lys Lys Ala
                115                 120                 125
Gly Ser Ser Val Gly Asp Asp Asp Asn Trp Gly Thr Arg Asp Leu Asn
130                 135                 140
Ala Cys Cys Gly Lys Met Gln Val Lys Ile Pro Ala Asp Ile Pro Ser
145                 150                 155                 160
Gly Asp Tyr Leu Leu Arg Ala Glu Ala Leu Ala Leu His Thr Ala Gly
                165                 170                 175
Gln Val Gly Gly Ala Gln Phe Tyr Met Ser Cys Tyr Gln Ile Thr Val
                180                 185                 190
Ser Gly Gly Gly Ser Ala Ser Pro Ala Thr Val Lys Phe Pro Gly Ala
                195                 200                 205
Tyr Ser Ala Asn Asp Pro Gly Ile His Ile Asn Ile His Ala Ala Val
                210                 215                 220
Ser Asn Tyr Val Ala Pro Gly Pro Ala Val Tyr Ser Gly Gly Thr Thr
225                 230                 235                 240
Lys Val Ala Gly Ser Gly Cys Gln Gly Cys Glu Asn Thr Cys Lys Val
                245                 250                 255
Gly Ser Ser Pro Thr Ala Thr Ala Pro Ser Gly Lys Ser Gly Ala Gly
                260                 265                 270
Ser Asp Gly Gly Ala Gly Thr Asp Gly Gly Ser Ser Ser Ser Ser Pro
                275                 280                 285
Asp Thr Gly Ser Ala Cys Ser Val Gln Ala Tyr Gly Gln Cys Gly Gly
                290                 295                 300
Asn Gly Tyr Ser Gly Cys Thr Gln Cys Ala Pro Gly Tyr Thr Cys Lys
305                 310                 315                 320
Ala Val Ser Pro Pro Tyr Tyr Ser Gln Cys Ala Pro Ser Ser
                325                 330
```

<210> SEQ ID NO 43
<211> LENGTH: 798
<212> TYPE: DNA
<213> ORGANISM: Thielavia terrestris

<400> SEQUENCE: 43

```
atgaagctga gcgttgccat cgccgtgctg gcgtcggctc ttgccgaggc tcactgtgag    60
tgcatcgtct cactccagct actgcgaagc ttgctgacga tggtccctag acaccttccc   120
cagcatcgga acaccgctga ctggcagtag tgtgcggatt acaacgaact accagagcaa   180
cgggccggtg acggacgtca cctcggatca aattcggtgc tacgaacgga acccaggcac   240
gggagcgcag ggcatataca acgtcaccgc cggccagacc atcaactaca acgcgaaggc   300
```

-continued

```
gtccatctcc cacccggggc ccatgtcctt ctacattgct aaggttcccg ccggccaaac    360
cgctgcgacc tgggacggta aggggggctgt gtggaccaag atctaccagg acatgcccaa    420
gttcggcagc agcctgacct ggcccaccat gggtaagaat tctcaccctg gaaatgaacg    480
cacatttgca cagatctaac atggcctaca ggcgccaagt ctgtcccgt caccatccct    540 cgttgcctcc agaacggcga ttaccttctg cgagccgagc acatcgctct acacagcgcg    600
agcagcgtcg gtggcgccca gttctacctc tcgtgcgccc agcttactgt cagcggcggc    660
agtggcacct ggaaccccaa gaaccgggtc tccttccccg gcgcttacaa ggcaacagac    720
ccgggcatct tgatcaacat ctactacccc gtgccgacca gctactcgcc gcccggcccg    780
ccggctgaga cgtgctaa                                                   798
```

<210> SEQ ID NO 44
<211> LENGTH: 227
<212> TYPE: PRT
<213> ORGANISM: Thielavia terrestris

<400> SEQUENCE: 44

```
Met Lys Leu Ser Val Ala Ile Ala Val Leu Ala Ser Ala Leu Ala Glu
1               5                   10                  15

Ala His Tyr Thr Phe Pro Ser Ile Gly Asn Thr Ala Asp Trp Gln Tyr
            20                  25                  30

Val Arg Ile Thr Thr Asn Tyr Gln Ser Asn Gly Pro Val Thr Asp Val
        35                  40                  45

Thr Ser Asp Gln Ile Arg Cys Tyr Glu Arg Asn Pro Gly Thr Gly Ala
50                  55                  60

Gln Gly Ile Tyr Asn Val Thr Ala Gly Gln Thr Ile Asn Tyr Asn Ala
65                  70                  75                  80

Lys Ala Ser Ile Ser His Pro Gly Pro Met Ser Phe Tyr Ile Ala Lys
                85                  90                  95

Val Pro Ala Gly Gln Thr Ala Ala Thr Trp Asp Gly Lys Gly Ala Val
            100                 105                 110

Trp Thr Lys Ile Tyr Gln Asp Met Pro Lys Phe Gly Ser Ser Leu Thr
        115                 120                 125

Trp Pro Thr Met Gly Ala Lys Ser Val Pro Val Thr Ile Pro Arg Cys
130                 135                 140

Leu Gln Asn Gly Asp Tyr Leu Leu Arg Ala Glu His Ile Ala Leu His
145                 150                 155                 160

Ser Ala Ser Ser Val Gly Gly Ala Gln Phe Tyr Leu Ser Cys Ala Gln
                165                 170                 175

Leu Thr Val Ser Gly Gly Ser Gly Thr Trp Asn Pro Lys Asn Arg Val
            180                 185                 190

Ser Phe Pro Gly Ala Tyr Lys Ala Thr Asp Pro Gly Ile Leu Ile Asn
        195                 200                 205

Ile Tyr Tyr Pro Val Pro Thr Ser Tyr Ser Pro Gly Pro Pro Ala
    210                 215                 220

Glu Thr Cys
225
```

<210> SEQ ID NO 45
<211> LENGTH: 1107
<212> TYPE: DNA
<213> ORGANISM: Thielavia terrestris

<400> SEQUENCE: 45

```
atgccttctt tcgcctccaa gactctcctt tccaccctgg cgggtgccgc atccgtggcc      60
gcccacgggc acgtgtcgaa catcgtcatc aacggggtct cgtaccaggg ttacgatccg     120
acctccttcc cttacatgca gaacccgccc atcgtggtcg gctggactgc cgccgacacg     180
gacaacggct tgttgccccc ggatgccttc gccagtggcg atatcatctg ccacaagaac     240
gccaccaacg ccaagggcca cgccgtggtc gccgcgggag acaagatctt catccagtgg     300
aacacatggc ccgagtccca ccacggcccc gtcatcgact acctcgcgag ctgcggcagc     360
gcgtcctgcg agaccgtcga caagaccaag ctcgagttct tcaagatcga cgaggtcggc     420
ctggtcgacg gcagctcggc gcccggtgtg tggggctccg accagctcat cgccaacaac     480
aactcgtggc tcgtcgagat cccgcccacc atcgcgccgg gcaactacgt cctgcgccac     540
gagatcatcg cgctgcacag cgccgaaaac gccgacggcg cccagaacta cccgcagtgc     600
ttcaacctgc agatcaccgg caccggcacc gccacccccct ccggcgtccc cggcacctcg     660
ctctacaccc cgaccgaccc gggcatcctc gtcaacatct cagcgcccc gatcacctac     720
accgtcccgg ggccggccct catctccggc gccgtcagca tcgcccagtc ctcctccgcc     780
atcaccgcct ccggcaccgc cctgaccggc tctgccaccg cacccgccgc cgccgctgct     840
accacaactt ccaccaccaa cgccgcggct gctgctacct ctgctgctgc tgctgctggt     900
acttccacaa ccaccaccag cgccgcggcc gtggtccaga cctcctcctc ctcctcctcc     960
gccccgtcct ctgccgccgc cgccgccacc accaccgcgg ctgccagcgc ccgcccgacc    1020
ggctgctcct ctggccgctc caggaagcag ccgcgccgcc acgcgcggga tatggtggtt    1080
gcgcgagggg ctgaggaggc aaactga                                        1107

<210> SEQ ID NO 46
<211> LENGTH: 368
<212> TYPE: PRT
<213> ORGANISM: Thielavia terrestris

<400> SEQUENCE: 46

Met Pro Ser Phe Ala Ser Lys Thr Leu Leu Ser Thr Leu Ala Gly Ala
1               5                   10                  15

Ala Ser Val Ala Ala His Gly His Val Ser Asn Ile Val Ile Asn Gly
                20                  25                  30

Val Ser Tyr Gln Gly Tyr Asp Pro Thr Ser Phe Pro Tyr Met Gln Asn
            35                  40                  45

Pro Pro Ile Val Val Gly Trp Thr Ala Ala Asp Thr Asp Asn Gly Phe
        50                  55                  60

Val Ala Pro Asp Ala Phe Ala Ser Gly Asp Ile Ile Cys His Lys Asn
65                  70                  75                  80

Ala Thr Asn Ala Lys Gly His Ala Val Val Ala Gly Asp Lys Ile
                85                  90                  95

Phe Ile Gln Trp Asn Thr Trp Pro Glu Ser His His Gly Pro Val Ile
            100                 105                 110

Asp Tyr Leu Ala Ser Cys Gly Ser Ala Ser Cys Glu Thr Val Asp Lys
        115                 120                 125

Thr Lys Leu Glu Phe Phe Lys Ile Asp Glu Val Gly Leu Val Asp Gly
    130                 135                 140

Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
                165                 170                 175
```

```
Val Leu Arg His Glu Ile Ile Ala Leu His Ser Ala Glu Asn Ala Asp
            180                 185                 190

Gly Ala Gln Asn Tyr Pro Gln Cys Phe Asn Leu Gln Ile Thr Gly Thr
        195                 200                 205

Gly Thr Ala Thr Pro Ser Gly Val Pro Gly Ser Leu Tyr Thr Pro
    210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
                245                 250                 255

Ser Ser Ser Ala Ile Thr Ala Ser Gly Thr Ala Leu Thr Gly Ser Ala
            260                 265                 270

Thr Ala Pro Ala Ala Ala Ala Thr Thr Thr Ser Thr Thr Asn Ala
        275                 280                 285

Ala Ala Ala Ala Thr Ser Ala Ala Ala Ala Gly Thr Ser Thr Thr
    290                 295                 300

Thr Thr Ser Ala Ala Ala Val Val Gln Thr Ser Ser Ser Ser Ser Ser
305                 310                 315                 320

Ala Pro Ser Ser Ala Ala Ala Ala Thr Thr Ala Ala Ala Ser
                325                 330                 335

Ala Arg Pro Thr Gly Cys Ser Ser Gly Arg Ser Arg Lys Gln Pro Arg
            340                 345                 350

Arg His Ala Arg Asp Met Val Val Ala Arg Gly Ala Glu Glu Ala Asn
            355                 360                 365

<210> SEQ ID NO 47
<211> LENGTH: 993
<212> TYPE: DNA
<213> ORGANISM: Thielavia terrestris

<400> SEQUENCE: 47
atgccgcccg cactccctca actcctaacc acggtcctga ccgccctcac cctcggttcc      60
accgccctcg cccactcaca cctcgcgtac attatcgtta acggcaagct ctaccagggc     120
ttcgacccgc gcccgcacca ggccaactac ccttcccggg tcggtggtc caccggcgcc      180 gtcgacgacg gcttcgtcac gccggccaac tactccaccc cggacatcat ttgccacatc     240
gccggcacca gccggccgg ccacgcgccc gtgcgcccgg cgaccgcat ccacgtccag       300 tggaacggct ggccggtcgg ccacatcggt cccgtgctgt cgtacctcgc ccgctgcgag     360
tcggacacgg gctgcacggg ccagaacaag accgcgctgc ggtggaccaa gatcgacgac    420
tccagcccga ccatgcagaa cgtcgccggc gcgggcaccc agggcgaggg caccccggc     480 aagcgctggg ccaccgacgt gctgatcgcc gccaacaaca gctggcaggt cgccgtgccg   540
gcggggctgc cgaccggcgc gtacgtgctg cgcaacgaga tcatcgcgct gcactacgcg    600
gcgaggaaga acggggcgca gaactatccg ctctgcatga acctgtgggt ggacgccagt    660
ggtgataata gtagtgtggc tgcaacgacg gcggcggtga cggcgggggg tctgcagatg    720
gatgcgtatg acgcgcgcgg gttctacaag gagaacgatc cgggcgtgct ggtcaatgtc    780
acggccgcgc tgtcgtcgta tgtcgtgccc gggccgacgg tggcggcggg cgccacgccg   840
gtgccgtacg cgcagcagag cccgagcgtg tcgacggcgg cgggcacgcc cgtcgtcgtt    900
acaaggacta gcgagacggc gccgtacacg ggcgccatga cgccgacggt tgcggcgagg   960 atgaaggggga gggggtatga tcggcggggt tag                                  993
```

<210> SEQ ID NO 48
<211> LENGTH: 330
<212> TYPE: PRT
<213> ORGANISM: Thielavia terrestris

<400> SEQUENCE: 48

Met Pro Pro Ala Leu Pro Gln Leu Leu Thr Val Leu Thr Ala Leu
1               5                   10                  15

Thr Leu Gly Ser Thr Ala Leu Ala His Ser His Leu Ala Tyr Ile Ile
            20                  25                  30

Val Asn Gly Lys Leu Tyr Gln Gly Phe Asp Pro Arg Pro His Gln Ala
        35                  40                  45

Asn Tyr Pro Ser Arg Val Gly Trp Ser Thr Gly Ala Val Asp Asp Gly
    50                  55                  60

Phe Val Thr Pro Ala Asn Tyr Ser Thr Pro Asp Ile Ile Cys His Ile
65                  70                  75                  80

Ala Gly Thr Ser Pro Ala Gly His Ala Pro Val Arg Pro Gly Asp Arg
                85                  90                  95

Ile His Val Gln Trp Asn Gly Trp Pro Val Gly His Ile Gly Pro Val
            100                 105                 110

Leu Ser Tyr Leu Ala Arg Cys Glu Ser Asp Thr Gly Cys Thr Gly Gln
        115                 120                 125

Asn Lys Thr Ala Leu Arg Trp Thr Lys Ile Asp Asp Ser Ser Pro Thr
    130                 135                 140

Met Gln Asn Val Ala Gly Ala Gly Thr Gln Gly Glu Gly Thr Pro Gly
145                 150                 155                 160

Lys Arg Trp Ala Thr Asp Val Leu Ile Ala Ala Asn Asn Ser Trp Gln
                165                 170                 175

Val Ala Val Pro Ala Gly Leu Pro Thr Gly Ala Tyr Val Leu Arg Asn
            180                 185                 190

Glu Ile Ile Ala Leu His Tyr Ala Ala Arg Lys Asn Gly Ala Gln Asn
        195                 200                 205

Tyr Pro Leu Cys Met Asn Leu Trp Val Asp Ala Ser Gly Asp Asn Ser
    210                 215                 220

Ser Val Ala Ala Thr Thr Ala Ala Val Thr Ala Gly Gly Leu Gln Met
225                 230                 235                 240

Asp Ala Tyr Asp Ala Arg Gly Phe Tyr Lys Glu Asn Asp Pro Gly Val
                245                 250                 255

Leu Val Asn Val Thr Ala Ala Leu Ser Ser Tyr Val Val Pro Gly Pro
            260                 265                 270

Thr Val Ala Ala Gly Ala Thr Pro Val Pro Tyr Ala Gln Gln Ser Pro
        275                 280                 285

Ser Val Ser Thr Ala Ala Gly Thr Pro Val Val Val Thr Arg Thr Ser
    290                 295                 300

Glu Thr Ala Pro Tyr Thr Gly Ala Met Thr Pro Thr Val Ala Ala Arg
305                 310                 315                 320

Met Lys Gly Arg Gly Tyr Asp Arg Arg Gly
                325                 330

<210> SEQ ID NO 49
<211> LENGTH: 1221
<212> TYPE: DNA
<213> ORGANISM: Thielavia terrestris

<400> SEQUENCE: 49

```
atgaagacat tcaccgccct cctggccgca gccggcctcg tcgccggcca tggatatgtc    60
gacaacgcca ccattggcgg ccagttttat caggtactct accgcttcac ccaaggtccg   120
ctggccacaa ctctataggt gtcataaatt aacaagccac cgtcccgcag ttctatcagg   180
tgtgctcgct accgaccatg tggtcccgtc tcagcaagcc actcacacgc ccatgatccc   240
ctagccttac gtcgacccgt atttagcaac cttggcacgt agtatttatt gtcccaaata   300
ttgagctgaa ctgcacctcc ctagaatccc gcggtgctaa cattctttca gcccgacagg   360
gtctctcgat ccatcccggg caacggcccg gtcacggacg tcactctcat cgacctgcag   420
tgcaacgcca attccacccc ggccaagctc acgccactg ccgctgccgg tcggacgtg    480
attctccgct ggacgctctg gcctgagtcg cacgttggcc ccgtcatcac ctacatggcc   540
cgctgccccg acacgggctg ccaggactgg atgccgggca cttcgtagga gcccatcttg   600
caccatatcc atttcaaccg ccacacgca ctgacccata tgtctgtcta cccctgcagt   660
gcggtctggt tcaagatcaa ggagggcggc cgcgacggca cttccaacac ctgggccgac   720
gtacgtgtac cccgtcccag agagccaaag cccccccttc aacaaagcaa acatctcaat   780
agcccgagcc tacgcactaa cccctctcct tccccctcga aaacacagac cccgctgatg   840
acggcgccca cctcgtacac gtacacgatc ccctcctgcc tgaagaaggg ctactacctg   900
gtccgccacg agatcatcgc gctgcacgcc gcctacacct accccggcgc gcagttctac   960
ccgggctgcc accagctcaa cgtcacgggc ggcgggtcca ccgtaccgtc gagcggcctg  1020
gtggcctttc ccggggcgta caagggcagt gaccccggga ttacgtacga tgcgtataaa  1080
ggtgggttgg ctggttggcc caggtcttgg tgatggggga atgtggtgat gaggtttatt  1140
atttgggatc ccgtggctaa cgtaaccctg ggtgtagcgc aaacgtacca gattcctggg  1200
ccggcggtct ttacttgctg a                                            1221
```

<210> SEQ ID NO 50
<211> LENGTH: 236
<212> TYPE: PRT
<213> ORGANISM: Thielavia terrestris

<400> SEQUENCE: 50

Met Lys Thr Phe Thr Ala Leu Leu Ala Ala Ala Gly Leu Val Ala Gly
1               5                   10                  15

His Gly Tyr Val Asp Asn Ala Thr Ile Gly Gly Gln Phe Tyr Gln Asn
                20                  25                  30

Pro Ala Val Leu Thr Phe Phe Gln Pro Asp Arg Val Ser Arg Ser Ile
            35                  40                  45

Pro Gly Asn Gly Pro Val Thr Asp Val Thr Leu Ile Asp Leu Gln Cys
        50                  55                  60

Asn Ala Asn Ser Thr Pro Ala Lys Leu His Thr Ala Ala Ala Gly
65                  70                  75                  80

Ser Asp Val Ile Leu Arg Trp Thr Leu Trp Pro Glu Ser His Val Gly
                85                  90                  95

Pro Val Ile Thr Tyr Met Ala Arg Cys Pro Asp Thr Gly Cys Gln Asp
            100                 105                 110

Trp Met Pro Gly Thr Ser Ala Val Trp Phe Lys Ile Lys Glu Gly Gly
        115                 120                 125

Arg Asp Gly Thr Ser Asn Thr Trp Ala Asp Thr Pro Leu Met Thr Ala
    130                 135                 140

Pro Thr Ser Tyr Thr Tyr Thr Ile Pro Ser Cys Leu Lys Lys Gly Tyr
145                 150                 155                 160

Tyr Leu Val Arg His Glu Ile Ile Ala Leu His Ala Ala Tyr Thr Tyr
            165                 170                 175

Pro Gly Ala Gln Phe Tyr Pro Gly Cys His Gln Leu Asn Val Thr Gly
            180                 185                 190

Gly Gly Ser Thr Val Pro Ser Ser Gly Leu Val Ala Phe Pro Gly Ala
            195                 200                 205

Tyr Lys Gly Ser Asp Pro Gly Ile Thr Tyr Asp Ala Tyr Lys Ala Gln
            210                 215                 220

Thr Tyr Gln Ile Pro Gly Pro Ala Val Phe Thr Cys
225                 230                 235

<210> SEQ ID NO 51
<211> LENGTH: 933
<212> TYPE: DNA
<213> ORGANISM: Thielavia terrestris

<400> SEQUENCE: 51

```
atggccttgc tgctcttggc aggcttggcc attctggccg gccggctca tgcccacggc      60
ggcctcgcca actacacagt gggcaacacc tggtataggg ggtgcgtaag gggggcaccg     120
acaacgcctg cttagtaact ccaccatttc gagcgggcta acaccgggcg cagctacgac     180
cccttcacgc cggcggccga ccagatcggc cagccgtgga tgatccaacg cgcgtgggac     240
tcgatcgacc cgatcttcag cgtcaacgac aaggcgctcg cctgcaacac cccggccacg     300
gcgccgacct cttacattcc catccgcgcg ggcgagaaca tcacggccgt gtactggtac     360
tggctgcacc cggtgggccc catgacggcg tggctggcgc ggtgcgacgg cgactgccgc     420
gacgccgacg tcaacgaggc gcgctggttc aagatctggg aggccggcct gctcagcggg     480
ccgaacctgg ccgagggcat gtggtaccag aaggcgttcc agaactggga cggcagcccg     540
gacctgtggc ccgtcacgat cccggccggg ctgaagagcg gcctgtacat gatccggcac     600
gagatcttgt cgatccacgt cgaggataaa ccgcagtttt atcccgagtg tgcgcatctg     660
aatgtgaccg ggggtgggga cctgctgccg cctgatgagt ttttggtgaa gttcccgggc     720
gcttacaaag aagatagtga gtgaaacgcg aagcttcggt agccattggg ttgcgctgat     780
ggaggttaga cccgtcgatc aagatcaata tctactcgga ccagtacgcc aatacaacgg     840
tgagtgtaac aggtcgagca aaaccaaaca gatgccgatg actgatgatc tcagaattac     900
acaattcccg gagggccgat atgggatggg tga                                  933
```

<210> SEQ ID NO 52
<211> LENGTH: 250
<212> TYPE: PRT
<213> ORGANISM: Thielavia terrestris

<400> SEQUENCE: 52

Met Ala Leu Leu Leu Leu Ala Gly Leu Ala Ile Leu Ala Gly Pro Ala
1               5                   10                  15

His Ala His Gly Gly Leu Ala Asn Tyr Thr Val Gly Asn Thr Trp Tyr
            20                  25                  30

Arg Gly Tyr Asp Pro Phe Thr Pro Ala Ala Asp Gln Ile Gly Gln Pro
        35                  40                  45

Trp Met Ile Gln Arg Ala Trp Asp Ser Ile Asp Pro Ile Phe Ser Val
    50                  55                  60

Asn Asp Lys Ala Leu Ala Cys Asn Thr Pro Ala Thr Ala Pro Thr Ser
65                  70                  75                  80

-continued

```
Tyr Ile Pro Ile Arg Ala Gly Glu Asn Ile Thr Ala Val Tyr Trp Tyr
            85                   90                   95
Trp Leu His Pro Val Gly Pro Met Thr Ala Trp Leu Ala Arg Cys Asp
        100                 105                 110
Gly Asp Cys Arg Asp Ala Asp Val Asn Glu Ala Arg Trp Phe Lys Ile
            115                 120                 125
Trp Glu Ala Gly Leu Leu Ser Gly Pro Asn Leu Ala Glu Gly Met Trp
    130                 135                 140
Tyr Gln Lys Ala Phe Gln Asn Trp Asp Gly Ser Pro Asp Leu Trp Pro
145                 150                 155                 160
Val Thr Ile Pro Ala Gly Leu Lys Ser Gly Leu Tyr Met Ile Arg His
                165                 170                 175
Glu Ile Leu Ser Ile His Val Glu Asp Lys Pro Gln Phe Tyr Pro Glu
            180                 185                 190
Cys Ala His Leu Asn Val Thr Gly Gly Gly Asp Leu Leu Pro Pro Asp
        195                 200                 205
Glu Phe Leu Val Lys Phe Pro Gly Ala Tyr Lys Glu Asp Asn Pro Ser
    210                 215                 220
Ile Lys Ile Asn Ile Tyr Ser Asp Gln Tyr Ala Asn Thr Thr Asn Tyr
225                 230                 235                 240
Thr Ile Pro Gly Gly Pro Ile Trp Asp Gly
                245                 250
```

<210> SEQ ID NO 53
<211> LENGTH: 1584
<212> TYPE: DNA
<213> ORGANISM: Thielavia terrestris

<400> SEQUENCE: 53

```
atgatgccgt cccttgttcg cttctcaatg ggtctggcga ccgccttcgc ctcgctgtcc      60
acagcacata ccgtcttcac cacgcttttc atcaacggcg tcgaccaagg ggacgggacc     120
tgcatccgca tggccaagaa gggcagcgtt tgcacccatc ccattgctgg tggcctcgac     180
agcccagaca tggcttgtgg tatgccctct gcgtttcccc tgcgagagct ttcctcgagc     240
taacccaatg ccgcgttgcc caggccgaga cggacaacaa gccgtggcat tcacctgccc     300
agccccggcg ggctccaagt tgagcttcga gttccgcatg tgggccgacg cctctcagcc     360
cggctctatc gacccatccc acctcggctc gacggcaatc tacctcaaac aagtctccaa     420
catcagctcc gactcggctg ccggccctgg ctggttcaag atctacgccg agggctacga     480
cacagccgcc aagaagtggg ccacagagaa gctcatcgac aacggcggcc tgctgagcat     540
cgagcttccg cccactctgc cggcgggata ctacctcgcc cgcagcgaga tcgtcaccat     600
ccagaacgtc accaacgacc acgtcgaccc gcagttctac gttggctgcg cacagctctt     660
cgtccagggg cctccgacca cccccaccgt cccgccagac agactcgtct ccatcccggg     720
ccacgtccat gcctccgacc cggggctgac cttcaacatc tggcgcgacg acccctccaa     780
gacggcctac accgtcgtcg gcccggcccc cttctccccc accgccgccc ccaccccac      840
ctccaccaac accaacgggc agcaacaaca acaacagcaa caggcgataa agcagacgga     900
cggcgtgatc cccgccgact gccagctcaa gaacgccaac tggtgcggcg ccgaggtgcc     960
cgcgtacgcc gacgaggccg gctgctgggc gtcgtcggcc gactgcttcg cccagctgga    1020
cgcctgctac acgtcggcgc cgcccacggg cagccgcggc tgccggctgt gggaggactg    1080
gtgcaccggc attcagcagg gctgccgcgc ggggcggtgg cggggccgc cgcccttca     1140
```

-continued

```
tggggaggggg gcagcagcgg aggtgtgaac ggttcgggga cgggtggcgg tggtggtggt    1200
ggtggtggtg gcactggctc ttcttcggct tctgccccga cggagacggc ctctgctggc    1260 cggggggggcg caagaatagc tgccgtggcc ggctgcggag cgggacagg  agacatggtt    1320 gaagaggttt  cctcttttta ttgggacgct tgcagcggct ggcgacggag ccgtggtggt    1380
ggttcgattc ttgcgaggct tatccttcat gtccttcttc cacttttgag accgaggcga    1440 gccctcgag  tccatttact tctcttccac ctgtacctca acttctgtta tccaggaacc    1500
agtggtttct ataatcgcct gagcattaaa ctaggcatat ggccaagcaa aatgtcgcct    1560
gatgtagcgc attacgtgaa ataa                                            1584
```

<210> SEQ ID NO 54
<211> LENGTH: 478
<212> TYPE: PRT
<213> ORGANISM: Thielavia terrestris

<400> SEQUENCE: 54

```
Met Met Pro Ser Leu Val Arg Phe Ser Met Gly Leu Ala Thr Ala Phe
1               5                   10                  15

Ala Ser Leu Ser Thr Ala His Thr Val Phe Thr Thr Leu Phe Ile Asn
            20                  25                  30

Gly Val Asp Gln Gly Asp Gly Thr Cys Ile Arg Met Ala Lys Lys Gly
        35                  40                  45

Ser Val Cys Thr His Pro Ile Ala Gly Gly Leu Ser Pro Asp Met
    50                  55                  60

Ala Cys Gly Arg Asp Gly Gln Gln Ala Val Ala Phe Thr Cys Pro Ala
65                  70                  75                  80

Pro Ala Gly Ser Lys Leu Ser Phe Glu Phe Arg Met Trp Ala Asp Ala
                85                  90                  95

Ser Gln Pro Gly Ser Ile Asp Pro Ser His Leu Gly Ser Thr Ala Ile
            100                 105                 110

Tyr Leu Lys Gln Val Ser Asn Ile Ser Ser Asp Ser Ala Ala Gly Pro
        115                 120                 125

Gly Trp Phe Lys Ile Tyr Ala Glu Gly Tyr Asp Thr Ala Ala Lys Lys
    130                 135                 140

Trp Ala Thr Glu Lys Leu Ile Asp Asn Gly Gly Leu Leu Ser Ile Glu
145                 150                 155                 160

Leu Pro Pro Thr Leu Pro Ala Gly Tyr Tyr Leu Ala Arg Ser Glu Ile
                165                 170                 175

Val Thr Ile Gln Asn Val Thr Asn Asp His Val Asp Pro Gln Phe Tyr
            180                 185                 190

Val Gly Cys Ala Gln Leu Phe Val Gln Gly Pro Thr Thr Pro Thr
        195                 200                 205

Val Pro Pro Asp Arg Leu Val Ser Ile Pro Gly His Val His Ala Ser
    210                 215                 220

Asp Pro Gly Leu Thr Phe Asn Ile Trp Arg Asp Pro Ser Lys Thr
225                 230                 235                 240

Ala Tyr Thr Val Val Gly Pro Ala Pro Phe Ser Pro Thr Ala Ala Pro
                245                 250                 255

Thr Pro Thr Ser Thr Asn Thr Asn Gly Gln Gln Gln Gln Gln Gln
            260                 265                 270

Gln Ala Ile Lys Gln Thr Asp Gly Val Ile Pro Ala Asp Cys Gln Leu
        275                 280                 285

Lys Asn Ala Asn Trp Cys Gly Ala Glu Val Pro Ala Tyr Ala Asp Glu
```

```
            290                 295                 300
Ala Gly Cys Trp Ala Ser Ser Ala Asp Cys Phe Ala Gln Leu Asp Ala
305                 310                 315                 320

Cys Tyr Thr Ser Ala Pro Pro Thr Gly Ser Arg Gly Cys Arg Leu Trp
                325                 330                 335

Glu Asp Trp Cys Thr Gly Ile Gln Gln Gly Cys Arg Ala Gly Arg Trp
            340                 345                 350

Arg Gly Pro Pro Pro Phe His Gly Glu Gly Ala Ala Glu Thr Ala
        355                 360                 365

Ser Ala Gly Arg Gly Gly Ala Arg Ile Ala Ala Val Ala Gly Cys Gly
370                 375                 380

Gly Gly Thr Gly Asp Met Val Glu Glu Val Phe Leu Phe Tyr Trp Asp
385                 390                 395                 400

Ala Cys Ser Gly Trp Arg Arg Ser Arg Gly Gly Ser Ile Leu Ala
                405                 410                 415

Arg Leu Ile Leu His Val Leu Leu Pro Leu Leu Arg Pro Arg Arg Ala
            420                 425                 430

Pro Arg Val His Leu Leu Leu Phe His Leu Tyr Leu Asn Phe Cys Tyr
                435                 440                 445

Pro Gly Thr Ser Gly Phe Tyr Asn Arg Leu Ser Ile Lys Leu Gly Ile
        450                 455                 460

Trp Pro Ser Lys Met Ser Pro Asp Val Ala His Tyr Val Lys
465                 470                 475
```

<210> SEQ ID NO 55
<211> LENGTH: 868
<212> TYPE: DNA
<213> ORGANISM: Thielavia terrestris

<400> SEQUENCE: 55

```
atgcagctcc tcgtgggctt gctgcttgca gccgtggctg ctcgagcaca ttgtatttct    60 accccttttcc gcgtgcctcc cagcctcaag gcaagaagac gcacgcagca gctaacggac   120
cctatcagac acatttccca gactcgtggt aaatgggcag cccgaggaca aggactggtc   180
ggttacgcgc atgaccaaga acgcgcagag caagcaggga gtccaggacc cgaccagtcc   240
cgacattcgc tgctacacgt cgcagacggc gcctaacgtg ctacggtccc tgccggagc    300 caccgtccat tacatatcga ctcagcagat caaccacccg ggcccgacgc agtactacct   360
cgccaaggta ccggcggggt cgtcggccaa gacgtgggac gggtcagggg ccgtctggtt   420
caagatctcg accaccatgc cttacttgga acaacaaag cagcttgtct ggccgaatca    480
gagtaggaac aattcccgct ccaatcttcg atttggcctt gagctacggc cgattgcatg   540
ggagagaccg ttgactgacg gggcaaccca accttcatca gacacgtaca cgacggtcaa   600
cacgaccatc cccgccgata cgcccagtgg ggaatacctc ctccgggtcg agcagatcgc   660
gctgcacctg gcctcgcagc ccaacggggc tcagttctac ctggcctgct cgcagatcca   720
gattacgggc ggcggcaacg gcacgcccgg cccgctagtc gcgttgccgg ggcgtacaa    780 gagcaacgac ccgggcattt tggtcaacat ctactctatg cagcccggcg attacaagcc   840
gcccgggccg ccggtgtgga gtggctga                                      868
```

<210> SEQ ID NO 56
<211> LENGTH: 230
<212> TYPE: PRT
<213> ORGANISM: Thielavia terrestris

<400> SEQUENCE: 56

```
Met Gln Leu Leu Val Gly Leu Leu Ala Ala Val Ala Ala Arg Ala
1               5                   10                  15

His Tyr Thr Phe Pro Arg Leu Val Asn Gly Gln Pro Glu Asp Lys
            20                  25                  30

Asp Trp Ser Val Thr Arg Met Thr Lys Asn Ala Gln Ser Lys Gln Gly
        35                  40                  45

Val Gln Asp Pro Thr Ser Pro Asp Ile Arg Cys Tyr Thr Ser Gln Thr
50                  55                  60

Ala Pro Asn Val Ala Thr Val Pro Ala Gly Ala Thr Val His Tyr Ile
65                  70                  75                  80

Ser Thr Gln Gln Ile Asn His Pro Gly Pro Thr Gln Tyr Tyr Leu Ala
                85                  90                  95

Lys Val Pro Ala Gly Ser Ser Ala Lys Thr Trp Asp Gly Ser Gly Ala
            100                 105                 110

Val Trp Phe Lys Ile Ser Thr Thr Met Pro Tyr Leu Asp Asn Asn Lys
            115                 120                 125

Gln Leu Val Trp Pro Asn Gln Asn Thr Tyr Thr Thr Val Asn Thr Thr
130                 135                 140

Ile Pro Ala Asp Thr Pro Ser Gly Glu Tyr Leu Leu Arg Val Glu Gln
145                 150                 155                 160

Ile Ala Leu His Leu Ala Ser Gln Pro Asn Gly Ala Gln Phe Tyr Leu
                165                 170                 175

Ala Cys Ser Gln Ile Gln Ile Thr Gly Gly Gly Asn Gly Thr Pro Gly
            180                 185                 190

Pro Leu Val Ala Leu Pro Gly Ala Tyr Lys Ser Asn Asp Pro Gly Ile
            195                 200                 205

Leu Val Asn Ile Tyr Ser Met Gln Pro Gly Asp Tyr Lys Pro Pro Gly
            210                 215                 220

Pro Pro Val Trp Ser Gly
225                 230
```

<210> SEQ ID NO 57
<211> LENGTH: 1068
<212> TYPE: DNA
<213> ORGANISM: Thielavia terrestris

<400> SEQUENCE: 57

```
atgaagctgt acctggcggc ctttctaggc gccgtcgcca ccccgggagc gttcgctcat     60
cgtaggttcc ccgtctatct ccctaggggt agcaccacga ctaatttctc gtcgtccccc    120
tgtagaaatc cacgggattc tacttgtcaa cggcaccgaa acgccggaat ggaaatacgt    180
ccggtaatat ctaccttgct ctccttcttc cacaaccagc taacacatc atcagtgacg     240
tggcctggga gggcgcctac gaaccggaaa ataccccaa caccgagttc tttaagacgc     300
ccccgcagac ggacatcaac aacccgaaca tcacctgcgg caggaacgcg ttcgactcgg    360
ccagcaagac tgagacggcc gacatactgg ccggctcaga ggtcggcttc cgcgtctcgt    420
gggacggcaa cggcaagtac ggcgtgttct ggcatcccgg gccggggcag atctacctct    480
ctcgtgctcc gaacgacgac ctggaggact accgcggcga cggagactgg ttcaagatcg    540
caaccggcgc cgccgtctcc aataccgagt ggctgctgtg aacaagcat gacgtgagcc     600
ccaacattcc tcgcccaatc gatcccaac ctggtcacca tggcggcgtc cgggatgcaa     660
agagactaac tccagaggaa cctacctagt tcaacttcac catccccaag acgacgccgc    720
```

-continued

```
cgggcaagta cctgatgcgc atcgagcagt tcatgccctc cacggtcgaa tacagccagt      780
ggtacgtcaa ctgcgcccac gtcaacatca tcggccccgg cggaggcacg ccgacgggct      840
ttgccaggtt tcccggcacc tacactgttg acgatcccgg taagccggac ctaccggaca      900
cagaggcctc gggatagctt gctaaccttg tttgctctct ctcttttcct ctcccgacta      960
ggcatcaagg tgccgttgaa ccagatcgtc aacagcggag agttgccgca ggaccaactg     1020
aggctgctcg agtacaagcc cccgggccca gcgctgtgga ctggttga                  1068
```

<210> SEQ ID NO 58
<211> LENGTH: 257
<212> TYPE: PRT
<213> ORGANISM: Thielavia terrestris

<400> SEQUENCE: 58

```
Met Lys Leu Tyr Leu Ala Ala Phe Leu Gly Ala Val Ala Thr Pro Gly
1               5                   10                  15

Ala Phe Ala His Gln Ile His Gly Ile Leu Leu Val Asn Gly Thr Glu
            20                  25                  30

Thr Pro Glu Trp Lys Tyr Val Arg Asp Val Ala Trp Glu Gly Ala Tyr
        35                  40                  45

Glu Pro Glu Lys Tyr Pro Asn Thr Glu Phe Phe Lys Thr Pro Pro Gln
    50                  55                  60

Thr Asp Ile Asn Asn Pro Asn Ile Thr Cys Gly Arg Asn Ala Phe Asp
65                  70                  75                  80

Ser Ala Ser Lys Thr Glu Thr Ala Asp Ile Leu Ala Gly Ser Glu Val
                85                  90                  95

Gly Phe Arg Val Ser Trp Asp Gly Asn Gly Lys Tyr Gly Val Phe Trp
            100                 105                 110

His Pro Gly Pro Gly Gln Ile Tyr Leu Ser Arg Ala Pro Asn Asp Asp
        115                 120                 125

Leu Glu Asp Tyr Arg Gly Asp Gly Asp Trp Phe Lys Ile Ala Thr Gly
    130                 135                 140

Ala Ala Val Ser Asn Thr Glu Trp Leu Leu Trp Asn Lys His Asp Phe
145                 150                 155                 160

Asn Phe Thr Ile Pro Lys Thr Thr Pro Gly Lys Tyr Leu Met Arg
                165                 170                 175

Ile Glu Gln Phe Met Pro Ser Thr Val Glu Tyr Ser Gln Trp Tyr Val
            180                 185                 190

Asn Cys Ala His Val Asn Ile Ile Gly Pro Gly Gly Thr Pro Thr
        195                 200                 205

Gly Phe Ala Arg Phe Pro Gly Thr Tyr Thr Val Asp Asp Pro Gly Ile
    210                 215                 220

Lys Val Pro Leu Asn Gln Ile Val Asn Ser Gly Glu Leu Pro Gln Asp
225                 230                 235                 240

Gln Leu Arg Leu Leu Glu Tyr Lys Pro Pro Gly Pro Ala Leu Trp Thr
                245                 250                 255

Gly
```

<210> SEQ ID NO 59
<211> LENGTH: 871
<212> TYPE: DNA
<213> ORGANISM: Thermoascus crustaceus

<400> SEQUENCE: 59

```
atggccttt cccagataat ggctattacc ggcgttttc ttgcctctgc ttccctggtg      60
```

```
gctggccatg gctttgttca gaatatcgtg attgatggta aaaggtacct aactacctac    120
cttactatct gatgtcattt acaagaaagg cacagacac  aagcggcaaa aaaaagaaag    180
aaagaaagaa agaaagaaag ctgacaaaaa ttcaacaagt tatggcgggt acatcgtgaa    240
ccaatatcca tacatgtcag atcctccgga ggtcgtcggc tggtctacca ccgcaaccga    300
cctcggattc gtggacggta ccggatacca aggacctgat atcatctgcc acagggcgc    360
caagcctgca gccctgactg cccaagtggc cgccggagga accgtcaagc tggaatggac    420
tccatggcct gattctcacc acggcccggt gatcaactac cttgctcctt gcaacggtga    480
ctgttccacc gtggacaaga cccaattgaa attcttcaag atcgcccagg ccggtctcat    540
cgatgacaac agtcctcctg gtatctgggc ctcagacaat ctgatagcgg ccaacaacag    600
ctggactgtc accatcccaa ccacaactgc acctggaaac tatgttctaa ggcatgagat    660
cattgctctc cactcagctg gaacaagga  tggtgcgcag aactatcccc agtgcatcaa    720
cctgaaggtc actggaaatg gttctggcaa tcctcctgct ggtgctcttg gaacggcact    780
ctacaaggat acagatccgg gaattctgat caatatctac cagaaacttt ccagctatgt    840
tattcctggt cctgctttgt acactggtta g                                   871

<210> SEQ ID NO 60
<211> LENGTH: 251
<212> TYPE: PRT
<213> ORGANISM: Thermoascus crustaceus

<400> SEQUENCE: 60

Met Ala Phe Ser Gln Ile Met Ala Ile Thr Gly Val Phe Leu Ala Ser
1               5                   10                  15

Ala Ser Leu Val Ala Gly His Gly Phe Val Gln Asn Ile Val Ile Asp
            20                  25                  30

Gly Lys Ser Tyr Gly Gly Tyr Ile Val Asn Gln Tyr Pro Tyr Met Ser
        35                  40                  45

Asp Pro Pro Glu Val Val Gly Trp Ser Thr Thr Ala Thr Asp Leu Gly
    50                  55                  60

Phe Val Asp Gly Thr Gly Tyr Gln Gly Pro Asp Ile Ile Cys His Arg
65                  70                  75                  80

Gly Ala Lys Pro Ala Ala Leu Thr Ala Gln Val Ala Ala Gly Gly Thr
                85                  90                  95

Val Lys Leu Glu Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Lys Phe Phe Lys Ile Ala Gln Ala Gly Leu Ile Asp Asp
    130                 135                 140

Asn Ser Pro Pro Gly Ile Trp Ala Ser Asp Asn Leu Ile Ala Ala Asn
145                 150                 155                 160

Asn Ser Trp Thr Val Thr Ile Pro Thr Thr Thr Ala Pro Gly Asn Tyr
                165                 170                 175

Val Leu Arg His Glu Ile Ile Ala Leu His Ser Ala Gly Thr Lys Asp
            180                 185                 190

Gly Ala Gln Asn Tyr Pro Gln Cys Ile Asn Leu Lys Val Thr Gly Asn
        195                 200                 205

Gly Ser Gly Asn Pro Pro Ala Gly Ala Leu Gly Thr Ala Leu Tyr Lys
    210                 215                 220
```

Asp Thr Asp Pro Gly Ile Leu Ile Asn Ile Tyr Gln Lys Leu Ser Ser
225                 230                 235                 240

Tyr Val Ile Pro Gly Pro Ala Leu Tyr Thr Gly
                245                 250

<210> SEQ ID NO 61
<211> LENGTH: 1102
<212> TYPE: DNA
<213> ORGANISM: Thermoascus crustaceus

<400> SEQUENCE: 61

```
atgtcattct cgaagatact tgctatcgct ggggccatta cctacgcatc ttcagctgcc    60
gctcatggtt atgtccaggg aattgttgtc gatggcagct agtatgtcac tctggatgga   120
accttcagca cgtactgtac taacaatcag cagctacggg ggatatatgg tgacccaata   180
tccctacacc gctcaacctc cggaactcat cgcctggtcc actaaagcaa ccgatcttgg   240
gtttgtggac ggcagtggct atacttctcc tgatatcatc tgccataagg gtgctgagcc   300
tggtgcccag agcgccaaag tggcagctgg agggaccgtt gagctgcagt ggacggcatg   360
gccccgagtct cacaagggcc cagttattga ctacctcgcc gcctgcgacg gggactgctc   420
atctgttgat aagactgcac taaagttctt taagattgac gagagtggtc tgattgacgg   480
caacggtgct ggaacatggg cctctgatac gttgatcaaa ataacaaca gctggactgt   540
caccatccca agcacaattg cttccggaaa ctacgtacta agacacgaaa taattgcgct   600
ccattctgcc ggaaacaaag atggtgctca gaactatccc cagtgtatca acctcgaggt   660
cactggtagt ggcaccgaaa accctgctgg cactctcgga acagcgcttt acacagacac   720
tgatcctggc cttctggtca acatctacca gggtctgtcc aactattcaa tccctggtcc   780
tgctctgtat agcggcaaca gtgataacgc tggttccctc aaccctacca ccacgccgtc   840
aattcagaat gctgctgctg ctccctccac ttccacagca tctgttgtca ctgattcttc   900
gtcagccacc cagactgcta gtgtcgccgc cacgactcca gcctccactt cggctgttac   960
agcctcacca gctcccgata ctggaagcga cgtaaccaaa tatctggatt cgatgagctc  1020
ggatgaggtc ctcaccctgg tgcgcgggac cctgtcttgg ctggtttcta acaagaaaca  1080
tgcgcgggat ctttctcact ga                                           1102
```

<210> SEQ ID NO 62
<211> LENGTH: 349
<212> TYPE: PRT
<213> ORGANISM: Thermoascus crustaceus

<400> SEQUENCE: 62

Met Ser Phe Ser Lys Ile Leu Ala Ile Ala Gly Ala Ile Thr Tyr Ala
1               5                   10                  15

Ser Ser Ala Ala Ala His Gly Tyr Val Gln Gly Ile Val Val Asp Gly
                20                  25                  30

Ser Tyr Tyr Gly Gly Tyr Met Val Thr Gln Tyr Pro Tyr Thr Ala Gln
            35                  40                  45

Pro Pro Glu Leu Ile Ala Trp Ser Thr Lys Ala Thr Asp Leu Gly Phe
        50                  55                  60

Val Asp Gly Ser Gly Tyr Thr Ser Pro Asp Ile Ile Cys His Lys Gly
65                  70                  75                  80

Ala Glu Pro Gly Ala Gln Ser Ala Lys Val Ala Ala Gly Gly Thr Val
                85                  90                  95

Glu Leu Gln Trp Thr Ala Trp Pro Glu Ser His Lys Gly Pro Val Ile

```
              100                 105                 110
Asp Tyr Leu Ala Ala Cys Asp Gly Asp Cys Ser Ser Val Asp Lys Thr
        115                 120                 125

Ala Leu Lys Phe Phe Lys Ile Asp Glu Ser Gly Leu Ile Asp Gly Asn
    130                 135                 140

Gly Ala Gly Thr Trp Ala Ser Asp Thr Leu Ile Lys Asn Asn Asn Ser
145                 150                 155                 160

Trp Thr Val Thr Ile Pro Ser Thr Ile Ala Ser Gly Asn Tyr Val Leu
                165                 170                 175

Arg His Glu Ile Ile Ala Leu His Ser Ala Gly Asn Lys Asp Gly Ala
            180                 185                 190

Gln Asn Tyr Pro Gln Cys Ile Asn Leu Glu Val Thr Gly Ser Gly Thr
        195                 200                 205

Glu Asn Pro Ala Gly Thr Leu Gly Thr Ala Leu Tyr Thr Asp Thr Asp
    210                 215                 220

Pro Gly Leu Leu Val Asn Ile Tyr Gln Gly Leu Ser Asn Tyr Ser Ile
225                 230                 235                 240

Pro Gly Pro Ala Leu Tyr Ser Gly Asn Ser Asp Asn Ala Gly Ser Leu
                245                 250                 255

Asn Pro Thr Thr Thr Pro Ser Ile Gln Asn Ala Ala Ala Pro Ser
            260                 265                 270

Thr Ser Thr Ala Ser Val Val Thr Asp Ser Ser Ala Thr Gln Thr
        275                 280                 285

Ala Ser Val Ala Ala Thr Thr Pro Ala Ser Thr Ser Ala Val Thr Ala
    290                 295                 300

Ser Pro Ala Pro Asp Thr Gly Ser Asp Val Thr Lys Tyr Leu Asp Ser
305                 310                 315                 320

Met Ser Ser Asp Glu Val Leu Thr Leu Val Arg Gly Thr Leu Ser Trp
                325                 330                 335

Leu Val Ser Asn Lys Lys His Ala Arg Asp Leu Ser His
            340                 345

<210> SEQ ID NO 63
<211> LENGTH: 1493
<212> TYPE: DNA
<213> ORGANISM: Thermoascus crustaceus

<400> SEQUENCE: 63
atgttgtcat tcattcccac caagtcagct gcgctgacga ctcttctact tcttggaaca    60
gctcatgctc acactttgat gaccaccatg tttgtggacg gcgtcaacca gggagatggt   120
gtctgcattc gcatgaacaa tgacggcgga actgccaata cctatatcca gcctatcacg   180
agcaaggata tcgcctgcgg taagtaccca gatgtcatca tactctgcca taacatccgt   240
catatctact agaatcggag caatgttaag tatttccagg catccaaggc gaaatcggcg   300
cctcccgagt ctgcccagtc aaggcatctt ccaccctaac cttccaattc gcgagcaac    360
ccaacaaccc aaactcctcc cctctcgatc catcgcacaa aggccccgcc gcggtgtacc   420
tgaaaaaggt cgactccgcc atcgcgagca caacgccgc cggagacagc tggttcaaga   480
tctgggagtc cgtctacgac gagtccacgg gcaaatgggg cacgaccaag atgatcgaga   540
acaacgggca catctccgtc aaggtgcccg atgatatcga gggtggttac tatcttgccc   600
ggacggagct gctggcgcta cattctgcgg atcaggggga tccgcagttc tatgttggct   660
gtgcgcagct gtttatcgat tcggatggga cggcgaaacc gcccactgtt tctattggag   720
```

```
agggacgta cgatctgagc atgcctgcca tgacgtataa tatctgggag acaccgttgg    780
ctctgccgta tccgatgtat gggcctcctg tctatacgcc tggctctggt tctggatcag    840
tccgtgcgac gagctcttct gctgtcccta ctgcaaccga atcctctttt gtagaggaaa    900
gagcaaaccc cgtcacggca aacagtgttt attctgcaag gggcaaattc aaaacctgga    960
ttgataaact gtcatggcgc gggaaggtcc gtgagaacgt cagacaagcc gcgggaagaa   1020
gaagcactct cgtccagact gtgggtctaa agccaaaagg ctgcatcttc gtcaatggaa   1080
actggtgcgg cttcgaggtt cccgactaca acgatgcgga gagctgctgg gctgtatgtt   1140
cccctcctta gcctcttaca tccctaagta ctacatttga aaacaacaaa aagaaatgta   1200
tatactaact acgtacgctc tactctaggc ctccgacaac tgctggaaac agtccgacgc   1260
ctgctggaac aagacccaac ccacgggcta caataactgc cagatctggc aggacaagaa   1320
atgcaaggtc atccaggatt cctgtagcgg acccaacccg catggaccac cgaataaggg   1380
caaggatttg actccggagt ggccgccact gaagggctcg atggatacgt tctccaagcg   1440
tactatcggt taccgcgatt ggattgttag aaggagaggt gcatgagggt gta           1493
```

<210> SEQ ID NO 64
<211> LENGTH: 436
<212> TYPE: PRT
<213> ORGANISM: Thermoascus crustaceus

<400> SEQUENCE: 64

```
Met Leu Ser Phe Ile Pro Thr Lys Ser Ala Ala Leu Thr Thr Leu Leu
1               5                   10                  15

Leu Leu Gly Thr Ala His Ala His Thr Leu Met Thr Thr Met Phe Val
                20                  25                  30

Asp Gly Val Asn Gln Gly Asp Gly Val Cys Ile Arg Met Asn Asn Asp
            35                  40                  45

Gly Gly Thr Ala Asn Thr Tyr Ile Gln Pro Ile Thr Ser Lys Asp Ile
        50                  55                  60

Ala Cys Gly Ile Gln Gly Glu Ile Gly Ala Ser Arg Val Cys Pro Val
65                  70                  75                  80

Lys Ala Ser Ser Thr Leu Thr Phe Gln Phe Arg Glu Gln Pro Asn Asn
                85                  90                  95

Pro Asn Ser Ser Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Ser Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ser Ala Asp Gln Gly Asp Pro Gln Phe Tyr Val
            180                 185                 190

Gly Cys Ala Gln Leu Phe Ile Asp Ser Asp Gly Thr Ala Lys Pro Pro
        195                 200                 205

Thr Val Ser Ile Gly Glu Gly Thr Tyr Asp Leu Ser Met Pro Ala Met
    210                 215                 220

Thr Tyr Asn Ile Trp Glu Thr Pro Leu Ala Leu Pro Tyr Pro Met Tyr
225                 230                 235                 240
```

Gly Pro Pro Val Tyr Thr Pro Gly Ser Gly Ser Val Arg Ala
            245                 250                 255

Thr Ser Ser Ala Val Pro Thr Ala Thr Glu Ser Ser Phe Val Glu
    260                 265                 270

Glu Arg Ala Asn Pro Val Thr Ala Asn Ser Val Tyr Ser Ala Arg Gly
        275                 280                 285

Lys Phe Lys Thr Trp Ile Asp Lys Leu Ser Trp Arg Gly Lys Val Arg
    290                 295                 300

Glu Asn Val Arg Gln Ala Ala Gly Arg Arg Ser Thr Leu Val Gln Thr
305                 310                 315                 320

Val Gly Leu Lys Pro Lys Gly Cys Ile Phe Val Asn Gly Asn Trp Cys
            325                 330                 335

Gly Phe Glu Val Pro Asp Tyr Asn Asp Ala Glu Ser Cys Trp Ala Ala
            340                 345                 350

Ser Asp Asn Cys Trp Lys Gln Ser Asp Ala Cys Trp Asn Lys Thr Gln
        355                 360                 365

Pro Thr Gly Tyr Asn Asn Cys Gln Ile Trp Gln Asp Lys Lys Cys Lys
    370                 375                 380

Val Ile Gln Asp Ser Cys Ser Gly Pro Asn Pro His Gly Pro Pro Asn
385                 390                 395                 400

Lys Gly Lys Asp Leu Thr Pro Glu Trp Pro Pro Leu Lys Gly Ser Met
            405                 410                 415

Asp Thr Phe Ser Lys Arg Thr Ile Gly Tyr Arg Asp Trp Ile Val Arg
            420                 425                 430

Arg Arg Gly Ala
        435

<210> SEQ ID NO 65
<211> LENGTH: 1377
<212> TYPE: DNA
<213> ORGANISM: Trichoderma reesei

<400> SEQUENCE: 65
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccggggggtg cgtggcccag acacctcgg tggtccttga ctggaactac     180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga ccagtacat gcccagcagc     360 tctggcgggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccggtgccaa ctacgggagc ggctactgcg atgctcagtg ccccgtccag     600
acatggagga acggcaccct caacactagc caccagggct tctgctgcaa cgagatggat     660
atcctggagg gcaactcgag ggcgaatgcc ttgaccccctc actcttgcac ggccacggcc     720
tgcgactctg ccggttgcgg cttcaaccc tatggcagcg gctacaaaag ctactacggc     780
cccggagata ccgttgacac ctccaagacc ttcaccatca tcacccagtt caacacggac     840
aacggctcgc cctcgggcaa ccttgtgagc atcacccgca agtaccagca aacggcgtc     900 gacatcccca gcgcccagcc cggcggcgac accatctcgt cctgcccgtc cgcctcagcc     960

```
tacggcggcc tcgccaccat gggcaaggcc ctgagcagcg gcatggtgct cgtgttcagc   1020
atttggaacg acaacagcca gtacatgaac tggctcgaca gcggcaacgc cggcccctgc   1080
agcagcaccg agggcaaccc atccaacatc ctggccaaca accccaacac gcacgtcgtc   1140
ttctccaaca tccgctgggg agacattggg tctactacga actcgactgc gccccgccc   1200 ccgcctgcgt ccagcacgac gttttcgact acacggagga gctcgacgac ttcgagcagc   1260
ccgagctgca cgcagactca ctgggggcag tgcggtggca ttgggtacag cgggtgcaag   1320
acgtgcacgt cgggcactac gtgccagtat agcaacgact actactcgca atgcctt     1377
```

<210> SEQ ID NO 66
<211> LENGTH: 459
<212> TYPE: PRT
<213> ORGANISM: Trichoderma reesei

<400> SEQUENCE: 66

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
                20                  25                  30

His Pro Lys Leu Thr Thr Tyr Lys Cys Thr Lys Ser Gly Gly Cys Val
            35                  40                  45

Ala Gln Asp Thr Ser Val Val Leu Asp Trp Asn Tyr Arg Trp Met His
        50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300
```

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
            325                 330                 335

Leu Val Phe Ser Ile Trp Asn Asp Asn Ser Gln Tyr Met Asn Trp Leu
        340                 345                 350

Asp Ser Gly Asn Ala Gly Pro Cys Ser Ser Thr Glu Gly Asn Pro Ser
    355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
            405                 410                 415

Thr Ser Ser Ser Pro Ser Cys Thr Gln Thr His Trp Gly Gln Cys Gly
        420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455

<210> SEQ ID NO 67
<211> LENGTH: 1254
<212> TYPE: DNA
<213> ORGANISM: Trichoderma reesei

<400> SEQUENCE: 67
atgaacaagt ccgtggctcc attgctgctt gcagcgtcca tactatatgg cggcgccgtc      60
gcacagcaga ctgtctgggg ccagtgtgga ggtattggtt ggagcggacc tacgaattgt     120
gctcctggct cagcttgttc gaccctcaat ccttattatg cgcaatgtat tccgggagcc     180
actactatca ccacttcgac ccggccacca tccggtccaa ccaccaccac cagggctacc     240
tcaacaagct catcaactcc acccacgagc tctgggtcc gatttgccgg cgttaacatc     300
gcgggttttg actttggctg taccacagat ggcacttgcg ttacctcgaa ggtttatcct     360
ccgttgaaga acttcaccgg ctcaaacaac taccccgatg catcggcca gatgcagcac     420 ttcgtcaacg aggacgggat gactattttc cgcttacctg tcggatggca gtacctcgtc     480
aacaacaatt tgggcggcaa tcttgattcc acgagcattt ccaagtatga tcagcttgtt     540
caggggtgcc tgtctctggg cgcatactgc atcgtcgaca tccacaatta tgctcgatgg     600
aacggtggga tcattggtca gggcggccct actaatgctc aattcacgag cctttggtcg     660
cagttggcat caaagtacgc atctcagtcg agggtgtggt tcggcatcat gaatgagccc     720
cacgacgtga acatcaacac ctgggctgcc acggtccaag aggttgtaac cgcaatccgc     780
aacgctggtg ctacgtcgca attcatctct ttgcctggaa atgattggca atctgctggg     840
gctttcatat ccgatggcag tgcagccgcc ctgtctcaag tcacgaaccc ggatgggtca     900
acaacgaatc tgattttga cgtgcacaaa tacttggact cagacaactc cggtactcac     960
gccgaatgta ctacaaataa cattgacggc gccttttctc cgcttgccac ttggctccga    1020
cagaacaatc gccaggctat cctgacagaa accggtggtg gcaacgttca gtcctgcata    1080
caagacatgt gccagcaaat ccaatatctc aaccagaact cagatgtcta tcttggctat    1140
gttggttggg gtgccggatc atttgatagc acgtatgtcc tgacggaaac accgactagc    1200
agtggtaact catggacgga cacatccttg gtcagctcgt gtctcgcaag aaag           1254

<210> SEQ ID NO 68
<211> LENGTH: 418
<212> TYPE: PRT
<213> ORGANISM: Trichoderma reesei

<400> SEQUENCE: 68

```
Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
290                 295                 300

Ile Phe Asp Val His Lys Tyr Leu Asp Ser Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
```

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys

<210> SEQ ID NO 69
<211> LENGTH: 702
<212> TYPE: DNA
<213> ORGANISM: Trichoderma reesei

<400> SEQUENCE: 69

```
atgaagttcc ttcaagtcct ccctgccctc ataccggccg ccctggccca aaccagctgt    60
gaccagtggg caaccttcac tggcaacggc tacacagtca gcaacaacct tggggagca   120
tcagccggct ctggatttgg ctgcgtgacg gcggtatcgc tcagcggcgg ggcctcctgg   180
cacgcagact ggcagtggtc cggcggccag aacaacgtca gtcgtacca gaactctcag    240
attgccattc cccagaagag gaccgtcaac agcatcagca gcatgccac cactgccagc    300
tggagctaca gcgggagcaa catccgcgct aatgttgcgt atgacttgtt caccgcagcc   360
aacccgaatc atgtcacgta ctcgggagac tacgaactca tgatctggct tggcaaatac   420
ggcgatattg gccgattgg gtcctcacag gaacagtca acgtcggtgg ccagagctgg    480
acgtctacta tggctacaa cggagccatg caagtctatt cctttgtggc ccagaccaac   540
actaccaact acagcggaga gtcaagaac ttcttcaatt atctccgaga caataaagga    600
tacaacgctg caggccaata tgttcttagc taccaatttg gtaccgagcc cttcacgggc   660
agtggaactc tgaacgtcgc atcctggacc gcatctatca ac                     702
```

<210> SEQ ID NO 70
<211> LENGTH: 234
<212> TYPE: PRT
<213> ORGANISM: Trichoderma reesei

<400> SEQUENCE: 70

Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

```
Thr Leu Tyr Tyr Gly Tyr Asn Gly Ala Met Gln Val Tyr Ser Phe Val
            165                 170                 175

Ala Gln Thr Asn Thr Thr Asn Tyr Ser Gly Asp Val Lys Asn Phe Phe
        180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```

<210> SEQ ID NO 71
<211> LENGTH: 726
<212> TYPE: DNA
<213> ORGANISM: Trichoderma reesei

<400> SEQUENCE: 71

```
atgaaggcaa ctctggttct cggctccctc attgtaggcg ccgtttccgc gtacaaggcc      60
accaccacgc gctactacga tgggcaggag ggtgcttgcg gatgcggctc gagctccggc     120
gcattcccgt ggcagctcgg catcggcaac ggagtctaca cggctgccgg ctcccaggct     180
ctcttcgaca cggccggagc ttcatggtgc ggcgccggct gcggtaaatg ctaccagctc     240
acctcgacgg gccaggcgcc ctgctccagc tgcggcacgg gcggtgctgc tggccagagc     300
atcatcgtca tggtgaccaa cctgtgcccg aacaatggga acgcgcagtg gtgcccggtg     360
gtcggcggca ccaaccaata cggctacagc taccattttcg acatcatggc gcagaacgag     420
atctttggag acaatgtcgt cgtcgacttt gagcccattg cttgccccgg gcaggctgcc     480
tctgactggg gacgtgcct ctgcgtggga cagcaagaga cggatcccac gcccgtcctc     540
ggcaacgaca cgggctcaac tcctcccggg agctcgccgc cagcgacatc gtcgagtccg     600
ccgtctggcg gcggccagca gacgctctat ggccagtgtg gaggtgccgg ctggacggga     660
cctacgacgt gccaggcccc agggacctgc aaggttcaga accagtggta ctcccagtgt     720
cttcct                                                                726
```

<210> SEQ ID NO 72
<211> LENGTH: 242
<212> TYPE: PRT
<213> ORGANISM: Trichoderma reesei

<400> SEQUENCE: 72

```
Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110
```

Gly Asn Ala Gln Trp Cys Pro Val Gly Gly Thr Asn Gln Tyr Gly
          115                 120                 125

Tyr Ser Tyr His Phe Asp Ile Met Ala Gln Asn Glu Ile Phe Gly Asp
130                 135                 140

Asn Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
              165                 170                 175

Thr Pro Val Leu Gly Asn Asp Thr Gly Ser Thr Pro Pro Gly Ser Ser
              180                 185                 190

Pro Pro Ala Thr Ser Ser Ser Pro Pro Ser Gly Gly Gln Gln Thr
          195                 200                 205

Leu Tyr Gly Gln Cys Gly Gly Ala Gly Trp Thr Gly Pro Thr Thr Cys
210                 215                 220

Gln Ala Pro Gly Thr Cys Lys Val Gln Asn Gln Trp Tyr Ser Gln Cys
225                 230                 235                 240

Leu Pro

<210> SEQ ID NO 73
<211> LENGTH: 923
<212> TYPE: DNA
<213> ORGANISM: Trichoderma reesei

<400> SEQUENCE: 73

```
atgcgttcct ccccccctcct ccgctccgcc gttgtggccg ccctgccggt gttggccctt      60
gccgctgatg gcaggtccac ccgctactgg gactgctgca agccttcgtg cggctgggcc     120
aagaaggctc ccgtgaacca gcctgtcttt cctgcaacg ccaacttcca gcgtatcacg      180
gacttcgacg ccaagtccgg ctgcgagccg ggcggtgtcg cctactcgtg cgccgaccag     240
accccatggg ctgtgaacga cgacttcgcg ctcggttttg ctgccacctc tattgccggc     300
agcaatgagg cgggctggtg ctgcgcctgc tacgagctca ccttcacatc cggtcctgtt    360
gctggcaaga gatggtcgt ccagtccacc agcactggcg gtgatcttgg cagcaaccac     420
ttcgatctca acatcccgg cggcggcgtc ggcatcttcg acggatgcac tccccagttc      480
ggcggtctgc ccggccagcg ctacggcggc atctcgtccc gcaacgagtg cgatcggttc     540
cccgacgccc tcaagcccgg ctgctactgg cgcttcgact ggttcaagaa cgccgacaat     600
ccgagcttca gcttccgtca ggtccagtgc ccagccgagc tcgtcgctcg caccggatgc     660
cgccgcaacg acgacggcaa cttccctgcc gtccagatcc cctccagcag caccagctct     720
ccggtcaacc agcctaccag caccagcacc acgtccacct ccaccacctc gagcccgcca     780
gtccagccta cgactcccag cggctgcact gctgagaggt gggctcagtg cggcggcaat     840
ggctggagcg gctgcaccac ctgcgtcgct ggcagcactt gcacgaagat taatgactgg     900
taccatcagt gcctgtagaa ttc                                             923
```

<210> SEQ ID NO 74
<211> LENGTH: 305
<212> TYPE: PRT
<213> ORGANISM: Trichoderma reesei

<400> SEQUENCE: 74

Met Arg Ser Ser Pro Leu Leu Arg Ser Ala Val Val Ala Ala Leu Pro
1                 5                  10                  15

Val Leu Ala Leu Ala Ala Asp Gly Arg Ser Thr Arg Tyr Trp Asp Cys
              20                  25                  30

Cys Lys Pro Ser Cys Gly Trp Ala Lys Lys Ala Pro Val Asn Gln Pro
            35                  40                  45

Val Phe Ser Cys Asn Ala Asn Phe Gln Arg Ile Thr Asp Phe Asp Ala
 50                  55                  60

Lys Ser Gly Cys Glu Pro Gly Val Ala Tyr Ser Cys Ala Asp Gln
 65                  70                  75                  80

Thr Pro Trp Ala Val Asn Asp Asp Phe Ala Leu Gly Phe Ala Ala Thr
                    85                  90                  95

Ser Ile Ala Gly Ser Asn Glu Ala Gly Trp Cys Cys Ala Cys Tyr Glu
                   100                 105                 110

Leu Thr Phe Thr Ser Gly Pro Val Ala Gly Lys Lys Met Val Val Gln
                115                 120                 125

Ser Thr Ser Thr Gly Gly Asp Leu Gly Ser Asn His Phe Asp Leu Asn
            130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
                180                 185                 190

Asp Trp Phe Lys Asn Ala Asp Asn Pro Ser Phe Ser Phe Arg Gln Val
                195                 200                 205

Gln Cys Pro Ala Glu Leu Val Ala Arg Thr Gly Cys Arg Arg Asn Asp
                210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
                260                 265                 270

Arg Trp Ala Gln Cys Gly Gly Asn Gly Trp Ser Gly Cys Thr Thr Cys
                275                 280                 285

Val Ala Gly Ser Thr Cys Thr Lys Ile Asn Asp Trp Tyr His Gln Cys
                290                 295                 300

Leu
305

<210> SEQ ID NO 75
<211> LENGTH: 1188
<212> TYPE: DNA
<213> ORGANISM: Myceliophthora thermophila

<400> SEQUENCE: 75
cgacttgaaa cgccccaaat gaagtcctcc atcctcgcca gcgtcttcgc cacgggcgcc        60
gtggctcaaa gtggtccgtg cagcaatgt ggtggcatcg gatggcaagg atcgaccgac        120
tgtgtgtcgg gctaccactg cgtctaccag aacgattggt acagccagtg cgtgcctggc       180
gcggcgtcga caacgctgca gacatcgacc acgtccaggc ccaccgccac cagcaccgcc       240
cctccgtcgt ccaccacctc gcctagcaag ggcaagctga gtggctcgg cagcaacgag        300 tcgggcgccg agttcgggga gggcaattac cccggcctct ggggcaagca cttcatcttc       360
ccgtcgactt cggcgattca gacgctcatc aatgatggat acaacatctt ccggatcgac       420
ttctcgatgg agcgtctggt gcccaaccag ttgacgtcgt ccttcgacca gggttacctc       480

```
cgcaacctga ccgaggtggt caacttcgtg acgaacgcgg gcaagtacgc cgtcctggac      540
ccgcacaact acggccggta ctacggcaac atcatcacgg acacgaacgc gttccggacc      600
ttctggacca acctggccaa gcagttcgcc tccaactcgc tcgtcatctt cgacaccaac      660
aacgagtaca acacgatgga ccagaccctg gtgctcaacc tcaaccaggc cgccatcgac      720
ggcatccggg ccgccggcgc gacctcgcag tacatcttcg tcgagggcaa cgcgtggagc      780
ggggcctgga gctggaacac gaccaacacc aacatggccg ccctgacgga cccgcagaac      840
aagatcgtgt acgagatgca ccagtacctc gactcggaca gctcgggcac ccacgccgag      900
tgcgtcagca gcaccatcgg cgcccagcgc gtcgtcggag ccacccagtg gctccgcgcc      960
aacggcaagc tcggcgtcct cggcgagttc gccggcggcg ccaacgccgt ctgccagcag     1020
gccgtcaccg cctcctcga ccacctccag gacaacagcg acgtctggct gggtgccctc     1080
tggtgggccg ccggtccctg gtggggcgac tacatgtact cgttcgagcc tccttcgggc     1140
accggctatg tcaactacaa ctcgatcttg aagaagtact gccgtaa              1188
```

<210> SEQ ID NO 76
<211> LENGTH: 389
<212> TYPE: PRT
<213> ORGANISM: Myceliophthora thermophila

<400> SEQUENCE: 76

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Gln Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Ile Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255
```

```
Trp Ser Trp Asn Thr Thr Asn Thr Asn Met Ala Ala Leu Thr Asp Pro
            260                 265                 270
Gln Asn Lys Ile Val Tyr Glu Met His Gln Tyr Leu Asp Ser Asp Ser
        275                 280                 285
Ser Gly Thr His Ala Glu Cys Val Ser Ser Thr Ile Gly Ala Gln Arg
    290                 295                 300
Val Val Gly Ala Thr Gln Trp Leu Arg Ala Asn Gly Lys Leu Gly Val
305                 310                 315                 320
Leu Gly Glu Phe Ala Gly Gly Ala Asn Ala Val Cys Gln Gln Ala Val
                325                 330                 335
Thr Gly Leu Leu Asp His Leu Gln Asp Asn Ser Asp Val Trp Leu Gly
            340                 345                 350
Ala Leu Trp Trp Ala Ala Gly Pro Trp Trp Gly Asp Tyr Met Tyr Ser
        355                 360                 365
Phe Glu Pro Pro Ser Gly Thr Gly Tyr Val Asn Tyr Asn Ser Ile Leu
    370                 375                 380
Lys Lys Tyr Leu Pro
385
```

<210> SEQ ID NO 77
<211> LENGTH: 1232
<212> TYPE: DNA
<213> ORGANISM: BASIDIOMYCETE CBS 495.95

<400> SEQUENCE: 77

```
ggatccactt agtaacggcc gccagtgtgc tggaaagcat gaagtctctc ttcctgtcac      60
ttgtagcgac cgtcgcgctc agctcgccag tattctctgt cgcagtctgg gggcaatgcg     120
gcggcattgg cttcagcgga agcaccgtct gtgatgcagg cgccggctgt gtgaagctca     180
acgactatta ctctcaatgc caacccggcg ctcccactgc tacatccgcg cgccaagta     240
gcaacgcacc gtccggcact tcgacggcct cggccccctc ctccagcctt tgctctggca     300
gccgcacgcc gttccagttc ttcggtgtca acgaatccgg cgcggagttc ggcaacctga     360
acatccccgg tgttctgggc accgactaca cctggccgtc gccatccagc attgacttct     420
tcatgggcaa gggaatgaat accttccgta ttccgttcct catggagcgt cttgtccccc     480
ctgccactgg catcacagga cctctcgacc agacgtactt gggcggcctg cagacgattg     540
tcaactacat caccggcaaa ggcggctttg ctctcattga cccgcacaac tttatgatct     600
acaatggcca gacgatctcc agtaccagcg acttccagaa gttctggcag aacctcgcag     660
gagtgtttaa atcgaacagt cacgtcatct tcgatgttat gaacgagcct cacgatattc     720
ccgcccagac cgtgttccaa ctgaaccaag ccgctgtcaa tggcatccgt gcgagcggtg     780
cgacgtcgca gctcattctg gtcgagggca caagctggac tggagcctgg acctggacga     840
cctctggcaa cagcgatgca ttcggtgcca ttaaggatcc caacaacaac gtcgcgatcc     900
agatgcatca gtacctggat agcgatggct ctggcacttc gcagacctgc gtgtctccca     960
ccatcggtgc cgagcggttg caggctgcga ctcaatggtt gaagcagaac aacctcaagg    1020
gcttcctggg cgagatcggc gccggctcta actccgcttg catcagcgct gtgcagggtg    1080
cgttgtgttc gatgcagcaa tctggtgtgt ggctcggcgc tctctggtgg gctgcgggcc    1140
cgtggtgggg cgactactac cagtccatcg agccgccctc tggcccggcg gtgtccgcga    1200
tcctcccgca ggccctgctg ccgttcgcgt aa                                   1232
```

<210> SEQ ID NO 78
<211> LENGTH: 397
<212> TYPE: PRT
<213> ORGANISM: BASIDIOMYCETE CBS 495.95

<400> SEQUENCE: 78

```
Met Lys Ser Leu Phe Leu Ser Leu Val Ala Thr Val Ala Leu Ser Ser
1               5                   10                  15

Pro Val Phe Ser Val Ala Val Trp Gly Gln Cys Gly Gly Ile Gly Phe
            20                  25                  30

Ser Gly Ser Thr Val Cys Asp Ala Gly Ala Gly Cys Val Lys Leu Asn
        35                  40                  45

Asp Tyr Tyr Ser Gln Cys Gln Pro Gly Ala Pro Thr Ala Thr Ser Ala
50                  55                  60

Ala Pro Ser Ser Asn Ala Pro Ser Gly Thr Ser Thr Ala Ser Ala Pro
65                  70                  75                  80

Ser Ser Ser Leu Cys Ser Gly Ser Arg Thr Pro Phe Gln Phe Phe Gly
                85                  90                  95

Val Asn Glu Ser Gly Ala Glu Phe Gly Asn Leu Asn Ile Pro Gly Val
            100                 105                 110

Leu Gly Thr Asp Tyr Thr Trp Pro Ser Pro Ser Ser Ile Asp Phe Phe
        115                 120                 125

Met Gly Lys Gly Met Asn Thr Phe Arg Ile Pro Phe Leu Met Glu Arg
130                 135                 140

Leu Val Pro Pro Ala Thr Gly Ile Thr Gly Pro Leu Asp Gln Thr Tyr
145                 150                 155                 160

Leu Gly Gly Leu Gln Thr Ile Val Asn Tyr Ile Thr Gly Lys Gly Gly
                165                 170                 175

Phe Ala Leu Ile Asp Pro His Asn Phe Met Ile Tyr Asn Gly Gln Thr
            180                 185                 190

Ile Ser Ser Thr Ser Asp Phe Gln Lys Phe Trp Gln Asn Leu Ala Gly
        195                 200                 205

Val Phe Lys Ser Asn Ser His Val Ile Phe Asp Val Met Asn Glu Pro
210                 215                 220

His Asp Ile Pro Ala Gln Thr Val Phe Gln Leu Asn Gln Ala Ala Val
225                 230                 235                 240

Asn Gly Ile Arg Ala Ser Gly Ala Thr Ser Gln Leu Ile Leu Val Glu
                245                 250                 255

Gly Thr Ser Trp Thr Gly Ala Trp Thr Trp Thr Thr Ser Gly Asn Ser
            260                 265                 270

Asp Ala Phe Gly Ala Ile Lys Asp Pro Asn Asn Val Ala Ile Gln
        275                 280                 285

Met His Gln Tyr Leu Asp Ser Asp Gly Ser Gly Thr Ser Gln Thr Cys
290                 295                 300

Val Ser Pro Thr Ile Gly Ala Glu Arg Leu Gln Ala Ala Thr Gln Trp
305                 310                 315                 320

Leu Lys Gln Asn Asn Leu Lys Gly Phe Leu Gly Glu Ile Gly Ala Gly
                325                 330                 335

Ser Asn Ser Ala Cys Ile Ser Ala Val Gln Gly Ala Leu Cys Ser Met
            340                 345                 350

Gln Gln Ser Gly Val Trp Leu Gly Ala Leu Trp Trp Ala Ala Gly Pro
        355                 360                 365

Trp Trp Gly Asp Tyr Tyr Gln Ser Ile Glu Pro Pro Ser Gly Pro Ala
370                 375                 380
```

Val Ser Ala Ile Leu Pro Gln Ala Leu Leu Pro Phe Ala
385                 390                 395

<210> SEQ ID NO 79
<211> LENGTH: 1303
<212> TYPE: DNA
<213> ORGANISM: BASIDIOMYCETE CBS 495.95

<400> SEQUENCE: 79

```
ggaaagcgtc agtatggtga aatttgcgct tgtggcaact gtcggcgcaa tcttgagcgc     60
ttctgcggcc aatgcggctt ctatctacca gcaatgtgga ggcattggat ggtctgggtc    120
cactgtttgc gacgccggtc tcgcttgcgt tatcctcaat gcgtactact ttcagtgctt    180
gacgcccgcc gcgggccaga caacgacggg ctcgggcgca ccggcgtcaa catcaacctc    240
tcactcaacg gtcactacgg ggagctcaca ctcaacaacc gggacgacgg cgacgaaaac    300
aactaccact ccgtcgacca ccacgaccct acccgccatc tctgtgtctg gtcgcgtctg    360
ctctggctcc aggacgaagt tcaagttctt cggtgtgaat gaaagcggcg ccgaattcgg    420
gaacactgct tggccagggc agctcgggaa agactataca tggccttcgc ctagcagcgt    480
ggactacttc atgggggctg gattcaatac attccgtatc accttcttga tggagcgtat    540
gagccctccg gctaccggac tcactggccc attcaaccag acgtacctgt cgggcctcac    600
caccattgtc gactacatca cgaacaaagg aggatacgct cttattgacc ccacaacctt    660
catgcgttac aacaacggca taatcagcag cacatctgac ttcgcgactt ggtggagcaa    720
tttggccact gtattcaaat ccacgaagaa cgccatcttc gacatccaga acgagccgta    780
cggaatcgat gcgcagaccg tatacgaact gaatcaagct gccatcaatt cgatccgcgc    840
cgctggcgct acgtcacagt tgattctggt tgaaggaacg tcatacactg agcttggac    900
gtgggtctcg tccggaaacg gagctgcttt cgcggccgtt acggatcctt acaacaacac    960
ggcaattgaa atgcaccaat acctcgacag cgacggttct gggacaaacg aagactgtgt   1020
ctcctccacc attgggtcgc aacgtctcca agctgccact gcgtggctgc aacaaacagg   1080
actcaaggga ttcctcggag agacgggtgc tgggtcgaat cccagtgca tcgacgccgt   1140
gttcgatgaa ctttgctata tgcaacagca aggcggctcc tggatcggtg cactctggtg   1200
ggctgcgggt ccctggtggg cacgtacat ttactcgatt gaacctccga gcggtgccgc   1260
tatcccagaa gtccttcctc agggtctcgc tccattcctc tag                     1303
```

<210> SEQ ID NO 80
<211> LENGTH: 429
<212> TYPE: PRT
<213> ORGANISM: BASIDIOMYCETE CBS 495.95

<400> SEQUENCE: 80

Met Val Lys Phe Ala Leu Val Ala Thr Val Gly Ala Ile Leu Ser Ala
1               5                   10                  15

Ser Ala Ala Asn Ala Ala Ser Ile Tyr Gln Gln Cys Gly Gly Ile Gly
            20                  25                  30

Trp Ser Gly Ser Thr Val Cys Asp Ala Gly Leu Ala Cys Val Ile Leu
        35                  40                  45

Asn Ala Tyr Tyr Phe Gln Cys Leu Thr Pro Ala Ala Gly Gln Thr Thr
    50                  55                  60

Thr Gly Ser Gly Ala Pro Ala Ser Thr Ser Thr Ser His Ser Thr Val
65                  70                  75                  80

Thr Thr Gly Ser Ser His Ser Thr Thr Gly Thr Thr Ala Thr Lys Thr

```
                85                  90                  95
Thr Thr Thr Pro Ser Thr Thr Thr Leu Pro Ala Ile Ser Val Ser
            100                 105                 110
Gly Arg Val Cys Ser Gly Ser Arg Thr Lys Phe Lys Phe Gly Val
            115                 120                 125
Asn Glu Ser Gly Ala Glu Phe Gly Asn Thr Ala Trp Pro Gly Gln Leu
            130                 135                 140
Gly Lys Asp Tyr Thr Trp Pro Ser Pro Ser Ser Val Asp Tyr Phe Met
145                 150                 155                 160
Gly Ala Gly Phe Asn Thr Phe Arg Ile Thr Phe Leu Met Glu Arg Met
                165                 170                 175
Ser Pro Pro Ala Thr Gly Leu Thr Gly Pro Phe Asn Gln Thr Tyr Leu
            180                 185                 190
Ser Gly Leu Thr Thr Ile Val Asp Tyr Ile Thr Asn Lys Gly Gly Tyr
            195                 200                 205
Ala Leu Ile Asp Pro His Asn Phe Met Arg Tyr Asn Gly Ile Ile
            210                 215                 220
Ser Ser Thr Ser Asp Phe Ala Thr Trp Trp Ser Asn Leu Ala Thr Val
225                 230                 235                 240
Phe Lys Ser Thr Lys Asn Ala Ile Phe Asp Ile Gln Asn Glu Pro Tyr
                245                 250                 255
Gly Ile Asp Ala Gln Thr Val Tyr Glu Leu Asn Gln Ala Ala Ile Asn
            260                 265                 270
Ser Ile Arg Ala Ala Gly Ala Thr Ser Gln Leu Ile Leu Val Glu Gly
            275                 280                 285
Thr Ser Tyr Thr Gly Ala Trp Thr Trp Val Ser Ser Gly Asn Gly Ala
290                 295                 300
Ala Phe Ala Ala Val Thr Asp Pro Tyr Asn Asn Thr Ala Ile Glu Met
305                 310                 315                 320
His Gln Tyr Leu Asp Ser Asp Gly Ser Gly Thr Asn Glu Asp Cys Val
                325                 330                 335
Ser Ser Thr Ile Gly Ser Gln Arg Leu Gln Ala Ala Thr Ala Trp Leu
            340                 345                 350
Gln Gln Thr Gly Leu Lys Gly Phe Leu Gly Glu Thr Gly Ala Gly Ser
            355                 360                 365
Asn Ser Gln Cys Ile Asp Ala Val Phe Asp Glu Leu Cys Tyr Met Gln
            370                 375                 380
Gln Gln Gly Gly Ser Trp Ile Gly Ala Leu Trp Trp Ala Ala Gly Pro
385                 390                 395                 400
Trp Trp Gly Thr Tyr Ile Tyr Ser Ile Glu Pro Pro Ser Gly Ala Ala
                405                 410                 415
Ile Pro Glu Val Leu Pro Gln Gly Leu Ala Pro Phe Leu
            420                 425

<210> SEQ ID NO 81
<211> LENGTH: 1580
<212> TYPE: DNA
<213> ORGANISM: Thielavia terrestris

<400> SEQUENCE: 81
agccccccgt tcaggcacac ttggcatcag atcagcttag cagcgcctgc acagcatgaa     60
gctctcgcag tcggccgcgc tggcggcact caccgcgacg gcgctcgccg ccccctcgcc    120
cacgacgccg caggcgccga ggcaggcttc agccggctgc tcgtctgcgg tcacgctcga    180
```

-continued

```
cgccagcacc aacgtttgga agaagtacac gctgcacccc aacagctact accgcaagga    240
ggttgaggcc gcggtggcgc agatctcgga cccggacctc gccgccaagg ccaagaaggt    300
ggccgacgtc ggcaccttcc tgtggctcga ctcgatcgag aacatcggca agctggagcc    360
ggcgatccag gacgtgccct gcgagaacat cctgggcctg gtcatctacg acctgccggg    420
ccgcgactgc gcggccaagg cgtccaacgg cgagctcaag gtcggcgaga tcgaccgcta    480
caagaccgag tacatcgaca gtgagtgctg ccccccgggt tcgagaagag cgtgggggaa    540
agggaaaggg ttgactgact gacacggcgc actgcagaga tcgtgtcgat cctcaaggca    600
caccccaaca cggcgttcgc gctggtcatc gagccggact cgctgcccaa cctggtgacc    660
aacagcaact tggacacgtg ctcgagcagc gcgtcgggct accgcgaagg cgtggcttac    720
gccctcaaga acctcaacct gcccaacgtg atcatgtacc tcgacgccgg ccacggcggc    780
tggctcggct gggacgccaa cctgcagccc ggcgcgcagg agctagccaa ggcgtacaag    840
aacgccggct cgcccaagca gctccgcggc ttctcgacca acgtggccgg ctggaactcc    900
tggtgagctt ttttccattc catttcttct tcctcttctc tcttcgctcc cactctgcag    960
cccccctcc cccaagcacc cactggcgtt ccggcttgct gactcggcct cccttttcccc   1020
gggcaccagg gatcaatcgc ccggcgaatt ctcccaggcg tccgacgcca agtacaacaa   1080
gtgccagaac gagaagatct acgtcagcac cttcggctcc gcgctccagt cggccggcat   1140
gcccaaccac gccatcgtcg acacgggccg caacggcgtc accggcctgc gcaaggagtg   1200
gggtgactgg tgcaacgtca acggtgcagg ttcgttgtct tctttttctc ctcttttgtt   1260
tgcacgtcgt ggtcctttc aagcagccgt gtttggttgg gggagatgga ctccggctga   1320
tgttctgctt cctctctagg cttcggcgtg cgcccgacga gcaacacggg cctcgagctg   1380
gccgacgcgt tcgtgtgggt caagcccggc ggcgagtcgg acggaccagc gacagctcg    1440
tcgccgcgct acgacagctt ctgcggcaag gacgacgcct tcaagccctc gcccgaggcc   1500
ggcacctgga cgaggccta cttcgagatg ctgctcaaga cgccgtgcc gtcgttctaa    1560
gacggtccag catcatccgg                                                1580
```

<210> SEQ ID NO 82
<211> LENGTH: 396
<212> TYPE: PRT
<213> ORGANISM: Thielavia terrestris

<400> SEQUENCE: 82

```
Met Lys Leu Ser Gln Ser Ala Ala Leu Ala Ala Leu Thr Ala Thr Ala
  1               5                  10                  15

Leu Ala Ala Pro Ser Pro Thr Thr Pro Gln Ala Pro Arg Gln Ala Ser
             20                  25                  30

Ala Gly Cys Ser Ser Ala Val Thr Leu Asp Ala Ser Thr Asn Val Trp
         35                  40                  45

Lys Lys Tyr Thr Leu His Pro Asn Ser Tyr Tyr Arg Lys Glu Val Glu
     50                  55                  60

Ala Ala Val Ala Gln Ile Ser Asp Pro Asp Leu Ala Ala Lys Ala Lys
 65                  70                  75                  80

Lys Val Ala Asp Val Gly Thr Phe Leu Trp Leu Asp Ser Ile Glu Asn
                 85                  90                  95

Ile Gly Lys Leu Glu Pro Ala Ile Gln Asp Val Pro Cys Glu Asn Ile
            100                 105                 110

Leu Gly Leu Val Ile Tyr Asp Leu Pro Gly Arg Asp Cys Ala Ala Lys
        115                 120                 125
```

```
Ala Ser Asn Gly Glu Leu Lys Val Gly Glu Ile Asp Arg Tyr Lys Thr
    130                 135                 140

Glu Tyr Ile Asp Lys Ile Val Ser Ile Leu Lys Ala His Pro Asn Thr
145                 150                 155                 160

Ala Phe Ala Leu Val Ile Glu Pro Asp Ser Leu Pro Asn Leu Val Thr
                165                 170                 175

Asn Ser Asn Leu Asp Thr Cys Ser Ser Ala Ser Gly Tyr Arg Glu
            180                 185                 190

Gly Val Ala Tyr Ala Leu Lys Asn Leu Asn Leu Pro Asn Val Ile Met
        195                 200                 205

Tyr Leu Asp Ala Gly His Gly Gly Trp Leu Gly Trp Asp Ala Asn Leu
    210                 215                 220

Gln Pro Gly Ala Gln Glu Leu Ala Lys Ala Tyr Lys Asn Ala Gly Ser
225                 230                 235                 240

Pro Lys Gln Leu Arg Gly Phe Ser Thr Asn Val Ala Gly Trp Asn Ser
                245                 250                 255

Trp Asp Gln Ser Pro Gly Glu Phe Ser Gln Ala Ser Asp Ala Lys Tyr
            260                 265                 270

Asn Lys Cys Gln Asn Glu Lys Ile Tyr Val Ser Thr Phe Gly Ser Ala
        275                 280                 285

Leu Gln Ser Ala Gly Met Pro Asn His Ala Ile Val Asp Thr Gly Arg
    290                 295                 300

Asn Gly Val Thr Gly Leu Arg Lys Glu Trp Gly Asp Trp Cys Asn Val
305                 310                 315                 320

Asn Gly Ala Gly Phe Gly Val Arg Pro Thr Ser Asn Thr Gly Leu Glu
                325                 330                 335

Leu Ala Asp Ala Phe Val Trp Val Lys Pro Gly Gly Glu Ser Asp Gly
            340                 345                 350

Thr Ser Asp Ser Ser Ser Pro Arg Tyr Asp Ser Phe Cys Gly Lys Asp
    355                 360                 365

Asp Ala Phe Lys Pro Ser Pro Glu Ala Gly Thr Trp Asn Glu Ala Tyr
370                 375                 380

Phe Glu Met Leu Leu Lys Asn Ala Val Pro Ser Phe
385                 390                 395

<210> SEQ ID NO 83
<211> LENGTH: 1203
<212> TYPE: DNA
<213> ORGANISM: Thielavia terrestris

<400> SEQUENCE: 83
atgaagtacc tcaacctcct cgcagctctc ctcgccgtcg ctcctctctc cctcgctgca      60
cccagcatcg aggccagaca gtcgaacgtc aacccataca tcggcaagag cccgctcgtt     120
attaggtcgt acgcccaaaa gcttgaggag accgtcagga ccttccagca acgtggcgac     180
cagctcaacg ctgcgaggac acggacggtg cagaacgttg cgactttcgc ctggatctcg     240
gataccaatg gtattggagc cattcgacct ctcatccaag atgctctcgc ccagcaggct     300
cgcactggac agaaggtcat cgtccaaatc gtcgtctaca acctcccaga tcgcgactgc     360
tctgccaacg cctcgactgg agagttcacc gtaggaaacg acggtctcaa ccgatacaag     420
aactttgtca acaccatcgc ccgcgagctc tcgactgctg acgctgacaa gctccacttt     480
gccctcctcc tcgaacccga cgcacttgcc aacctcgtca ccaacgcgaa tgccccagg      540 tgccgaatcg ccgctcccgc ttacaaggag ggtatcgcct acaccctcgc caccttgtcc     600
```

-continued

```
aagcccaacg tcgacgtcta catcgacgcc gccaacggtg gctggctcgg ctggaacgac    660
aacctccgcc ccttcgccga actcttcaag gaagtctacg acctcgcccg ccgcatcaac    720
cccaacgcca aggtccgcgg cgtccccgtc aacgtctcca actacaacca gtaccgcgct    780
gaagtccgcg agcccttcac cgagtggaag gacgcctggg acgagagccg ctacgtcaac    840
gtcctcaccc cgcacctcaa cgccgtcggc ttctccgcgc acttcatcgt tgaccaggga    900
cgcggtggca agggcggtat caggacgag tggggccagt ggtgcaacgt taggaacgct    960
gggttcggta tcaggcctac tgcggatcag ggcgtgctcc agaacccgaa tgtggatgcg   1020
attgtgtggg ttaagccggg tggagagtcg gatggcacga gtgatttgaa ctcgaacagg   1080
tatgatccta cgtgcaggag tccggtggcg catgttcccg ctcctgaggc tggccagtgg   1140
ttcaacgagt atgttgttaa cctcgttttg aacgctaacc cccctcttga gcctacctgg   1200
taa                                                                 1203
```

<210> SEQ ID NO 84
<211> LENGTH: 400
<212> TYPE: PRT
<213> ORGANISM: Thielavia terrestris

<400> SEQUENCE: 84

```
Met Lys Tyr Leu Asn Leu Leu Ala Ala Leu Ala Val Ala Pro Leu
1               5                   10                  15

Ser Leu Ala Ala Pro Ser Ile Glu Ala Arg Gln Ser Asn Val Asn Pro
            20                  25                  30

Tyr Ile Gly Lys Ser Pro Leu Val Ile Arg Ser Tyr Ala Gln Lys Leu
        35                  40                  45

Glu Glu Thr Val Arg Thr Phe Gln Gln Arg Gly Asp Gln Leu Asn Ala
    50                  55                  60

Ala Arg Thr Arg Thr Val Gln Asn Val Ala Thr Phe Ala Trp Ile Ser
65                  70                  75                  80

Asp Thr Asn Gly Ile Gly Ala Ile Arg Pro Leu Ile Gln Asp Ala Leu
                85                  90                  95

Ala Gln Gln Ala Arg Thr Gly Gln Lys Val Ile Val Gln Ile Val Val
            100                 105                 110

Tyr Asn Leu Pro Asp Arg Asp Cys Ser Ala Asn Ala Ser Thr Gly Glu
        115                 120                 125

Phe Thr Val Gly Asn Asp Gly Leu Asn Arg Tyr Lys Asn Phe Val Asn
    130                 135                 140

Thr Ile Ala Arg Glu Leu Ser Thr Ala Asp Ala Asp Lys Leu His Phe
145                 150                 155                 160

Ala Leu Leu Leu Glu Pro Asp Ala Leu Ala Asn Leu Val Thr Asn Ala
                165                 170                 175

Asn Ala Pro Arg Cys Arg Ile Ala Ala Pro Ala Tyr Lys Glu Gly Ile
            180                 185                 190

Ala Tyr Thr Leu Ala Thr Leu Ser Lys Pro Asn Val Asp Val Tyr Ile
        195                 200                 205

Asp Ala Ala Asn Gly Gly Trp Leu Gly Trp Asn Asp Asn Leu Arg Pro
    210                 215                 220

Phe Ala Glu Leu Phe Lys Glu Val Tyr Asp Leu Ala Arg Arg Ile Asn
225                 230                 235                 240

Pro Asn Ala Lys Val Arg Gly Val Pro Val Asn Val Ser Asn Tyr Asn
                245                 250                 255
```

```
Gln Tyr Arg Ala Glu Val Arg Glu Pro Phe Thr Glu Trp Lys Asp Ala
            260                 265                 270

Trp Asp Glu Ser Arg Tyr Val Asn Val Leu Thr Pro His Leu Asn Ala
        275                 280                 285

Val Gly Phe Ser Ala His Phe Ile Val Asp Gln Gly Arg Gly Gly Lys
    290                 295                 300

Gly Gly Ile Arg Thr Glu Trp Gly Gln Trp Cys Asn Val Arg Asn Ala
305                 310                 315                 320

Gly Phe Gly Ile Arg Pro Thr Ala Asp Gln Gly Val Leu Gln Asn Pro
                325                 330                 335

Asn Val Asp Ala Ile Val Trp Val Lys Pro Gly Gly Glu Ser Asp Gly
            340                 345                 350

Thr Ser Asp Leu Asn Ser Asn Arg Tyr Asp Pro Thr Cys Arg Ser Pro
        355                 360                 365

Val Ala His Val Pro Ala Pro Glu Ala Gly Gln Trp Phe Asn Glu Tyr
    370                 375                 380

Val Val Asn Leu Val Leu Asn Ala Asn Pro Pro Leu Glu Pro Thr Trp
385                 390                 395                 400

<210> SEQ ID NO 85
<211> LENGTH: 1501
<212> TYPE: DNA
<213> ORGANISM: Thielavia terrestris

<400> SEQUENCE: 85
gccgttgtca agatgggcca gaagacgctg cacggattcg ccgccacggc tttggccgtt    60
ctcccctttg tgaaggctca gcagcccggc aacttcacgc cggaggtgca cccgcaactg   120
ccaacgtgga agtgcacgac cgccggcggc tgcgttcagc aggacacttc ggtggtgctc   180
gactggaact accgttggat ccacaatgcc gacggcaccg cctcgtgcac gacgtccagc   240
ggggtcgacc acacgctgtg tccagatgag gcgacctgcg cgaagaactg cttcgtggaa   300
ggcgtcaact acacgagcag cggtgtcacc acatccggca gttcgctgac gatgaggcag   360
tatttcaagg ggagcaacgg gcagaccaac agcgtttcgc ctcgtctcta cctgctcggc   420
tcggatggaa actacgtaat gctcaagctg ctcggccagg agctgagctt cgatgtcgat   480
ctctccacgc tcccctgcgg cgagaacggc gcgctgtacc tgtccgagat ggacgcgacc   540
ggtggcagga accagtacaa caccggcggt gccaactacg gctcgggcta ctgtgacgcc   600
cagtgtcccg tgcagacgtg gatgaacggc acgctgaaca ccaacgggca gggctactgc   660
tgcaacgaga tggacatcct cgaggccaac tcccgcgcca acgcgatgac acctcacccc   720
tgcgccaacg gcagctgcga caagagcggg tgcggactca cccctacgc gagggctac    780 aagagctact acggaccggg cctcacggtt gacacgtcga agcccttcac catcattacc   840
cgcttcatca ccgacgacgg cacgaccagc ggcaccctca ccagatcca gcggatctat   900 gtgcagaatg gcaagacggt cgcgtcggct cgtccggag cgacatcat acggcatcc    960 ggctgcacct cggcccaggc gttcggcggg ctggccaaca tgggcgcggc gcttggacgg  1020
ggcatggtgc tgaccttcag catctggaac gacgctgggg gctacatgaa ctggctcgac  1080
agcggcaaca acgccgtg cagcagcacc gagggcaacc cgtccaacat cctgccaac   1140 tacccggaca cccacgtggt cttctccaac atccgctggg gagacatcgg ctcgacggtc  1200
caggtctcgg gaggcggcaa cggcggctcg accaccacca gtcgaccac cacgctgagg  1260 acctcgacca cgaccaccac caccgccccg acggccactg ccacgcactg ggacaatgc  1320
```

-continued

```
ggcggaatcg gggtacgtca accgcctcct gcattctgtt gaggaagtta actaacgtgg   1380
cctacgcagt ggactggacc gaccgtctgc gaatcgccgt acgcatgcaa ggagctgaac   1440
ccctggtact accagtgcct ctaaagtatt gcagtgaagc catactccgt gctcggcatg   1500
g                                                                   1501
```

```
<210> SEQ ID NO 86
<211> LENGTH: 464
<212> TYPE: PRT
<213> ORGANISM: Thielavia terrestris

<400> SEQUENCE: 86
```

| | | | | | | | | | | | | | | |
|---|---|---|---|---|---|---|---|---|---|---|---|---|---|---|
| Met | Gly | Gln | Lys | Thr | Leu | His | Gly | Phe | Ala | Ala | Thr | Ala | Leu | Ala | Val |
| 1 | | | | 5 | | | | | 10 | | | | | 15 | |
| Leu | Pro | Phe | Val | Lys | Ala | Gln | Gln | Pro | Gly | Asn | Phe | Thr | Pro | Glu | Val |
| | | | 20 | | | | | 25 | | | | | 30 | | |
| His | Pro | Gln | Leu | Pro | Thr | Trp | Lys | Cys | Thr | Thr | Ala | Gly | Gly | Cys | Val |
| | | | 35 | | | | | 40 | | | | | 45 | | |
| Gln | Gln | Asp | Thr | Ser | Val | Val | Leu | Asp | Trp | Asn | Tyr | Arg | Trp | Ile | His |
| | 50 | | | | | 55 | | | | | 60 | | | | |
| Asn | Ala | Asp | Gly | Thr | Ala | Ser | Cys | Thr | Thr | Ser | Ser | Gly | Val | Asp | His |
| 65 | | | | | 70 | | | | | 75 | | | | | 80 |
| Thr | Leu | Cys | Pro | Asp | Glu | Ala | Thr | Cys | Ala | Lys | Asn | Cys | Phe | Val | Glu |
| | | | | 85 | | | | | 90 | | | | | 95 | |
| Gly | Val | Asn | Tyr | Thr | Ser | Ser | Gly | Val | Thr | Thr | Ser | Gly | Ser | Ser | Leu |
| | | | 100 | | | | | 105 | | | | | 110 | | |
| Thr | Met | Arg | Gln | Tyr | Phe | Lys | Gly | Ser | Asn | Gly | Gln | Thr | Asn | Ser | Val |
| | | 115 | | | | | 120 | | | | | 125 | | | |
| Ser | Pro | Arg | Leu | Tyr | Leu | Leu | Gly | Ser | Asp | Gly | Asn | Tyr | Val | Met | Leu |
| | 130 | | | | | 135 | | | | | 140 | | | | |
| Lys | Leu | Leu | Gly | Gln | Glu | Leu | Ser | Phe | Asp | Val | Asp | Leu | Ser | Thr | Leu |
| 145 | | | | | 150 | | | | | 155 | | | | | 160 |
| Pro | Cys | Gly | Glu | Asn | Gly | Ala | Leu | Tyr | Leu | Ser | Glu | Met | Asp | Ala | Thr |
| | | | | 165 | | | | | 170 | | | | | 175 | |
| Gly | Gly | Arg | Asn | Gln | Tyr | Asn | Thr | Gly | Gly | Ala | Asn | Tyr | Gly | Ser | Gly |
| | | | 180 | | | | | 185 | | | | | 190 | | |
| Tyr | Cys | Asp | Ala | Gln | Cys | Pro | Val | Gln | Thr | Trp | Met | Asn | Gly | Thr | Leu |
| | | 195 | | | | | 200 | | | | | 205 | | | |
| Asn | Thr | Asn | Gly | Gln | Gly | Tyr | Cys | Cys | Asn | Glu | Met | Asp | Ile | Leu | Glu |
| | 210 | | | | | 215 | | | | | 220 | | | | |
| Ala | Asn | Ser | Arg | Ala | Asn | Ala | Met | Thr | Pro | His | Pro | Cys | Ala | Asn | Gly |
| 225 | | | | | 230 | | | | | 235 | | | | | 240 |
| Ser | Cys | Asp | Lys | Ser | Gly | Cys | Gly | Leu | Asn | Pro | Tyr | Ala | Glu | Gly | Tyr |
| | | | | 245 | | | | | 250 | | | | | 255 | |
| Lys | Ser | Tyr | Tyr | Gly | Pro | Gly | Leu | Thr | Val | Asp | Thr | Ser | Lys | Pro | Phe |
| | | | 260 | | | | | 265 | | | | | 270 | | |
| Thr | Ile | Ile | Thr | Arg | Phe | Ile | Thr | Asp | Asp | Gly | Thr | Thr | Ser | Gly | Thr |
| | | 275 | | | | | 280 | | | | | 285 | | | |
| Leu | Asn | Gln | Ile | Gln | Arg | Ile | Tyr | Val | Gln | Asn | Gly | Lys | Thr | Val | Ala |
| | 290 | | | | | 295 | | | | | 300 | | | | |
| Ser | Ala | Ala | Ser | Gly | Gly | Asp | Ile | Ile | Thr | Ala | Ser | Gly | Cys | Thr | Ser |
| 305 | | | | | 310 | | | | | 315 | | | | | 320 |
| Ala | Gln | Ala | Phe | Gly | Gly | Leu | Ala | Asn | Met | Gly | Ala | Ala | Leu | Gly | Arg |
| | | | | 325 | | | | | 330 | | | | | 335 | |

```
Gly Met Val Leu Thr Phe Ser Ile Trp Asn Asp Ala Gly Gly Tyr Met
            340                 345                 350

Asn Trp Leu Asp Ser Gly Asn Asn Gly Pro Cys Ser Thr Glu Gly
        355                 360                 365

Asn Pro Ser Asn Ile Leu Ala Asn Tyr Pro Asp Thr His Val Val Phe
    370                 375                 380

Ser Asn Ile Arg Trp Gly Asp Ile Gly Ser Thr Val Gln Val Ser Gly
385                 390                 395                 400

Gly Gly Asn Gly Gly Ser Thr Thr Thr Ser Thr Thr Thr Leu Arg
            405                 410                 415

Thr Ser Thr Thr Thr Thr Thr Thr Ala Pro Ala Thr Ala Thr His
            420                 425                 430

Trp Gly Gln Cys Gly Gly Ile Gly Trp Thr Gly Pro Thr Val Cys Glu
            435                 440                 445

Ser Pro Tyr Ala Cys Lys Glu Leu Asn Pro Trp Tyr Tyr Gln Cys Leu
            450                 455                 460

<210> SEQ ID NO 87
<211> LENGTH: 1368
<212> TYPE: DNA
<213> ORGANISM: Thielavia terrestris

<400> SEQUENCE: 87
accgatccgc tcgaagatgg cgcccaagtc tacagttctg gccgcctggc tgctctcctc      60
gctggccgcg gcccagcaga tcggcaaagc cgtgcccgag gtccaccccc aactgacaac     120
gcagaagtgc actctccgcg gcgggtgcaa gcctgtccgc acctcggtcg tgctcgactc     180
gtccgcgcgc tcgctgcaca aggtcgggga ccccaacacc agctgcagcg tcggcggcga     240
cctgtgctcg gacgcgaagt cgtgcggcaa gaactgcgcg ctcgagggcg tcgactacgc     300
ggcccacggc gtggcgacca agggcgacgc cctcacgctg caccagtggc tcaaggggc     360
cgacggcacc tacaggaccg tctcgccgcg cgtataccctc ctgggcgagg acgggaagaa     420
ctacgaggac ttcaagctgc tcaacgccga gctcagcttc gacgtcgacg tgtcccagct     480
cgtctgcggc atgaacggcg ccctgtactt ctccgagatg gagatggacg gcggccgcag     540
cccgctgaac ccggcgggcg ccacgtacgg cacgggctac tgcgacgcgc agtgccccaa     600
gttggacttt atcaacggcg aggtatttct tctctcttct gttttctttt tccatcgctt     660
tttctgaccg gaatccgccc tcttagctca acaccaacca cacgtacggg gcgtgctgca     720
acgagatgga catctgggag gccaacgcgc tggcgcaggc gctcacgccg cacccgtgca     780
acgcgacgcg ggtgtacaag tgcgacacgg cggacgagtg cgggcagccg gtgggcgtgt     840
gcgacgaatg ggggtgctcg tacaacccgt ccaacttcgg ggtcaaggac tactacgggc     900
gcaacctgac ggtggacacg aaccgcaagt tcacggtgac gacgcagttc gtgacgtcca     960
acggcgggc ggacgcgag ctgaccgaga tccggcggct gtacgtgcag acggcgtgg    1020
tgatccagaa ccacgcgggtc acggcgggcg gggcgacgta cgacagcatc acggacggct    1080
tctgcaacgc gacggccacc tggacgcagc agcggggcgg gctcgcgcgc atgggcgagg    1140
ccatcggccg cggcatggtg ctcatcttca gcctgtgggt tgacaacggc ggcttcatga    1200
actggctcga cagcggcaac gccgggccct gcaacgccac cgagggcgac ccggccctga    1260
tcctgcagca gcacccggac gccagcgtca ccttctccaa catccgatgg ggcgagatcg    1320
gcagcacgta caagagcgag tgcagccact agagtagagc ttgtaatt                 1368
```

<210> SEQ ID NO 88
<211> LENGTH: 423
<212> TYPE: PRT
<213> ORGANISM: Thielavia terrestris

<400> SEQUENCE: 88

| Met | Ala | Pro | Lys | Ser | Thr | Val | Leu | Ala | Ala | Trp | Leu | Leu | Ser | Ser | Leu |
|---|---|---|---|---|---|---|---|---|---|---|---|---|---|---|---|
| 1 | | | | 5 | | | | | 10 | | | | | 15 | |

Ala Ala Ala Gln Gln Ile Gly Lys Ala Val Pro Glu Val His Pro Lys
            20                  25                  30

Leu Thr Thr Gln Lys Cys Thr Leu Arg Gly Gly Cys Lys Pro Val Arg
                35                  40                  45

Thr Ser Val Val Leu Asp Ser Ser Ala Arg Ser Leu His Lys Val Gly
    50                  55                  60

Asp Pro Asn Thr Ser Cys Ser Val Gly Gly Asp Leu Cys Ser Asp Ala
65                  70                  75                  80

Lys Ser Cys Gly Lys Asn Cys Ala Leu Glu Gly Val Asp Tyr Ala Ala
                85                  90                  95

His Gly Val Ala Thr Lys Gly Asp Ala Leu Thr Leu His Gln Trp Leu
            100                 105                 110

Lys Gly Ala Asp Gly Thr Tyr Arg Thr Val Ser Pro Arg Val Tyr Leu
        115                 120                 125

Leu Gly Glu Asp Gly Lys Asn Tyr Glu Asp Phe Lys Leu Leu Asn Ala
    130                 135                 140

Glu Leu Ser Phe Asp Val Asp Val Ser Gln Leu Val Cys Gly Met Asn
145                 150                 155                 160

Gly Ala Leu Tyr Phe Ser Glu Met Glu Met Asp Gly Gly Arg Ser Pro
                165                 170                 175

Leu Asn Pro Ala Gly Ala Thr Tyr Gly Thr Gly Tyr Cys Asp Ala Gln
            180                 185                 190

Cys Pro Lys Leu Asp Phe Ile Asn Gly Glu Leu Asn Thr Asn His Thr
        195                 200                 205

Tyr Gly Ala Cys Cys Asn Glu Met Asp Ile Trp Glu Ala Asn Ala Leu
    210                 215                 220

Ala Gln Ala Leu Thr Pro His Pro Cys Asn Ala Thr Arg Val Tyr Lys
225                 230                 235                 240

Cys Asp Thr Ala Asp Glu Cys Gly Gln Pro Val Gly Val Cys Asp Glu
                245                 250                 255

Trp Gly Cys Ser Tyr Asn Pro Ser Asn Phe Gly Val Lys Asp Tyr Tyr
            260                 265                 270

Gly Arg Asn Leu Thr Val Asp Thr Asn Arg Lys Phe Thr Val Thr Thr
        275                 280                 285

Gln Phe Val Thr Ser Asn Gly Arg Ala Asp Gly Glu Leu Thr Glu Ile
    290                 295                 300

Arg Arg Leu Tyr Val Gln Asp Gly Val Val Ile Gln Asn His Ala Val
305                 310                 315                 320

Thr Ala Gly Gly Ala Thr Tyr Asp Ser Ile Thr Asp Gly Phe Cys Asn
                325                 330                 335

Ala Thr Ala Thr Trp Thr Gln Gln Arg Gly Gly Leu Ala Arg Met Gly
            340                 345                 350

Glu Ala Ile Gly Arg Gly Met Val Leu Ile Phe Ser Leu Trp Val Asp
        355                 360                 365

Asn Gly Gly Phe Met Asn Trp Leu Asp Ser Gly Asn Ala Gly Pro Cys
    370                 375                 380

Asn Ala Thr Glu Gly Asp Pro Ala Leu Ile Leu Gln Gln His Pro Asp
385                 390                 395                 400

Ala Ser Val Thr Phe Ser Asn Ile Arg Trp Gly Glu Ile Gly Ser Thr
            405                 410                 415

Tyr Lys Ser Glu Cys Ser His
            420

<210> SEQ ID NO 89
<211> LENGTH: 1011
<212> TYPE: DNA
<213> ORGANISM: Thielavia terrestris

<400> SEQUENCE: 89

```
atgaccctac ggctccctgt catcagcctg ctggcctcgc tggcagcagg cgccgtcgtc    60
gtcccacggg cggagtttca ccccctctc ccgacttgga atgcacgac ctccggggc      120
tgcgtgcagc agaacaccag cgtcgtcctg accgtgact cgaagtacgc cgcacacagc    180
gccggctcgc ggacggaatc ggattacgcg gcaatgggag tgtccacttc gggcaatgcc   240
gtgacgctgt accactacgt caagaccaac ggcaccctcg tccccgcttc gccgcgcatc   300
tacctcctgg gcgcggacgg caagtacgtg cttatggacc tcctcaacca ggagctgtcg   360
gtggacgtcg acttctcggc gctgccgtgc ggcgagaacg gggccttcta cctgtccgag   420
atggcggcgg acgggcgggg cgacgcgggg cgggcgacg ggtactgcga cgcgcagtgc    480
cagggctact gctgcaacga gatggacatc ctcgaggcca actcgatggc gacggccatg   540
acgccgcacc cgtgcaaggg caacaactgc gaccgcagcg gctgcggcta caacccgtac   600
gccagcggcc agcgcggctt ctacgggccc ggcaagacgg tcgacacgag caagcccttc   660
accgtcgtca cgcagttcgc cgccagcggc ggcaagctga cccagatcac ccgcaagtac   720
atccagaacg gccgggagat cggcggcggc ggcaccatct ccagctgcgg ctccgagtct   780
tcgacgggcg gcctgaccgg catgggcgag gcgctgggc gcggaatggt gctggccatg   840
agcatctgga cgacgcggc ccaggagatg gcatggctcg atgccggcaa caacggccct    900
tgcgccagtg gccagggcag cccgtccgtc attcagtcgc agcatcccga cacccacgtc   960
gtcttctcca acatcaggtg gggcgacatc gggtctacca cgaagaacta g           1011
```

<210> SEQ ID NO 90
<211> LENGTH: 336
<212> TYPE: PRT
<213> ORGANISM: Thielavia terrestris

<400> SEQUENCE: 90

Met Thr Leu Arg Leu Pro Val Ile Ser Leu Leu Ala Ser Leu Ala Ala
1               5                   10                  15

Gly Ala Val Val Val Pro Arg Ala Glu Phe His Pro Pro Leu Pro Thr
                20                  25                  30

Trp Lys Cys Thr Thr Ser Gly Gly Cys Val Gln Gln Asn Thr Ser Val
            35                  40                  45

Val Leu Asp Arg Asp Ser Lys Tyr Ala Ala His Ser Ala Gly Ser Arg
    50                  55                  60

Thr Glu Ser Asp Tyr Ala Ala Met Gly Val Ser Thr Ser Gly Asn Ala
65                  70                  75                  80

Val Thr Leu Tyr His Tyr Val Lys Thr Asn Gly Thr Leu Val Pro Ala
                85                  90                  95

Ser Pro Arg Ile Tyr Leu Leu Gly Ala Asp Gly Lys Tyr Val Leu Met
                100                 105                 110

```
Asp Leu Leu Asn Gln Glu Leu Ser Val Asp Val Asp Phe Ser Ala Leu
        115                 120                 125
Pro Cys Gly Glu Asn Gly Ala Phe Tyr Leu Ser Glu Met Ala Ala Asp
    130                 135                 140
Gly Arg Gly Asp Ala Gly Ala Gly Asp Gly Tyr Cys Asp Ala Gln Cys
145                 150                 155                 160
Gln Gly Tyr Cys Cys Asn Glu Met Asp Ile Leu Glu Ala Asn Ser Met
                165                 170                 175
Ala Thr Ala Met Thr Pro His Pro Cys Lys Gly Asn Asn Cys Asp Arg
            180                 185                 190
Ser Gly Cys Gly Tyr Asn Pro Tyr Ala Ser Gly Gln Arg Gly Phe Tyr
        195                 200                 205
Gly Pro Gly Lys Thr Val Asp Thr Ser Lys Pro Phe Thr Val Val Thr
    210                 215                 220
Gln Phe Ala Ala Ser Gly Gly Lys Leu Thr Gln Ile Thr Arg Lys Tyr
225                 230                 235                 240
Ile Gln Asn Gly Arg Glu Ile Gly Gly Gly Thr Ile Ser Ser Cys
                245                 250                 255
Gly Ser Glu Ser Ser Thr Gly Gly Leu Thr Gly Met Gly Glu Ala Leu
            260                 265                 270
Gly Arg Gly Met Val Leu Ala Met Ser Ile Trp Asn Asp Ala Ala Gln
        275                 280                 285
Glu Met Ala Trp Leu Asp Ala Gly Asn Asn Gly Pro Cys Ala Ser Gly
    290                 295                 300
Gln Gly Ser Pro Ser Val Ile Gln Ser Gln His Pro Asp Thr His Val
305                 310                 315                 320
Val Phe Ser Asn Ile Arg Trp Gly Asp Ile Gly Ser Thr Thr Lys Asn
                325                 330                 335
```

<210> SEQ ID NO 91
<211> LENGTH: 1480
<212> TYPE: DNA
<213> ORGANISM: Cladorrhinum foecundissimum

<400> SEQUENCE: 91

| | | | | | |
|---|---|---|---|---|---|
| gatccgaatt | cctcctctcg | ttctttagtc | acagaccaga | catctgccca | cgatggttca | 60 |
| caagttcgcc | ctcctcaccg | gcctcgccgc | ctccctcgca | tctgcccagc | agatcggcac | 120 |
| cgtcgtcccc | gagtctcacc | ccaagcttcc | caccaagcgc | tgcactctcg | ccggtggctg | 180 |
| ccagaccgtc | gacacctcca | tcgtcatcga | cgccttccag | cgtcccctcc | acaagatcgg | 240 |
| cgacccttcc | actccttgcg | tcgtcggcgg | ccctctctgc | ccgacgcca | agtcctgcgc | 300 |
| tgagaactgc | gcgctcgagg | gtgtcgacta | tgcctcctgg | ggcatcaaga | ccgagggcga | 360 |
| cgccctaact | ctcaaccagt | ggatgcccga | cccggcgaac | cctggccagt | acaagacgac | 420 |
| tactccccgt | acttaccttg | ttgctgagga | cggcaagaac | tacgaggatg | tgaagctcct | 480 |
| ggctaaggag | atctcgtttg | atgccgatgt | cagcaacctt | ccctgcggca | tgaacggtgc | 540 |
| tttctacttg | tctgagatgt | tgatggatgg | tggacgtggc | gacctcaacc | ctgctggtgc | 600 |
| cgagtatggt | accggttact | gtgatgcgca | gtgcttcaag | ttggatttca | tcaacggcga | 660 |
| ggccaacatc | gaccaaaagc | acggcgcctg | ctgcaacgaa | atggacattt | tcgaatccaa | 720 |
| ctcgcgcgcc | aagaccttcg | tccccacccc | ctgcaacatc | acgcaggtct | acaagtgcga | 780 |
| aggcgaagac | gagtgcggcc | agcccgtcgg | cgtgtgcgac | aagtgggggt | gcggcttcaa | 840 |

```
cgagtacaaa tggggcgtcg agtccttcta cggccggggc tcgcagttcg ccatcgactc    900
ctccaagaag ttcaccgtca ccacgcagtt cctgaccgac aacggcaagg aggacggcgt    960
cctcgtcgag atccgccgct gtggcacca ggatggcaag ctgatcaaga caccgctat    1020 ccaggttgag gagaactaca gcacggactc ggtgagcacc gagttctgcg agaagactgc   1080
ttctttcacc atgcagcgcg gtggtctcaa ggcgatgggc gaggctatcg gtcgtggtat   1140
ggtgctggtt ttcagcatct gggcggatga ttcgggtttt atgaactggt tggatgcgga   1200
gggtaatggc ccttgcagcg cgactgaggg cgatccgaag gagattgtca agaataagcc   1260
ggatgctagg gttacgttct caaacattag gattggtgag gttggtagca cgtatgctcc   1320
gggtgggaag tgcggtgtta agagcagggt tgctagggg cttactgctt cttaaggggg    1380
gtgtgaagag aggaggaggt gttgttgggg gttggagatg ataattgggc gagatggtgt   1440
agagcgggtt ggttggatat gaatacgttg aattggatgt                         1480

<210> SEQ ID NO 92
<211> LENGTH: 440
<212> TYPE: PRT
<213> ORGANISM: Cladorrhinum foecundissimum

<400> SEQUENCE: 92

Met Val His Lys Phe Ala Leu Leu Thr Gly Leu Ala Ala Ser Leu Ala
1               5                   10                  15

Ser Ala Gln Gln Ile Gly Thr Val Val Pro Glu Ser His Pro Lys Leu
                20                  25                  30

Pro Thr Lys Arg Cys Thr Leu Ala Gly Gly Cys Gln Thr Val Asp Thr
            35                  40                  45

Ser Ile Val Ile Asp Ala Phe Gln Arg Pro Leu His Lys Ile Gly Asp
        50                  55                  60

Pro Ser Thr Pro Cys Val Val Gly Gly Pro Leu Cys Pro Asp Ala Lys
65                  70                  75                  80

Ser Cys Ala Glu Asn Cys Ala Leu Glu Gly Val Asp Tyr Ala Ser Trp
                85                  90                  95

Gly Ile Lys Thr Glu Gly Asp Ala Leu Thr Leu Asn Gln Trp Met Pro
            100                 105                 110

Asp Pro Ala Asn Pro Gly Gln Tyr Lys Thr Thr Pro Arg Thr Tyr
        115                 120                 125

Leu Val Ala Glu Asp Gly Lys Asn Tyr Glu Asp Val Lys Leu Leu Ala
    130                 135                 140

Lys Glu Ile Ser Phe Asp Ala Asp Val Ser Asn Leu Pro Cys Gly Met
145                 150                 155                 160

Asn Gly Ala Phe Tyr Leu Ser Glu Met Leu Met Asp Gly Gly Arg Gly
                165                 170                 175

Asp Leu Asn Pro Ala Gly Ala Glu Tyr Gly Thr Gly Tyr Cys Asp Ala
            180                 185                 190

Gln Cys Phe Lys Leu Asp Phe Ile Asn Gly Glu Ala Asn Ile Asp Gln
        195                 200                 205

Lys His Gly Ala Cys Cys Asn Glu Met Asp Ile Phe Glu Ser Asn Ser
    210                 215                 220

Arg Ala Lys Thr Phe Val Pro His Pro Cys Asn Ile Thr Gln Val Tyr
225                 230                 235                 240

Lys Cys Glu Gly Glu Asp Glu Cys Gly Gln Pro Val Gly Val Cys Asp
                245                 250                 255

Lys Trp Gly Cys Gly Phe Asn Glu Tyr Lys Trp Gly Val Glu Ser Phe
```

```
                260                 265                 270
Tyr Gly Arg Gly Ser Gln Phe Ala Ile Asp Ser Ser Lys Lys Phe Thr
            275                 280                 285
Val Thr Thr Gln Phe Leu Thr Asp Asn Gly Lys Glu Asp Gly Val Leu
            290                 295                 300
Val Glu Ile Arg Arg Leu Trp His Gln Asp Gly Lys Leu Ile Lys Asn
305                 310                 315                 320
Thr Ala Ile Gln Val Glu Glu Asn Tyr Ser Thr Asp Ser Val Ser Thr
                325                 330                 335
Glu Phe Cys Glu Lys Thr Ala Ser Phe Thr Met Gln Arg Gly Gly Leu
            340                 345                 350
Lys Ala Met Gly Glu Ala Ile Gly Arg Gly Met Val Leu Val Phe Ser
            355                 360                 365
Ile Trp Ala Asp Asp Ser Gly Phe Met Asn Trp Leu Asp Ala Glu Gly
            370                 375                 380
Asn Gly Pro Cys Ser Ala Thr Glu Gly Asp Pro Lys Glu Ile Val Lys
385                 390                 395                 400
Asn Lys Pro Asp Ala Arg Val Thr Phe Ser Asn Ile Arg Ile Gly Glu
                405                 410                 415
Val Gly Ser Thr Tyr Ala Pro Gly Gly Lys Cys Gly Val Lys Ser Arg
            420                 425                 430
Val Ala Arg Gly Leu Thr Ala Ser
            435                 440

<210> SEQ ID NO 93
<211> LENGTH: 1380
<212> TYPE: DNA
<213> ORGANISM: Trichoderma reesei

<400> SEQUENCE: 93
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccgggggggtg cgtggcccag acacctcgg tggtccttga ctggaactac     180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga accagtacat gcccagcagc     360
tctggcggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccggtgccaa ctacgggagc ggctactgcg atgctcagtg ccccgtccag     600
acatggagga acggcacccct caacactagc accagggct tctgctgcaa cgagatggat     660
atcctggagg caactcgag ggcgaatgcc ttgacccctc actcttgcac ggccacggcc     720
tgcgactctg ccggttgcgg cttcaacccc tatggcagcg gctacaaaag ctactacggc     780
cccggagata ccgttgacac ctccaagacc ttcaccatca tcacccagtt caacacggac     840
aacggctcgc cctcgggcaa ccttgtgagc atccccgca agtaccagca aaacggcgtc     900
gacatcccca gcgcccagcc cggcggcgac accatctcgt cctgcccgtc gcctcagcc     960 tacgcgggcc tcgccaccat gggcaaggcc ctgagcagcg gcatggtgct cgtgttcagc    1020
atttggaacg acaacagcca gtacatgaac tggctcgaca cggcaacgc cggccctgc    1080
```

```
agcagcaccg agggcaaccc atccaacatc ctggccaaca accccaacac gcacgtcgtc      1140
ttctccaaca tccgctgggg agacattggg tctactacga actcgactgc gcccccgccc      1200
ccgcctgcgt ccagcacgac gttttcgact acacggagga gctcgacgac ttcgagcagc      1260
ccgagctgca cgcagactca ctggggggcag tgcggtggca ttgggtacag cgggtgcaag      1320
acgtgcacgt cgggcactac gtgccagtat agcaacgact actactcgca atgcctttag      1380
```

<210> SEQ ID NO 94
<211> LENGTH: 459
<212> TYPE: PRT
<213> ORGANISM: Trichoderma reesei

<400> SEQUENCE: 94

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
```

```
                  325                 330                 335
Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
            355                 360                 365

Asn Ile Leu Ala Asn Asn Pro Asn Thr His Val Val Phe Ser Asn Ile
            370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
            450                 455

<210> SEQ ID NO 95
<211> LENGTH: 1545
<212> TYPE: DNA
<213> ORGANISM: Trichoderma reesei

<400> SEQUENCE: 95
```

| | | |
|---|---|---|
| atgtatcgga agttggccgt catctcggcc ttcttggcca cagctcgtgc tcagtcggcc | 60 |
| tgcactctcc aatcggagac tcacccgcct ctgacatggc agaaatgctc gtctggtggc | 120 |
| acgtgcactc aacagacagg ctccgtggtc atcgacgcca actggcgctg gactcacgct | 180 |
| acgaacagca gcacgaactg ctacgatggc aacacttgga gctcgaccct atgtcctgac | 240 |
| aacgagacct gcgcgaagaa ctgctgtctg acggtgccgc ctacgcgtc acgtacgga | 300 |
| gttaccacga gcggtaacag cctctccatt ggctttgtca cccagtctgc gcagaagaac | 360 |
| gttggcgctc gcctttacct tatggcgagc gacacgacct accaggaatt caccctgctt | 420 |
| ggcaacgagt tctcttttcga tgttgatgtt tcgcagctgc cgtgcggctt gaacggagct | 480 |
| ctctacttcg tgtccatgga cgcggatggt ggcgtgagca agtatcccac caacaccgct | 540 |
| ggcgccaagt acggcacggg gtactgtgac agccagtgtc ccgcgatct gaagttcatc | 600 |
| aatggccagg ccaacgttga gggctggagc cgtcatcca caacgcgaa cacgggcatt | 660 |
| ggaggacacg gaagctgctg ctctgagatg gatatctggg aggccaactc catctccgag | 720 |
| gctcttaccc cccacccttg cacgactgtc ggccaggaga tctgcgaggg tgatgggtgc | 780 |
| ggcggaactt actccgataa cagatatggc ggcacttgcg atcccgatgg ctgcgactgg | 840 |
| aacccatacc gcctgggcaa caccagcttc tacggccctg gctcaagctt taccctcgat | 900 |
| accaccaaga aattgaccgt tgtcacccag ttcgagacgt cgggtgccat caaccgatac | 960 |
| tatgtccaga atggcgtcac tttccagcag cccaacgccg agcttggtag ttactctggc | 1020 |
| aacgagctca cgatgattac tgcacagct gaggaggcag aattcggcgg atcctctttc | 1080 |
| tcagacaagg gcggcctgac tcagttcaag aaggctacct ctggcggcat ggttctggtc | 1140 |
| atgagtctgt gggatgatta ctacgccaac atgctgtggc tggactccac ctacccgaca | 1200 |
| aacgagacct cctccacacc cggtgccgtg cgcggaagct gctccaccag ctccggtgtc | 1260 |
| cctgctcagt cgaatctca gtctcccaac gccaaggtca ccttctccaa catcaagttc | 1320 |
| ggacccattg gcagcaccgg caaccctagc ggcggcaacc ctcccggcgg aaacccgcct | 1380 |

```
ggcaccacca ccacccgccg cccagccact accactggaa gctctcccgg acctacccag   1440
tctcactacg gccagtgcgg cggtattggc tacagcggcc ccacggtctg cgccagcggc   1500
acaacttgcc aggtcctgaa cccttactac tctcagtgcc tgtaa                  1545
```

<210> SEQ ID NO 96
<211> LENGTH: 514
<212> TYPE: PRT
<213> ORGANISM: Trichoderma reesei

<400> SEQUENCE: 96

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
```

```
                     340             345             350
Ala Glu Phe Gly Gly Ser Ser Phe Ser Asp Lys Gly Gly Leu Thr Gln
                355                 360                 365

Phe Lys Lys Ala Thr Ser Gly Gly Met Val Leu Val Met Ser Leu Trp
            370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
            450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 97
<211> LENGTH: 1611
<212> TYPE: DNA
<213> ORGANISM: Trichoderma reesei

<400> SEQUENCE: 97
atgattgtcg gcattctcac cacgctggct acgctggcca cactcgcagc tagtgtgcct      60
ctagaggagc ggcaagcttg ctcaagcgtc tggtaattat gtgaaccctc tcaagagacc     120
caaatactga gatatgtcaa ggggccaatg tggtggccag aattggtcgg gtccgacttg     180
ctgtgcttcc ggaagcacat gcgtctactc aacgactat tactcccagt gtcttcccgg     240
cgctgcaagc tcaagctcgt ccacgcgcgc gcgtcgacg acttctcgag tatcccccac     300
aacatcccgg tcgagctccg cgacgcctcc acctggttct actactacca gagtacctcc     360
agtcggatcg ggaaccgcta cgtattcagg caacccttt gttggggtca ctccttgggc     420
caatgcatat tacgcctctg aagttagcag cctcgctatt cctagcttga ctggagccat     480
ggccactgct gcagcagctg tcgcaaaggt tccctctttt atgtggctgt aggtcctccc     540
ggaaccaagg caatctgtta ctgaaggctc atcattcact gcagagatac tcttgacaag     600
acccctctca tggagcaaac cttggccgac atccgcaccg ccaacaagaa tggcggtaac     660
tatgccggac agtttgtggt gtatgacttg ccggatcgcg attgcgctgc ccttgcctcg     720
aatggcgaat actctattgc cgatggtggc gtcgccaaat ataagaacta tatcgacacc     780
attcgtcaaa ttgtcgtgga atattccgat atccggaccc tcctggttat tggtatgagt     840
ttaaacacct gcctcccccc cccttccct tcctttcccg ccggcatctt gtcgttgtgc     900
taactattgt tccctcttcc agagcctgac tctcttgcca acctggtgac caacctcggt     960
actccaaagt gtgccaatgc tcagtcagcc taccttgagt gcatcaacta cgccgtcaca    1020
cagctgaact ttccaaatgt tgcgatgtat ttggacgctg gccatgcagg atggcttggc    1080
tggccggcaa accaagaccc ggccgctcag ctatttgcaa atgtttacaa gaatgcatcg    1140
```

```
tctccgagag ctcttcgcgg attggcaacc aatgtcgcca actacaacgg gtggaacatt    1200
accagccccc catcgtacac gcaaggcaac gctgtctaca acgagaagct gtacatccac    1260
gctattggac gtcttcttgc caatcacggc tggtccaacg ccttcttcat cactgatcaa    1320
ggtcgatcgg gaaagcagcc taccggacag caacagtggg gagactggtg caatgtgatc    1380
ggcaccggat ttggtattcg cccatccgca aacactgggg actcgttgct ggattcgttt    1440
gtctgggtca agccaggcgg cgagtgtgac ggcaccagcg acagcagtgc gccacgattt    1500
gactcccact gtgcgctccc agatgccttg caaccggcgc ctcaagctgg tgcttggttc    1560
caagcctact ttgtgcagct tctcacaaac gcaaacccat cgttcctgta a             1611
```

<210> SEQ ID NO 98
<211> LENGTH: 471
<212> TYPE: PRT
<213> ORGANISM: Trichoderma reesei

<400> SEQUENCE: 98

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285
```

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
    435                 440                 445

Pro Gln Ala Gly Ala Trp Phe Gln Ala Tyr Phe Val Gln Leu Leu Thr
    450                 455                 460

Asn Ala Asn Pro Ser Phe Leu
465             470

```
<210> SEQ ID NO 99
<211> LENGTH: 2046
<212> TYPE: DNA
<213> ORGANISM: Humicola insolens

<400> SEQUENCE: 99
```

| | | | | | |
|---|---|---|---|---|---|
| gccgtgacct | tgcgcgcttt | gggtggcggt | ggcgagtcgt | ggacggtgct | tgctggtcgc | 60 |
| cggccttccc | ggcgatccgc | gtgatgagag | ggccaccaac | ggcgggatga | tgctccatgg | 120 |
| ggaacttccc | catggagaag | agagagaaac | ttgcggagcc | gtgatctggg | aaagatgct | 180 |
| ccgtgtctcg | tctatataac | tcgagtctcc | ccgagccctc | aacaccacca | gctctgatct | 240 |
| caccatcccc | atcgacaatc | acgcaaacac | agcagttgtc | gggccattcc | ttcagacaca | 300 |
| tcagtcaccc | tccttcaaaa | tgcgtaccgc | caagttcgcc | accctcgccg | cccttgtggc | 360 |
| ctcggccgcc | gcccagcagg | cgtgcagtct | caccaccgag | aggcaccctt | ccctctcttg | 420 |
| gaacaagtgc | accgccggcg | gccagtgcca | gaccgtccag | gcttccatca | ctctcgactc | 480 |
| caactggcgc | tggactcacc | aggtgtctgg | ctccaccaac | tgctacacgg | gcaacaagtg | 540 |
| ggatactagc | atctgcactg | atgccaagtc | gtgcgctcag | aactgctgcg | tcgatggtgc | 600 |
| cgactacacc | agcacctatg | gcatcaccac | caacggtgat | tccctgagcc | tcaagttcgt | 660 |
| caccaagggc | cagcactcga | ccaacgtcgg | ctcgcgtacc | tacctgatgg | acggcgagga | 720 |
| caagtatcag | agtacgttct | atcttcagcc | ttctcgcgcc | ttgaatcctg | gctaacgttt | 780 |
| acacttcaca | gccttcgagc | tcctcggcaa | cgagttcacc | ttcgatgtcg | atgtctccaa | 840 |
| catcggctgc | ggtctcaacg | gcgccctgta | cttcgtctcc | atggacgccg | atggtggtct | 900 |
| cagccgctat | cctggcaaca | aggctggtgc | caagtacggt | accggctact | gcgatgctca | 960 |
| gtgccccccgt | gacatcaagt | tcatcaacgg | cgaggccaac | attgagggct | ggaccggctc | 1020 |
| caccaacgac | cccaacgccg | gcgcgggccg | ctatggtacc | tgctgctctg | agatggatat | 1080 |

```
ctgggaagcc aacaacatgg ctactgcctt cactcctcac ccttgcacca tcattggcca   1140
gagccgctgc gagggcgact cgtgcggtgg cacctacagc aacgagcgct acgccggcgt   1200
ctgcgacccc gatggctgcg acttcaactc gtaccgccag ggcaacaaga ccttctacgg   1260
caagggcatg accgtcgaca ccaccaagaa gatcactgtc gtcacccagt cctcaagga   1320 tgccaacggc gatctcggcg agatcaagcg cttctacgtc caggatggca agatcatccc   1380
caactccgag tccaccatcc ccggcgtcga gggcaattcc atcacccagg actggtgcga   1440
ccgccagaag gttgcctttg cgacattga cgacttcaac cgcaagggcg catgaagca   1500 gatgggcaag ccctcgccg gccccatggt cctggtcatg tccatctggg atgaccacgc   1560
ctccaacatg ctctggctcg actcgacctt ccctgtcgat gccgctggca agcccggcgc   1620
cgagcgcggt gcctgcccga ccacctcggg tgtccctgct gaggttgagg ccgaggcccc   1680
caacagcaac gtcgtcttct ccaacatccg cttcggcccc atcggctcga ccgttgctgg   1740 tctcccggc gcgggcaacg gcggcaacaa cggcggcaac cccccgcccc ccaccaccac   1800
cacctcctcg gctccggcca ccaccaccac cgccagcgct ggccccaagg ctggccgctg   1860
gcagcagtgc ggcggcatcg gcttcactgg cccgacccag tgcgaggagc cctacatttg   1920
caccaagctc aacgactggt actctcagtg cctgtaaatt ctgagtcgct gactcgacga   1980
tcacggccgg tttttgcatg aaaggaaaca aacgaccgcg ataaaaatgg agggtaatga   2040
gatgtc                                                              2046
```

<210> SEQ ID NO 100  
<211> LENGTH: 525  
<212> TYPE: PRT  
<213> ORGANISM: Humicola insolens

<400> SEQUENCE: 100

```
Met Arg Thr Ala Lys Phe Ala Thr Leu Ala Ala Leu Val Ala Ser
1               5                   10                  15

Ala Ala Gln Gln Ala Cys Ser Leu Thr Thr Glu Arg His Pro Ser Leu
                20                  25                  30

Ser Trp Asn Lys Cys Thr Ala Gly Gly Gln Cys Gln Thr Val Gln Ala
            35                  40                  45

Ser Ile Thr Leu Asp Ser Asn Trp Arg Trp Thr His Gln Val Ser Gly
        50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190
```

```
Ala Gln Cys Pro Arg Asp Ile Lys Phe Ile Asn Gly Glu Ala Asn Ile
            195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
    290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
    370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
        515                 520                 525

<210> SEQ ID NO 101
<211> LENGTH: 1812
<212> TYPE: DNA
<213> ORGANISM: Myceliophthora thermophila

<400> SEQUENCE: 101
atggccaaga agctttttcat caccgccgcc cttgcggctg ccgtgttggc ggccccgtc      60 attgaggagc gccagaactg cggcgctgtg tggtaagaaa gcccggtctg agtttcccat    120
gactttctca tcgagtaatg gcataaggcc caccccttcg actgactgtg agaatcgatc    180
aaatccagga ctcaatgcgg cggcaacggg tggcagggtc ccacatgctg cgcctcgggc    240
```

```
tcgacctgcg ttgcgcagaa cgagtggtac tctcagtgcc tgcccaacaa tcaggtgacg      300
agttccaaca ctccgtcgtc gacttccacc tcgcagcgca gcagcagcac ctccagcagc      360
agcaccagga gcggcagctc ctcctcctcc accaccacgc ccctcccgt ctccagcccc       420 gtgactagca ttcccggcgg tgcgaccacc acggcgagct actctggcaa cccccttctcg     480 ggcgtccggc tcttcgccaa cgactactac aggtccgagg tccacaatct cgccattcct     540
agcatgaccg gtactctggc ggccaaggct tccgccgtcg ccgaagtccc tagcttccag     600
tggctcgacc ggaacgtcac catcgacacc ctgatggtcc agactctgtc ccagatccgg     660
gctgccaata atgccggtgc caatcctccc tatgctggtg agttacatgg cggcgacttg     720
ccttctcgtc ccccacccttt cttgacggga tcggttacct gacctggagg caaaacaaaa   780
ccagcccaac ttgtcgtcta cgacctcccc gaccgtgact gcgccgccgc tgcgtccaac     840
ggcgagtttt cgattgcaaa cggcggcgcc gccaactaca ggagctacat cgacgctatc     900
cgcaagcaca tcattgagta ctcggacatc cggatcatcc tggttatcga gcccgactcg     960
atggccaaca tggtgaccaa catgaacgtg ccaagtgca gcaacgccgc gtcgacgtac     1020
cacgagttga ccgtgtacgc gctcaagcag ctgaacctgc caacgtcgc catgtatctc    1080 gacgccggcc acgccggctg gctcggctgg cccgccaaca tccagcccgc cgccgacctg    1140
tttgccggca tctacaatga cgccggcaag ccggctgccg tccgcggcct ggccactaac    1200
gtcgccaact acaacgcctg gagtatcgct tcggccccgt cgtacacgtc ccctaaccct    1260
aactacgacg agaagcacta catcgaggcc ttcagcccgc tcctgaacgc ggccggcttc    1320
cccgcacgct tcattgtcga cactggccgc aacggcaaac aacctaccgg tatggttttt    1380
ttcttttttt ttctctgttc ccctccccct tccccttcag ttggcgtcca caaggtctct    1440
tagtcttgct tcttctcgga ccaaccttcc cccaccccca aaacgcaccg cccacaaccg    1500
ttcgactcta tactcttggg aatgggcgcc gaaactgacc gttcgacagg ccaacaacag    1560
tggggtgact ggtgcaatgt caagggcact ggctttggcg tgcccgac ggccaacacg      1620 ggccacgacc tggtcgatgc ctttgtctgg gtcaagcccg gcggcgagtc cgacggcaca    1680
agcgacacca gcgccgcccg ctacgactac cactgcggcc tgtccgatgc cctgcagcct    1740
gctccggagg ctggacagtg gttccaggcc tacttcgagc agctgctcac caacgccaac    1800
ccgcccttct aa                                                          1812
```

<210> SEQ ID NO 102
<211> LENGTH: 482
<212> TYPE: PRT
<213> ORGANISM: Myceliophthora thermophila

<400> SEQUENCE: 102

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Asn Gln Val Thr Ser Ser Asn Thr Pro Ser Ser Thr Ser Thr Ser Gln
65                  70                  75                  80

Arg Ser Ser Ser Thr Ser Ser Ser Ser Thr Arg Ser Gly Ser Ser Ser
                85                  90                  95
```

```
Ser Ser Thr Thr Thr Pro Pro Val Ser Ser Pro Val Thr Ser Ile
            100                 105                 110

Pro Gly Gly Ala Thr Thr Ala Ser Tyr Ser Gly Asn Pro Phe Ser
    115                 120                 125

Gly Val Arg Leu Phe Ala Asn Asp Tyr Tyr Arg Ser Glu Val His Asn
130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ala Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Asp Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe

<210> SEQ ID NO 103
<211> LENGTH: 1802
<212> TYPE: DNA
```

<213> ORGANISM: Myceliophthora thermophila

<400> SEQUENCE: 103

```
atggccaaga agcttttcat caccgccgcg cttgcggctg ccgtgttggc ggccccgtc      60
attgaggagc gccagaactg cggcgctgtg tggtaagaaa gcccggtccg agtctcccat    120
gattttctcg tcgagtaatg cataagggc cacccctctcg actgaccgtg agaatcgatc    180
aaatccagga ctcaatgcgg cggtaacggg tggcaaggtc ccacatgctg cgcctcgggc    240
tcgacctgcg ttgcgcagaa cgagtggtac tctcagtgcc tgcccaacag ccaggtgacg    300
agttccacca ctccgtcgtc gacttccacc tcgcagcgca gcaccagcac tccagcagc    360
accaccagga gcggcagctc ctcctcctcc tccaccacgc cccgcccgt ctccagcccc     420
gtgaccagca ttcccggcgg tgcgacctcc acgcgagct actctggcaa ccccttctcg     480
ggcgtccggc tcttcgccaa cgactactac aggtccgagg tccacaatct cgccattcct    540
agcatgactg gtactctggc ggccaaggct tccgccgtcg ccgaagtccc tagcttccag    600
tggctcgacc ggaacgtcac catcgacacc ctgatggtcc agactctgtc ccaggtccgg    660
gctctcaata aggccggtgc caatcctccc tatgctggtg agttacatgg cgacttgcct    720
tctcgtcccc tacctttctt gacgggatcg gttacctgac ctggaggcaa acaacaaca    780
gcccaactcg tcgtctacga cctccccgac cgtgactgtg ccgccgctgc gtccaacggc    840
gagttttcga ttgcaaacgg cggcgccgcc aactacagga gctacatcga cgctatccgc    900
aagcacatca ttgagtactc ggacatccgg atcatcctgg ttatcgagcc cgactcgatg    960
gccaacatg tgaccaacat gaacgtggcc aagtgcagca acgccgcgtc gacgtaccac   1020
gagttgaccg tgtacgcgct caagcagctg aacctgccca acgtcgccat gtatctcgac   1080
gccggccacg ccggctggct cggctggccc gccaacatcc agcccgccgc cgagctgttt   1140
gccggcatct acaatgatgc cggcaagccg gctgccgtcc gcggcctggc cactaacgtc   1200
gccaactaca acgcctggag catcgcttcg gccccgtcgt acacgtcgcc taaccctaac   1260
tacgacgaga gcactacat cgaggccttc agcccgctct gaactcggc cggcttcccc     1320
gcacgcttca ttgtcgacac tggccgcaac ggcaaacaac ctaccggtat gttttttttt   1380
cttttgtctc tgtcccccc ttttctcccc cttcagttgg cgtccacaag gtctcttagt    1440
cctgcttcat ctgtgaccaa cctccccccc ccggcaccg cccacaaccg tttgactcta    1500
tactcttggg aatgggcgcc gaaactgacc gttccacagg ccaacaacag tggggtgact   1560
ggtgcaatgt caagggcacc ggcttttggcg tgcgcccgac ggccaacacg ggccacgagc  1620
tggtcgatgc ctttgtctgg gtcaagcccg cggcgagtc cgacggcaca agcgacacca    1680
gcgccgcccg ctacgactac cactgcggcc tgtccgatgc cctgcagcct gccccgagg    1740
ctggacagtg gttccaggcc tacttcgagc agctgctcac caacgccaac ccgcccttct   1800
aa                                                                  1802
```

<210> SEQ ID NO 104
<211> LENGTH: 481
<212> TYPE: PRT
<213> ORGANISM: Myceliophthora thermophila

<400> SEQUENCE: 104

```
Met Ala Lys Lys Leu Phe Ile Thr Ala Ala Leu Ala Ala Ala Val Leu
1               5                   10                  15
Ala Ala Pro Val Ile Glu Glu Arg Gln Asn Cys Gly Ala Val Trp Thr
            20                  25                  30
```

```
Gln Cys Gly Gly Asn Gly Trp Gln Gly Pro Thr Cys Cys Ala Ser Gly
         35                  40                  45

Ser Thr Cys Val Ala Gln Asn Glu Trp Tyr Ser Gln Cys Leu Pro Asn
     50                  55                  60

Ser Gln Val Thr Ser Thr Thr Pro Ser Ser Thr Ser Thr Ser Gln
 65              70                  75                  80

Arg Ser Thr Ser Thr Ser Ser Ser Thr Thr Arg Ser Gly Ser Ser Ser
                 85                  90                  95

Ser Ser Ser Thr Thr Pro Pro Val Ser Ser Pro Val Thr Ser Ile
                100             105             110

Pro Gly Gly Ala Thr Ser Thr Ala Ser Tyr Ser Gly Asn Pro Phe Ser
            115                 120                 125

Gly Val Arg Leu Phe Ala Asn Asp Tyr Tyr Arg Ser Glu Val His Asn
        130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445
```

Tyr His Cys Gly Leu Ser Asp Ala Leu Gln Pro Ala Pro Glu Ala Gly
        450                 455                 460

Gln Trp Phe Gln Ala Tyr Phe Glu Gln Leu Leu Thr Asn Ala Asn Pro
465                 470                 475                 480

Pro

<210> SEQ ID NO 105
<211> LENGTH: 1446
<212> TYPE: DNA
<213> ORGANISM: Thielavia terrestris

<400> SEQUENCE: 105

```
atggctcaga agctccttct cgccgccgcc cttgcggcca gcgccctcgc tgctcccgtc      60
gtcgaggagc gccagaactg cggttccgtc tggagccaat gcggcggcat tggctggtcc     120
ggcgcgacct gctgcgcttc gggcaatacc tgcgttgagc tgaacccgta ctactcgcag     180
tgcctgccca cagccaggt gactacctcg accagcaaga ccacctccac caccaccagg     240
agcagcacca ccagccacag cagcggtccc accagcacga gcaccaccac caccagcagt     300
cccgtggtca ctaccccgcc gagtacctcc atccccggcg gtgcctcgtc aacggccagc     360
tggtccggca acccgttctc gggcgtgcag atgtgggcca acgactacta cgcctccgag     420
gtctcgtcgc tggccatccc cagcatgacg ggcgccatgg ccaccaaggc ggccgaggtg     480
gccaaggtgc ccagcttcca gtggcttgac cgcaacgtca ccatcgacac gctgttcgcc     540
cacacgctgt cgcagatccg cgcggccaac cagaaaggcg ccaacccgcc ctacgcgggc     600
atcttcgtgg tctacgacct tccggaccgc gactgcgccg ccgccgcgtc caacggcgag     660
ttctccatcg cgaacaacgg ggcggccaac tacaagacgt acatcgacgc gatccggagc     720
ctcgtcatcc agtactcaga catccgcatc atcttcgtca tcgagcccga ctcgctggcc     780
aacatggtga ccaacctgaa cgtggccaag tgcgccaacg ccgagtcgac ctacaaggag     840
ttgaccgtct acgcgctgca gcagctgaac ctgcccaacg tggccatgta cctggacgcc     900
ggccacgccg gctggctcgg ctggcccgcc aacatccagc cggccgccaa cctcttcgcc     960
gagatctaca cgagcgccgg caagccggcc gccgtgcgcg gcctcgccac caacgtggcc    1020
aactacaacg gctggagcct ggccacgccg ccctcgtaca cccagggcga ccccaactac    1080
gacgagagcc actacgtcca ggccctcgcc ccgctgctca ccgccaacgg cttccccgcc    1140
cacttcatca ccgacaccgg ccgcaacggc aagcagccga ccggacaacg gcaatgggga    1200
gactggtgca acgttatcgg aactggcttc ggcgtgcgcc cgacgacaaa caccggcctc    1260
gacatcgagg acgccttcgt ctgggtcaag cccggcggcg agtgcgacgg cacgagcaac    1320
acgacctctc ccgctacga ctaccactgc ggcctgtcgg acgcgctgca gcctgctccg    1380
gaggccggca cttggttcca ggcctacttc gagcagctcc tgaccaacgc caacccgccc    1440
ttttaa                                                              1446
```

<210> SEQ ID NO 106
<211> LENGTH: 481
<212> TYPE: PRT
<213> ORGANISM: Thielavia terrestris

<400> SEQUENCE: 106

Met Ala Gln Lys Leu Leu Leu Ala Ala Ala Leu Ala Ala Ser Ala Leu
1               5                   10                  15

Ala Ala Pro Val Val Glu Glu Arg Gln Asn Cys Gly Ser Val Trp Ser
            20                  25                  30

```
Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Ser Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
            115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
            195                 200                 205

Asp Arg Asp Cys Ala Ala Ala Ser Asn Gly Glu Phe Ser Ile Ala
    210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
            275                 280                 285

Leu Asn Leu Pro Asn Val Ala Met Tyr Leu Asp Ala Gly His Ala Gly
            290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
            355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
            435                 440                 445
```

His Cys Gly Leu Ser Asp Ala Leu Gln Pro Ala Pro Glu Ala Gly Thr
450                 455                 460

Trp Phe Gln Ala Tyr Phe Glu Gln Leu Leu Thr Asn Ala Asn Pro Pro
465                 470                 475                 480

Phe

<210> SEQ ID NO 107
<211> LENGTH: 1593
<212> TYPE: DNA
<213> ORGANISM: Chaetomium thermophilum

<400> SEQUENCE: 107

| | |
|---|---|
| atgatgtaca agaagttcgc cgctctcgcc gccctcgtgg ctggcgccgc cgcccagcag | 60 |
| gcttgctccc tcaccactga gacccacccc agactcactt ggaagcgctg cacctctggc | 120 |
| ggcaactgct cgaccgtgaa cggcgccgtc accatcgatg ccaactggcg ctggactcac | 180 |
| actgtttccg gctcgaccaa ctgctacacc ggcaacgagt gggataccct catctgctct | 240 |
| gatggcaaga gctgcgccca gacctgctgc gtcgacggcg ctgactactc ttcgacctat | 300 |
| ggtatcacca ccagcggtga ctccctgaac ctcaagttcg tcaccaagca ccagcacggc | 360 |
| accaatgtcg gctctcgtgt ctacctgatg gagaacgaca ccagtaccaa gatgttcgag | 420 |
| ctcctcggca acgagttcac cttcgatgtc gatgtctcta acctgggctg cggtctcaac | 480 |
| ggcgccctct acttcgtctc catggacgct gatggtggta tgagcaagta ctctggcaac | 540 |
| aaggctggcg ccaagtacgg taccggctac tgcgatgctc agtgcccgcg cgaccttaag | 600 |
| ttcatcaacg gcgaggccaa cattgagaac tggacccctt cgaccaatga tgccaacgcc | 660 |
| ggtttcggcc gctatggcag ctgctgctct gagatggata tctgggatgc aacaacatg | 720 |
| gctactgcct tcactcctca cccttgcacc attatcggcc agagccgctg cgagggcaac | 780 |
| agctgcggtg gcacctacag ctctgagcgc tatgctggtg tttgcgatcc tgatggctgc | 840 |
| gacttcaacg cctaccgcca gggcgacaag accttctacg caagggcat gaccgtcgac | 900 |
| accaccaaga gatgaccgt cgtcacccag ttccacaaga actcggctgg cgtcctcagc | 960 |
| gagatcaagc gcttctacgt tcaggacggc aagatcattg ccaacgccga gtccaagatc | 1020 |
| cccggcaacc ccggcaactc catcacccag gagtggtgcg atgcccagaa ggtcgccttc | 1080 |
| ggtgacatcg atgacttcaa ccgcaagggc ggtatggctc agatgagcaa ggccctcgag | 1140 |
| ggccctatgg tcctggtcat gtccgtctgg gatgaccact acgccaacat gctctggctc | 1200 |
| gactcgacct accccattga caaggccggc acccccggcg ccgagcgcgg tgcttgcccg | 1260 |
| accacctccg gtgtccctgc cgagattgag gcccaggtcc ccaacagcaa cgttatcttc | 1320 |
| tccaacatcc gcttcggccc catcggctcg accgtccctg cctcgacgg cagcaccccc | 1380 |
| agcaacccga ccgccaccgt tgctcctccc acttctacca ccaccagcgt gagaagcagc | 1440 |
| actactcaga tttccacccc gactagccag cccggcggct gcaccaccca gaagtggggc | 1500 |
| cagtgcggtg gtatcggcta caccggctgc actaactgcg ttgctggcac tacctgcact | 1560 |
| gagctcaacc cctggtacag ccagtgcctg taa | 1593 |

<210> SEQ ID NO 108
<211> LENGTH: 530
<212> TYPE: PRT
<213> ORGANISM: Chaetomium thermophilum

<400> SEQUENCE: 108

Met Met Tyr Lys Lys Phe Ala Ala Leu Ala Ala Leu Val Ala Gly Ala

```
1               5                   10                  15
Ala Ala Gln Gln Ala Cys Ser Leu Thr Thr Glu Thr His Pro Arg Leu
                20                  25                  30

Thr Trp Lys Arg Cys Thr Ser Gly Gly Asn Cys Ser Thr Val Asn Gly
                35                  40                  45

Ala Val Thr Ile Asp Ala Asn Trp Arg Trp Thr His Thr Val Ser Gly
                50                  55                  60

Ser Thr Asn Cys Tyr Thr Gly Asn Glu Trp Asp Thr Ser Ile Cys Ser
65                      70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
                100                 105                 110

Phe Val Thr Lys His Gln His Gly Thr Asn Val Gly Ser Arg Val Tyr
                115                 120                 125

Leu Met Glu Asn Asp Thr Lys Tyr Gln Met Phe Glu Leu Leu Gly Asn
                130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
                180                 185                 190

Ala Gln Cys Pro Arg Asp Leu Lys Phe Ile Asn Gly Glu Ala Asn Ile
                195                 200                 205

Glu Asn Trp Thr Pro Ser Thr Asn Asp Ala Asn Ala Gly Phe Gly Arg
                210                 215                 220

Tyr Gly Ser Cys Cys Ser Glu Met Asp Ile Trp Asp Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
                260                 265                 270

Gly Val Cys Asp Pro Asp Gly Cys Asp Phe Asn Ala Tyr Arg Gln Gly
                275                 280                 285

Asp Lys Thr Phe Tyr Gly Lys Gly Met Thr Val Asp Thr Thr Lys Lys
                290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Trp
                340                 345                 350

Cys Asp Ala Gln Lys Val Ala Phe Gly Asp Ile Asp Asp Phe Asn Arg
                355                 360                 365

Lys Gly Gly Met Ala Gln Met Ser Lys Ala Leu Glu Gly Pro Met Val
                370                 375                 380

Leu Val Met Ser Val Trp Asp Asp His Tyr Ala Asn Met Leu Trp Leu
385                 390                 395                 400

Asp Ser Thr Tyr Pro Ile Asp Lys Ala Gly Thr Pro Gly Ala Glu Arg
                405                 410                 415

Gly Ala Cys Pro Thr Thr Ser Gly Val Pro Ala Glu Ile Glu Ala Gln
                420                 425                 430
```

```
Val Pro Asn Ser Asn Val Ile Phe Ser Asn Ile Arg Phe Gly Pro Ile
        435                 440                 445

Gly Ser Thr Val Pro Gly Leu Asp Gly Ser Thr Pro Ser Asn Pro Thr
    450                 455                 460

Ala Thr Val Ala Pro Pro Thr Ser Thr Thr Thr Ser Val Arg Ser Ser
465                 470                 475                 480

Thr Thr Gln Ile Ser Thr Pro Thr Ser Gln Pro Gly Gly Cys Thr Thr
                485                 490                 495

Gln Lys Trp Gly Gln Cys Gly Gly Ile Gly Tyr Thr Gly Cys Thr Asn
            500                 505                 510

Cys Val Ala Gly Thr Thr Cys Thr Glu Leu Asn Pro Trp Tyr Ser Gln
        515                 520                 525

Cys Leu
    530

<210> SEQ ID NO 109
<211> LENGTH: 1434
<212> TYPE: DNA
<213> ORGANISM: Chaetomium thermophilum

<400> SEQUENCE: 109
atggctaagc agctgctgct cactgccgct cttgcggcca cttcgctggc tgcccctctc      60
cttgaggagc gccagagctg ctcctccgtc tggggtcaat gcggtggcat caattacaac     120
ggcccgacct gctgccagtc cggcagtgtt tgcacttacc tgaatgactg gtacagccag     180
tgcattcccg gtcaggctca gcccggcacg actagcacca cggctcggac caccagcacc     240
agcaccacca gcacttcgtc ggtccgcccg accacctcga atacccctgt gacgactgct     300
cccccgacga ccaccatccc gggcggcgcc tcgagcacgg ccagctacaa cggcaacccg     360
ttttcgggtg ttcaactttg gccaacacc tactactcgt ccgaggtgca cactttggcc     420
atccccagct tgtctcctga gctggctgcc aaggccgcca aggtcgctga ggttcccagc     480
ttccagtggc tcgaccgcaa tgtgactgtt gacactctct tctccggcac tcttgccgaa     540
atccgcgccg ccaaccagcg cggtgccaac ccgccttatg ccggcatttt cgtggtttat     600
gacttaccag accgtgattg cgcggctgct gcttcgaacg gcgagtggtc tatcgccaac     660
aatggtgcca caactacaa gcgctacatc gaccggatcc gtgagctcct tatccagtac     720
tccgatatcc gcactattct ggtcattgaa cctgattccc tggccaacat ggtcaccaac     780
atgaacgtcc agaagtgctc gaacgctgcc tccacttaca aggagcttac tgtctatgcc     840
ctcaaacagc tcaatcttcc tcacgttgcc atgtacatgg atgctggcca cgctggctgg     900
cttggctggc cgccaacat ccagcctgct gctgagctct ttgctcaaat ctaccgcgac     960
gctggcaggc ccgctgctgt ccgcggtctt gcgaccaacg ttgccaacta caatgcttgg    1020
tcgatcgcca gccctccgtc ctacacctct cctaacccga actacgacga gaagcactat    1080
attgaggcct ttgctcctct tctccgcaac cagggcttcg acgcaaagtt catcgtcgac    1140
accggccgta acggcaagca gcccactggc cagcttgaat ggggtcactg gtgcaatgtc    1200
aagggaactg gcttcggtgt gcgccctact gctaacactg gcatgaact tgttgatgct    1260 ttcgtgtggg tcaagcccgg tggcgagtcc gacggcacca gtgcggacac cagcgctgct    1320
cgttatgact atcactgcgg cctttccgac gcactgactc cggcgcctga ggctggccaa    1380
tggttccagg cttatttcga acagctgctc atcaatgcca ccctccgct ctga           1434
```

<210> SEQ ID NO 110
<211> LENGTH: 477
<212> TYPE: PRT
<213> ORGANISM: Chaetomium thermophilum

<400> SEQUENCE: 110

| | | | | | | | | | | | | | | |
|---|---|---|---|---|---|---|---|---|---|---|---|---|---|---|
| Met | Ala | Lys | Gln | Leu | Leu | Leu | Thr | Ala | Ala | Leu | Ala | Ala | Thr | Ser | Leu |
| 1 | | | | 5 | | | | | 10 | | | | | 15 | |
| Ala | Ala | Pro | Leu | Leu | Glu | Glu | Arg | Gln | Ser | Cys | Ser | Ser | Val | Trp | Gly |
| | | | 20 | | | | | 25 | | | | | 30 | | |
| Gln | Cys | Gly | Gly | Ile | Asn | Tyr | Asn | Gly | Pro | Thr | Cys | Cys | Gln | Ser | Gly |
| | | | 35 | | | | 40 | | | | | 45 | | | |
| Ser | Val | Cys | Thr | Tyr | Leu | Asn | Asp | Trp | Tyr | Ser | Gln | Cys | Ile | Pro | Gly |
| | 50 | | | | | 55 | | | | | 60 | | | | |
| Gln | Ala | Gln | Pro | Gly | Thr | Thr | Ser | Thr | Thr | Ala | Arg | Thr | Thr | Ser | Thr |
| 65 | | | | 70 | | | | | 75 | | | | | 80 | |
| Ser | Thr | Thr | Ser | Thr | Ser | Ser | Val | Arg | Pro | Thr | Thr | Ser | Asn | Thr | Pro |
| | | | | 85 | | | | | 90 | | | | | 95 | |
| Val | Thr | Thr | Ala | Pro | Pro | Thr | Thr | Thr | Ile | Pro | Gly | Gly | Ala | Ser | Ser |
| | | | | 100 | | | | | 105 | | | | | 110 | |
| Thr | Ala | Ser | Tyr | Asn | Gly | Asn | Pro | Phe | Ser | Gly | Val | Gln | Leu | Trp | Ala |
| | | | 115 | | | | | 120 | | | | | 125 | | |
| Asn | Thr | Tyr | Tyr | Ser | Ser | Glu | Val | His | Thr | Leu | Ala | Ile | Pro | Ser | Leu |
| 130 | | | | | 135 | | | | | 140 | | | | | |
| Ser | Pro | Glu | Leu | Ala | Ala | Lys | Ala | Ala | Lys | Val | Ala | Glu | Val | Pro | Ser |
| 145 | | | | | 150 | | | | | 155 | | | | | 160 |
| Phe | Gln | Trp | Leu | Asp | Arg | Asn | Val | Thr | Val | Asp | Thr | Leu | Phe | Ser | Gly |
| | | | | 165 | | | | | 170 | | | | | 175 | |
| Thr | Leu | Ala | Glu | Ile | Arg | Ala | Ala | Asn | Gln | Arg | Gly | Ala | Asn | Pro | Pro |
| | | | 180 | | | | | 185 | | | | | 190 | | |
| Tyr | Ala | Gly | Ile | Phe | Val | Val | Tyr | Asp | Leu | Pro | Asp | Arg | Asp | Cys | Ala |
| | | 195 | | | | | 200 | | | | | 205 | | | |
| Ala | Ala | Ala | Ser | Asn | Gly | Glu | Trp | Ser | Ile | Ala | Asn | Asn | Gly | Ala | Asn |
| 210 | | | | | 215 | | | | | 220 | | | | | |
| Asn | Tyr | Lys | Arg | Tyr | Ile | Asp | Arg | Ile | Arg | Glu | Leu | Leu | Ile | Gln | Tyr |
| 225 | | | | | 230 | | | | | 235 | | | | | 240 |
| Ser | Asp | Ile | Arg | Thr | Ile | Leu | Val | Ile | Glu | Pro | Asp | Ser | Leu | Ala | Asn |
| | | | | 245 | | | | | 250 | | | | | 255 | |
| Met | Val | Thr | Asn | Met | Asn | Val | Gln | Lys | Cys | Ser | Asn | Ala | Ala | Ser | Thr |
| | | | 260 | | | | | 265 | | | | | 270 | | |
| Tyr | Lys | Glu | Leu | Thr | Val | Tyr | Ala | Leu | Lys | Gln | Leu | Asn | Leu | Pro | His |
| | | 275 | | | | | 280 | | | | | 285 | | | |
| Val | Ala | Met | Tyr | Met | Asp | Ala | Gly | His | Ala | Gly | Trp | Leu | Gly | Trp | Pro |
| | 290 | | | | | 295 | | | | | 300 | | | | |
| Ala | Asn | Ile | Gln | Pro | Ala | Ala | Glu | Leu | Phe | Ala | Gln | Ile | Tyr | Arg | Asp |
| 305 | | | | | 310 | | | | | 315 | | | | | 320 |
| Ala | Gly | Arg | Pro | Ala | Ala | Val | Arg | Gly | Leu | Ala | Thr | Asn | Val | Ala | Asn |
| | | | | 325 | | | | | 330 | | | | | 335 | |
| Tyr | Asn | Ala | Trp | Ser | Ile | Ala | Ser | Pro | Pro | Ser | Tyr | Thr | Ser | Pro | Asn |
| | | | 340 | | | | | 345 | | | | | 350 | | |
| Pro | Asn | Tyr | Asp | Glu | Lys | His | Tyr | Ile | Glu | Ala | Phe | Ala | Pro | Leu | Leu |
| | | 355 | | | | | 360 | | | | | 365 | | | |
| Arg | Asn | Gln | Gly | Phe | Asp | Ala | Lys | Phe | Ile | Val | Asp | Thr | Gly | Arg | Asn |
| | 370 | | | | | 375 | | | | | 380 | | | | |

Gly Lys Gln Pro Thr Gly Gln Leu Glu Trp Gly His Trp Cys Asn Val
385                 390                 395                 400

Lys Gly Thr Gly Phe Gly Val Arg Pro Thr Ala Asn Thr Gly His Glu
            405                 410                 415

Leu Val Asp Ala Phe Val Trp Val Lys Pro Gly Gly Glu Ser Asp Gly
            420                 425                 430

Thr Ser Ala Asp Thr Ser Ala Ala Arg Tyr Asp Tyr His Cys Gly Leu
            435                 440                 445

Ser Asp Ala Leu Thr Pro Ala Pro Glu Ala Gly Gln Trp Phe Gln Ala
    450                 455                 460

Tyr Phe Glu Gln Leu Leu Ile Asn Ala Asn Pro Pro Leu
465                 470                 475

<210> SEQ ID NO 111
<211> LENGTH: 2586
<212> TYPE: DNA
<213> ORGANISM: Aspergillus oryzae

<400> SEQUENCE: 111

| | | |
|---|---|---|
| atgaagcttg gttggatcga ggtggccgca ttggcggctg cctcagtagt cagtgccaag | 60 |
| gatgatctcg cgtactcccc tcctttctac ccttccccat gggcagatgg tcagggtgaa | 120 |
| tgggcggaag tatacaaacg cgctgtagac atagtttccc agatgacgtt gacagagaaa | 180 |
| gtcaacttaa cgactggaac aggatggcaa ctagagaggt gtgttggaca aactggcagt | 240 |
| gttcccagac tcaacatccc cagcttgtgt ttgcaggata gtcctcttgg tattcgtttc | 300 |
| tcggactaca attcagcttt ccctgcgggt gttaatgtcg ctgccacctg ggacaagacg | 360 |
| ctcgcctacc ttcgtggtca ggcaatgggt gaggagttca gtgataaggg tattgacgtt | 420 |
| cagctgggtc ctgctgctgg ccctctcggt gctcatccgg atggcggtag aaactgggaa | 480 |
| ggtttctcac cagatccagc cctcaccggt gtactttttg cggagacgat taagggtatt | 540 |
| caagatgctg gtgtcattgc gacagctaag cattatatca tgaacgaaca agagcatttc | 600 |
| cgccaacaac ccgaggctgc gggttacgga ttcaacgtaa gcgacagttt gagttccaac | 660 |
| gttgatgaca agactatgca tgaattgtac ctctggccct cgcggatgc agtacgcgct | 720 |
| ggagtcggtg ctgtcatgtg ctcttacaac caaatcaaca acagctacgg ttgcgagaat | 780 |
| agcgaaactc tgaacaagct tttgaaggcg gagcttggtt tccaaggctt cgtcatgagt | 840 |
| gattggaccg ctcatcacag cggcgtaggc gctgctttag caggtctgga tatgtcgatg | 900 |
| cccggtgatg ttaccttcga tagtggtacg tctttctggg gtgcaaactt gacggtcggt | 960 |
| gtccttaacg gtacaatccc ccaatggcgt gttgatgaca tggctgtccg tatcatggcc | 1020 |
| gcttattaca aggttggccg cgacaccaaa tacaccctc ccaacttcag ctcgtggacc | 1080 |
| agggacgaat atggtttcgc gcataaccat gtttcggaag gtgcttacga gagggtcaac | 1140 |
| gaattcgtgg acgtgcaacg cgatcatgcc gacctaatcc gtcgcatcgg cgcgcagagc | 1200 |
| actgttctgc tgaagaacaa gggtgccttg cccttgagcc gcaaggaaaa gctggtcgcc | 1260 |
| cttctgggag aggatgcggg ttccaactcg tggggcgcta acggctgtga tgaccgtggt | 1320 |
| tgcgataacg gtaccttgc catggcctgg gtagcggta ctgcgaattt cccatacctc | 1380 |
| gtgacaccag agcaggcgat tcagaacgaa gttcttcagg gccgtggtaa tgtcttcgcc | 1440 |
| gtgaccgaca gttgggcgct cgacaagatc gctgcggctg cccgccaggc cagcgtatct | 1500 |
| ctcgtgttcg tcaactccga ctcaggagaa ggctatctta gtgtggatgg aaatgagggc | 1560 |
| gatcgtaaca acatcactct gtggaagaac ggcgacaatg tggtcaagac cgcagcgaat | 1620 |

```
aactgtaaca acaccgttgt catcatccac tccgtcggac cagttttgat cgatgaatgg    1680
tatgaccacc ccaatgtcac tggtattctc tgggctggtc tgccaggcca ggagtctggt    1740
aactccattg ccgatgtgct gtacggtcgt gtcaaccctg cgccaagtc tcctttcact     1800
tggggcaaga cccgggagtc gtatggttct cccttggtca aggatgccaa caatggcaac    1860
ggagcgcccc agtctgattt cacccagggt gttttcatcg attaccgcca tttcgataag    1920
ttcaatgaga cccctatcta cgagtttggc tacggcttga gctacaccac cttcgagctc    1980
tccgacctcc atgttcagcc cctgaacgcg tcccgataca ctcccaccag tggcatgact    2040
gaagctgcaa gaactttggg tgaaattggc gatgcgtcgg agtacgtgta ccggaggggg    2100
ctggaaagga tccatgagtt tatctatccc tggatcaact ctaccgacct gaaggcatcg    2160
tctgacgatt ctaactacgg ctgggaagac tccaagtata ttcccgaagg cgccacggat    2220
gggtctgccc agccccgttt gccgctagt ggtggtgccg aggaaaccc cggtctgtac      2280
gaggatcttt tccgcgtctc tgtgaaggtc aagaacacgg gcaatgtcgc cggtgatgaa    2340
gttcctcagc tgtacgtttc cctaggcggc ccgaatgagc ccaaggtggt actgcgcaag    2400
tttgagcgta ttcacttggc cccttcgcag gaggccgtgt ggacaacgac ccttacccgt    2460
cgtgaccttg caaactggga cgtttcggct caggactgga ccgtcactcc ttaccccaag    2520
acgatctacg ttggaaactc ctcacggaaa ctgccgctcc aggcctcgct gcctaaggcc    2580
cagtaa                                                               2586
```

<210> SEQ ID NO 112
<211> LENGTH: 861
<212> TYPE: PRT
<213> ORGANISM: Aspergillus oryzae

<400> SEQUENCE: 112

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190
```

```
Ile Met Asn Glu Gln Glu His Phe Arg Gln Gln Pro Glu Ala Ala Gly
        195                 200                 205
Tyr Gly Phe Asn Val Ser Asp Ser Leu Ser Ser Asn Val Asp Asp Lys
    210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Glu Asn Ser Glu Thr Leu Asn Lys Leu Leu Lys Ala Glu Leu
            260                 265                 270
Gly Phe Gln Gly Phe Val Met Ser Asp Trp Thr Ala His His Ser Gly
        275                 280                 285
Val Gly Ala Ala Leu Ala Gly Leu Asp Met Ser Met Pro Gly Asp Val
    290                 295                 300
Thr Phe Asp Ser Gly Thr Ser Phe Trp Gly Ala Asn Leu Thr Val Gly
305                 310                 315                 320
Val Leu Asn Gly Thr Ile Pro Gln Trp Arg Val Asp Asp Met Ala Val
                325                 330                 335
Arg Ile Met Ala Ala Tyr Tyr Lys Val Gly Arg Asp Thr Lys Tyr Thr
            340                 345                 350
Pro Pro Asn Phe Ser Ser Trp Thr Arg Asp Glu Tyr Gly Phe Ala His
        355                 360                 365
Asn His Val Ser Glu Gly Ala Tyr Glu Arg Val Asn Glu Phe Val Asp
    370                 375                 380
Val Gln Arg Asp His Ala Asp Leu Ile Arg Ile Gly Ala Gln Ser
385                 390                 395                 400
Thr Val Leu Leu Lys Asn Lys Gly Ala Leu Pro Leu Ser Arg Lys Glu
                405                 410                 415
Lys Leu Val Ala Leu Leu Gly Glu Asp Ala Gly Ser Asn Ser Trp Gly
            420                 425                 430
Ala Asn Gly Cys Asp Asp Arg Gly Cys Asp Asn Gly Thr Leu Ala Met
        435                 440                 445
Ala Trp Gly Ser Gly Thr Ala Asn Phe Pro Tyr Leu Val Thr Pro Glu
    450                 455                 460
Gln Ala Ile Gln Asn Glu Val Leu Gln Gly Arg Gly Asn Val Phe Ala
465                 470                 475                 480
Val Thr Asp Ser Trp Ala Leu Asp Lys Ile Ala Ala Ala Arg Gln
                485                 490                 495
Ala Ser Val Ser Leu Val Phe Val Asn Ser Asp Ser Gly Glu Gly Tyr
            500                 505                 510
Leu Ser Val Asp Gly Asn Glu Gly Asp Arg Asn Asn Ile Thr Leu Trp
        515                 520                 525
Lys Asn Gly Asp Asn Val Val Lys Thr Ala Ala Asn Asn Cys Asn Asn
    530                 535                 540
Thr Val Val Ile Ile His Ser Val Gly Pro Val Leu Ile Asp Glu Trp
545                 550                 555                 560
Tyr Asp His Pro Asn Val Thr Gly Ile Leu Trp Ala Gly Leu Pro Gly
                565                 570                 575
Gln Glu Ser Gly Asn Ser Ile Ala Asp Val Leu Tyr Gly Arg Val Asn
            580                 585                 590
Pro Gly Ala Lys Ser Pro Phe Thr Trp Gly Lys Thr Arg Glu Ser Tyr
        595                 600                 605
Gly Ser Pro Leu Val Lys Asp Ala Asn Asn Gly Asn Gly Ala Pro Gln
```

610                615                620
Ser Asp Phe Thr Gln Gly Val Phe Ile Asp Tyr Arg His Phe Asp Lys
625                630                635                640

Phe Asn Glu Thr Pro Ile Tyr Glu Phe Gly Tyr Gly Leu Ser Tyr Thr
                645                650                655

Thr Phe Glu Leu Ser Asp Leu His Val Gln Pro Leu Asn Ala Ser Arg
            660                665                670

Tyr Thr Pro Thr Ser Gly Met Thr Glu Ala Ala Lys Asn Phe Gly Glu
        675                680                685

Ile Gly Asp Ala Ser Glu Tyr Val Tyr Pro Glu Gly Leu Glu Arg Ile
    690                695                700

His Glu Phe Ile Tyr Pro Trp Ile Asn Ser Thr Asp Leu Lys Ala Ser
705                710                715                720

Ser Asp Asp Ser Asn Tyr Gly Trp Glu Asp Ser Lys Tyr Ile Pro Glu
                725                730                735

Gly Ala Thr Asp Gly Ser Ala Gln Pro Arg Leu Pro Ala Ser Gly Gly
            740                745                750

Ala Gly Gly Asn Pro Gly Leu Tyr Glu Asp Leu Phe Arg Val Ser Val
        755                760                765

Lys Val Lys Asn Thr Gly Asn Val Ala Gly Asp Glu Val Pro Gln Leu
    770                775                780

Tyr Val Ser Leu Gly Gly Pro Asn Glu Pro Lys Val Val Leu Arg Lys
785                790                795                800

Phe Glu Arg Ile His Leu Ala Pro Ser Gln Glu Ala Val Trp Thr Thr
                805                810                815

Thr Leu Thr Arg Arg Asp Leu Ala Asn Trp Asp Val Ser Ala Gln Asp
            820                825                830

Trp Thr Val Thr Pro Tyr Pro Lys Thr Ile Tyr Val Gly Asn Ser Ser
        835                840                845

Arg Lys Leu Pro Leu Gln Ala Ser Leu Pro Lys Ala Gln
    850                855                860

<210> SEQ ID NO 113
<211> LENGTH: 3060
<212> TYPE: DNA
<213> ORGANISM: Aspergillus fumigatus

<400> SEQUENCE: 113
atgagattcg gttggctcga ggtggccgct ctgacggccg cttctgtagc caatgcccag      60
gtttgtgatg ctttcccgtc attgtttcgg atatagttga caatagtcat ggaaataatc     120
aggaattggc tttctctcca ccattctacc cttcgccttg gctgatggca cagggagagt     180
gggcagatgc ccatcgacgc gccgtcgaga tcgtttctca gatgacactg gcggagaagg     240
ttaaccttac aacgggtact gggtgggttg cgacttttt gttgacagtg agctttcttc     300
actgaccatc tacacagatg ggaaatggac cgatgcgtcg gtcaaaccgg cagcgttccc     360
aggtaagctt gcaattctgc aacaacgtgc aagtgtagtt gctaaaacgc ggtggtgcag     420
acttggtatc aactggggtc tttgtggcca ggattcccct tgggtatcc gtttctgtga     480 gctatacccg cggagtcttt cagtccttgt attatgtgct gatgattgtc tctgtatagc     540
tgacctcaac tccgccttcc ctgctggtac taatgtcgcc gcgacatggg acaagacact     600
cgcctacctt cgtggcaagg ccatgggtga ggaattcaac gacaagggcg tggacatttt     660
gctggggcct gctgctggtc ctctcggcaa ataccccggac ggcggcagaa tctgggaagg     720

```
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta acacatcacg gagacgatca gctccaacgt    900
ggatgacaag accatgcacg agttgtacct ttggtgagta gttgacactg caaatgagga    960
ccttgattga tttgactgac ctggaatgca ggccctttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt cccctaact tcagctcctg gacccgggat    1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttccctta ccttgtcacc   1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt ttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaacccct cctgaaggct ggcggcgctc ctggtggtaa ccctacccct   2700
tatcaggatc ttgttagggt gtcggccacc ataaccaaca ctggtaacgt cgccggttat   2760
gaagtccctc aattggtgag tgacccgcat gttccttgcg ttgcaatttg gctaactcgc   2820
ttctagtatg tttcactggg cggaccgaac gagcctcggg tcgttctgcg caagttcgac   2880
cgaatcttcc tggctcctgg ggagcaaaag gtttggacca cgactcttaa ccgtcgtgat   2940
ctcgccaatt gggatgtgga ggctcaggac tgggtcatca caaagtaccc caagaaagtg   3000
cacgtcggca gctcctcgcg taagctgcct ctgagagcgc tctgccccg tgtctactag    3060
```

<210> SEQ ID NO 114
<211> LENGTH: 863
<212> TYPE: PRT
<213> ORGANISM: Aspergillus fumigatus

<400> SEQUENCE: 114

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380
```

```
Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
            405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
        450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
        770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
```

```
                    805                 810                 815
Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
            850                 855                 860

<210> SEQ ID NO 115
<211> LENGTH: 2800
<212> TYPE: DNA
<213> ORGANISM: Penicillium brasilianum

<400> SEQUENCE: 115
tgaaaatgca gggttctaca atctttctgg ctttcgcctc atgggcgagc caggttgctg     60
ccattgcgca gcccatacag aagcacgagg tttgttttat cttgctcatg acgtgctttt    120
gacttgacta attgttttac atacagcccg gatttctgca cgggccccaa gccatagaat    180
cgttctcaga accgttctac ccgtcgccct ggatgaatcc tcacgccgag ggctgggagg    240
ccgcatatca gaaagctcaa gattttgtct cgcaactcac tatcttggag aaaataaatc    300
tgaccaccgg tgttgggtaa gtctctccga ctgcttctgg gtcacggtgc gacgagccac    360 tgacttttg aagctgggaa atgggccgt gtgtaggaaa cactggatca attcctcgtc    420
tcggattcaa aggattttgt acccaggatt caccacaggg tgttcggttc gcagattatt    480
cctccgcttt cacatctagc caaatggccg ccgcaacatt tgaccgctca attctttatc    540
aacgaggcca agccatggca caggaacaca aggctaaggg tatcacaatt caattgggcc    600
ctgttgccgg ccctctcggt cgcatccccg agggcggccg caactgggaa ggattctccc    660
ctgatcctgt cttgactggt atagccatgg ctgagacaat taagggcatg caggatactg    720
gagtgattgc ttgcgctaaa cattatattg gaaacgagca ggagcacttc cgtcaagtgg    780
gtgaagctgc gggtcacgga tacactattt ccgatactat ttcatctaat attgacgacc    840
gtgctatgca tgagctatac ttgtggccat ttgctgatgc cgttcgcgct ggtgtgggtt    900
cttccatgtg ctcatactct cagatcaaca actcctacgg atgccaaaac agtcagaccc    960
tcaacaagct cctcaagagc gaattgggct tccaaggctt tgtcatgagc gattggggtg   1020
cccatcactc tggagtgtca tcggcgtag ctggacttga tatgagcatg ccgggtgata   1080
ccgaatttga ttctggcttg agcttctggg gctctaacct caccattgca attctgaacg   1140
gcacggttcc cgaatggcgc ctggatgaca tggcgatgcg aattatggct gcatacttca   1200
aagttggcct tactattgag atcaaccag atgtcaactt caatgcctgg acccatgaca   1260
cctacggata taaatacgct tatagcaagg aagattacga gcaggtcaac tggcatgtcg   1320
atgttcgcag cgaccacaat aagctcattc gcgagactgc cgcgaagggt acagttctgc   1380
tgaagaacaa ctttcatgct ctccctctga gcagcccag gttcgtggcc gtcgttggtc   1440
aggatgccgg gccaaacccc aagggcccta acggctgcgc agaccgagga tgcgaccaag   1500
gcactctcgc aatgggatgg ggctcagggt ctaccgaatt cccttacctg gtcactcctg   1560
acactgctat tcagtcaaag gtcctcgaat acggggtcg atacgagagt attttgata   1620 actatgacga caatgctatc ttgtcgcttg tctcacagcc tgatgcaacc tgtatcgttt   1680
ttgcaaatgc cgattccggt gaaggctaca tcactgtcga caacaactgg ggtgaccgca   1740
acaatctgac cctctggcaa aatgccgatc aagtgattag cactgtcagc tcgcgatgca   1800
```

```
acaacacaat cgttgttctc cactctgtcg gaccagtgtt gctaaatggt atatatgagc    1860
acccgaacat cacagctatt gtctgggcag ggatgccagg cgaagaatct ggcaatgctc    1920
tcgtggatat tctttggggc aatgttaacc ctgccggtcg cactccgttc acctgggcca    1980
aaagtcgaga ggactatggc actgatataa tgtacgagcc caacaacggc cagcgtgcgc    2040
ctcagcagga tttcaccgag agcatctacc tcgactaccg ccatttcgac aaagctggta    2100
tcgagccaat ttacgagttt ggattcggcc tctcctatac caccttcgaa tactctgacc    2160
tccgtgttgt gaagaagtat gttcaaccat acagtcccac gaccggcacc ggtgctcaag    2220
caccttccat cggacagcca cctagccaga acctggatac ctacaagttc cctgctacat    2280
acaagtacat caaaaccttc atttatccct acctgaacag cactgtctcc ctccgcgctg    2340
cttccaagga tcccgaatac ggtcgtacag actttatccc accccacgcg cgtgatggct    2400
cccctcaacc tctcaacccc gctggagacc cagtggccag tggtggaaac aacatgctct    2460
acgacgaact ttacgaggtc actgcacaga tcaaaaacac tggcgacgtg gccggcgacg    2520
aagtcgtcca gctttacgta gatctcgggg gtgacaaccc gcctcgtcag ttgagaaact    2580
ttgacaggtt ttatctgctg cccggtcaga gctcaacatt ccgggctaca ttgacgcgcc    2640
gtgatttgag caactgggat attgaggcgc agaactggcg agttacggaa tcgcctaaga    2700
gagtgtatgt tggacggtcg agtcgggatt tgccgctgag ctcacaattg gagtaatgat    2760
catgtctacc aatagatgtt gaatgtctgg tgtggatatt                          2800
```

<210> SEQ ID NO 116
<211> LENGTH: 878
<212> TYPE: PRT
<213> ORGANISM: Penicillium brasilianum

<400> SEQUENCE: 116

```
Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125

Met Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
```

```
                195                 200                 205
Tyr Ile Gly Asn Glu Gln Glu His Phe Arg Gln Val Gly Glu Ala Ala
        210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
        275                 280                 285

Leu Gly Phe Gln Gly Phe Val Met Ser Asp Trp Gly Ala His His Ser
    290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
            340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
    370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Val Gly Gln Asp Ala Gly Pro Asn Pro Lys
        435                 440                 445

Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asp Asn Ala Ile Leu Ser Leu Val Ser
            500                 505                 510

Gln Pro Asp Ala Thr Cys Ile Val Phe Ala Asn Ala Asp Ser Gly Glu
        515                 520                 525

Gly Tyr Ile Thr Val Asp Asn Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
            580                 585                 590

Pro Gly Glu Glu Ser Gly Asn Ala Leu Val Asp Ile Leu Trp Gly Asn
        595                 600                 605

Val Asn Pro Ala Gly Arg Thr Pro Phe Thr Trp Ala Lys Ser Arg Glu
    610                 615                 620
```

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
            645                 650                 655

Asp Lys Ala Gly Ile Glu Pro Ile Tyr Glu Phe Gly Phe Gly Leu Ser
        660                 665                 670

Tyr Thr Thr Phe Glu Tyr Ser Asp Leu Arg Val Val Lys Lys Tyr Val
    675                 680                 685

Gln Pro Tyr Ser Pro Thr Thr Gly Thr Gly Ala Gln Ala Pro Ser Ile
690                 695                 700

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
            725                 730                 735

Ser Leu Arg Ala Ala Ser Lys Asp Pro Glu Tyr Gly Arg Thr Asp Phe
        740                 745                 750

Ile Pro Pro His Ala Arg Asp Gly Ser Pro Gln Pro Leu Asn Pro Ala
    755                 760                 765

Gly Asp Pro Val Ala Ser Gly Asn Asn Met Leu Tyr Asp Glu Leu
770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
            805                 810                 815

Gln Leu Arg Asn Phe Asp Arg Phe Tyr Leu Leu Pro Gly Gln Ser Ser
        820                 825                 830

Thr Phe Arg Ala Thr Leu Thr Arg Arg Asp Leu Ser Asn Trp Asp Ile
    835                 840                 845

Glu Ala Gln Asn Trp Arg Val Thr Glu Ser Pro Lys Arg Val Tyr Val
850                 855                 860

Gly Arg Ser Ser Arg Asp Leu Pro Leu Ser Ser Gln Leu Glu
865                 870                 875

<210> SEQ ID NO 117
<211> LENGTH: 2583
<212> TYPE: DNA
<213> ORGANISM: Aspergillus niger

<400> SEQUENCE: 117
atgaggttca ctttgatcga ggcggtggct ctgactgccg tctcgctggc cagcgctgat      60
gaattggcct actccccacc gtattaccca tccccttggg ccaatggcca gggcgactgg     120
gcgcaggcat accagcgcgc tgttgatatt gtctcgcaaa tgacattgga tgagaaggtc     180
aatctgacca caggaactgg atgggaattg aactatgtg ttggtcagac tggcggtgtt     240
ccccgattgg gagttccggg aatgtgttta caggatagcc ctctgggcgt tcgcgactcc     300
gactacaact ctgctttccc tgccggcatg aacgtggctg caacctggga caagaatctg     360
gcataccttc gcggcaaggc tatgggtcag gaatttagtg acaagggtgc cgatatccaa     420
ttgggtccag ctgccggccc tctcggtaga agtcccgacg tggtcgtaa ctgggagggc     480 ttctccccag accctgccct aagtggtgtg ctctttgccg agaccatcaa gggtatccaa     540
gatgctggtg tggttgcgac ggctaagcac tacattgctt acgagcaaga gcatttccgt     600
caggcgcctg aagcccaagg ttttggattt aatatttccg agagtggaag tgcgaacctc     660

```
gatgataaga ctatgcacga gctgtacctc tggcccttcg cggatgccat ccgtgcaggt    720
gctggcgctg tgatgtgctc ctacaaccag atcaacaaca gttatggctg ccagaacagc    780
tacactctga acaagctgct caaggccgag ctgggcttcc agggctttgt catgagtgat    840
tgggctgctc accatgctgg tgtgagtggt gctttggcag gattggatat gtctatgcca    900
ggagacgtcg actacgacag tggtacgtct tactggggta caaacttgac cattagcgtg    960
ctcaacggaa cggtgcccca atggcgtgtt gatgacatgg ctgtccgcat catggccgcc   1020
tactacaagg tcggccgtga ccgtctgtgg actcctccca acttcagctc atggaccaga   1080
gatgaatacg ctacaagta ctactacgtg tcggagggac cgtacgagaa ggtcaaccag   1140
tacgtgaatg tgcaacgcaa ccacagcgaa ctgattcgcc gcattggagc ggacagcacg   1200
gtgctcctca agaacgacgg cgctctgcct ttgactggta aggagcgcct ggtcgcgctt   1260
atcggagaag atgcgggctc caaccccttat ggtgccaacg gctgcagtga ccgtggatgc   1320
gacaatggaa cattggcgat gggctgggga agtggtactg ccaacttccc atacctggtg   1380
accccccgagc aggccatctc aaacgaggtg cttaagcaca gaatggtgt attcaccgcc   1440
accgataact gggctatcga tcagattgag gcgcttgcta agaccgccag tgtctctctt   1500
gtctttgtca cgccgactc tggtgagggt tacatcaatg tggacggaaa cctgggtgac   1560
cgcaggaacc tgaccctgtg gaggaacggc gataatgtga tcaaggctgc tgctagcaac   1620
tgcaacaaca caatcgttgt cattcactct gtcggaccag tcttggttaa cgagtggtac   1680
gacaaccca atgttaccgc tatcctctgg ggtggtttgc ccggtcagga gtctggcaac   1740
tctcttgccg acgtcctcta tggccgtgtc aaccccggtg ccagtcgcc ctttacctgg   1800
ggcaagactc gtgaggccta ccaagactac ttggtcaccg agcccaacaa cggcaacgga   1860
gcccctcagg aagactttgt cgaggcgtc ttcattgact accgtggatt tgacaagcgc   1920
aacgagaccc cgatctacga gttcggctat ggtctgagct acaccactt caactactcg   1980
aaccttgagg tgcaggtgct gagcgcccct gcatacgagc ctgcttcggg tgagaccgag   2040
gcagcgccaa ccttcggaga ggttggaaat gcgtcggatt acctctaccc cagcggattg   2100
cagagaatta ccaagttcat ctaccccctgg ctcaacggta ccgatctcga ggcatcttcc   2160
ggggatgcta gctacgggca ggactcctcc gactatcttc ccgagggagc caccgatggc   2220
tctgcgcaac cgatcctgcc tgccggtggc ggtcctggcg caaccctcg cctgtacgac   2280
gagctcatcc gcgtgtcagt gaccatcaag aacaccggca aggttgctgg tgatgaagtt   2340
ccccaactgt atgtttccct tggcggtccc aatgagccca agatcgtgct gcgtcaattc   2400
gagcgcatca cgctgcagcc gtcggaggag acgaagtgga gcacgactct gacgcgccgt   2460
gaccttgcaa actggaatgt tgagaagcag gactgggaga ttacgtcgta tcccaagatg   2520
gtgtttgtcg gaagctcctc gcggaagctg ccgctccggg cgtctctgcc tactgttcac   2580
taa                                                                   2583
```

<210> SEQ ID NO 118
<211> LENGTH: 860
<212> TYPE: PRT
<213> ORGANISM: Aspergillus niger

<400> SEQUENCE: 118

Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
                20                  25                  30

```
Trp Ala Asn Gly Gln Gly Asp Trp Ala Gln Ala Tyr Gln Arg Ala Val
            35                  40                  45

Asp Ile Val Ser Gln Met Thr Leu Asp Glu Lys Val Asn Leu Thr Thr
 50                  55                  60

Gly Thr Gly Trp Glu Leu Glu Leu Cys Val Gly Gln Thr Gly Gly Val
 65                  70                  75                  80

Pro Arg Leu Gly Val Pro Gly Met Cys Leu Gln Asp Ser Pro Leu Gly
                 85                  90                  95

Val Arg Asp Ser Asp Tyr Asn Ser Ala Phe Pro Ala Gly Met Asn Val
                100                 105                 110

Ala Ala Thr Trp Asp Lys Asn Leu Ala Tyr Leu Arg Gly Lys Ala Met
            115                 120                 125

Gly Gln Glu Phe Ser Asp Lys Gly Ala Asp Ile Gln Leu Gly Pro Ala
        130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
                180                 185                 190

Ala Tyr Glu Gln Glu His Phe Arg Gln Ala Pro Glu Ala Gln Gly Phe
            195                 200                 205

Gly Phe Asn Ile Ser Glu Ser Gly Ser Ala Asn Leu Asp Asp Lys Thr
        210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
                260                 265                 270

Phe Gln Gly Phe Val Met Ser Asp Trp Ala Ala His His Ala Gly Val
            275                 280                 285

Ser Gly Ala Leu Ala Gly Leu Asp Met Ser Met Pro Gly Asp Val Asp
        290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
                340                 345                 350

Pro Asn Phe Ser Ser Trp Thr Arg Asp Glu Tyr Gly Tyr Lys Tyr Tyr
            355                 360                 365

Tyr Val Ser Glu Gly Pro Tyr Glu Lys Val Asn Gln Tyr Val Asn Val
        370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
                420                 425                 430

Asn Gly Cys Ser Asp Arg Gly Cys Asp Asn Gly Thr Leu Ala Met Gly
            435                 440                 445
```

```
Trp Gly Ser Gly Thr Ala Asn Phe Pro Tyr Leu Val Thr Pro Glu Gln
    450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
                500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
    595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
    675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
    755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
    835                 840                 845

Lys Leu Pro Leu Arg Ala Ser Leu Pro Thr Val His
850                 855                 860
```

<210> SEQ ID NO 119
<211> LENGTH: 2583
<212> TYPE: DNA
<213> ORGANISM: Aspergillus aculeatus

<400> SEQUENCE: 119

| | | | | | |
|---|---|---|---|---|---|
| atgaagctca | gttggcttga | ggcggctgcc | ttgacggctg | cttcagtcgt | cagcgctgat | 60 |
| gaactggcgt | tctctcctcc | tttctacccc | tctccgtggg | ccaatggcca | gggagagtgg | 120 |
| gcggaagcct | accagcgtgc | agtggccatt | gtatcccaga | tgactctgga | tgagaaggtc | 180 |
| aacctgacca | ccggaactgg | atgggagctg | agaagtgcg | tcggtcagac | tggtggtgtc | 240 |
| ccaagactga | catcggtgg | catgtgtctt | caggacagtc | ccttgggaat | tcgtgatagt | 300 |
| gactacaatt | cggctttccc | tgctggtgtc | aacgttgctg | cgacatggga | caagaacctt | 360 |
| gcttatctac | gtggtcaggc | tatgggtcaa | gagttcagtg | acaaaggaat | tgatgttcaa | 420 |
| ttgggaccgg | ccgcgggtcc | cctcggcagg | agccctgatg | gaggtcgcaa | ctgggaaggt | 480 |
| ttctctccag | acccggctct | tactggtgtg | ctctttgcgg | agacgattaa | gggtattcaa | 540 |
| gacgctggtg | tcgtggcgac | agccaagcat | tacattctca | tgagcaaga | gcatttccgc | 600 |
| caggtcgcag | aggctgcggg | ctacggattc | aatatctccg | cacgatcag | ctctaacgtt | 660 |
| gatgacaaga | ccattcatga | aatgtacctc | tggcccttcg | cggatgccgt | tcgcgccggc | 720 |
| gttggcgcca | tcatgtgttc | ctacaaccag | atcaacaaca | gctacggttg | ccagaacagt | 780 |
| tacactctga | caagcttct | gaaggccgag | ctcggcttcc | agggctttgt | gatgtctgac | 840 |
| tggggtgctc | accacagtgg | tgttggctct | gctttggccg | gcttggatat | gtcaatgcct | 900 |
| ggcgatatca | ccttcgattc | tgccactagt | ttctggggta | ccaacctgac | cattgctgtg | 960 |
| ctcaacggta | ccgtcccgca | gtggcgcgtt | gacgacatgg | ctgtccgtat | catggctgcc | 1020 |
| tactacaagg | ttggccgcga | ccgcctgtac | cagccgccta | acttcagctc | ctggactcgc | 1080 |
| gatgaatacg | gcttcaagta | tttctacccc | caggaagggc | cctatgagaa | ggtcaatcac | 1140 |
| tttgtcaatg | tgcagcgcaa | ccacagcgag | gttattcgca | gttgggagc | agacagtact | 1200 |
| gttctactga | gaacaacaa | tgccctgccg | ctgaccggaa | aggagcgcaa | agttgcgatc | 1260 |
| ctgggtgaag | atgctggatc | caactcgtac | ggtgccaatg | ctgctctga | ccgtggctgt | 1320 |
| gacaacggta | ctcttgctat | ggcttgggt | agcggcactg | ccgaattccc | atatctcgtg | 1380 |
| acccctgagc | aggctattca | agccgagtg | ctcaagcata | agggcagcgt | ctacgccatc | 1440 |
| acggacaact | gggcgctgag | ccaggtggag | accctcgcta | acaagccag | tgtctctctt | 1500 |
| gtatttgtca | actcggacgc | gggagagggc | tatatctccg | tggacggaaa | cgagggcgac | 1560 |
| cgcaacaacc | tcaccctctg | gaagaacggc | gacaacctca | tcaaggctgc | tgcaaacaac | 1620 |
| tgcaacaaca | ccatcgttgt | catccactcc | gttggacctg | ttttggttga | cgagtggtat | 1680 |
| gaccaccca | acgttactgc | catcctctgg | gcgggcttgc | ctggccagga | gtctggcaac | 1740 |
| tccttggctg | acgtgctcta | cggccgcgtc | aacccgggcg | ccaaatctcc | attcacctgg | 1800 |
| ggcaagacga | gggaggcgta | cggggattac | cttgtccgtg | agctcaacaa | cggcaacgga | 1860 |
| gctcccccaag | atgatttctc | ggaaggtgtt | ttcattgact | accgcggatt | cgacaagcgc | 1920 |
| aatgagaccc | cgatctacga | gttcggacat | ggtctgagct | acaccacttt | caactactct | 1980 |
| ggccttcaca | tccaggttct | caacgcttcc | tccaacgctc | aagtagccac | tgagactggc | 2040 |
| gccgctccca | ccttcggaca | agtcggcaat | gcctctgact | acgtgtaccc | tgagggattg | 2100 |
| accagaatca | gcaagttcat | ctatccctgg | cttaattcca | cagacctgaa | ggcctcatct | 2160 |

-continued

```
ggcgacccgt actatggagt cgacaccgcg gagcacgtgc ccgagggtgc tactgatggc    2220
tctccgcagc ccgttctgcc tgccggtggt ggctctggtg gtaacccgcg cctctacgat    2280
gagttgatcc gtgtttcggt gacagtcaag aacactggtc gtgttgccgg tgatgctgtg    2340
cctcaattgt atgtttccct tggtggaccc aatgagccca aggttgtgtt gcgcaaattc    2400
gaccgcctca ccctcaagcc ctccgaggag acggtgtgga cgactaccct gacccgccgc    2460
gatctgtcta ctgggacgt tgcggctcag gactgggtca tcacttctta cccgaagaag    2520
gtccatgttg gtagctcttc gcgtcagctg ccccttcacg cggcgctccc gaaggtgcaa    2580
tga                                                                  2583
```

<210> SEQ ID NO 120
<211> LENGTH: 860
<212> TYPE: PRT
<213> ORGANISM: Aspergillus aculeatus

<400> SEQUENCE: 120

| Met | Lys | Leu | Ser | Trp | Leu | Glu | Ala | Ala | Leu | Thr | Ala | Ala | Ser | Val |
|---|---|---|---|---|---|---|---|---|---|---|---|---|---|---|
| 1 | | | | 5 | | | | | 10 | | | | | 15 |

| Val | Ser | Ala | Asp | Glu | Leu | Ala | Phe | Ser | Pro | Pro | Phe | Tyr | Pro | Ser | Pro |
|---|---|---|---|---|---|---|---|---|---|---|---|---|---|---|---|
| | | 20 | | | | | 25 | | | | | 30 | | | |

| Trp | Ala | Asn | Gly | Gln | Gly | Glu | Trp | Ala | Glu | Ala | Tyr | Gln | Arg | Ala | Val |
|---|---|---|---|---|---|---|---|---|---|---|---|---|---|---|---|
| | | | 35 | | | | | 40 | | | | | 45 | | |

| Ala | Ile | Val | Ser | Gln | Met | Thr | Leu | Asp | Glu | Lys | Val | Asn | Leu | Thr | Thr |
|---|---|---|---|---|---|---|---|---|---|---|---|---|---|---|---|
| | 50 | | | | | 55 | | | | | 60 | | | | |

| Gly | Thr | Gly | Trp | Glu | Leu | Glu | Lys | Cys | Val | Gly | Gln | Thr | Gly | Val |
|---|---|---|---|---|---|---|---|---|---|---|---|---|---|---|
| 65 | | | | | 70 | | | | | 75 | | | | | 80 |

| Pro | Arg | Leu | Asn | Ile | Gly | Gly | Met | Cys | Leu | Gln | Asp | Ser | Pro | Leu | Gly |
|---|---|---|---|---|---|---|---|---|---|---|---|---|---|---|---|
| | | | | 85 | | | | | 90 | | | | | 95 | |

| Ile | Arg | Asp | Ser | Asp | Tyr | Asn | Ser | Ala | Phe | Pro | Ala | Gly | Val | Asn | Val |
|---|---|---|---|---|---|---|---|---|---|---|---|---|---|---|---|
| | | | 100 | | | | | 105 | | | | | 110 | | |

| Ala | Ala | Thr | Trp | Asp | Lys | Asn | Leu | Ala | Tyr | Leu | Arg | Gly | Gln | Ala | Met |
|---|---|---|---|---|---|---|---|---|---|---|---|---|---|---|---|
| | | 115 | | | | | 120 | | | | | 125 | | | |

| Gly | Gln | Glu | Phe | Ser | Asp | Lys | Gly | Ile | Asp | Val | Gln | Leu | Gly | Pro | Ala |
|---|---|---|---|---|---|---|---|---|---|---|---|---|---|---|---|
| | 130 | | | | | 135 | | | | | 140 | | | | |

| Ala | Gly | Pro | Leu | Gly | Arg | Ser | Pro | Asp | Gly | Gly | Arg | Asn | Trp | Glu | Gly |
|---|---|---|---|---|---|---|---|---|---|---|---|---|---|---|---|
| 145 | | | | | 150 | | | | | 155 | | | | | 160 |

| Phe | Ser | Pro | Asp | Pro | Ala | Leu | Thr | Gly | Val | Leu | Phe | Ala | Glu | Thr | Ile |
|---|---|---|---|---|---|---|---|---|---|---|---|---|---|---|---|
| | | | | 165 | | | | | 170 | | | | | 175 | |

| Lys | Gly | Ile | Gln | Asp | Ala | Gly | Val | Val | Ala | Thr | Ala | Lys | His | Tyr | Ile |
|---|---|---|---|---|---|---|---|---|---|---|---|---|---|---|---|
| | | | 180 | | | | | 185 | | | | | 190 | | |

| Leu | Asn | Glu | Gln | Glu | His | Phe | Arg | Gln | Val | Ala | Glu | Ala | Gly | Tyr |
|---|---|---|---|---|---|---|---|---|---|---|---|---|---|---|
| | | 195 | | | | | 200 | | | | | 205 | | |

| Gly | Phe | Asn | Ile | Ser | Asp | Thr | Ile | Ser | Ser | Asn | Val | Asp | Asp | Lys | Thr |
|---|---|---|---|---|---|---|---|---|---|---|---|---|---|---|---|
| | 210 | | | | | 215 | | | | | 220 | | | | |

| Ile | His | Glu | Met | Tyr | Leu | Trp | Pro | Phe | Ala | Asp | Ala | Val | Arg | Ala | Gly |
|---|---|---|---|---|---|---|---|---|---|---|---|---|---|---|---|
| 225 | | | | | 230 | | | | | 235 | | | | | 240 |

| Val | Gly | Ala | Ile | Met | Cys | Ser | Tyr | Asn | Gln | Ile | Asn | Asn | Ser | Tyr | Gly |
|---|---|---|---|---|---|---|---|---|---|---|---|---|---|---|---|
| | | | | 245 | | | | | 250 | | | | | 255 | |

| Cys | Gln | Asn | Ser | Tyr | Thr | Leu | Asn | Lys | Leu | Leu | Lys | Ala | Glu | Leu | Gly |
|---|---|---|---|---|---|---|---|---|---|---|---|---|---|---|---|
| | | | 260 | | | | | 265 | | | | | 270 | | |

| Phe | Gln | Gly | Phe | Val | Met | Ser | Asp | Trp | Gly | Ala | His | His | Ser | Gly | Val |
|---|---|---|---|---|---|---|---|---|---|---|---|---|---|---|---|
| | | 275 | | | | | 280 | | | | | 285 | | | |

Gly Ser Ala Leu Ala Gly Leu Asp Met Ser Met Pro Gly Asp Ile Thr

```
              290                 295                 300
Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
                340                 345                 350

Pro Asn Phe Ser Ser Trp Thr Arg Asp Glu Tyr Gly Phe Lys Tyr Phe
                355                 360                 365

Tyr Pro Gln Glu Gly Pro Tyr Glu Lys Val Asn His Phe Val Asn Val
                370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
                420                 425                 430

Asn Gly Cys Ser Asp Arg Gly Cys Asp Asn Gly Thr Leu Ala Met Ala
                435                 440                 445

Trp Gly Ser Gly Thr Ala Glu Phe Pro Tyr Leu Val Thr Pro Glu Gln
450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile
                500                 505                 510

Ser Val Asp Gly Asn Glu Gly Asp Arg Asn Asn Leu Thr Leu Trp Lys
                515                 520                 525

Asn Gly Asp Asn Leu Ile Lys Ala Ala Ala Asn Asn Cys Asn Asn Thr
                530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
                580                 585                 590

Gly Ala Lys Ser Pro Phe Thr Trp Gly Lys Thr Arg Glu Ala Tyr Gly
                595                 600                 605

Asp Tyr Leu Val Arg Glu Leu Asn Asn Gly Asn Gly Ala Pro Gln Asp
                610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
                660                 665                 670

Ala Gln Val Ala Thr Glu Thr Gly Ala Ala Pro Thr Phe Gly Gln Val
                675                 680                 685

Gly Asn Ala Ser Asp Tyr Val Tyr Pro Glu Gly Leu Thr Arg Ile Ser
                690                 695                 700

Lys Phe Ile Tyr Pro Trp Leu Asn Ser Thr Asp Leu Lys Ala Ser Ser
705                 710                 715                 720
```

```
Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
    770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860

<210> SEQ ID NO 121
<211> LENGTH: 3294
<212> TYPE: DNA
<213> ORGANISM: Aspergillus oryzae

<400> SEQUENCE: 121
atgcgttcct ccccctcct ccgctccgcc gttgtggccg ccctgccggt gttggccctt      60
gccgctgatg caggtccac cgctactgg gactgctgca agccttcgtg cggctgggcc     120
aagaaggctc ccgtgaacca gcctgtcttt tcctgcaacg ccaacttcca gcgtatcacg     180
gacttcgacg ccaagtccgg ctgcgagccg ggcggtgtcg cctactcgtg cgccgaccag     240
accccatggg ctgtgaacga cgacttcgcg ctcggttttg ctgccaccct tattgccggc     300
agcaatgagg cgggctggtg ctgcgcctgc tacgagctca ccttcacatc cggtcctgtt     360
gctggcaaga gatggtcgt ccagtccacc agcactggcg gtgatcttgg cagcaaccac     420
ttcgatctca acatccccgg cggcggcgtc ggcatcttcg acggatgcac tccccagttc     480
ggtggtctgc ccgccagcg ctacggcggc atctcgtccc gcaacgagtg cgatcggttc     540
cccgacgccc tcaagcccgg ctgctactgg cgcttcgact ggttcaagaa cgccgacaat     600
ccgagcttca gcttccgtca ggtccagtgc ccagccgagc tcgtcgctcg accggatgc     660 cgccgcaacg acgacggcaa cttccctgcc gtccagatcc ccatgcgttc ctccccctc     720 ctccgctccg ccgttgtggc cgccctgccg gtgttggccc ttgccaagga tgatctcgcg     780
tactcccctc ctttctaccc ttcccatgg gcagatggtc agggtgaatg gcggaagta     840 tacaaacgcg ctgtagacat agtttcccag atgacgttga cagagaaagt caacttaacg     900 actgaacag gatggcaact agagaggtgt gttggacaaa ctggcagtgt cccagactc     960 aacatcccca gcttgtgttt gcaggatagt cctcttggta ttcgtttctc ggactacaat    1020
tcagctttcc ctgcgggtgt taatgtcgct gccacctggg acaagacgct cgcctacctt    1080
cgtggtcagg caatgggtga ggagttcagt gataagggta ttgacgttca gctgggtcct    1140
gctgctggcc ctctcggtgc tcatccggat ggcggtagaa actgggaagg tttctcacca    1200
gatccagccc tcaccggtgt acttttttgcg gagacgatta gggtattca agatgctggt    1260 gtcattgcga cagctaagca ttatatcatg aacgaacaag agcatttccg ccaacaaccc    1320
```

-continued

```
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gtcatgtgct cttacaacca aatcaacaac agctacggtt gcgagaatag cgaaactctg   1500
aacaagcttt tgaaggcgga gcttggtttc caaggcttcg tcatgagtga ttggaccgct   1560
catcacagcg gcgtaggcgc tgctttagca ggtctggata tgtcgatgcc cggtgatgtt   1620
accttcgata gtggtacgtc tttctgtggt gcaaacttga cggtcggtgt ccttaacggt   1680
acaatccccc aatggcgtgt tgatgacatg gctgtccgta tcatggccgc ttattacaag   1740
gttggccgcg acaccaaata caccctcccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acggtcgtgt caaccctggc gccaagtctc ctttcacttg gggcaagacc   2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
aactacggct gggaagactc caagtatatt cccgaaggcg ccacggatgg gtctgcccag   2940
ccccgttttgc ccgctagtgg tggtgccgga ggaaaccccg gtctgtacga ggatcttttc   3000
cgcgtctctg tgaaggtcaa gaacacgggc aatgtcgccg gtgatgaagt tcctcagctg   3060
tacgtttccc taggcggccc gaatgagccc aaggtggtac tgcgcaagtt tgagcgtatt   3120
cacttggccc cttcgcagga ggccgtgtgg acaacgaccc ttacccgtcg tgaccttgca   3180
aactgggacg tttcggctca ggactggacc gtcactcctt accccaagac gatctacgtt   3240
ggaaactcct cacggaaact gccgctccag gcctcgctgc ctaaggccca gtaa           3294
```

<210> SEQ ID NO 122
<211> LENGTH: 1097
<212> TYPE: PRT
<213> ORGANISM: Aspergillus oryzae

<400> SEQUENCE: 122

Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys

-continued

```
                20                  25                  30
Cys Lys Pro Ser Cys Gly Trp Ala Lys Lys Ala Pro Val Asn Gln Pro
                35                  40                  45
Val Phe Ser Cys Asn Ala Asn Phe Gln Arg Ile Thr Asp Phe Asp Ala
 50                  55                  60
Lys Ser Gly Cys Glu Pro Gly Val Ala Tyr Ser Cys Ala Asp Gln
 65                  70                  75                  80
Thr Pro Trp Ala Val Asn Asp Asp Phe Ala Leu Gly Phe Ala Ala Thr
                85                  90                  95
Ser Ile Ala Gly Ser Asn Glu Ala Gly Trp Cys Cys Ala Cys Tyr Glu
                100                 105                 110
Leu Thr Phe Thr Ser Gly Pro Val Ala Gly Lys Lys Met Val Val Gln
                115                 120                 125
Ser Thr Ser Thr Gly Gly Asp Leu Gly Ser Asn His Phe Asp Leu Asn
                130                 135                 140
Ile Pro Gly Gly Gly Val Gly Ile Phe Asp Gly Cys Thr Pro Gln Phe
145                 150                 155                 160
Gly Gly Leu Pro Gly Gln Arg Tyr Gly Gly Ile Ser Ser Arg Asn Glu
                165                 170                 175
Cys Asp Arg Phe Pro Asp Ala Leu Lys Pro Gly Cys Tyr Trp Arg Phe
                180                 185                 190
Asp Trp Phe Lys Asn Ala Asp Asn Pro Ser Phe Ser Phe Arg Gln Val
                195                 200                 205
Gln Cys Pro Ala Glu Leu Val Ala Arg Thr Gly Cys Arg Arg Asn Asp
                210                 215                 220
Asp Gly Asn Phe Pro Ala Val Gln Ile Pro Met Arg Ser Ser Pro Leu
225                 230                 235                 240
Leu Arg Ser Ala Val Val Ala Ala Leu Pro Val Leu Ala Leu Ala Lys
                245                 250                 255
Asp Asp Leu Ala Tyr Ser Pro Pro Phe Tyr Pro Ser Pro Trp Ala Asp
                260                 265                 270
Gly Gln Gly Glu Trp Ala Glu Val Tyr Lys Arg Ala Val Asp Ile Val
                275                 280                 285
Ser Gln Met Thr Leu Thr Glu Lys Val Asn Leu Thr Thr Gly Thr Gly
                290                 295                 300
Trp Gln Leu Glu Arg Cys Val Gly Gln Thr Gly Ser Val Pro Arg Leu
305                 310                 315                 320
Asn Ile Pro Ser Leu Cys Leu Gln Asp Ser Pro Leu Gly Ile Arg Phe
                325                 330                 335
Ser Asp Tyr Asn Ser Ala Phe Pro Ala Gly Val Asn Val Ala Ala Thr
                340                 345                 350
Trp Asp Lys Thr Leu Ala Tyr Leu Arg Gly Gln Ala Met Gly Glu Glu
                355                 360                 365
Phe Ser Asp Lys Gly Ile Asp Val Gln Leu Gly Pro Ala Ala Gly Pro
                370                 375                 380
Leu Gly Ala His Pro Asp Gly Gly Arg Asn Trp Glu Gly Phe Ser Pro
385                 390                 395                 400
Asp Pro Ala Leu Thr Gly Val Leu Phe Ala Glu Thr Ile Lys Gly Ile
                405                 410                 415
Gln Asp Ala Gly Val Ile Ala Thr Ala Lys His Tyr Ile Met Asn Glu
                420                 425                 430
Gln Glu His Phe Arg Gln Pro Glu Ala Ala Gly Tyr Gly Phe Asn
                435                 440                 445
```

```
Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
            485                 490                 495

Ser Glu Thr Leu Asn Lys Leu Leu Lys Ala Glu Leu Gly Phe Gln Gly
        500                 505                 510

Phe Val Met Ser Asp Trp Thr Ala His His Ser Gly Val Gly Ala Ala
    515                 520                 525

Leu Ala Gly Leu Asp Met Ser Met Pro Gly Asp Val Thr Phe Asp Ser
530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Arg Gln Ala Ser Val Ser
                725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Asn Cys Asn Asn Thr Val Val Ile
770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
            820                 825                 830

Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
    850                 855                 860
```

```
Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
            885                 890                 895

Ser Asp Leu His Val Gln Pro Leu Asn Ala Ser Arg Tyr Thr Pro Thr
        900                 905                 910

Ser Gly Met Thr Glu Ala Ala Lys Asn Phe Gly Glu Ile Gly Asp Ala
            915                 920                 925

Ser Glu Tyr Val Tyr Pro Glu Gly Leu Glu Arg Ile His Glu Phe Ile
        930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
            965                 970                 975

Gly Ser Ala Gln Pro Arg Leu Pro Ala Ser Gly Ala Gly Gly Asn
        980                 985                 990

Pro Gly Leu Tyr Glu Asp Leu Phe Arg Val Ser Val Lys Val Lys Asn
            995                1000                1005

Thr Gly Asn Val Ala Gly Asp Glu Val Pro Gln Leu Tyr Val Ser
    1010                1015                1020

Leu Gly Gly Pro Asn Glu Pro Lys Val Val Leu Arg Lys Phe Glu
    1025                1030                1035

Arg Ile His Leu Ala Pro Ser Gln Glu Ala Val Trp Thr Thr Thr
    1040                1045                1050

Leu Thr Arg Arg Asp Leu Ala Asn Trp Asp Val Ser Ala Gln Asp
    1055                1060                1065

Trp Thr Val Thr Pro Tyr Pro Lys Thr Ile Tyr Val Gly Asn Ser
    1070                1075                1080

Ser Arg Lys Leu Pro Leu Gln Ala Ser Leu Pro Lys Ala Gln
    1085                1090                1095

<210> SEQ ID NO 123
<211> LENGTH: 3294
<212> TYPE: DNA
<213> ORGANISM: Aspergillus oryzae

<400> SEQUENCE: 123
atgcgttcct cccccctcct ccgctccgcc gttgtggccg ccctgccggt gttggccctt    60
gccgctgatg caggtccacc cgctactggg gactgctgca agccttcgtg cggctgggcc   120
aagaaggctc ccgtgaacca gcctgtcttt tcctgcaacg ccaacttcca gcgtatcacg   180
gacttcgacg ccaagtccgg ctgcgagccg ggcggtgtcg cctactcgtg cgccgaccag   240 acccatggg ctgtgaacga cgacttcgcg ctcggttttg ctgccacctc tattgccggc   300
agcaatgagg cgggctggtg ctgcgcctgc tacgagctca ccttcacatc cggtcctgtt   360
gctggcaaga gatggtcgt ccagtccacc agcactggcg gtgatcttgg cagcaaccac   420
ttcgatctca acatccccgg cggcggcgtc ggcatcttcg acggatgcac tccccagttc   480
ggtggtctgc ccggccagcg ctacggcggc atctcgtccc gcaacgagtg cgatcggttc   540
cccgacgccc tcaagcccgg ctgctactgg cgcttcgact ggttcaagaa cgccgacaat   600
ccgagcttca gcttccgtca ggtccagtgc ccagccgagc tcgtcgctcg caccggatgc   660
cgccgcaacg acgacggcaa cttccctgcc gtccagatcc ccatgcgttc ctccccccctc   720 ctccgctccg ccgttgtggc cgccctgccg gtgttggccc ttgccaagga tgatctcgcg   780
```

```
tactcccctc ctttctaccc ttccccatgg gcagatggtc agggtgaatg ggcggaagta    840
tacaaacgcg ctgtagacat agtttcccag atgacgttga cagagaaagt caacttaacg    900
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaaag tttctcacca   1200
gatccagccc tcaccggtgt acttttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gttatgtgct cttacaacca aatcaacaac agctacggtt gcgagaatag cgaaactctg   1500
aacaagcttt tgaaggcgga gcttggtttc caaggcttcg tcatgagtga ttggaccgct   1560
caacacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata caccccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acggtcgtgt caaccctggc gccaagtctc ctttcacttg gggcaagacc   2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
aactacggct gggaagactc caagtatatt cccgaaggcg ccacggatgg gtctgcccag   2940
ccccgtttgc ccgctagtgg tggtgccgga ggaaacccccg gtctgtacga ggatctttctc   3000 cgcgtctctg tgaaggtcaa gaacacgggc aatgtcgccg gtgatgaagt tcctcagctg   3060
tacgtttccc taggcggccc gaatgagccc aaggtggtac tgcgcaagtt tgagcgtatt   3120
cacttggccc cttcgcagga ggccgtgtgg acaacgaccc ttacccgtcg tgaccttgca   3180
```

```
aactgggacg tttcggctca ggactggacc gtcactcctt accccaagac gatctacgtt    3240
ggaaactcct cacggaaact gccgctccag gcctcgctgc ctaaggccca gtaa           3294
```

<210> SEQ ID NO 124
<211> LENGTH: 1097
<212> TYPE: PRT
<213> ORGANISM: Aspergillus oryzae

<400> SEQUENCE: 124

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350
```

```
Trp Asp Lys Thr Leu Ala Tyr Leu Arg Gly Gln Ala Met Gly Glu Glu
            355                 360                 365

Phe Ser Asp Lys Gly Ile Asp Val Gln Leu Gly Pro Ala Ala Gly Pro
        370                 375                 380

Leu Gly Ala His Pro Asp Gly Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala Gln His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Arg Gln Ala Ser Val Ser
                725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Asn Cys Asn Asn Thr Val Val Ile
```

```
                770             775             780
Ile His Ser Val Gly Pro Val Leu Ile Asp Glu Trp Tyr Asp His Pro
785             790             795             800

Asn Val Thr Gly Ile Leu Trp Ala Gly Leu Pro Gly Gln Glu Ser Gly
            805             810             815

Asn Ser Ile Ala Asp Val Leu Tyr Gly Arg Val Asn Pro Gly Ala Lys
            820             825             830

Ser Pro Phe Thr Trp Gly Lys Thr Arg Glu Ser Tyr Gly Ser Pro Leu
            835             840             845

Val Lys Asp Ala Asn Asn Gly Asn Gly Ala Pro Gln Ser Asp Phe Thr
            850             855             860

Gln Gly Val Phe Ile Asp Tyr Arg His Phe Asp Lys Phe Asn Glu Thr
865             870             875             880

Pro Ile Tyr Glu Phe Gly Tyr Gly Leu Ser Tyr Thr Thr Phe Glu Leu
            885             890             895

Ser Asp Leu His Val Gln Pro Leu Asn Ala Ser Arg Tyr Thr Pro Thr
            900             905             910

Ser Gly Met Thr Glu Ala Ala Lys Asn Phe Gly Glu Ile Gly Asp Ala
            915             920             925

Ser Glu Tyr Val Tyr Pro Glu Gly Leu Glu Arg Ile His Glu Phe Ile
            930             935             940

Tyr Pro Trp Ile Asn Ser Thr Asp Leu Lys Ala Ser Ser Asp Asp Ser
945             950             955             960

Asn Tyr Gly Trp Glu Asp Ser Lys Tyr Ile Pro Glu Gly Ala Thr Asp
            965             970             975

Gly Ser Ala Gln Pro Arg Leu Pro Ala Ser Gly Gly Ala Gly Gly Asn
            980             985             990

Pro Gly Leu Tyr Glu Asp Leu Phe Arg Val Ser Val Lys Val Lys Asn
            995             1000            1005

Thr Gly Asn Val Ala Gly Asp Glu Val Pro Gln Leu Tyr Val Ser
        1010            1015            1020

Leu Gly Gly Pro Asn Glu Pro Lys Val Val Leu Arg Lys Phe Glu
        1025            1030            1035

Arg Ile His Leu Ala Pro Ser Gln Glu Ala Val Trp Thr Thr Thr
        1040            1045            1050

Leu Thr Arg Arg Asp Leu Ala Asn Trp Asp Val Ser Ala Gln Asp
        1055            1060            1065

Trp Thr Val Thr Pro Tyr Pro Lys Thr Ile Tyr Val Gly Asn Ser
        1070            1075            1080

Ser Arg Lys Leu Pro Leu Gln Ala Ser Leu Pro Lys Ala Gln
        1085            1090            1095

<210> SEQ ID NO 125
<211> LENGTH: 20
<212> TYPE: DNA
<213> ORGANISM: Thermoascus aurantiacus
<220> FEATURE:
<221> NAME/KEY: misc_feature
<222> LOCATION: (3)..(3)
<223> OTHER INFORMATION: Y=T OR C
<220> FEATURE:
<221> NAME/KEY: misc_feature
<222> LOCATION: (6)..(6)
<223> OTHER INFORMATION: R=A OR G
<220> FEATURE:
<221> NAME/KEY: misc_feature
<222> LOCATION: (9)..(9)
<223> OTHER INFORMATION: n is a, c, g, or t
```

```
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 125
aaygartcng gngcngaatt                                        20

<210> SEQ ID NO 126
<211> LENGTH: 20
<212> TYPE: DNA
<213> ORGANISM: Thermoascus aurantiacus
<220> FEATURE:
<221> NAME/KEY: misc_feature
<222> LOCATION: (3)..(3)
<223> OTHER INFORMATION: Y=T OR C
<220> FEATURE:
<221> NAME/KEY: misc_feature
<222> LOCATION: (6)..(6)
<223> OTHER INFORMATION: R=A OR G
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 126
aaygartcng gngcngagtt                                        20

<210> SEQ ID NO 127
<211> LENGTH: 20
<212> TYPE: DNA
<213> ORGANISM: Thermoascus aurantiacus
<220> FEATURE:
<221> NAME/KEY: misc_feature
<222> LOCATION: (3)..(3)
<223> OTHER INFORMATION: Y=T OR C
<220> FEATURE:
<221> NAME/KEY: misc_feature
<222> LOCATION: (6)..(6)
<223> OTHER INFORMATION: R=A OR G
<220> FEATURE:
<221> NAME/KEY: misc_feature
<222> LOCATION: (9)..(9)
<223> OTHER INFORMATION: Y=T OR C
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 127
aaygaragyg gngcngaatt                                        20

<210> SEQ ID NO 128
<211> LENGTH: 20
<212> TYPE: DNA
<213> ORGANISM: Thermoascus aurantiacus
<220> FEATURE:
```

```
<221> NAME/KEY: misc_feature
<222> LOCATION: (3)..(3)
<223> OTHER INFORMATION: Y=T OR C
<220> FEATURE:
<221> NAME/KEY: misc_feature
<222> LOCATION: (6)..(6)
<223> OTHER INFORMATION: R=A OR G
<220> FEATURE:
<221> NAME/KEY: misc_feature
<222> LOCATION: (9)..(9)
<223> OTHER INFORMATION: Y=T OR C
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 128
aaygaragyg gngcngagtt                                              20

<210> SEQ ID NO 129
<211> LENGTH: 26
<212> TYPE: DNA
<213> ORGANISM: Thermoascus aurantiacus

<400> SEQUENCE: 129
gatctcatga agctcggctc tctcgt                                       26

<210> SEQ ID NO 130
<211> LENGTH: 32
<212> TYPE: DNA
<213> ORGANISM: Thermoascus aurantiacus

<400> SEQUENCE: 130
ttaattaatc aaagatacgg agtcaaaata gg                                32

<210> SEQ ID NO 131
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M, OR V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X=E OR Q
<220> FEATURE:
<221> NAME/KEY: misc_feature
```

<222> LOCATION: (15)..(18)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X=H,N, OR Q

<400> SEQUENCE: 131

Xaa Pro Xaa Xaa Xaa Xaa Gly Xaa Tyr Xaa Xaa Arg Xaa Xaa Xaa Xaa
1               5                   10                  15

Xaa Xaa Xaa

<210> SEQ ID NO 132
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,M, OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X=H,N, OR Q

<400> SEQUENCE: 132

Xaa Pro Xaa Xaa Xaa Xaa Xaa Gly Xaa Tyr Xaa Xaa Arg Xaa Xaa Xaa
1               5                   10                  15

Xaa Xaa Xaa Xaa
            20

<210> SEQ ID NO 133
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE

```
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 133

His Xaa Gly Pro Xaa Xaa Xaa Xaa Xaa
1               5

<210> SEQ ID NO 134
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= Y OR W

<400> SEQUENCE: 134

His Xaa Xaa Gly Pro Xaa Xaa Xaa Xaa Xaa
1               5                   10

<210> SEQ ID NO 135
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 135
```

```
Xaa Xaa Tyr Xaa Xaa Cys Xaa Xaa Xaa Xaa
1               5                   10
```

<210> SEQ ID NO 136
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 136

```
His Xaa Gly Pro Xaa Xaa Xaa Xaa Xaa
1               5
```

<210> SEQ ID NO 137
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 137

```
His Xaa Xaa Gly Pro Xaa Xaa Xaa Xaa Xaa
1               5                   10
```

<210> SEQ ID NO 138
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:

```
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 138

Xaa Xaa Tyr Xaa Xaa Cys Xaa Xaa Xaa Xaa Xaa
1               5                   10

<210> SEQ ID NO 139
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 139

His Xaa Gly Pro Xaa Xaa Xaa Xaa Xaa
1               5

<210> SEQ ID NO 140
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 140

His Xaa Xaa Gly Pro Xaa Xaa Xaa Xaa Xaa
1               5                   10

<210> SEQ ID NO 141
<211> LENGTH: 11
<212> TYPE: PRT
```

```
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 141

Xaa Xaa Tyr Xaa Xaa Cys Xaa Xaa Xaa Xaa Xaa
1               5                   10

<210> SEQ ID NO 142
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 142

His Xaa Gly Pro Xaa Xaa Xaa Xaa Xaa
1               5

<210> SEQ ID NO 143
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
```

-continued

```
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 143

His Xaa Xaa Gly Pro Xaa Xaa Xaa Xaa Xaa
1               5                   10

<210> SEQ ID NO 144
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 144

Xaa Xaa Tyr Xaa Xaa Cys Xaa Xaa Xaa Xaa Xaa
1               5                   10

<210> SEQ ID NO 145
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M OR V
<220> FEATURE:
```

```
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X= E OR Q
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X= H,N, OR Q

<400> SEQUENCE: 145

Xaa Pro Xaa Xaa Xaa Xaa Gly Xaa Tyr Xaa Xaa Arg Xaa Xaa Xaa Xaa
1               5                   10                  15

Xaa Ala Xaa

<210> SEQ ID NO 146
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,M OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X= H,N, OR Q

<400> SEQUENCE: 146

Xaa Pro Xaa Xaa Xaa Xaa Xaa Gly Xaa Tyr Xaa Xaa Arg Xaa Xaa Xaa
1               5                   10                  15

Xaa Xaa Ala Xaa
            20

<210> SEQ ID NO 147
```

```
<211> LENGTH: 1035
<212> TYPE: DNA
<213> ORGANISM: Aspergillus aculeatus

<400> SEQUENCE: 147
atgaagtata ttcctctcgt tattgcagtt gctgccggcc tggcacgtcc ggctactgcc      60
cactacatct tcagcaagct cgtgctgaac ggagaggcat ctgcggactg gcaatacatc     120
cgcgagacta ctcgcagcat agtctatgag ccgaccaagt acacctctac cttcgataac     180
ctaacaccca gcgatagcga cttccgctgt aatctcggtt ccttcagcaa tgctgcgaag     240
accgaggtcg ctgaggttgc ggcaggcgat accatcgcaa tgaagctatt ctacgacacc     300
agtattgcgc atcctggccc gggacaagtt tatatgtcca aggcaccgac cggcaatgtt     360
caggaatacc aaggagacgg ggattggttc aaaatctggg aaaagaccct ttgcaacacg     420
gatggtgatc tgactacaga ggcctggtgc acctggggca tgtcacagtt tgaatttcaa     480
atcccagctg cgaccccggc aggagagtac ctagtgcgcg ccgagcatat aggcctgcat     540
ggcgctcaag cgaacgaggc cgaattcttc tacagctgtg cgcagatcaa ggttacaggc     600
tcgggaactg gatctcccag tctcacgtat caaattcctg gtctctataa cgacactatg     660
accctgttca atggcctcaa tctttggact gattcagccg agaaggtgca gctggatttc     720
ctggagacgc caattgggga cgacgtgtgg agcggagcag gctcggggag cccatctgct     780
gccacctctt cgaccagcgg tgcaactctt gcagctcagg gtacaactac ctctgccgcg     840
catgctcagg cccagaccac cattaccacc agcaccagca ccatcacgtc tctcgaatca     900
gccagctcaa ccgatctcgt tgcgcagtat ggtcagtgcg gaggccttaa ctggtccggt     960
ccaaccgagt gtgagacacc ttatacctgt gtgcagcaga acccttacta ccatcaatgc    1020
gtgaattcgt gctga                                                      1035

<210> SEQ ID NO 148
<211> LENGTH: 344
<212> TYPE: PRT
<213> ORGANISM: Aspergillus aculeatus

<400> SEQUENCE: 148

Met Lys Tyr Ile Pro Leu Val Ile Ala Val Ala Ala Gly Leu Ala Arg
1               5                   10                  15

Pro Ala Thr Ala His Tyr Ile Phe Ser Lys Leu Val Leu Asn Gly Glu
            20                  25                  30

Ala Ser Ala Asp Trp Gln Tyr Ile Arg Glu Thr Thr Arg Ser Ile Val
        35                  40                  45

Tyr Glu Pro Thr Lys Tyr Thr Ser Thr Phe Asp Asn Leu Thr Pro Ser
    50                  55                  60

Asp Ser Asp Phe Arg Cys Asn Leu Gly Ser Phe Ser Asn Ala Ala Lys
65                  70                  75                  80

Thr Glu Val Ala Glu Val Ala Ala Gly Asp Thr Ile Ala Met Lys Leu
                85                  90                  95

Phe Tyr Asp Thr Ser Ile Ala His Pro Gly Pro Gly Gln Val Tyr Met
            100                 105                 110

Ser Lys Ala Pro Thr Gly Asn Val Gln Glu Tyr Gln Gly Asp Gly Asp
        115                 120                 125

Trp Phe Lys Ile Trp Glu Lys Thr Leu Cys Asn Thr Asp Gly Asp Leu
    130                 135                 140

Thr Thr Glu Ala Trp Cys Thr Trp Gly Met Ser Gln Phe Glu Phe Gln
145                 150                 155                 160
```

```
Ile Pro Ala Ala Thr Pro Ala Gly Glu Tyr Leu Val Arg Ala Glu His
                165                 170                 175
Ile Gly Leu His Gly Ala Gln Ala Asn Glu Ala Glu Phe Phe Tyr Ser
            180                 185                 190
Cys Ala Gln Ile Lys Val Thr Gly Ser Gly Thr Gly Ser Pro Ser Leu
        195                 200                 205
Thr Tyr Gln Ile Pro Gly Leu Tyr Asn Asp Thr Met Thr Leu Phe Asn
    210                 215                 220
Gly Leu Asn Leu Trp Thr Asp Ser Ala Glu Lys Val Gln Leu Asp Phe
225                 230                 235                 240
Leu Glu Thr Pro Ile Gly Asp Asp Val Trp Ser Gly Ala Gly Ser Gly
                245                 250                 255
Ser Pro Ser Ala Ala Thr Ser Ser Thr Ser Gly Ala Thr Leu Ala Ala
                260                 265                 270
Gln Gly Thr Thr Thr Ser Ala Ala His Ala Gln Ala Gln Thr Thr Ile
            275                 280                 285
Thr Thr Ser Thr Ser Thr Ile Thr Ser Leu Glu Ser Ala Ser Ser Thr
        290                 295                 300
Asp Leu Val Ala Gln Tyr Gly Gln Cys Gly Gly Leu Asn Trp Ser Gly
305                 310                 315                 320
Pro Thr Glu Cys Glu Thr Pro Tyr Thr Cys Val Gln Gln Asn Pro Tyr
                325                 330                 335
Tyr His Gln Cys Val Asn Ser Cys
            340

<210> SEQ ID NO 149
<211> LENGTH: 1170
<212> TYPE: DNA
<213> ORGANISM: Aspergillus aculeatus

<400> SEQUENCE: 149
atgaagtcct ctactttcgg tatgctcgct ctggcagcag cagccaagat ggtcgatgcc      60
cacaccaccg tcttcgccgt ctggatcaac ggcgaggacc agggtctggg caacagtgcc     120
agtggctaca tccggtctcc ccccagcaac agccccgtca aggacgtgac ctcgaccgac     180
atcacctgca acgtcaacgg cgaccaggcg gcggctaaga ccctctccgt caagggcggc     240
gacgtcgtca ccttcgagtg gcaccacgac agccgggacg cctccgacga catcatcgcc     300
tcctcccaca agggccccgt catggtctac atggccccga ccaccgccgg cagcagcggc     360
aagaactggg tcaagatcgc cgaggacgga tactccgacg gcacctgggc cgtcgacacc     420
ctgatcgcca acagcggcaa gcacaacatc accgtccccg acgtccccgc cggcgactac     480
ctcttccgcc cggagatcat cgccctccac gaggccgaga cgagggcgg cgcccagttc     540 tacatggagt gtgtccagtt caaggtcacc tccgacggtg ccaacactct gcccgacggt     600
gtcagcctgc ccggcgccta ctccgccact gaccccggta tcctcttcaa catgtacggc     660
tccttcgaca gctatcccat ccccggtccc tccgtctggg atggcactag ctctggctct     720
tcctcttctt cctcttcttc ctcttccagc tcttccgccg ccgctgccgt tgttgccacc     780
tcctcttcct cttcctctgc ttccatcgag gccgtgacca ccaagggtgc cgtcgccgcc     840
gtctccaccg ccgccgccgt ggctcctacc accaccaccg ctgcccccac caccttcgcc     900
acggccgtcg cctccaccaa gaaggccact gcctgccgca acaagaccaa gtcctcctcc     960
gctgccacca ccgccgccgc cgtcgccgag accacctctt ccaccgctgc cgccaccgct    1020
```

```
gctgcttcct ctgcctcttc cgcctccggc accgccggca agtacgagcg ctgcggtggc    1080
cagggctgga ccggtgccac cacctgcgtt gatggctgga cctgcaagca gtggaaccct    1140
tactactacc agtgcgttga gtctgcctag                                      1170
```

<210> SEQ ID NO 150
<211> LENGTH: 389
<212> TYPE: PRT
<213> ORGANISM: Aspergillus aculeatus

<400> SEQUENCE: 150

```
Met Lys Ser Ser Thr Phe Gly Met Leu Ala Leu Ala Ala Ala Lys
1               5                   10                  15

Met Val Asp Ala His Thr Thr Val Phe Ala Val Trp Ile Asn Gly Glu
            20                  25                  30

Asp Gln Gly Leu Gly Asn Ser Ala Ser Gly Tyr Ile Arg Ser Pro Pro
        35                  40                  45

Ser Asn Ser Pro Val Lys Asp Val Thr Ser Thr Asp Ile Thr Cys Asn
    50                  55                  60

Val Asn Gly Asp Gln Ala Ala Lys Thr Leu Ser Val Lys Gly Gly
65                  70                  75                  80

Asp Val Val Thr Phe Glu Trp His His Asp Ser Arg Asp Ala Ser Asp
                85                  90                  95

Asp Ile Ile Ala Ser Ser His Lys Gly Pro Val Met Val Tyr Met Ala
            100                 105                 110

Pro Thr Thr Ala Gly Ser Ser Gly Lys Asn Trp Val Lys Ile Ala Glu
        115                 120                 125

Asp Gly Tyr Ser Asp Gly Thr Trp Ala Val Asp Thr Leu Ile Ala Asn
    130                 135                 140

Ser Gly Lys His Asn Ile Thr Val Pro Asp Val Pro Ala Gly Asp Tyr
145                 150                 155                 160

Leu Phe Arg Pro Glu Ile Ile Ala Leu His Glu Ala Glu Asn Glu Gly
                165                 170                 175

Gly Ala Gln Phe Tyr Met Glu Cys Val Gln Phe Lys Val Thr Ser Asp
            180                 185                 190

Gly Ala Asn Thr Leu Pro Asp Gly Val Ser Leu Pro Gly Ala Tyr Ser
        195                 200                 205

Ala Thr Asp Pro Gly Ile Leu Phe Asn Met Tyr Gly Ser Phe Asp Ser
    210                 215                 220

Tyr Pro Ile Pro Gly Pro Ser Val Trp Asp Gly Thr Ser Ser Gly Ser
225                 230                 235                 240

Ser Ser Ser Ser Ser Ser Ser Ser Ser Ser Ala Ala Ala
                245                 250                 255

Val Val Ala Thr Ser Ser Ser Ser Ser Ala Ser Ile Glu Ala Val
            260                 265                 270

Thr Thr Lys Gly Ala Val Ala Ala Val Ser Thr Ala Ala Val Ala
        275                 280                 285

Pro Thr Thr Thr Thr Ala Ala Pro Thr Thr Phe Ala Thr Val Ala
    290                 295                 300

Ser Thr Lys Lys Ala Thr Ala Cys Arg Asn Lys Thr Lys Ser Ser Ser
305                 310                 315                 320

Ala Ala Thr Thr Ala Ala Ala Val Ala Glu Thr Thr Ser Ser Thr Ala
                325                 330                 335

Ala Ala Thr Ala Ala Ala Ser Ser Ala Ser Ser Ala Ser Gly Thr Ala
            340                 345                 350
```

Gly Lys Tyr Glu Arg Cys Gly Gly Gln Gly Trp Thr Gly Ala Thr Thr
            355                 360                 365

Cys Val Asp Gly Trp Thr Cys Lys Gln Trp Asn Pro Tyr Tyr Tyr Gln
        370                 375                 380

Cys Val Glu Ser Ala
385

<210> SEQ ID NO 151
<211> LENGTH: 1221
<212> TYPE: DNA
<213> ORGANISM: Aspergillus aculeatus

<400> SEQUENCE: 151

```
atgcgtcagg ctcagtcttt gtccctcttg acagctcttc tgtctgccac gcgtgtggct      60
ggacacggtc acgtcactaa cgttgtcgtc aacggtgttt actacgaggg cttcgatatc     120
aacagcttcc cctacgagtc cgatccccct aaggtggcgg cttggaccac tcctaacact     180
ggcaacggtt tcatttcccc cagcgactac ggtaccgatg acattatttg ccaccagaat     240
gccaccaacg cccaggccca cattgttgtt gcggctggtg acaagatcaa catccagtgg     300
accgcgtggc ccgattccca ccacggtcct gtccttgact acctcgctcg ctgcgacggt     360
gagtgtgaga cggttgataa gaccactctt gagtttttca agatcgacgg cgtcggtctc     420
atcagtgaca ccgaagtgcc cggtacctgg ggagatgacc agctgatcgc aacaacaac      480
agctggttgg tcgagatccc cccgaccatt gctcctggca actatgttct cgccacgag      540
cttatcgctc tccacagcgc cggcactgaa atggtgctc agaactaccc ccagtgtttc      600
aacctccagg tcactggctc cggtactgac gagcccgctg gtaccctcgg caccaagctc     660
tacactgagg atgaggctgg tatcgttgtg aacatctaca cctctctgtc ttcctatgcc     720
gtccccggcc ccacccagta cagcggcgcc gtctctgtca gccaatccac ttcggccatt     780
acctccaccg gaactgctgt tgtcggtagc ggcagcgctc ttgccacctc tgccgccgcg     840
gctaccacca gcgctgctgc ttcttctgcc gctgctgcta ccaccgctgc tgccgttacc     900
agcgccaatg ccaacactca gattgcccag cccagcagca gctcttctta ctcccagatc     960
gccgtgcagg tgcctcctc ctggaccacc cttgtgaccg tcactcctcc cgccgccgcc    1020
gccaccaccc ctgctgccgt ccctgagcct cagacccct ctgccagctc tggagccacc    1080
actaccagca gcagcagcgg cgccgcccag tctctctacg ccagtgcgg tggtatcaac    1140
tggaccggag ctacctcttg cgttgagggc gctacttgct accagtacaa cccttactac    1200
taccagtgca tctctgccta a                                              1221
```

<210> SEQ ID NO 152
<211> LENGTH: 406
<212> TYPE: PRT
<213> ORGANISM: Aspergillus aculeatus

<400> SEQUENCE: 152

Met Arg Gln Ala Gln Ser Leu Ser Leu Leu Thr Ala Leu Leu Ser Ala
1               5                   10                  15

Thr Arg Val Ala Gly His Gly His Val Thr Asn Val Val Asn Gly
            20                  25                  30

Val Tyr Tyr Glu Gly Phe Asp Ile Asn Ser Phe Pro Tyr Glu Ser Asp
        35                  40                  45

Pro Pro Lys Val Ala Ala Trp Thr Thr Pro Asn Thr Gly Asn Gly Phe
    50                  55                  60

```
Ile Ser Pro Ser Asp Tyr Gly Thr Asp Asp Ile Ile Cys His Gln Asn
 65                  70                  75                  80

Ala Thr Asn Ala Gln Ala His Ile Val Val Ala Ala Gly Asp Lys Ile
                 85                  90                  95

Asn Ile Gln Trp Thr Ala Trp Pro Asp Ser His His Gly Pro Val Leu
            100                 105                 110

Asp Tyr Leu Ala Arg Cys Asp Gly Glu Cys Glu Thr Val Asp Lys Thr
        115                 120                 125

Thr Leu Glu Phe Phe Lys Ile Asp Gly Val Gly Leu Ile Ser Asp Thr
130                 135                 140

Glu Val Pro Gly Thr Trp Gly Asp Gln Leu Ile Ala Asn Asn Asn
145                 150                 155                 160

Ser Trp Leu Val Glu Ile Pro Pro Thr Ile Ala Pro Gly Asn Tyr Val
                165                 170                 175

Leu Arg His Glu Leu Ile Ala Leu His Ser Ala Gly Thr Glu Asp Gly
            180                 185                 190

Ala Gln Asn Tyr Pro Gln Cys Phe Asn Leu Gln Val Thr Gly Ser Gly
        195                 200                 205

Thr Asp Glu Pro Ala Gly Thr Leu Gly Thr Lys Leu Tyr Thr Glu Asp
210                 215                 220

Glu Ala Gly Ile Val Val Asn Ile Tyr Thr Ser Leu Ser Ser Tyr Ala
225                 230                 235                 240

Val Pro Gly Pro Thr Gln Tyr Ser Gly Ala Val Ser Val Ser Gln Ser
                245                 250                 255

Thr Ser Ala Ile Thr Ser Thr Gly Thr Ala Val Val Gly Ser Gly Ser
            260                 265                 270

Ala Val Ala Thr Ser Ala Ala Ala Thr Thr Ser Ala Ala Ala Ser
        275                 280                 285

Ser Ala Ala Ala Ala Thr Thr Ala Ala Ala Val Thr Ser Ala Asn Ala
290                 295                 300

Asn Thr Gln Ile Ala Gln Pro Ser Ser Ser Ser Tyr Ser Gln Ile
305                 310                 315                 320

Ala Val Gln Val Pro Ser Ser Trp Thr Thr Leu Val Thr Val Thr Pro
                325                 330                 335

Pro Ala Ala Ala Thr Thr Pro Ala Ala Val Pro Glu Pro Gln Thr
            340                 345                 350

Pro Ser Ala Ser Ser Gly Ala Thr Thr Thr Ser Ser Ser Gly Ala
        355                 360                 365

Ala Gln Ser Leu Tyr Gly Gln Cys Gly Gly Ile Asn Trp Thr Gly Ala
370                 375                 380

Thr Ser Cys Val Glu Gly Ala Thr Cys Tyr Gln Tyr Asn Pro Tyr Tyr
385                 390                 395                 400

Tyr Gln Cys Ile Ser Ala
                405

<210> SEQ ID NO 153
<211> LENGTH: 1284
<212> TYPE: DNA
<213> ORGANISM: Aspergillus aculeatus

<400> SEQUENCE: 153
atgtctcttt ccaagattgc cactcttctg ctgggctcgg tctcgctggt cgctggtcat    60
gggtatgtct cgagcatcga ggtggacggt accacctatg agggtacttg gtcgacact    120
```

-continued

```
tattactacg aatccgaccc gcccgagtta atcgcctggt ccacaaatgc cacggatgat    180
ggctatgtat cgccctccga ctacgagagc gtgaacatca tctgccacaa ggggtctgcg    240
cccggcgcgt tgtcggcccc tgtcgcgccc ggaggctggg tgcagatgac ctggaacacc    300
tggcccaccg accatcacgg ccctgtcatc acgtatatgg ccaattgcca cggttcttgc    360
gcagatgtgg acaagaccac cctcgagttc ttcaagatcg atgctggcgg cttgatcgat    420
gacacggacg tgcctggaac ttgggcgacc gatgagctca ttgaagatag ctatagtcgc    480
aacatcacta tccccagcga tattgccccc gggtactatg ttttgcgaca cgagatcatt    540
gctctgcaca gcgccgagaa cctggacgga gcccagaact accccagtg catcaatctg    600
gaagtcaccg gcagcgagac agcaaccccg agtggcacct gggcactgc tctgtacaag    660
gagaccgacc ccggcatcta tgttgacatc tggaacacgt tgagcacgta actattccc    720
ggccccgcgc tgtacactgc tggtagcact gcgaccgcag ccgctgctgc cgataccacc    780
actacttctg ctggcaccac cgctgaggcc accaccgctg ccgccgccgt gagtaccacc    840
gcggacgctg ttccgaccga gtcttcagct ccttccgaga ccagcgcgac taccgcgaac    900
cctgctcggc ccactgccgg cagcgacatc cgcttccagc ccggtcaggt caaggctggt    960
gcttcagtca caactcggc tactgagact tcctctggtg agtctgccac gacgaccaca   1020
acatcagtgg ccactgcggc ttcgagcgcg gattcgtcga cgacttctgg ggttttgagt   1080
ggcgcctgca gccaggaggg ctactggtac tgcaacgggg gcactgcgtt ccagcgctgt   1140
gtcaacgggg aatgggatgc gtcccagagt gtggctgcgg gcacggtctg caccgccggt   1200
atctcggaga ccatcaccat ttcagccgcc gccacgcgcc gggatgccat gcgtcgtcat   1260
ctggcgcgtc caagcgtca ctga                                            1284
```

<210> SEQ ID NO 154
<211> LENGTH: 427
<212> TYPE: PRT
<213> ORGANISM: Aspergillus aculeatus

<400> SEQUENCE: 154

```
Met Ser Leu Ser Lys Ile Ala Thr Leu Leu Gly Ser Val Ser Leu
1               5                   10                  15

Val Ala Gly His Gly Tyr Val Ser Ser Ile Glu Val Asp Gly Thr Thr
            20                  25                  30

Tyr Gly Gly Tyr Leu Val Asp Thr Tyr Tyr Glu Ser Asp Pro Pro
        35                  40                  45

Glu Leu Ile Ala Trp Ser Thr Asn Ala Thr Asp Gly Tyr Val Ser
50                  55                  60

Pro Ser Asp Tyr Glu Ser Val Asn Ile Ile Cys His Lys Gly Ser Ala
65                  70                  75                  80

Pro Gly Ala Leu Ser Ala Pro Val Ala Pro Gly Gly Trp Val Gln Met
            85                  90                  95

Thr Trp Asn Thr Trp Pro Thr Asp His His Gly Pro Val Ile Thr Tyr
            100                 105                 110

Met Ala Asn Cys His Gly Ser Cys Ala Asp Val Asp Lys Thr Thr Leu
        115                 120                 125

Glu Phe Phe Lys Ile Asp Ala Gly Gly Leu Ile Asp Asp Thr Asp Val
    130                 135                 140

Pro Gly Thr Trp Ala Thr Asp Glu Leu Ile Glu Asp Ser Tyr Ser Arg
145                 150                 155                 160

Asn Ile Thr Ile Pro Ser Asp Ile Ala Pro Gly Tyr Tyr Val Leu Arg
```

```
                    165                 170                 175
His Glu Ile Ile Ala Leu His Ser Ala Glu Asn Leu Asp Gly Ala Gln
                180                 185                 190

Asn Tyr Pro Gln Cys Ile Asn Leu Glu Val Thr Gly Ser Glu Thr Ala
            195                 200                 205

Thr Pro Ser Gly Thr Leu Gly Thr Ala Leu Tyr Lys Glu Thr Asp Pro
        210                 215                 220

Gly Ile Tyr Val Asp Ile Trp Asn Thr Leu Ser Thr Tyr Thr Ile Pro
225                 230                 235                 240

Gly Pro Ala Leu Tyr Thr Ala Gly Ser Thr Ala Thr Ala Ala Ala
                245                 250                 255

Ala Asp Thr Thr Thr Thr Ser Ala Gly Thr Thr Ala Glu Ala Thr Thr
                260                 265                 270

Ala Ala Ala Ala Val Ser Thr Thr Ala Asp Ala Val Pro Thr Glu Ser
                275                 280                 285

Ser Ala Pro Ser Glu Thr Ser Ala Thr Thr Ala Asn Pro Ala Arg Pro
            290                 295                 300

Thr Ala Gly Ser Asp Ile Arg Phe Gln Pro Gly Gln Val Lys Ala Gly
305                 310                 315                 320

Ala Ser Val Asn Asn Ser Ala Thr Glu Thr Ser Ser Gly Glu Ser Ala
                325                 330                 335

Thr Thr Thr Thr Thr Ser Val Ala Thr Ala Ser Ser Ala Asp Ser
                340                 345                 350

Ser Thr Thr Ser Gly Val Leu Ser Gly Ala Cys Ser Gln Glu Gly Tyr
            355                 360                 365

Trp Tyr Cys Asn Gly Gly Thr Ala Phe Gln Arg Cys Val Asn Gly Glu
        370                 375                 380

Trp Asp Ala Ser Gln Ser Val Ala Ala Gly Thr Val Cys Thr Ala Gly
385                 390                 395                 400

Ile Ser Glu Thr Ile Thr Ile Ser Ala Ala Ala Thr Arg Arg Asp Ala
                405                 410                 415

Met Arg Arg His Leu Ala Arg Pro Lys Arg His
                420                 425

<210> SEQ ID NO 155
<211> LENGTH: 804
<212> TYPE: DNA
<213> ORGANISM: Aspergillus aculeatus

<400> SEQUENCE: 155
atgcttgtca aactcatctc ttttctttca gctgctacca gcgtagctgc tcatggtcat      60
gtgtcaaaca ttgtgatcaa cggggtgtcc taccgcggat gggacatcaa ttcggaccct     120
tacaattcca accctccggt ggtggttgca tggcaaacac ccaacacagc taatggcttc     180
atctcccctg atgcatacga cacagatgat gttatttgcc atctgagcgc tacgaatgcc     240
agaggccacg cagtcgtcgc tgctggcgac aagatcagcc tccagtggac gacctggcct     300
gacagtcacc atggccctgt catcagctac ctagccaact gcggctccag ctgcgagaca     360
gtcgataaga ccaccctcga gttcttcaag atcgatggtg ttggcttggt ggatgagagc     420
aatccccctg gtatctgggg agacgatgag ctcattgcca acaacaactc ttggctggta     480
gagattccag ctagtatcgc gccaggatac tatgtgctgc gtcacgagtt gatcgctctg     540
catggagcag ggagtgagaa tggagcccag aattacatgc aatgtttcaa ccttcaggtt     600
actgggactg gcacggtcca gccttccggg gtcctgggca cggagctgta caaacccaca     660
```

```
gacgctggaa ttcttgtcaa tatctaccag tcgctctcca cctatgttgt tcctggcccg    720
accctgatcc cccaggccgt ttccctcgtt cagtcgagct ccaccattac cgcctcgggc    780
acggcagtga caaccacggc ttga                                            804
```

<210> SEQ ID NO 156
<211> LENGTH: 267
<212> TYPE: PRT
<213> ORGANISM: Aspergillus aculeatus

<400> SEQUENCE: 156

```
Met Leu Val Lys Leu Ile Ser Phe Leu Ser Ala Ala Thr Ser Val Ala
1               5                   10                  15

Ala His Gly His Val Ser Asn Ile Val Ile Asn Gly Val Ser Tyr Arg
            20                  25                  30

Gly Trp Asp Ile Asn Ser Asp Pro Tyr Asn Ser Asn Pro Val Val
        35                  40                  45

Val Ala Trp Gln Thr Pro Asn Thr Ala Asn Gly Phe Ile Ser Pro Asp
    50                  55                  60

Ala Tyr Asp Thr Asp Asp Val Ile Cys His Leu Ser Ala Thr Asn Ala
65                  70                  75                  80

Arg Gly His Ala Val Ala Ala Gly Asp Lys Ile Ser Leu Gln Trp
                85                  90                  95

Thr Thr Trp Pro Asp Ser His His Gly Pro Val Ile Ser Tyr Leu Ala
            100                 105                 110

Asn Cys Gly Ser Ser Cys Glu Thr Val Asp Lys Thr Thr Leu Glu Phe
        115                 120                 125

Phe Lys Ile Asp Gly Val Gly Leu Val Asp Glu Ser Asn Pro Pro Gly
    130                 135                 140

Ile Trp Gly Asp Asp Glu Leu Ile Ala Asn Asn Asn Ser Trp Leu Val
145                 150                 155                 160

Glu Ile Pro Ala Ser Ile Ala Pro Gly Tyr Tyr Val Leu Arg His Glu
                165                 170                 175

Leu Ile Ala Leu His Gly Ala Gly Ser Glu Asn Gly Ala Gln Asn Tyr
            180                 185                 190

Met Gln Cys Phe Asn Leu Gln Val Thr Gly Thr Gly Thr Val Gln Pro
        195                 200                 205

Ser Gly Val Leu Gly Thr Glu Leu Tyr Lys Pro Thr Asp Ala Gly Ile
    210                 215                 220

Leu Val Asn Ile Tyr Gln Ser Leu Ser Thr Tyr Val Val Pro Gly Pro
225                 230                 235                 240

Thr Leu Ile Pro Gln Ala Val Ser Leu Val Gln Ser Ser Ser Thr Ile
                245                 250                 255

Thr Ala Ser Gly Thr Ala Val Thr Thr Thr Ala
            260                 265
```

<210> SEQ ID NO 157
<211> LENGTH: 822
<212> TYPE: DNA
<213> ORGANISM: Aspergillus aculeatus

<400> SEQUENCE: 157

```
atgaagtatc ttgcgatctt cgcggcagca gcagctggac tggcccgccc gacagcagcg     60
cactacatct tcagcaagct gattctggac ggcgaagtct ctgaggactg gcagtatatt    120
cgtaaaacca cccgggagac atgctatttg ccgaccaagt tcaccgacac cttcgacaac    180
```

```
ttgactccga acgaccagga tttccggtgc aatctcggct cgttcagcaa cgccgccaag      240
accgaagtgg ccgaggtgga agcgggctcc acgattggca tgcagctttt cgctggtagc      300
cacatgcgtc acccgggacc tgcgcaagtc ttcatgtcta aggccccgtc cggcaacgta      360
cagagctacg agggtgacgg ctcctggttc aagatctggg agcgtacact ctgcgacaaa      420
agtggcgatc tgactggaga tgcgtggtgt acatacggcc agaccgagat cgagtttcaa      480
atccccgagg cgaccccgac gggcgaatac ctggtccgag cggagcacat cggtcttcac      540
cgcgcacaga gtaatcaagc cgagttctac tacagctgcg cccaggtcaa ggtcacgggc      600
aatggtaccg gggtgccgag ccagacatat cagatccctg gcatgtacaa tgaccgctcg      660
gagcttttca acgggctgaa cttgtggtcc tactcggtgg agaacgtcga ggcagccatg      720
aagaattcta tcgtgggtga tgaaatttgg aatggaagtt ctgttccctc tgagtcccat      780
gtcccgaagt ataagaagag tcatgcttgt cgtgtttatt ga                        822
```

<210> SEQ ID NO 158
<211> LENGTH: 273
<212> TYPE: PRT
<213> ORGANISM: Aspergillus aculeatus

<400> SEQUENCE: 158

```
Met Lys Tyr Leu Ala Ile Phe Ala Ala Ala Ala Gly Leu Ala Arg
1               5                   10                  15

Pro Thr Ala Ala His Tyr Ile Phe Ser Lys Leu Ile Leu Asp Gly Glu
                20                  25                  30

Val Ser Glu Asp Trp Gln Tyr Ile Arg Lys Thr Thr Arg Glu Thr Cys
            35                  40                  45

Tyr Leu Pro Thr Lys Phe Thr Asp Thr Phe Asp Asn Leu Thr Pro Asn
        50                  55                  60

Asp Gln Asp Phe Arg Cys Asn Leu Gly Ser Phe Ser Asn Ala Ala Lys
65                  70                  75                  80

Thr Glu Val Ala Glu Val Ala Gly Ser Thr Ile Gly Met Gln Leu
                85                  90                  95

Phe Ala Gly Ser His Met Arg His Pro Gly Pro Ala Gln Val Phe Met
            100                 105                 110

Ser Lys Ala Pro Ser Gly Asn Val Gln Ser Tyr Glu Gly Asp Gly Ser
        115                 120                 125

Trp Phe Lys Ile Trp Glu Arg Thr Leu Cys Asp Lys Ser Gly Asp Leu
    130                 135                 140

Thr Gly Asp Ala Trp Cys Thr Tyr Gly Gln Thr Glu Ile Glu Phe Gln
145                 150                 155                 160

Ile Pro Glu Ala Thr Pro Thr Gly Glu Tyr Leu Val Arg Ala Glu His
                165                 170                 175

Ile Gly Leu His Arg Ala Gln Ser Asn Gln Ala Glu Phe Tyr Tyr Ser
            180                 185                 190

Cys Ala Gln Val Lys Val Thr Gly Asn Gly Thr Gly Val Pro Ser Gln
        195                 200                 205

Thr Tyr Gln Ile Pro Gly Met Tyr Asn Asp Arg Ser Glu Leu Phe Asn
    210                 215                 220

Gly Leu Asn Leu Trp Ser Tyr Ser Val Glu Asn Val Glu Ala Ala Met
225                 230                 235                 240

Lys Asn Ser Ile Val Gly Asp Glu Ile Trp Asn Gly Ser Ser Val Pro
                245                 250                 255
```

Ser Glu Ser His Val Pro Lys Tyr Lys Lys Ser His Ala Cys Arg Val
                260                 265                 270

Tyr

<210> SEQ ID NO 159
<211> LENGTH: 969
<212> TYPE: DNA
<213> ORGANISM: Aurantiporus alborubescens

<400> SEQUENCE: 159

```
atgcgaacca tcgccacgtt tgttacgctt gtagcctcag ttctccctgc ggtcctcgca    60
cacggaggtg tcctctccta ttcsaacggg gggaattggt actggggatg gaagccttac   120
aattcacctg acgggcagac caccatccaa cgcccgtggg caacatacaa tccgatcact   180
gatgcgacgg atcctaccat tgcttgcaac aacgacggga catctggagc tctgcagttg   240
actgcgacag tcgcggcggg atctgccatc acggcgtatt ggaaccaggt gtggccgcat   300
gataaagggc cgatgacgac atacctcgca caatgccccg cagtacctg cacaggagtc    360
aacgcgaaga ctctgaaatg gttcaagatc gatcacgccg ggttgctttc tggtactgtc   420
tacagtggct cgtgggcatc aggcaagatg attgcacaga actcgacctg dacaactacc   480
attccagcga cggtgccttc agggaactat ctgatacgtt tcgagactat tgccctgcac   540
tctttgccag cgcaatttta ccctgagtgc gcacaaattc aaatcacggg cggaggttcc   600
cgtgctccaa ccgctgcaga gcttgttagc ttccctggcg cgtacagcaa caatgatcct   660
ggtgtcaaca ttgacatcta ctccaatgcc gcgcagagtg caaccacata cgtaatacca   720
ggacctccat tgtacggcgg tgcttccgga tctggtccat cttccgcgcc tccatcaagt   780
accccaggta gttcgtccac ttcccacggt cccacgtccg tcagcacgtc cagcagtgct   840
gcaccatcga cgacaggaac cgtgacgcag tacggtcagt gcggtggcat tggttgggct   900
ggagctaccg gctgtatctc accattcaag tgcacggtca tcaacgatta ttactaccag   960
tgcctctga                                                           969
```

<210> SEQ ID NO 160
<211> LENGTH: 322
<212> TYPE: PRT
<213> ORGANISM: Aurantiporus alborubescens

<400> SEQUENCE: 160

Met Arg Thr Ile Ala Thr Phe Val Thr Leu Val Ala Ser Val Leu Pro
1               5                   10                  15

Ala Val Leu Ala His Gly Gly Val Leu Ser Tyr Ser Asn Gly Gly Asn
            20                  25                  30

Trp Tyr Trp Gly Trp Lys Pro Tyr Asn Ser Pro Asp Gly Gln Thr Thr
        35                  40                  45

Ile Gln Arg Pro Trp Ala Thr Tyr Asn Pro Ile Thr Asp Ala Thr Asp
    50                  55                  60

Pro Thr Ile Ala Cys Asn Asn Asp Gly Thr Ser Gly Ala Leu Gln Leu
65                  70                  75                  80

Thr Ala Thr Val Ala Ala Gly Ser Ala Ile Thr Ala Tyr Trp Asn Gln
                85                  90                  95

Val Trp Pro His Asp Lys Gly Pro Met Thr Thr Tyr Leu Ala Gln Cys
            100                 105                 110

Pro Gly Ser Thr Cys Thr Gly Val Asn Ala Lys Thr Leu Lys Trp Phe
        115                 120                 125

```
Lys Ile Asp His Ala Gly Leu Leu Ser Gly Thr Val Tyr Ser Gly Ser
130                 135                 140

Trp Ala Ser Gly Lys Met Ile Ala Gln Asn Ser Thr Trp Thr Thr
145                 150                 155                 160

Ile Pro Ala Thr Val Pro Ser Gly Asn Tyr Leu Ile Arg Phe Glu Thr
                165                 170                 175

Ile Ala Leu His Ser Leu Pro Ala Gln Phe Tyr Pro Glu Cys Ala Gln
                180                 185                 190

Ile Gln Ile Thr Gly Gly Gly Ser Arg Ala Pro Thr Ala Ala Glu Leu
                195                 200                 205

Val Ser Phe Pro Gly Ala Tyr Ser Asn Asn Asp Pro Gly Val Asn Ile
210                 215                 220

Asp Ile Tyr Ser Asn Ala Ala Gln Ser Ala Thr Thr Tyr Val Ile Pro
225                 230                 235                 240

Gly Pro Pro Leu Tyr Gly Gly Ala Ser Gly Ser Gly Pro Ser Ser Ala
                245                 250                 255

Pro Pro Ser Ser Thr Pro Gly Ser Ser Thr Ser His Gly Pro Thr
                260                 265                 270

Ser Val Ser Thr Ser Ser Ser Ala Ala Pro Ser Thr Thr Gly Thr Val
275                 280                 285

Thr Gln Tyr Gly Gln Cys Gly Gly Ile Gly Trp Ala Gly Ala Thr Gly
                290                 295                 300

Cys Ile Ser Pro Phe Lys Cys Thr Val Ile Asn Asp Tyr Tyr Tyr Gln
305                 310                 315                 320

Cys Leu

<210> SEQ ID NO 161
<211> LENGTH: 705
<212> TYPE: DNA
<213> ORGANISM: Aurantiporus alborubescens

<400> SEQUENCE: 161
atgaaggcta tcttggctat tttctcggcc cttgctccac ttgccgctgc cattatacc      60
ttccctgatt ttattgtcaa cggaacaaca actgccgatt gggtctacat ccgagagacc    120
gcgaaccact actcgaatgg tcctgtaacc aacgtgaacg atccagaatt ccgatgctac    180
gagctggacc tgcaaaacac ggcagcgagt accctcaccg ccacggtctc tgcaggctcc    240
agcgtcggct ttaaagctaa cagcgccctt taccatcctg gttatctcga tgtgtatatg    300
tccaaagcga ccccagctgc taattcaccc agtgctggaa cggaccaaag ctggttcaag    360
gtctatgaat ccgctccggt cttcgcgaat ggggccctaa gcttcccttc ggagaacatc    420
caatctttca cgttcacaat cccgaagtcc cttcccagtg ccaatatct catccgtgtg     480
gaacacatcg ctctccactc cgccagtagc tacgaggtg cacaattcta catcagctgc     540
gctcaagtca atgtcgtcaa cggcgggaac ggaaacccag accgttagt caagattccc     600
ggcgtttaca ctgggaacga gcctggcatc ctcatcaaca tctacagctt cccaccgggt    660
ttcagtggct accaatcccc gggacctgct gtgtggcgtg gttga                    705

<210> SEQ ID NO 162
<211> LENGTH: 234
<212> TYPE: PRT
<213> ORGANISM: Aurantiporus alborubescens

<400> SEQUENCE: 162

Met Lys Ala Ile Leu Ala Ile Phe Ser Ala Leu Ala Pro Leu Ala Ala
```

```
  1               5                  10                 15
Ala His Tyr Thr Phe Pro Asp Phe Ile Val Asn Gly Thr Thr Thr Ala
                20                  25                 30

Asp Trp Val Tyr Ile Arg Glu Thr Ala Asn His Tyr Ser Asn Gly Pro
                35                  40                 45

Val Thr Asn Val Asn Asp Pro Glu Phe Arg Cys Tyr Glu Leu Asp Leu
 50                  55                  60

Gln Asn Thr Ala Ala Ser Thr Leu Thr Ala Thr Val Ser Ala Gly Ser
 65                  70                  75                 80

Ser Val Gly Phe Lys Ala Asn Ser Ala Leu Tyr His Pro Gly Tyr Leu
                85                  90                 95

Asp Val Tyr Met Ser Lys Ala Thr Pro Ala Ala Asn Ser Pro Ser Ala
                100                 105                110

Gly Thr Asp Gln Ser Trp Phe Lys Val Tyr Glu Ser Ala Pro Val Phe
                115                 120                125

Ala Asn Gly Ala Leu Ser Phe Pro Ser Glu Asn Ile Gln Ser Phe Thr
130                 135                 140

Phe Thr Ile Pro Lys Ser Leu Pro Ser Gly Gln Tyr Leu Ile Arg Val
145                 150                 155                160

Glu His Ile Ala Leu His Ser Ala Ser Ser Tyr Gly Gly Ala Gln Phe
                165                 170                175

Tyr Ile Ser Cys Ala Gln Val Asn Val Val Asn Gly Asn Gly Asn
                180                 185                190

Pro Gly Pro Leu Val Lys Ile Pro Gly Val Tyr Thr Gly Asn Glu Pro
                195                 200                205

Gly Ile Leu Ile Asn Ile Tyr Ser Phe Pro Pro Gly Phe Ser Gly Tyr
                210                 215                220

Gln Ser Pro Gly Pro Ala Val Trp Arg Gly
225                 230
```

<210> SEQ ID NO 163
<211> LENGTH: 702
<212> TYPE: DNA
<213> ORGANISM: Trichophaea saccata

<400> SEQUENCE: 163

```
atgacgcccc tgaaactccg cccccttctc ctcctggtgc tttccacgac cctcagcctc      60
gtgcacgcgc actatcgctt ctacgaactg atcgccaacg ggccacccca cgcttccttc     120
gaatacatcc gccaatgggt gcccatctac agcaactctc ccgtaaccga cgtcaccagc     180
gtcaacctcc gctgcaacgt caacgccact cccgccgccg aggtgatcac cgttgctgcc     240
ggtagcaccg tcggcttcgt agcagacaca acagtaacgc accccggtgc gttcaccgcg     300
tacatggcga aagcgcccga agacatcacg gaatgggatg gcaacgggga ctggttcaag     360
atctgggaga agggtccaac gagtataacc agtagcggga taacctggga cgtcacggat     420
acccaatgga ccttcaccat cccttccgcg acaccaaacg gtcaatacct actccgcttc     480
gagcacatag cgctccacgc cgccagcacc gtgggggtg ctcaattcta catgtcgtgc     540
gcgcagatac aagtaacgaa cggcggcaac gggagtcccg ggccaccat caagttcccg      600
ggcggataca cgccacaga ccccggtatc ctgatcaata tctattatcc catccccact      660
agttacacta ttcctggtcc accggtttgg accggtaagt aa                        702
```

<210> SEQ ID NO 164
<211> LENGTH: 233

<210> TYPE: PRT
<213> ORGANISM: Trichophaea saccata

<400> SEQUENCE: 164

```
Met Thr Pro Leu Lys Leu Arg Pro Leu Leu Leu Val Leu Ser Thr
1               5                   10                  15

Thr Leu Ser Leu Val His Ala His Tyr Arg Phe Tyr Glu Leu Ile Ala
            20                  25                  30

Asn Gly Ala Thr His Ala Ser Phe Glu Tyr Ile Arg Gln Trp Val Pro
        35                  40                  45

Ile Tyr Ser Asn Ser Pro Val Thr Asp Val Thr Ser Val Asn Leu Arg
50                  55                  60

Cys Asn Val Asn Ala Thr Pro Ala Ala Glu Val Ile Thr Val Ala Ala
65                  70                  75                  80

Gly Ser Thr Val Gly Phe Val Ala Asp Thr Thr Val Thr His Pro Gly
                85                  90                  95

Ala Phe Thr Ala Tyr Met Ala Lys Ala Pro Glu Asp Ile Thr Glu Trp
            100                 105                 110

Asp Gly Asn Gly Asp Trp Phe Lys Ile Trp Glu Lys Gly Pro Thr Ser
        115                 120                 125

Ile Thr Ser Ser Gly Ile Thr Trp Asp Val Thr Asp Thr Gln Trp Thr
130                 135                 140

Phe Thr Ile Pro Ser Ala Thr Pro Asn Gly Gln Tyr Leu Leu Arg Phe
145                 150                 155                 160

Glu His Ile Ala Leu His Ala Ala Ser Thr Val Gly Gly Ala Gln Phe
                165                 170                 175

Tyr Met Ser Cys Ala Gln Ile Gln Val Thr Asn Gly Gly Asn Gly Ser
            180                 185                 190

Pro Gly Pro Thr Ile Lys Phe Pro Gly Gly Tyr Ser Ala Thr Asp Pro
        195                 200                 205

Gly Ile Leu Ile Asn Ile Tyr Tyr Pro Ile Pro Thr Ser Tyr Thr Ile
210                 215                 220

Pro Gly Pro Pro Val Trp Thr Gly Lys
225                 230
```

<210> SEQ ID NO 165
<211> LENGTH: 714
<212> TYPE: DNA
<213> ORGANISM: Trichophaea saccata

<400> SEQUENCE: 165

```
atgaaatgcc ttctctccct ccttctcgcc gcgacagcgg tctccgctca cacgatcttc      60
caagaaatcg gcataaacgg ggtgatgcaa gctcgctacg actacatgcg gctgccgtcc     120
tacgacggtc ccattacgga cgtaacgagc acctacatgg cgtgcaacgg tggtcccaat     180
ccattggtcc aaatctcgaa cgacgtcgct ttcgtaaaag ccggcgacag catcacgctg     240
caatgggcgc aaacgttgac gacagatttc aacacggggc tgatcatcga tccatcgcac     300
ttgggtcctg tgatggtcta catggccaaa gtaccctccg ccaccggtcc gatccccaac     360
agcggctggt caaaatctca cgaagacgg tacgacccga caacaaagac atgggcggta     420
accaagctca tcaacaacaa gggaaaagtg accgtcacca tcccatcgtg tctaccggca     480
ggggactact tgctgcgcgg tgaaatcatt gccttgcacg cggctagtac ctatccaggc     540
gcacagtttt acatggagtg tgcgcagttg cggcttacca gtggcggcac taagatgcct     600
accacgtata acattccggg gatctattcg cccactgatc cgggtgttac gttcaatctt     660
```

```
tacaatggat tcacgagtta taccattcct ggcccaaggc cgtttacatg ctag        714
```

<210> SEQ ID NO 166
<211> LENGTH: 237
<212> TYPE: PRT
<213> ORGANISM: Trichophaea saccata

<400> SEQUENCE: 166

```
Met Lys Cys Leu Leu Ser Leu Leu Ala Ala Thr Ala Val Ser Ala
1               5                   10                  15

His Thr Ile Phe Gln Glu Ile Gly Ile Asn Gly Val Met Gln Ala Arg
            20                  25                  30

Tyr Asp Tyr Met Arg Leu Pro Ser Tyr Asp Gly Pro Ile Thr Asp Val
        35                  40                  45

Thr Ser Thr Tyr Met Ala Cys Asn Gly Gly Pro Asn Pro Leu Val Gln
50                  55                  60

Ile Ser Asn Asp Val Ala Phe Val Lys Ala Gly Asp Ser Ile Thr Leu
65                  70                  75                  80

Gln Trp Ala Gln Thr Leu Thr Thr Asp Phe Asn Thr Gly Leu Ile Ile
                85                  90                  95

Asp Pro Ser His Leu Gly Pro Val Met Val Tyr Met Ala Lys Val Pro
            100                 105                 110

Ser Ala Thr Gly Pro Ile Pro Asn Ser Gly Trp Phe Lys Ile Tyr Glu
        115                 120                 125

Asp Gly Tyr Asp Pro Thr Thr Lys Thr Trp Ala Val Thr Lys Leu Ile
    130                 135                 140

Asn Asn Lys Gly Lys Val Thr Val Thr Ile Pro Ser Cys Leu Pro Ala
145                 150                 155                 160

Gly Asp Tyr Leu Leu Arg Gly Glu Ile Ile Ala Leu His Ala Ala Ser
                165                 170                 175

Thr Tyr Pro Gly Ala Gln Phe Tyr Met Glu Cys Ala Gln Leu Arg Leu
            180                 185                 190

Thr Ser Gly Gly Thr Lys Met Pro Thr Thr Tyr Asn Ile Pro Gly Ile
        195                 200                 205

Tyr Ser Pro Thr Asp Pro Gly Val Thr Phe Asn Leu Tyr Asn Gly Phe
    210                 215                 220

Thr Ser Tyr Thr Ile Pro Gly Pro Arg Pro Phe Thr Cys
225                 230                 235
```

<210> SEQ ID NO 167
<211> LENGTH: 1455
<212> TYPE: DNA
<213> ORGANISM: Penicillium thomii

<400> SEQUENCE: 167

```
atgtctctgt ctaagatttc tggattgatc ctcggatctg ctgccttggt ggctggccac        60
ggttacgtga gcggaatcgt cgttgacgat acctactatg tggatacct tgtcacccag        120 taccctatg agagtgacgc cccagagctc attgcctggt cggagcaaga gaccgatctg        180
ggttacatcg atggctctga gtatgccaac tccaacatca tctgtcacaa ggaggccaaa        240
cctggtgctt tggaagcacc cgttaaggct ggtggctccg tcgagctcca gtggaccact        300
tggcctacca gccaccacgg tcctgtcatt acctacatgg ccaactgtaa cggcgactgt        360
gacgacgttg acaagactac tttgcagttc ttcaagattg accagggtgg tttgatcagc        420
gataccaccg agcccggtac ctgggcaact gacaacctca tcgccaacaa caatagccgt        480
```

```
actgtcaccg tccccagcga cattgccgat ggaaactacg tcctccgtca cgagatcatt    540
gccctccact ccgccgggga gaccaacggt gcccagaact accccccaatg tatcaacttg   600 aaggtcactg gcggcggtag cgctactcct tctggtaccc tgggtaccgc cctgtacaag    660
aacaccgacc ccggtatcct gatcaacatc tacacttccc tcagcaccta cgatatcccc    720
ggcccaaccc tgtacactgc cggcgccgcc gctgctaccg ctgcctccac ggctgcctct    780
tccaccgccg ctgccgttac tactgccgac gccgtcacta ccgccgctgc cgtcaccagc    840
agctctgcat ccgtggaagt tgtgcccaca actactccca gctcatcaat cgtcagtgcc    900
ttcccaacct ggagccctc ttctaccca ccttctcca actcttccaa cggatggcgt       960
ccgtcattca gccgcggacc tggtggcccc cgcttcacat ctgctcctgc tcctcagttc   1020
tccgctccta gcggcgctca gcagaagcag tctgccactg ctaccccccat cgtggctacc   1080 cctgtcgtga tcaccatgac cgagaccagc acctcctggg tcaccgaaat ggttactctt   1140
actgacaagt ctgttgtgca gaccaccagc gctgtcccag tcgtcgtcgc cgccaccact   1200
acccttaccg agggaagcga gcctgctcag acagcctccc ccagcgttgt ctccggctcc   1260
tctagctccg gctctagctc ctcatctacc accaccacct caaagacctc aactggatcc   1320
gactacgtct ccagcgactg gatgtcttac ctcagctcct tgagcgctgc tgaggtcctc   1380
cagatgctgc gccagacctt ccgttggatg gtcagcaacg acaaggtgca cgctcgtgat   1440
attaccatca actag                                                    1455

<210> SEQ ID NO 168
<211> LENGTH: 484
<212> TYPE: PRT
<213> ORGANISM: Penicillium thomii

<400> SEQUENCE: 168

Met Ser Leu Ser Lys Ile Ser Gly Leu Ile Leu Gly Ser Ala Ala Leu
1               5                   10                  15

Val Ala Gly His Gly Tyr Val Ser Gly Ile Val Val Asp Asp Thr Tyr
            20                  25                  30

Tyr Gly Gly Tyr Leu Val Thr Gln Tyr Pro Tyr Glu Ser Asp Ala Pro
        35                  40                  45

Glu Leu Ile Ala Trp Ser Glu Gln Glu Thr Asp Leu Gly Tyr Ile Asp
    50                  55                  60

Gly Ser Glu Tyr Ala Asn Ser Asn Ile Ile Cys His Lys Glu Ala Lys
65                  70                  75                  80

Pro Gly Ala Leu Glu Ala Pro Val Lys Ala Gly Ser Val Glu Leu
            85                  90                  95

Gln Trp Thr Thr Trp Pro Thr Ser His His Gly Pro Val Ile Thr Tyr
            100                 105                 110

Met Ala Asn Cys Asn Gly Asp Cys Asp Asp Val Asp Lys Thr Thr Leu
        115                 120                 125

Gln Phe Phe Lys Ile Asp Gln Gly Gly Leu Ile Ser Asp Thr Thr Glu
    130                 135                 140

Pro Gly Thr Trp Ala Thr Asp Asn Leu Ile Ala Asn Asn Ser Arg
145                 150                 155                 160

Thr Val Thr Val Pro Ser Asp Ile Ala Asp Gly Asn Tyr Val Leu Arg
                165                 170                 175

His Glu Ile Ile Ala Leu His Ser Ala Gly Glu Thr Asn Gly Ala Gln
            180                 185                 190
```

Asn Tyr Pro Gln Cys Ile Asn Leu Lys Val Thr Gly Gly Ser Ala
            195                 200                 205

Thr Pro Ser Gly Thr Leu Gly Thr Ala Leu Tyr Lys Asn Thr Asp Pro
    210                 215                 220

Gly Ile Leu Ile Asn Ile Tyr Thr Ser Leu Ser Thr Tyr Asp Ile Pro
225                 230                 235                 240

Gly Pro Thr Leu Tyr Thr Ala Gly Ala Ala Ala Thr Ala Ala Ser
                245                 250                 255

Thr Ala Ala Ser Ser Thr Ala Ala Val Thr Thr Ala Asp Ala Val
            260                 265                 270

Thr Thr Ala Ala Ala Val Thr Ser Ser Ala Ser Val Glu Val Val
        275                 280                 285

Pro Thr Thr Thr Pro Ser Ser Ser Ile Val Ser Ala Phe Pro Thr Trp
    290                 295                 300

Ser Pro Ser Ser Thr Pro Pro Phe Ser Asn Ser Ser Asn Gly Trp Arg
305                 310                 315                 320

Pro Ser Phe Ser Arg Gly Pro Gly Gly Pro Arg Phe Thr Ser Ala Pro
                325                 330                 335

Ala Pro Gln Phe Ser Ala Pro Ser Gly Ala Gln Gln Lys Gln Ser Ala
            340                 345                 350

Thr Ala Thr Pro Ile Val Ala Thr Pro Val Val Ile Thr Met Thr Glu
        355                 360                 365

Thr Ser Thr Ser Trp Val Thr Glu Met Val Thr Leu Thr Asp Lys Ser
    370                 375                 380

Val Val Gln Thr Thr Ser Ala Val Pro Val Val Ala Ala Thr Thr
385                 390                 395                 400

Thr Leu Thr Glu Gly Ser Glu Pro Ala Gln Thr Ala Ser Pro Ser Val
                405                 410                 415

Val Ser Gly Ser Ser Ser Ser Gly Ser Ser Ser Ser Thr Thr Thr
            420                 425                 430

Thr Ser Lys Thr Ser Thr Gly Ser Asp Tyr Val Ser Ser Asp Trp Met
        435                 440                 445

Ser Tyr Leu Ser Ser Leu Ser Ala Ala Glu Val Leu Gln Met Leu Arg
    450                 455                 460

Gln Thr Phe Arg Trp Met Val Ser Asn Asp Lys Val His Ala Arg Asp
465                 470                 475                 480

Ile Thr Ile Asn

<210> SEQ ID NO 169
<211> LENGTH: 1021
<212> TYPE: DNA
<213> ORGANISM: Talaromyces stipitatus

<400> SEQUENCE: 169
atgccttcca ctaaagttgc tgctctatct gccgtcctgg ctttggcctc cacggttgct      60
ggccatggct ttgtgcaaaa tattgtcatt gacggtaaat cgtaagtgac ttgcttttgt     120
actatagagc tagataaata cttatactaa ataattcagc tacactggct acctcgtgaa     180
ccagtatcct taccagtcca acccaccagc tgttattggg tggtcaacca ctgcaaccga     240
cttgggattt gtcgatggat ctggatacac caacccggat atcatctgcc acaaaaacgc     300
caaacccggt cagcttttctg ctccggttgc cgcaggaggc aaggttgagc tcgaatggac     360
aacatggccc gagagccatc acggccctgt catcagctat ctcgccaatt gcaatggcga     420
ttgtactacc gtggataaga cgaagctcga atttgtcaaa atcgatcagc ggggtctgat     480

-continued

```
cgacgacagc aatcctcccg gtacatgggc cgccgaccag ctcatcgccg ccaacaacag        540
ctggactgta actattcccg agagcatcgc gcctggaaac tacgtccttc gccacgaaat        600
catcgctctt cactccgcca acaacgcaac cggagctcaa aactaccctc aatgcatcaa       660
cttgcaaatc actggcagcg ggacggccaa cccatctggt accctggcg agaaactcta        720 taccccaact gacccaggta tcttggtcaa catctaccag tcattgtcgt cttatgttat       780
tcccggtccg actttgtgga gtggtgctgc agcgcacgtt gttgccactg cagccggttc       840
tgctactggg gttgcttctg ccaccgctac tccgaccact cttgtgactg ccgtttcatc       900
gcctaccggt gctccttcag tggtgactcc tgaggctcct tcagtaacct cgttcgcccc       960
agtggtgact gttactgatg tcgttactgt gactaccgtc atcactacta ctatctctta      1020
g                                                                       1021
```

<210> SEQ ID NO 170
<211> LENGTH: 320
<212> TYPE: PRT
<213> ORGANISM: Talaromyces stipitatus

<400> SEQUENCE: 170

```
Met Pro Ser Thr Lys Val Ala Ala Leu Ser Ala Val Leu Ala Leu Ala
 1               5                  10                  15

Ser Thr Val Ala Gly His Gly Phe Val Gln Asn Ile Val Ile Asp Gly
            20                  25                  30

Lys Ser Tyr Thr Gly Tyr Leu Val Asn Gln Tyr Pro Tyr Gln Ser Asn
        35                  40                  45

Pro Pro Ala Val Ile Gly Trp Ser Thr Thr Thr Asp Leu Gly Phe
    50                  55                  60

Val Asp Gly Ser Gly Tyr Thr Asn Pro Asp Ile Ile Cys His Lys Asn
 65                  70                  75                  80

Ala Lys Pro Gly Gln Leu Ser Ala Pro Val Ala Gly Gly Lys Val
                85                  90                  95

Glu Leu Glu Trp Thr Thr Trp Pro Glu Ser His His Gly Pro Val Ile
            100                 105                 110

Ser Tyr Leu Ala Asn Cys Asn Gly Asp Cys Thr Thr Val Asp Lys Thr
        115                 120                 125

Lys Leu Glu Phe Val Lys Ile Asp Gln Arg Gly Leu Ile Asp Asp Ser
    130                 135                 140

Asn Pro Pro Gly Thr Trp Ala Ala Asp Gln Leu Ile Ala Ala Asn Asn
145                 150                 155                 160

Ser Trp Thr Val Thr Ile Pro Glu Ser Ile Ala Pro Gly Asn Tyr Val
                165                 170                 175

Leu Arg His Glu Ile Ile Ala Leu His Ser Ala Asn Asn Ala Thr Gly
            180                 185                 190

Ala Gln Asn Tyr Pro Gln Cys Ile Asn Leu Gln Ile Thr Gly Ser Gly
        195                 200                 205

Thr Ala Asn Pro Ser Gly Thr Pro Gly Glu Lys Leu Tyr Thr Pro Thr
    210                 215                 220

Asp Pro Gly Ile Leu Val Asn Ile Tyr Gln Ser Leu Ser Ser Tyr Val
225                 230                 235                 240

Ile Pro Gly Pro Thr Leu Trp Ser Gly Ala Ala His Val Val Ala
                245                 250                 255

Thr Ala Ala Gly Ser Ala Thr Gly Val Ala Ser Ala Thr Ala Thr Pro
            260                 265                 270
```

```
Thr Thr Leu Val Thr Ala Val Ser Ser Pro Thr Gly Ala Pro Ser Val
        275                 280                 285

Val Thr Pro Glu Ala Pro Ser Val Thr Ser Phe Ala Pro Val Val Thr
        290                 295                 300

Val Thr Asp Val Val Thr Val Thr Thr Val Ile Thr Thr Thr Ile Ser
305                 310                 315                 320
```

<210> SEQ ID NO 171
<211> LENGTH: 1008
<212> TYPE: DNA
<213> ORGANISM: Thermoascus aurantiacus

<400> SEQUENCE: 171

```
atgaagctcg gctctctcgt gctcgctctc agcgcagcta ggcttacact gtcggcccct      60
ctcgcagaca gaaagcagga gaccaagcgt gcgaaagtat tccaatggtt cggttcgaac     120
gagtccggtg ctgaattcgg aagccagaac cttccaggag tcgagggaaa ggattatata     180
tggcctgatc ccaacaccat tgacacattg atcagcaagg ggatgaacat ctttcgtgtc     240
cccttttatga tggagagatt ggttcccaac tcaatgaccg gctctccgga tccgaactac     300
ctggcagatc tcatagcgac tgtaaatgca atcacccaga aaggtgccta cgccgtcgtc     360
gatcctcata actacggcag atactacaat tctataatct cgagcccttc cgatttccag     420
accttctgga aaacggtcgc ctcacagttt gcttcgaatc cactggtcat cttcgacact     480
aataacgaat accacgatat ggaccagacc ttagtcctca atctcaacca ggccgctatc     540
gacggcatcc gttccgccgg agccacttcc cagtacatct tgtcgagggg caattcgtgg     600
accggggcat ggacctggac gaacgtgaac gataacatga aaagcctgac cgacccatct     660
gacaagatca tatacgagat gcaccagtac ctggactctg acggatccgg acatcagcg     720
acctgcgtat cttcgaccat cggtcaagag cgaatcacca gcgcaacgca gtggctcagg     780
gccaacggga gaagggcat catcggcgag tttgcgggcg gagccaacga cgtctgcgag     840
acggccatca cgggcatgct ggactacatg cccagaaca cagacgtctg gactggcgcc     900
atctggtggg cggccgggcc gtggtgggga gactacatat ctccatgga gccggacaat     960
ggcatcgcgt atcagcagat acttcctatt ttgactccgt atctttga               1008
```

<210> SEQ ID NO 172
<211> LENGTH: 335
<212> TYPE: PRT
<213> ORGANISM: Thermoascus aurantiacus

<400> SEQUENCE: 172

```
Met Lys Leu Gly Ser Leu Val Leu Ala Leu Ser Ala Ala Arg Leu Thr
1               5                   10                  15

Leu Ser Ala Pro Leu Ala Asp Arg Lys Gln Glu Thr Lys Arg Ala Lys
            20                  25                  30

Val Phe Gln Trp Phe Gly Ser Asn Glu Ser Gly Ala Glu Phe Gly Ser
        35                  40                  45

Gln Asn Leu Pro Gly Val Glu Gly Lys Asp Tyr Ile Trp Pro Asp Pro
    50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
```

-continued

```
                100                  105                   110
Gln Lys Gly Ala Tyr Ala Val Val Asp Pro His Asn Tyr Gly Arg Tyr
        115                 120                 125

Tyr Asn Ser Ile Ile Ser Ser Pro Ser Asp Phe Gln Thr Phe Trp Lys
        130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
                180                 185                 190

Ile Phe Val Glu Gly Asn Ser Trp Thr Gly Ala Trp Thr Trp Thr Asn
        195                 200                 205

Val Asn Asp Asn Met Lys Ser Leu Thr Asp Pro Ser Asp Lys Ile Ile
        210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
                260                 265                 270

Gly Gly Ala Asn Asp Val Cys Glu Thr Ala Ile Thr Gly Met Leu Asp
                275                 280                 285

Tyr Met Ala Gln Asn Thr Asp Val Trp Thr Gly Ala Ile Trp Trp Ala
        290                 295                 300

Ala Gly Pro Trp Trp Gly Asp Tyr Ile Phe Ser Met Glu Pro Asp Asn
305                 310                 315                 320

Gly Ile Ala Tyr Gln Gln Ile Leu Pro Ile Leu Thr Pro Tyr Leu
                325                 330                 335
```